United States Patent
Lindsay et al.

(10) Patent No.: US 11,938,129 B2
(45) Date of Patent: Mar. 26, 2024

(54) METHODS AND COMPOSITIONS FOR THE TREATMENT OF VASCULAR DISEASE

(71) Applicant: THE GENERAL HOSPITAL CORPORATION, Boston, MA (US)

(72) Inventors: Mark E. Lindsay, Winchester, MA (US); Christian Lacks Lino Cardenas, Boston, MA (US); Rajeev Malhotra, Boston, MA (US)

(73) Assignee: THE GENERAL HOSPITAL CORPORATION

( * ) Notice: Subject to any disclaimer, the term of this patent is extended or adjusted under 35 U.S.C. 154(b) by 407 days.

(21) Appl. No.: 16/969,743

(22) PCT Filed: Feb. 19, 2019

(86) PCT No.: PCT/US2019/018501
§ 371 (c)(1),
(2) Date: Aug. 13, 2020

(87) PCT Pub. No.: WO2019/161364
PCT Pub. Date: Aug. 22, 2019

(65) Prior Publication Data
US 2021/0038596 A1   Feb. 11, 2021

Related U.S. Application Data

(60) Provisional application No. 62/793,614, filed on Jan. 17, 2019, provisional application No. 62/632,105, filed on Feb. 19, 2018.

(51) Int. Cl.
*A61K 31/496* (2006.01)
*A61K 31/4178* (2006.01)
*A61P 9/00* (2006.01)

(52) U.S. Cl.
CPC ........ *A61K 31/496* (2013.01); *A61K 31/4178* (2013.01); *A61P 9/00* (2018.01)

(58) Field of Classification Search
CPC ................................ A61P 9/10; A61K 31/496
See application file for complete search history.

(56) References Cited

U.S. PATENT DOCUMENTS

| | | |
|---|---|---|
| 2005/0059682 A1 | 3/2005 | Rubinfeld |
| 2015/0133381 A1 | 5/2015 | Boileau et al. |
| 2016/0340674 A1* | 11/2016 | Jin ....................... A61K 31/713 |

FOREIGN PATENT DOCUMENTS

| | | | |
|---|---|---|---|
| WO | 2011136638 A1 | 11/2011 | |
| WO | WO-2011136638 A1 * | 11/2011 | ........... C12Q 1/6886 |
| WO | WO-2017153023 A1 * | 9/2017 | .............. A61P 43/00 |

OTHER PUBLICATIONS

Zhang (International Journal of Cardiology vol. 203 pp. 214-216. Published 2016). (Year: 2016).*
Han (Journal of Cardiovascular Pharmacology vol. 71 pp. 104-112 published Feb. 2018) (Year: 2018).*
Cardenas et al., "An HDAC9-MALAT1-BRG1 Complex Medlate Smooth Muscle Dysfunction in Thoracic Aortic Aneurysm" Nature Communication, 9(1): 1-14 (2018).
Cardenas et al., "Inhibition of the Methyltranferase EZH2 Improves Aortic Performance in Experimental Thoracic Aortic Aneurysm" Jci Insight 3(5) (2018).
Malhotra et al. "HDAC9 is implicated in atherosclerotic aortic calcification and affects vascular smooth muscle cell phenotype." Nature genetics 51(11): 1580-1587 (2019).
Yang et al., "Effectiveness of Combonation of Losartan Potassium and Doxycycline Versus Single-Drug Treatments in the Secondary Prevention of Thoracic Aortic Aneurysm in Marfan Syndrome" The Journal of thoracic and cardiovascular surgery 140(2): 305-312 (2010).
B3KUJ5, UniProtKB Accession No. B3KUJ5, Histone deacetylase, Sep. 2, 2008 [online]. [Retrieved on Jun. 10, 2019]. Retrieved from the internet <URL: https://www.uniprot.org/uniprot/B3KUJ5> Entire document.
Cao et al. "Histone deacetylase 9 represses cholesterol efflux and alternatively activated macrophages in atherosclerosis development." Arteriosclerosis, Thrombosis, and Vascular Biology 34(9): 1871-1879 (2014).
Li et al. "Tgfbr2 disruption in postnatal smooth muscle impairs aortic wall homeostasis." The Journal of Clinical Investigation 124(2): 755-767 (2014).
Maleszewska et al. "Enhancer of zeste homolog-2 (EZH2) methyltransferase regulates transgelin/smooth muscle-22α expression in endothelial cells in response to interleukin-1β and transforming growth factor-β2." Cellular Signalling 27(8): 1589-1596 (2015).

* cited by examiner

*Primary Examiner* — Theodore R. Howell
*Assistant Examiner* — George W Kosturko
(74) *Attorney, Agent, or Firm* — NIXON PEABODY LLP; David S. Resnick; Nicole D. Kling

(57) ABSTRACT

The technology described herein relates to methods and compositions to prevent or treat vascular disease by targeting the epigenetic regulation of gene expression of vascular smooth muscle cell cytoskeletal proteins.

2 Claims, 66 Drawing Sheets
Specification includes a Sequence Listing.

| Sample ID | Clinical Classification | Asc. Size (mm) | Dissection |
|---|---|---|---|
| Ao58 | Non-Syndromic | 4.9 | No |
| Ao269 | Marfan | 5.1 | No |
| Ao699 | Non-Syndromic | 4.2 | No |
| Ao204 | Marfan | 6.6 | Yes |
| Ao696 | Syndromic | 5.05 | No |
| Ao628 | Marfan | 5.3 | No |
| Ao282 | Marfan | 5.5 | No |
| Ao245 | Marfan | 6.7 | Yes |
| Ao203 | Marfan | 6.7 | Yes |

TGFR2$^{G357W}$ vs Wildtype

Cellular Function

- Wnt Signaling Pathway
- Oxytocin Signaling Pathway
- cAMP Signaling Pathway
- Renin Secretion
- PI3K-AKT Signaling Pathway
- Vascular Smooth Muscle Contraction
- Hippo Signaling Pathway
- Proteasome
- Calcium Signaling Pathway

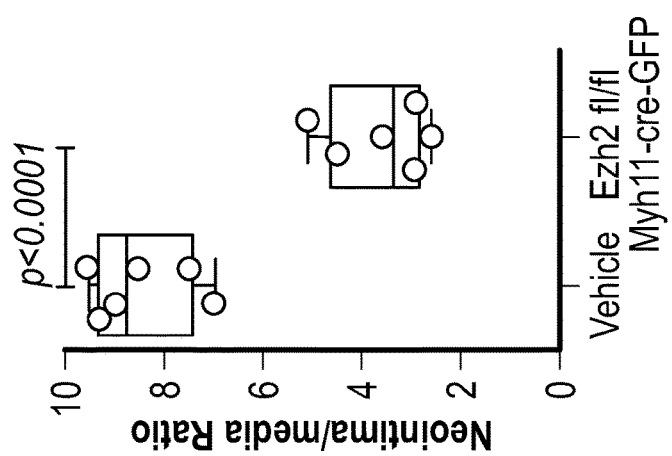
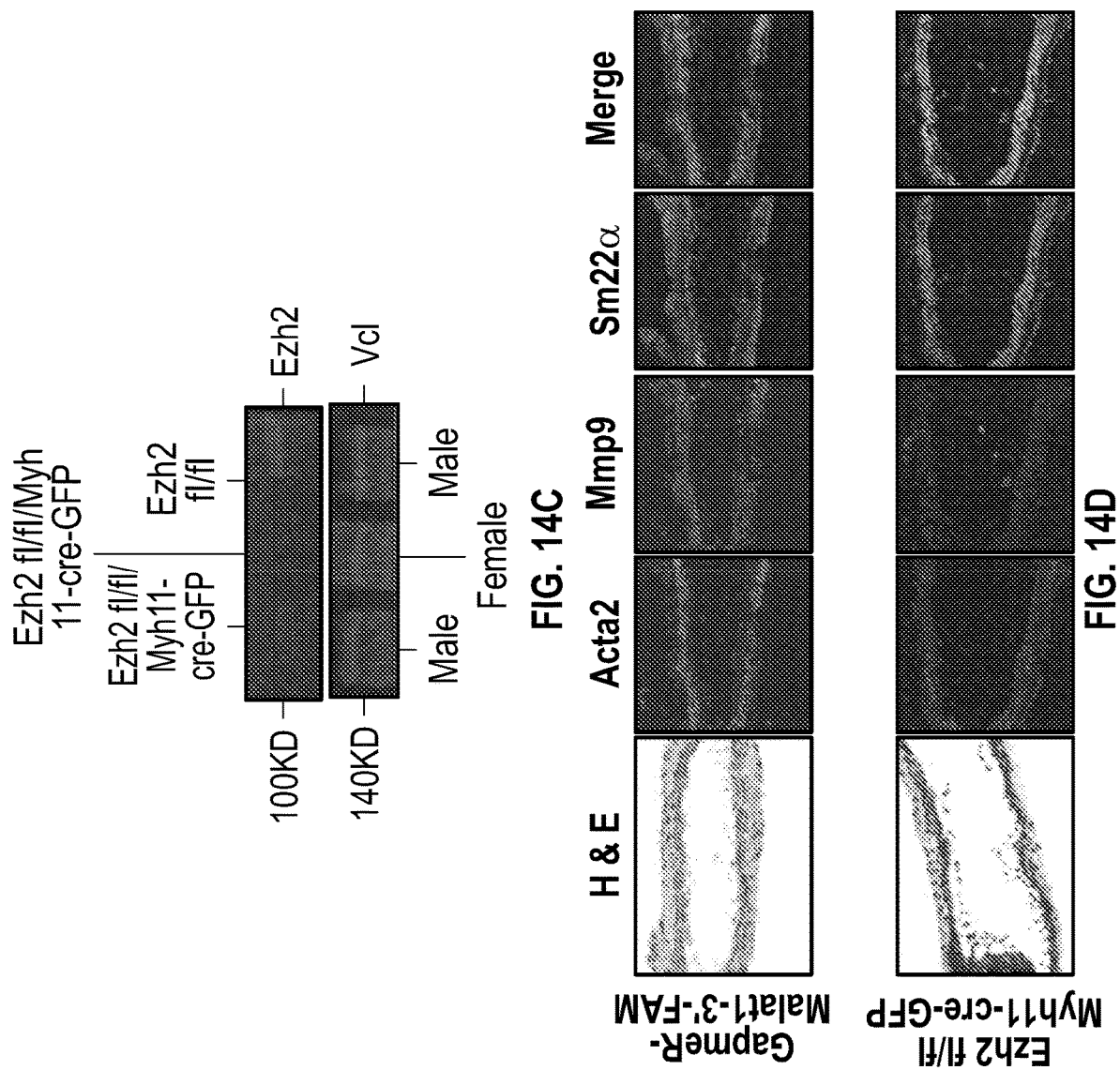
FIG. 14C
FIG. 14D
FIG. 14E

SEQUENCE LISTING

<160> NUMBER OF SEQ ID NOS: 65

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gtcacaatgc attcta    16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' 36-FAM

<400> SEQUENCE: 2
gtcacaatgc attcta    16

<210> SEQ ID NO 3
<211> LENGTH: 2151
<212> TYPE: DNA
<213> ORGANISM: Homo sapiens

<400> SEQUENCE: 3

| | |
|---|---|
| atggcgcctc agaagcacgg cggtgggggga gggggcggct cggggcccag cgcggggtcc | 60 |
| gggggaggcg gcttcggggg ttcggcggcg gtggcggcgg cgacggcttc gggcggcaaa | 120 |
| tccggcggcg ggagctgtgg aggggtggc agttactcgg cctcctcctc ctcctccgcg | 180 |
| gcggcagcgg cgggggctgc ggtgttaccg gtgaagaagc cgaaaatgga gcacgtccag | 240 |
| gctgaccacg agcttttcct ccaggccttt gagaagccaa cacagatcta tagatttctt | 300 |
| cgaactcgga atctcatagc accaatattt ttgcacagaa ctcttactta catgtctcat | 360 |
| cgaaactcca gaacaaacat caaaagcttg tcagctcatt tgcagcttac gtttactggt | 420 |
| ttcttccaca aaaatgataa gccatcacca aactcagaaa atgaacaaaa ttctgttacc | 480 |
| ctggaagtcc tgcttgtgaa agtttgccac aaaaaaagaa aggatgtaag ttgtccaata | 540 |
| aggcaagttc ccacaggtaa aaagcaggtg cctttgaatc ctgacctcaa tcaaacaaaa | 600 |
| cccggaaatt tcccgtccct tgcagtttcc agtaatgaat ttgaacctag taacagccat | 660 |
| atggtgaagt cttactcgtt gctatttaga gtgactcgtc aggaagaag agagtttaat | 720 |
| ggaatgatta atgaagaaac caatgaaaat attgatgtca atgaagagct tccagccaga | 780 |
| agaaacgaa atcgtgagga tggggaaaag acatttgttg cacaaatgac agtatttgat | 840 |
| aaaaacaggc gcttacagct tttagatggg aatatgaag tagccatgca ggaaatggaa | 900 |
| gaatgtccaa taagcaagaa aagagcaaca tgggagacta ttcttgatgg aagaggctg | 960 |
| cctccattcg aaacatttc tcagggacct acgttgcagt tcactcttcg ttggacagga | 1020 |
| gagaccaatg ataaatctac ggctcctatt gccaaacctc ttgccactag aaattcagag | 1080 |
| agtctccatc aggaaaacaa gcctggttca gttaaaccta ctcaaactat gctgttaaaa | 1140 |
| gaatcattga ctacagatct acaaacaaga aaagaaagg atactccaaa tgaaaaccga | 1200 |
| caaaaattaa gaatatttta tcagtttctc tataacaaca atacaaggca acaaactgaa | 1260 |
| gcaagagatg acctgcattg ccccttggtgt actctgaact gccgcaaact ttatagttta | 1320 |
| ctcaagcatc ttaaactctg ccatagcaga tttatcttca actatgttta tcatccaaaa | 1380 |
| ggtgctagga tagatgtttc tatcaatgag tgttatgatg ctccatgc aggaaatcct | 1440 |
| caggatattc atcgccaacc tggatttgct tttagtcgca acggaccagt taagagaaca | 1500 |
| cctatcacac atattcttgt gtgcaggcca aaacgaacaa aagcaagcat gtctgaattt | 1560 |

```
cttgaatctg aagatgggga agtagaacag caaagaacat atagtagtgg ccacaatcgt    1620
ctgtatttcc atagtgatac ctgcttacct ctccgtccac aagaaatgga agtagatagt    1680
gaagatgaaa aggatcctga atggctaaga gaaaaaacca ttacacaaat tgaagagttt    1740
tctgatgtta atgaaggaga gaaagaagtg atgaaactct ggaatctcca tgtcatgaag    1800
catgggttta ttgctgacaa tcaaatgaat catgcctgta tgctgtttgt agaaaattat    1860
ggacagaaaa taattaagaa gaatttatgt cgaaacttca tgcttcatct agtcagcatg    1920 catgactttta atcttattag cataatgtca atagataaag ctgttaccaa gctccgtgaa    1980
atgcagcaaa aattagaaaa gggggaatct gcttcccctg caaacgaaga ataactgaa     2040 gaacaaaatg ggacagcaaa tggatttagt gaaattaact caaagagaa agctttggaa     2100 acagatagtg tctcaggggt ttcaaaacag agcaaaaaac aaaaactctg a             2151
```

<210> SEQ ID NO 4
<211> LENGTH: 716
<212> TYPE: PRT
<213> ORGANISM: Homo sapiens

<400> SEQUENCE: 4

```
Met Ala Pro Gln Lys His Gly Gly Gly Gly Gly Gly Ser Gly Pro
1               5                   10                  15

Ser Ala Gly Ser Gly Gly Gly Phe Gly Gly Ser Ala Ala Val Ala
            20                  25                  30

Ala Ala Thr Ala Ser Gly Gly Lys Ser Gly Gly Gly Ser Cys Gly Gly
        35                  40                  45

Gly Gly Ser Tyr Ser Ala Ser Ser Ser Ser Ala Ala Ala Ala
    50                  55                  60

Gly Ala Ala Val Leu Pro Val Lys Lys Pro Lys Met Glu His Val Gln
65                  70                  75                  80

Ala Asp His Glu Leu Phe Leu Gln Ala Phe Glu Lys Pro Thr Gln Ile
                85                  90                  95

Tyr Arg Phe Leu Arg Thr Arg Asn Leu Ile Ala Pro Ile Phe Leu His
                100                 105                 110

Arg Thr Leu Thr Tyr Met Ser His Arg Asn Ser Arg Thr Asn Ile Lys
            115                 120                 125

Ser Leu Ser Ala His Leu Gln Leu Thr Phe Thr Gly Phe Phe His Lys
130                 135                 140

Asn Asp Lys Pro Ser Pro Asn Ser Glu Asn Glu Gln Asn Ser Val Thr
145                 150                 155                 160

Leu Glu Val Leu Leu Val Lys Val Cys His Lys Lys Arg Lys Asp Val
                165                 170                 175

Ser Cys Pro Ile Arg Gln Val Pro Thr Gly Lys Lys Gln Val Pro Leu
            180                 185                 190

Asn Pro Asp Leu Asn Gln Thr Lys Pro Gly Asn Phe Pro Ser Leu Ala
        195                 200                 205

Val Ser Ser Asn Glu Phe Glu Pro Ser Asn Ser His Met Val Lys Ser
    210                 215                 220

Tyr Ser Leu Leu Phe Arg Val Thr Arg Pro Gly Arg Arg Glu Phe Asn
225                 230                 235                 240

Gly Met Ile Asn Gly Glu Thr Asn Glu Asn Ile Asp Val Asn Glu Glu
                245                 250                 255

Leu Pro Ala Arg Arg Lys Arg Asn Arg Glu Asp Gly Glu Lys Thr Phe
            260                 265                 270
```

```
Val Ala Gln Met Thr Val Phe Asp Lys Asn Arg Arg Leu Gln Leu Leu
            275                 280                 285
Asp Gly Glu Tyr Glu Val Ala Met Gln Glu Met Glu Glu Cys Pro Ile
290                 295                 300
Ser Lys Lys Arg Ala Thr Trp Glu Thr Ile Leu Asp Gly Lys Arg Leu
305                 310                 315                 320
Pro Pro Phe Glu Thr Phe Ser Gln Gly Pro Thr Leu Gln Phe Thr Leu
            325                 330                 335
Arg Trp Thr Gly Glu Thr Asn Asp Lys Ser Thr Ala Pro Ile Ala Lys
                340                 345                 350
Pro Leu Ala Thr Arg Asn Ser Glu Ser Leu His Gln Glu Asn Lys Pro
            355                 360                 365
Gly Ser Val Lys Pro Thr Gln Thr Ile Ala Val Lys Glu Ser Leu Thr
370                 375                 380
Thr Asp Leu Gln Thr Arg Lys Glu Lys Asp Thr Pro Asn Glu Asn Arg
385                 390                 395                 400
Gln Lys Leu Arg Ile Phe Tyr Gln Phe Leu Tyr Asn Asn Asn Thr Arg
                405                 410                 415
Gln Gln Thr Glu Ala Arg Asp Asp Leu His Cys Pro Trp Cys Thr Leu
            420                 425                 430
Asn Cys Arg Lys Leu Tyr Ser Leu Leu Lys His Leu Lys Leu Cys His
            435                 440                 445
Ser Arg Phe Ile Phe Asn Tyr Val Tyr His Pro Lys Gly Ala Arg Ile
            450                 455                 460
Asp Val Ser Ile Asn Glu Cys Tyr Asp Gly Ser Tyr Ala Gly Asn Pro
465                 470                 475                 480
Gln Asp Ile His Arg Gln Pro Gly Phe Ala Phe Ser Arg Asn Gly Pro
                485                 490                 495
Val Lys Arg Thr Pro Ile Thr His Ile Leu Val Cys Arg Pro Lys Arg
                500                 505                 510
Thr Lys Ala Ser Met Ser Glu Phe Leu Glu Ser Glu Asp Gly Glu Val
            515                 520                 525
Glu Gln Gln Arg Thr Tyr Ser Ser Gly His Asn Arg Leu Tyr Phe His
            530                 535                 540
Ser Asp Thr Cys Leu Pro Leu Arg Pro Gln Glu Met Glu Val Asp Ser
545                 550                 555                 560
Glu Asp Glu Lys Asp Pro Glu Trp Leu Arg Glu Lys Thr Ile Thr Gln
                565                 570                 575
Ile Glu Glu Phe Ser Asp Val Asn Glu Gly Glu Lys Gly Val Met Lys
            580                 585                 590
Leu Trp Asn Leu His Val Met Lys His Gly Phe Ile Ala Asp Asn Gln
            595                 600                 605
Met Asn His Ala Cys Met Leu Phe Val Glu Asn Tyr Gly Gln Lys Ile
610                 615                 620
Ile Lys Lys Asn Leu Cys Arg Asn Phe Met Leu His Leu Val Ser Met
625                 630                 635                 640
His Asp Phe Asn Leu Ile Ser Ile Met Ser Ile Asp Lys Ala Val Thr
                645                 650                 655
Lys Leu Arg Glu Met Gln Gln Lys Leu Glu Lys Gly Glu Ser Ala Ser
            660                 665                 670
Pro Ala Asn Glu Glu Ile Thr Glu Glu Gln Asn Gly Thr Ala Asn Gly
            675                 680                 685
```

```
Phe Ser Glu Ile Asn Ser Lys Glu Lys Ala Leu Glu Thr Asp Ser Val
    690                 695                 700
Ser Gly Val Ser Lys Gln Ser Lys Lys Gln Lys Leu
705                 710                 715

<210> SEQ ID NO 5
<211> LENGTH: 1401
<212> TYPE: DNA
<213> ORGANISM: Homo sapiens

<400> SEQUENCE: 5
atgtccgaga gggaagtgtc gactgcgccg gcgggaacag acatgcctgc ggccaagaag      60
cagaagctga gcagtgacga gaacagcaat ccagacctct ctggagacga gatgatgac     120 gctgtcagta tagaaagtgg tacaaacact gaacgcctg atacacctac aaacacgcca     180
aatgcacctg gaggaaaag ttggggaaag ggaaaatgga agtcaaagaa atgcaaatat     240
tctttcaaat gtgtaaatag tctcaaggaa gatcataacc aaccattgtt tggagttcag     300
tttaactggc acagtaaaga aggagatcca ttagtgtttg caactgtagg aagcaacaga     360
gttaccttgt atgaatgtca ttcacaagga gaaatccggt tgttgcaatc ttacgtggat     420
gctgatgctg atgaaaactt ttacacttgt gcatggacct atgatagcaa tacgagccat     480
cctctgctgg ctgtagctgg atctagaggc ataattagga taataaatcc tataacaatg     540
cagtgtataa agcactatgt tggccatgga aatgctatca atgagctgaa attccatcca     600
agagatccaa atcttctcct gtcagtaagt aaagatcatg ctttacgatt atggaatatc     660
cagacggaca ctctggtggc aatatttgga ggcgtagaag ggcacagaga tgaagttcta     720
agtgctgatt atgatctttt gggtgaaaaa ataatgtcct gtggtatgga tcattctctt     780
aaactttgga ggatcaattc aaagagaatg atgaatgcaa ttaaggaatc ttatgattat     840
aatccaaata aaactaacag gccatttatt tctcagaaaa tccatttccc tgattttct     900 accagagaca tacataggaa ttatgttgat tgtgtgcgat ggttaggcga tttgatactt     960
tctaagagtg gccgtgccat tttacattcc caccagcaat gtatgagaga tccagtgtct    1020
ccgaatcttc gccagcattt gtcttgtgaa atgccattg tgtgctggaa acctggcaag    1080
atggaagatg atatagataa aattaaaccc agtgaatcta atgtgactat tcttgggcga    1140
tttgattaca gccagtgtga catttggtac atgaggtttt ctatggattt ctggcaaaag    1200
atgcttgcat tgggcaatca agttggcaaa ctttatgttt gggatttaga agtagaagat    1260
cctcataaag ccaaatgtac aacactgact catcataaat gtggtgctgc tattcgacaa    1320
accagtttta gcagggatag cagcattctt atagctgttt gtgatgatgc cagtatttgg    1380
cgctgggatc gacttcgata a                                              1401

<210> SEQ ID NO 6
<211> LENGTH: 466
<212> TYPE: PRT
<213> ORGANISM: Homo sapiens

<400> SEQUENCE: 6

Met Ser Glu Arg Glu Val Ser Thr Ala Pro Ala Gly Thr Asp Met Pro
1               5                   10                  15

Ala Ala Lys Lys Gln Lys Leu Ser Ser Asp Glu Asn Ser Asn Pro Asp
                20                  25                  30

Leu Ser Gly Asp Glu Asn Asp Asp Ala Val Ser Ile Glu Ser Gly Thr
            35                  40                  45
```

```
Asn Thr Glu Arg Pro Asp Thr Pro Thr Asn Thr Pro Asn Ala Pro Gly
    50                  55                  60

Arg Lys Ser Trp Gly Lys Gly Lys Trp Lys Ser Lys Lys Cys Lys Tyr
65                  70                  75                  80

Ser Phe Lys Cys Val Asn Ser Leu Lys Glu Asp His Asn Gln Pro Leu
                85                  90                  95

Phe Gly Val Gln Phe Asn Trp His Ser Lys Glu Gly Asp Pro Leu Val
            100                 105                 110

Phe Ala Thr Val Gly Ser Asn Arg Val Thr Leu Tyr Glu Cys His Ser
        115                 120                 125

Gln Gly Glu Ile Arg Leu Leu Gln Ser Tyr Val Asp Ala Asp Ala Asp
    130                 135                 140

Glu Asn Phe Tyr Thr Cys Ala Trp Thr Tyr Asp Ser Asn Thr Ser His
145                 150                 155                 160

Pro Leu Leu Ala Val Ala Gly Ser Arg Gly Ile Ile Arg Ile Ile Asn
                165                 170                 175

Pro Ile Thr Met Gln Cys Ile Lys His Tyr Val Gly His Gly Asn Ala
            180                 185                 190

Ile Asn Glu Leu Lys Phe His Pro Arg Asp Pro Asn Leu Leu Leu Ser
        195                 200                 205

Val Ser Lys Asp His Ala Leu Arg Leu Trp Asn Ile Gln Thr Asp Thr
    210                 215                 220

Leu Val Ala Ile Phe Gly Gly Val Glu Gly His Arg Asp Glu Val Leu
225                 230                 235                 240

Ser Ala Asp Tyr Asp Leu Leu Gly Glu Lys Ile Met Ser Cys Gly Met
                245                 250                 255

Asp His Ser Leu Lys Leu Trp Arg Ile Asn Ser Lys Arg Met Met Asn
            260                 265                 270

Ala Ile Lys Glu Ser Tyr Asp Tyr Asn Pro Asn Lys Thr Asn Arg Pro
        275                 280                 285

Phe Ile Ser Gln Lys Ile His Phe Pro Asp Phe Ser Thr Arg Asp Ile
    290                 295                 300

His Arg Asn Tyr Val Asp Cys Val Arg Trp Leu Gly Asp Leu Ile Leu
305                 310                 315                 320

Ser Lys Ser Gly Arg Ala Ile Leu His Ser His Gln Gln Cys Met Arg
                325                 330                 335

Asp Pro Val Ser Pro Asn Leu Arg Gln His Leu Ser Cys Glu Asn Ala
            340                 345                 350

Ile Val Cys Trp Lys Pro Gly Lys Met Glu Asp Ile Asp Lys Ile
        355                 360                 365

Lys Pro Ser Glu Ser Asn Val Thr Ile Leu Gly Arg Phe Asp Tyr Ser
    370                 375                 380

Gln Cys Asp Ile Trp Tyr Met Arg Phe Ser Met Asp Phe Trp Gln Lys
385                 390                 395                 400

Met Leu Ala Leu Gly Asn Gln Val Gly Lys Leu Tyr Val Trp Asp Leu
                405                 410                 415

Glu Val Glu Asp Pro His Lys Ala Lys Cys Thr Thr Leu Thr His His
            420                 425                 430

Lys Cys Gly Ala Ala Ile Arg Gln Thr Ser Phe Ser Arg Asp Ser Ser
        435                 440                 445

Ile Leu Ile Ala Val Cys Asp Asp Ala Ser Ile Trp Arg Trp Asp Arg
    450                 455                 460
```

Leu Arg
465

<210> SEQ ID NO 7
<211> LENGTH: 1275
<212> TYPE: DNA
<213> ORGANISM: Homo sapiens

<400> SEQUENCE: 7

| | | |
|---|---|---|
| atggccgaca aggaagcctt cgacgacgca gtggaagaac gagtgatcaa cgaggaatac | 60 |
| aaaatatgga aaagaacac ccctttctt tatgatttgg tgatgaccca tgctctggag | 120 |
| tggcccagcc taactgccca gtggcttcca gatgtaacca gaccagaagg gaaagatttc | 180 |
| agcattcatc gacttgtcct ggggacacac acatcggatg aacaaaacca tcttgttata | 240 |
| gccagtgtgc agctccctaa tgatgatgct cagtttgatg cgtcacacta cgacagtgag | 300 |
| aaaggagaat ttggaggttt tggttcagtt agtggaaaaa ttgaaataga aatcaagatc | 360 |
| aaccatgaag gagaagtaaa cagggcccgt tatatgcccc agaacccttg tatcatcgca | 420 |
| acaaagactc cttccagtga tgttcttgtt tttgactata caaaacatcc ttctaaacca | 480 |
| gatccttctg gagagtgcaa cccagacttg cgtctccgtg gacatcagaa ggaaggctat | 540 |
| gggctttctt ggaacccaaa tctcagtggg cacttactta gtgcttcaga tgaccatacc | 600 |
| atctgcctgt gggacatcag tgccgttcca aaggagggaa aagtggtaga tcgaagacc | 660 |
| atctttacag gcatacggc agtagtagaa gatgtttcct ggcatctact ccatgagtct | 720 |
| ctgtttgggt cagttgctga tgatcagaaa cttatgattt gggatactcg ttcaaacaat | 780 |
| acttccaaac caagccactc agttgatgct cacactgctg aagtgaactg cctttctttc | 840 |
| aatccttata gtgagttcat tcttgccaca ggatcagctg acaagactgt tgccttgtgg | 900 |
| gatctgagaa atctgaaact taagttgcat tcctttgagt cacataagga tgaaatattc | 960 |
| caggttcagt ggtcacctca caatgagact atttttagctt ccagtggtac tgatcgcaga | 1020 |
| ctgaatgtct gggatttaag taaaattgga gaggaacaat ccccagaaga tgcagaagac | 1080 |
| gggccaccag agttgttgtt tattcatggt ggtcatactg ccaagatatc tgatttctcc | 1140 |
| tggaatccca tgaaccttg ggtgatttgt tctgtatcag aagacaatat catgcaagtg | 1200 |
| tggcaaatgg cagagaacat ttataatgat gaagaccctg aaggaagcgt ggatccagaa | 1260 |
| ggacaagggt cctag | 1275 |

<210> SEQ ID NO 8
<211> LENGTH: 424
<212> TYPE: PRT
<213> ORGANISM: Homo sapiens

<400> SEQUENCE: 8

Met Ala Asp Lys Glu Ala Phe Asp Asp Ala Val Glu Glu Arg Val Ile
1               5                   10                  15

Asn Glu Glu Tyr Lys Ile Trp Lys Lys Asn Thr Pro Phe Leu Tyr Asp
                20                  25                  30

Leu Val Met Thr His Ala Leu Glu Trp Pro Ser Leu Thr Ala Gln Trp
            35                  40                  45

Leu Pro Asp Val Thr Arg Pro Glu Gly Lys Asp Phe Ser Ile His Arg
        50                  55                  60

Leu Val Leu Gly Thr His Thr Ser Asp Glu Gln Asn His Leu Val Ile
65                  70                  75                  80

Ala Ser Val Gln Leu Pro Asn Asp Asp Ala Gln Phe Asp Ala Ser His
            85                  90                  95

Tyr Asp Ser Glu Lys Gly Glu Phe Gly Gly Phe Gly Ser Val Ser Gly
            100                 105                 110

Lys Ile Glu Ile Glu Ile Lys Ile Asn His Glu Gly Val Asn Arg
        115                 120                 125

Ala Arg Tyr Met Pro Gln Asn Pro Cys Ile Ile Ala Thr Lys Thr Pro
130                 135                 140

Ser Ser Asp Val Leu Val Phe Asp Tyr Thr Lys His Pro Ser Lys Pro
145                 150                 155                 160

Asp Pro Ser Gly Glu Cys Asn Pro Asp Leu Arg Leu Arg Gly His Gln
                165                 170                 175

Lys Glu Gly Tyr Gly Leu Ser Trp Asn Pro Asn Leu Ser Gly His Leu
            180                 185                 190

Leu Ser Ala Ser Asp Asp His Thr Ile Cys Leu Trp Asp Ile Ser Ala
        195                 200                 205

Val Pro Lys Glu Gly Lys Val Val Asp Ala Lys Thr Ile Phe Thr Gly
210                 215                 220

His Thr Ala Val Val Glu Asp Val Ser Trp His Leu Leu His Glu Ser
225                 230                 235                 240

Leu Phe Gly Ser Val Ala Asp Asp Gln Lys Leu Met Ile Trp Asp Thr
                245                 250                 255

Arg Ser Asn Asn Thr Ser Lys Pro Ser His Ser Val Asp Ala His Thr
            260                 265                 270

Ala Glu Val Asn Cys Leu Ser Phe Asn Pro Tyr Ser Glu Phe Ile Leu
        275                 280                 285

Ala Thr Gly Ser Ala Asp Lys Thr Val Ala Leu Trp Asp Leu Arg Asn
290                 295                 300

Leu Lys Leu Lys Leu His Ser Phe Glu Ser His Lys Asp Glu Ile Phe
305                 310                 315                 320

Gln Val Gln Trp Ser Pro His Asn Glu Thr Ile Leu Ala Ser Ser Gly
                325                 330                 335

Thr Asp Arg Arg Leu Asn Val Trp Asp Leu Ser Lys Ile Gly Glu Glu
            340                 345                 350

Gln Ser Pro Glu Asp Ala Glu Asp Gly Pro Pro Glu Leu Leu Phe Ile
        355                 360                 365

His Gly Gly His Thr Ala Lys Ile Ser Asp Phe Ser Trp Asn Pro Asn
370                 375                 380

Glu Pro Trp Val Ile Cys Ser Val Ser Glu Asp Asn Ile Met Gln Val
385                 390                 395                 400

Trp Gln Met Ala Glu Asn Ile Tyr Asn Asp Glu Asp Pro Glu Gly Ser
                405                 410                 415

Val Asp Pro Glu Gly Gln Gly Ser
            420

<210> SEQ ID NO 9
<211> LENGTH: 2241
<212> TYPE: DNA
<213> ORGANISM: Homo sapiens

<400> SEQUENCE: 9
atgggccaga ctgggaagaa atctgagaag ggaccagttt gttggcggaa gcgtgtaaaa      60
tcagagtaca tgcgactgag acagctcaag aggttcagac gagctgatga agtaaagagt     120

```
atgtttagtt ccaatcgtca gaaaattttg gaaagaacgg aaatcttaaa ccaagaatgg      180
aaacagcgaa ggatacagcc tgtgcacatc ctgacttctg tgagctcatt gcgcgggact      240
agggagtgtt cggtgaccag tgacttggat tttccaacac aagtcatccc attaaagact      300
ctgaatgcag ttgcttcagt acccataatg tattcttggt ctcccctaca gcagaatttt      360
atggtggaag atgaaactgt tttacataac attccttata tgggagatga agttttagat      420
caggatggta ctttcattga agaactaata aaaaattatg atgggaaagt acacggggat      480
agagaatgtg ggtttataaa tgatgaaatt tttgtggagt tggtgaatgc ccttggtcaa      540
tataatgatg atgacgatga tgatgatgga gacgatcctg aagaaagaga agaaaagcag      600
aaagatctgg aggatcaccg agatgataaa gaaagccgcc cacctcggaa atttccttct      660
gataaaattt ttgaagccat ttcctcaatg tttccagata agggcacagc agaagaacta      720
aaggaaaaat ataagaact caccgaacag cagctcccag gcgcacttcc tcctgaatgt      780
acccccaaca tagatggacc aaatgctaaa tctgttcaga gagagcaaag cttacactcc      840
tttcatacgc ttttctgtag gcgatgtttt aaatatgact gcttcctaca tccttttcat      900
gcaacaccca cacttataa gcggaagaac acagaaacag ctctagacaa caaaccttgt      960
ggaccacagt gttaccagca tttggaggga gcaaaggagt tgctgctgc tctcaccgct      1020 gagcggataa agaccccacc aaaacgtcca ggaggccgca aagaggacg gcttcccaat      1080 aacagtagca ggcccagcac ccccaccatt aatgtgctgg aatcaaagga tacagacagt      1140
gatagggaag cagggactga acgggggga gagaacaatg ataaagaaga agaagagaag      1200
aaagatgaaa cttcgagctc ctctgaagca aattctcggt gtcaaacacc aataaagatg      1260
aagccaaata ttgaacctcc tgagaatgtg gagtggagtg gtgctgaagc ctcaatgttt      1320
agagtcctca ttggcactta ctatgacaat ttctgtgcca ttgctaggtt aattgggacc      1380
aaaacatgta gacaggtgta tgagtttaga gtcaaagaat ctagcatcat agctccagct      1440
cccgctgagg atgtggatac tcctccaagg aaaaagaaga ggaaacaccg gttgtgggct      1500
gcacactgca gaaagataca gctgaaaaag gacggctcct ctaaccatgt ttacaactat      1560
caaccctgtg atcatccacg gcagccttgt gacagttcgt gcccttgtgt gatagcacaa      1620
aatttttgtg aaaagttttg tcaatgtagt tcagagtgtc aaaaccgctt tccgggatgc      1680
cgctgcaaag cacagtgcaa caccaagcag tgcccgtgct acctggctgt ccagagtgt      1740 gaccctgacc tctgtcttac ttgtggagcc gctgaccatt gggacagtaa aaatgtgtcc      1800
tgcaagaact gcagtattca gcggggctcc aaaaagcatc tattgctggc accatctgac      1860
gtggcaggct gggggatttt tatcaaagat cctgtgcaga aaatgaatt catctcagaa      1920 tactgtggag agattatttc tcaagatgaa gctgacagaa gagggaaagt gtatgataaa      1980
tacatgtgca gctttctgtt caacttgaac aatgattttg tggtggatgc aacccgcaag      2040
ggtaacaaaa ttcgttttgc aaatcattcg gtaaatccaa actgctatgc aaaagttatg      2100
atggttaacg gtgatcacag gataggtatt tttgccaaga gagccatcca gactggcgaa      2160
gagctgtttt ttgattacag atacagccag gctgatgccc tgaagtatgt cggcatcgaa      2220
agagaaatgg aaatcccttg a                                                 2241
```

<210> SEQ ID NO 10
<211> LENGTH: 746
<212> TYPE: PRT
<213> ORGANISM: Homo sapiens

<400> SEQUENCE: 10

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
                100                 105                 110

Trp Ser Pro Leu Gln Gln Asn Phe Met Val Glu Asp Glu Thr Val Leu
            115                 120                 125

His Asn Ile Pro Tyr Met Gly Asp Glu Val Leu Asp Gln Asp Gly Thr
        130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
                180                 185                 190

Pro Glu Glu Arg Glu Lys Gln Lys Asp Leu Glu Asp His Arg Asp
            195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
                260                 265                 270

Gln Arg Glu Gln Ser Leu His Ser Phe His Thr Leu Phe Cys Arg Arg
            275                 280                 285

Cys Phe Lys Tyr Asp Cys Phe Leu His Pro Phe His Ala Thr Pro Asn
        290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Lys Arg Pro Gly Gly
                340                 345                 350

Arg Arg Arg Gly Arg Leu Pro Asn Asn Ser Ser Arg Pro Ser Thr Pro
            355                 360                 365

Thr Ile Asn Val Leu Glu Ser Lys Asp Thr Asp Ser Asp Arg Glu Ala
        370                 375                 380

Gly Thr Glu Thr Gly Gly Glu Asn Asn Asp Lys Glu Glu Glu Glu Lys
385                 390                 395                 400
```

Lys Asp Glu Thr Ser Ser Ser Glu Ala Asn Ser Arg Cys Gln Thr
            405                 410                 415

Pro Ile Lys Met Lys Pro Asn Ile Glu Pro Pro Glu Asn Val Glu Trp
        420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
    450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Lys Arg Lys His
                485                 490                 495

Arg Leu Trp Ala Ala His Cys Arg Lys Ile Gln Leu Lys Lys Asp Gly
                500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
    530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
                580                 585                 590

His Trp Asp Ser Lys Asn Val Ser Cys Lys Asn Cys Ser Ile Gln Arg
            595                 600                 605

Gly Ser Lys Lys His Leu Leu Leu Ala Pro Ser Asp Val Ala Gly Trp
    610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
    675                 680                 685

His Ser Val Asn Pro Asn Cys Tyr Ala Lys Val Met Met Val Asn Gly
690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 11
<211> LENGTH: 1767
<212> TYPE: DNA
<213> ORGANISM: Homo sapiens

<400> SEQUENCE: 11
atgatgagct cacctgcaca gcctgacctc atgtggaacc ttgtaccatg ggtgctattc    60
tgtggctgct gtaggatctt cccagatggg gtggctggac gagagcagct cttggctcag   120

| | |
|---|---|
| caaagaatgc acagtatgat cagctcagtg gatgtgaagt cagaagttcc tgtgggcctg | 180 |
| gagcccatct caccttttaga cctaaggaca gacctcagga tgatgatgcc cgtggtggac | 240 |
| cctgttgtcc gtgagaagca attgcagcag gaattacttc ttatccagca gcagcaacaa | 300 |
| atccagaagc agcttctgat agcagagttt cagaaacagc atgagaactt gacacggcag | 360 |
| caccaggctc agcttcagga gcatatcaag gaacttctag ccataaaaca gcaacaagaa | 420 |
| ctcctagaaa aggagcagaa actggagcag cagaggcaag aacaggaagt agagaggcat | 480 |
| cgcagagaac agcagcttcc tcctctcaga ggcaaagata gaggacgaga agggcagtg | 540 |
| gcaagtacag aagtaaagca gaagcttcaa gagttcctac tgagtaaatc agcaacgaaa | 600 |
| gacactccaa ctaatggaaa aaatcattcc gtgagccgcc atcccaagct ctggtacacg | 660 |
| gctgcccacc acacatcatt ggatcaaagc tctccacccc ttagtggaac atctccatcc | 720 |
| tacaagtaca cattaccagg agcacaagat gcaaggatg atttcccct tcgaaaaact | 780 |
| gaatcctcag tcagtagcag ttctccaggc tctggtccca gttcaccaaa caatgggcca | 840 |
| actggaagtg ttactgaaaa tgagacttcg gttttgcccc ctacccctca tgccgagcaa | 900 |
| atggtttcac agcaacgcat tctaattcat gaagattcca tgaacctgct aagtctttat | 960 |
| acctctcctt ctttgcccaa cattaccttg gggcttccgg cagtgccatc ccagctcaat | 1020 |
| gcttcgaatt cactcaaaga aaagcagaag tgtgagacgc agacgcttag gcaaggtgtt | 1080 |
| cctctgcctg ggcagtatgg aggcagcatc ccggcatctt ccagccaccc tcatgttact | 1140 |
| ttagagggaa agccacccaa cagcagccac caggctctcc tgcagcattt attattgaaa | 1200 |
| gaacaaatgc gacagcaaaa gcttcttgta gctggtggga ttcccttaca tcctcagtct | 1260 |
| cccttggcaa caaaagagag aatttcacct ggcattagag gtacccacaa attgccccgt | 1320 |
| cacagacccc tgaaccgaac ccagtctgca cctttgcctc agagcacgtt ggctcagctg | 1380 |
| gtcattcaac agcaacacca gcaattcttg gagaagcaga gcaatacca gcagcagatc | 1440 |
| cacatgaaca aactgctttc gaaatctatt gaacaactga gcaaccagg cagtcacctt | 1500 |
| gaggaagcag aggaagagct tcaggggac caggcgatgc aggaagacag agcgccctct | 1560 |
| agtggcaaca gcactaggag cgacagcagt gcttgtgtgg atgacacact gggacaagtt | 1620 |
| ggggctgtga aggtcaagga ggaaccagtg gacagtgatg aagatgctca gatccaggaa | 1680 |
| atggaatctg gggagcaggc tgcttttatg caacaggtaa taggcaaaga tttagctcca | 1740 |
| ggatttgtaa ttaaagtcat tatctga | 1767 |

<210> SEQ ID NO 12
<211> LENGTH: 588
<212> TYPE: PRT
<213> ORGANISM: Homo sapiens

<400> SEQUENCE: 12

```
Met Met Ser Ser Pro Ala Gln Pro Asp Leu Met Trp Asn Leu Val Pro
1               5                   10                  15

Trp Val Leu Phe Cys Gly Cys Cys Arg Ile Phe Pro Asp Gly Val Ala
                20                  25                  30

Gly Arg Glu Gln Leu Leu Ala Gln Gln Arg Met His Ser Met Ile Ser
            35                  40                  45

Ser Val Asp Val Lys Ser Glu Val Pro Val Gly Leu Glu Pro Ile Ser
        50                  55                  60

Pro Leu Asp Leu Arg Thr Asp Leu Arg Met Met Met Pro Val Val Asp
65                  70                  75                  80
```

```
Pro Val Val Arg Glu Lys Gln Leu Gln Gln Glu Leu Leu Leu Ile Gln
                85                  90                  95

Gln Gln Gln Gln Ile Gln Lys Gln Leu Leu Ile Ala Glu Phe Gln Lys
            100                 105                 110

Gln His Glu Asn Leu Thr Arg Gln His Gln Ala Gln Leu Gln Glu His
        115                 120                 125

Ile Lys Glu Leu Leu Ala Ile Lys Gln Gln Gln Glu Leu Leu Glu Lys
    130                 135                 140

Glu Gln Lys Leu Glu Gln Gln Arg Gln Glu Gln Glu Val Glu Arg His
145                 150                 155                 160

Arg Arg Glu Gln Gln Leu Pro Pro Leu Arg Gly Lys Asp Arg Gly Arg
                165                 170                 175

Glu Arg Ala Val Ala Ser Thr Glu Val Lys Gln Lys Leu Gln Glu Phe
            180                 185                 190

Leu Leu Ser Lys Ser Ala Thr Lys Asp Thr Pro Thr Asn Gly Lys Asn
        195                 200                 205

His Ser Val Ser Arg His Pro Lys Leu Trp Tyr Thr Ala Ala His His
    210                 215                 220

Thr Ser Leu Asp Gln Ser Ser Pro Leu Ser Gly Thr Ser Pro Ser
225                 230                 235                 240

Tyr Lys Tyr Thr Leu Pro Gly Ala Gln Asp Ala Lys Asp Asp Phe Pro
                245                 250                 255

Leu Arg Lys Thr Glu Ser Ser Val Ser Ser Ser Pro Gly Ser Gly
            260                 265                 270

Pro Ser Ser Pro Asn Asn Gly Pro Thr Gly Ser Val Thr Glu Asn Glu
        275                 280                 285

Thr Ser Val Leu Pro Pro Thr Pro His Ala Glu Gln Met Val Ser Gln
    290                 295                 300

Gln Arg Ile Leu Ile His Glu Asp Ser Met Asn Leu Leu Ser Leu Tyr
305                 310                 315                 320

Thr Ser Pro Ser Leu Pro Asn Ile Thr Leu Gly Leu Pro Ala Val Pro
                325                 330                 335

Ser Gln Leu Asn Ala Ser Asn Ser Leu Lys Glu Lys Gln Lys Cys Glu
            340                 345                 350

Thr Gln Thr Leu Arg Gln Gly Val Pro Leu Pro Gly Gln Tyr Gly Gly
        355                 360                 365

Ser Ile Pro Ala Ser Ser Ser His Pro His Val Thr Leu Glu Gly Lys
    370                 375                 380

Pro Pro Asn Ser Ser His Gln Ala Leu Leu Gln His Leu Leu Lys
385                 390                 395                 400

Glu Gln Met Arg Gln Gln Lys Leu Leu Val Ala Gly Gly Val Pro Leu
                405                 410                 415

His Pro Gln Ser Pro Leu Ala Thr Lys Glu Arg Ile Ser Pro Gly Ile
            420                 425                 430

Arg Gly Thr His Lys Leu Pro Arg His Arg Pro Leu Asn Arg Thr Gln
        435                 440                 445

Ser Ala Pro Leu Pro Gln Ser Thr Leu Ala Gln Leu Val Ile Gln Gln
    450                 455                 460

Gln His Gln Gln Phe Leu Glu Lys Gln Lys Gln Tyr Gln Gln Gln Ile
465                 470                 475                 480

His Met Asn Lys Leu Leu Ser Lys Ser Ile Glu Gln Leu Lys Gln Pro
                485                 490                 495
```

```
Gly Ser His Leu Glu Glu Ala Glu Glu Leu Gln Gly Asp Gln Ala
            500                 505                 510

Met Gln Glu Asp Arg Ala Pro Ser Gly Asn Ser Thr Arg Ser Asp
        515                 520                 525

Ser Ser Ala Cys Val Asp Asp Thr Leu Gly Gln Val Gly Ala Val Lys
    530                 535                 540

Val Lys Glu Glu Pro Val Asp Ser Asp Glu Asp Ala Gln Ile Gln Glu
545                 550                 555                 560

Met Glu Ser Gly Glu Gln Ala Ala Phe Met Gln Val Ile Gly Lys
                565                 570                 575

Asp Leu Ala Pro Gly Phe Val Ile Lys Val Ile Ile
            580                 585

<210> SEQ ID NO 13
<211> LENGTH: 4944
<212> TYPE: DNA
<213> ORGANISM: Homo sapiens

<400> SEQUENCE: 13
```

| | | | | | |
|---|---|---|---|---|---|
| atgtccactc | cagacccacc | cctgggcgga | actcctcggc | caggtccttc | cccgggccct | 60 |
| ggcccttccc | ctggagccat | gctgggccct | agcccgggtc | cctcgccggg | ctccgcccac | 120 |
| agcatgatgg | ggcccagccc | agggccgccc | tcagcaggac | accccatccc | acccaggggg | 180 |
| cctggagggt | accctcagga | caacatgcac | cagatgcaca | agcccatgga | gtccatgcat | 240 |
| gagaagggca | tgtcggacga | cccgcgctac | aaccagatga | aggaatggga | gatgcggtca | 300 |
| gggggccatg | ctgggatggg | gccccgccc | agcccatgg | accagcactc | ccaaggttac | 360 |
| ccctcgcccc | tgggtggctc | tgagcatgcc | tctagtccag | ttccagccag | tggcccgtct | 420 |
| tcggggcccc | agatgtcttc | cgggccagga | ggtgccccgc | tggatggtgc | tgaccccag | 480 |
| gccttgggc | agcagaaccg | ggcccaacc | ccatttaacc | agaaccagct | gcaccagctc | 540 |
| agagctcaga | tcatggccta | caagatgctg | gccaggggc | agcccctccc | cgaccacctg | 600 |
| cagatggcgg | tgcagggcaa | gcggccgatg | cccgggatgc | agcagcagat | gccaacgcta | 660 |
| cctccaccct | cggtgtccgc | aacaggaccc | ggccctggcc | ctggcccctgg | ccccggcccg | 720 |
| ggtcccggcc | cggcacctcc | aaattacagc | aggcctcatg | gtatgggagg | gcccaacatg | 780 |
| cctccccag | accctcggg | cgtgcccccc | gggatgccag | gccagcctcc | tggagggcct | 840 |
| cccaagccct | ggcctgaagg | acccatggcg | aatgctgctg | ccccacgag | cacccctcag | 900 |
| aagctgattc | ccccgcagcc | aacgggccgc | ccttcccccg | cgccccctgc | cgtcccaccc | 960 |
| gccgcctcgc | ccgtgatgcc | accgcagacc | cagtccccg | ggcagccggc | ccagcccgcg | 1020 |
| cccatggtgc | cactgcacca | gaagcagagc | cgcatcaccc | ccatccagaa | gccgcggggc | 1080 |
| ctcgaccctg | tggagatcct | gcaggagcgc | gagtacaggc | tgcaggctcg | catcgcacac | 1140 |
| cgaattcaga | aacttgaaaa | ccttcccggg | tccctggccg | gggatttgcg | aaccaaagcg | 1200 |
| accattgagc | tcaaggccct | caggctgctg | aacttccaga | ggcagctgcg | ccaggaggtg | 1260 |
| gtggtgtgca | tgcggaggga | cacagcgctg | gagacagccc | tcaatgctaa | ggcctacaag | 1320 |
| cgcagcaagc | gccagtccct | gcgcgaggcc | cgcatcactg | agaagctgga | gaagcagcag | 1380 |
| aagatcgagc | aggagcgcaa | gcgccggcag | aagcaccagg | aatacctcaa | tagcattctc | 1440 |
| cagcatgcca | aggatttcaa | ggaatatcac | agatccgtca | caggcaaaat | ccagaagctg | 1500 |
| accaaggcag | tggccacgta | ccatgccaac | acggagcggg | agcagaagaa | agagaacgag | 1560 |

```
cggatcgaga aggagcgcat gcggaggctc atggctgaag atgaggaggg gtaccgcaag    1620
ctcatcgacc agaagaagga caagcgcctg gcctacctct gcagcagac  agacgagtac    1680 gtggctaacc tcacggagct ggtgcggcag cacaaggctg cccaggtcgc caaggagaaa    1740
aagaagaaaa agaaaaagaa gaaggcagaa aatgcagaag acagacgcc  tgccattggg    1800 ccggatggcg agcctctgga cgagaccagc cagatgagcg acctcccggt gaaggtgatc    1860
cacgtggaga gtgggaagat cctcacaggc acagatgccc ccaaagccgg gcagctggag    1920
gcctggctcg agatgaaccc ggggtatgaa gtagctccga ggtctgatag tgaagaaagt    1980
ggctcagaag aagaggaaga ggaggaggag gaagagcagc cgcaggcagc acagcctccc    2040
accctgcccg tggaggagaa gaagaagatt ccagatccag acagcgatga cgtctctgag    2100
gtggacgcgc ggcacatcat tgagaatgcc aagcaagatg tcgatgatga atatggcgtg    2160
tcccaggccc ttgcacgtgg cctgcagtcc tactatgccg tggcccatgc tgtcactgag    2220
agagtggaca gcagtcagc  gcttatggtc aatggtgtcc tcaaacagta ccagatcaaa    2280
ggtttggagt ggctggtgtc cctgtacaac aacaacctga acggcatcct ggccgacgag    2340
atgggcctgg ggaagaccat ccagaccatc gcgctcatca cgtacctcat ggagcacaaa    2400
cgcatcaatg ggcccttcct catcatcgtg cctctctcaa cgctgtccaa ctgggcgtac    2460
gagtttgaca gtgggcccc  ctccgtggtg aaggtgtctt acaagggatc cccagcagca    2520
agacgggcct ttgtccccca gctccggagt gggaagttca acgtcttgct gacgacgtac    2580
gagtacatca tcaaagacaa gcacatcctc gccaagatcc gttggaagta catgattgtg    2640
gacgaaggtc accgcatgaa gaaccaccac tgcaagctga cgcaggtgct caacacgcac    2700
tatgtggcac cccgccgcct gctgctgacg ggcacaccgc tgcagaacaa gcttcccgag    2760
ctctgggcgc tgctcaactt cctgctgccc accatcttca agagctgcag caccttcgag    2820
cagtggttta acgcacccct tgccatgacc ggggaaaagg tggacctgaa tgaggaggaa    2880
accattctca tcatccggcg tctccacaaa gtgctgcggc ccttcttgct ccgacgactc    2940
aagaaggaag tcgaggccca gttgcccgaa aaggtggagt acgtcatcaa gtgcgacatg    3000
tctgcgctgc agcgagtgct ctaccgccac atgcaggcca agggcgtgct gctgactgat    3060
ggctccgaga aggacaagaa gggcaaaggc ggcaccaaga ccctgatgaa caccatcatg    3120
cagctgcgga gatctgcaa  ccaccccta  atgttccagc acatcgagga gtcctttttcc   3180 gagcacttgg ggttcactgg cggcattgtc caagggctgg acctgtaccg agcctcgggt    3240
aaatttgagc ttcttgatag aattcttccc aaactccgag caaccaacca caaagtgctg    3300
ctgttctgcc aaatgaccte cctcatgacc atcatggaag attactttgc gtatcgcggc    3360
tttaaatacc tcaggcttga tggaaccacg aaggcggagg accggggcat gctgctgaaa    3420
accttcaacg agcccggctc tgagtacttc atcttcctgc tcagcacccg ggctgggggg    3480
ctcggcctga acctccagtc ggcagacact gtgatcattt ttgacagcga ctggaatcct    3540
caccaggacc tgcaagcgca ggaccgagcc caccgcatcg gcagcagaa  cgaggtgcgt    3600 gtgctccgcc tctgcaccgt caacagcgtg gaggagaaga tcctagctgc agccaagtac    3660
aagctcaacg tggaccagaa ggtgatccag gccggcatgt tcgaccagaa gtcctccagc    3720
catgagcggc gcgccttcct gcaggccatc ctggagcacg aggagcagga tgagagcaga    3780
cactgcagca cgggcagcgg cagtgccagc ttcgcccaca ctgcccctcc gccagcgggc    3840
gtcaaccccg acttggagga gccacctcta aaggaggaag acgaggtgcc cgacgacgag    3900
accgtcaacc agatgatcgc ccggcacgag gaggagtttg atctgttcat gcgcatggac    3960
```

```
ctggaccgca ggcgcgagga ggcccgcaac cccaagcgga agccgcgcct catggaggag    4020
gacgagctcc cctcgtggat catcaaggac gacgcggagg tggagcggct gacctgtgag    4080
gaggaggagg agaagatgtt cggccgtggc tcccgccacc gcaaggaggt ggactacagc    4140
gactcactga cggagaagca gtggctcaag gccatcgagg agggcacgct ggaggagatc    4200
gaagaggagg tccggcagaa gaaatcatca cggaagcgca agcgagacag cgacgccggc    4260
tcctccaccc cgaccaccag cacccgcagc cgcgacaagg acgacgagag caagaagcag    4320
aagaagcgcg gcggccgcc tgccgagaaa ctctcccta acccacccaa cctcaccaag    4380
aagatgaaga agattgtgga tgccgtgatc aagtacaagg acagcagcag tggacgtcag    4440
ctcagcgagg tcttcatcca gctgccctcg cgaaaggagc tgcccgagta ctacgagctc    4500
atccgcaagc ccgtggactt caagaagata aaggagcgca ttcgcaacca caagtaccgc    4560
agcctcaacg acctagagaa ggacgtcatg ctcctgtgcc agaacgcaca gaccttcaac    4620
ctggagggct ccctgatcta tgaagactcc atcgtcttgc agtcggtctt caccagcgtg    4680
cggcagaaaa tcgagaagga ggatgacagt gaaggcgagg agagtgagga ggaggaagag    4740
ggcgaggagg aaggctccga atccgaatct cggtccgtca aagtgaagat caagcttggc    4800
cggaaggaga aggcacagga ccggctgaag ggcggccggc ggcggccgag ccgagggtcc    4860
cgagccaagc cggtcgtgag tgacgatgac agtgaggagg aacaagagga ggaccgctca    4920
ggaagtggca gcgaagaaga ctga                                         4944
```

<210> SEQ ID NO 14
<211> LENGTH: 1647
<212> TYPE: PRT
<213> ORGANISM: Homo sapiens

<400> SEQUENCE: 14

```
Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
                20                  25                  30

Gly Pro Ser Pro Gly Ser Ala His Ser Met Met Gly Pro Ser Pro Gly
            35                  40                  45

Pro Pro Ser Ala Gly His Pro Ile Pro Thr Gln Gly Pro Gly Gly Tyr
        50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190
```

-continued

```
Gly Gln Pro Leu Pro Asp His Leu Gln Met Ala Val Gln Gly Lys Arg
            195                 200                 205
Pro Met Pro Gly Met Gln Gln Met Pro Thr Leu Pro Pro Pro Ser
210                 215                 220
Val Ser Ala Thr Gly Pro Gly Pro Gly Pro Gly Pro Gly Pro Gly Pro
225                 230                 235                 240
Gly Pro Gly Pro Ala Pro Pro Asn Tyr Ser Arg Pro His Gly Met Gly
                245                 250                 255
Gly Pro Asn Met Pro Pro Pro Gly Pro Ser Gly Val Pro Pro Gly Met
            260                 265                 270
Pro Gly Gln Pro Pro Gly Gly Pro Pro Lys Pro Trp Pro Glu Gly Pro
            275                 280                 285
Met Ala Asn Ala Ala Ala Pro Thr Ser Thr Pro Gln Lys Leu Ile Pro
290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
            355                 360                 365
Glu Arg Glu Tyr Arg Leu Gln Ala Arg Ile Ala His Arg Ile Gln Glu
            370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
            435                 440                 445
Glu Ala Arg Ile Thr Glu Lys Leu Glu Lys Gln Gln Lys Ile Glu Gln
            450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
            515                 520                 525
Arg Leu Met Ala Glu Asp Glu Glu Gly Tyr Arg Lys Leu Ile Asp Gln
            530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Ala Glu Asn Ala
            580                 585                 590
Glu Gly Gln Thr Pro Ala Ile Gly Pro Asp Gly Glu Pro Leu Asp Glu
            595                 600                 605
```

```
Thr Ser Gln Met Ser Asp Leu Pro Val Lys Val Ile His Val Glu Ser
610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
            645                 650                 655

Ser Glu Glu Ser Gly Ser Glu Glu Glu Glu Glu Glu Glu Glu Glu Glu
            660                 665                 670

Gln Pro Gln Ala Ala Gln Pro Pro Thr Leu Pro Val Glu Glu Lys Lys
            675                 680                 685

Lys Ile Pro Asp Pro Asp Ser Asp Asp Val Ser Glu Val Asp Ala Arg
690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
                725                 730                 735

Ala Val Thr Glu Arg Val Asp Lys Gln Ser Ala Leu Met Val Asn Gly
            740                 745                 750

Val Leu Lys Gln Tyr Gln Ile Lys Gly Leu Glu Trp Leu Val Ser Leu
755                 760                 765

Tyr Asn Asn Asn Leu Asn Gly Ile Leu Ala Asp Glu Met Gly Leu Gly
770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
            820                 825                 830

Ser Tyr Lys Gly Ser Pro Ala Ala Arg Arg Ala Phe Val Pro Gln Leu
            835                 840                 845

Arg Ser Gly Lys Phe Asn Val Leu Leu Thr Thr Tyr Glu Tyr Ile Ile
850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
                900                 905                 910

Pro Leu Gln Asn Lys Leu Pro Glu Leu Trp Ala Leu Leu Asn Phe Leu
            915                 920                 925

Leu Pro Thr Ile Phe Lys Ser Cys Ser Thr Phe Glu Gln Trp Phe Asn
930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
            995                 1000                1005

Arg His Met Gln Ala Lys Gly Val Leu Leu Thr Asp Gly Ser Glu
    1010                1015                1020
```

```
Lys Asp Lys Lys Gly Lys Gly Gly Thr Lys Thr Leu Met Asn Thr
    1025            1030            1035

Ile Met Gln Leu Arg Lys Ile Cys Asn His Pro Tyr Met Phe Gln
    1040            1045            1050

His Ile Glu Glu Ser Phe Ser Glu His Leu Gly Phe Thr Gly Gly
    1055            1060            1065

Ile Val Gln Gly Leu Asp Leu Tyr Arg Ala Ser Gly Lys Phe Glu
    1070            1075            1080

Leu Leu Asp Arg Ile Leu Pro Lys Leu Arg Ala Thr Asn His Lys
    1085            1090            1095

Val Leu Leu Phe Cys Gln Met Thr Ser Leu Met Thr Ile Met Glu
    1100            1105            1110

Asp Tyr Phe Ala Tyr Arg Gly Phe Lys Tyr Leu Arg Leu Asp Gly
    1115            1120            1125

Thr Thr Lys Ala Glu Asp Arg Gly Met Leu Leu Lys Thr Phe Asn
    1130            1135            1140

Glu Pro Gly Ser Glu Tyr Phe Ile Phe Leu Leu Ser Thr Arg Ala
    1145            1150            1155

Gly Gly Leu Gly Leu Asn Leu Gln Ser Ala Asp Thr Val Ile Ile
    1160            1165            1170

Phe Asp Ser Asp Trp Asn Pro His Gln Asp Leu Gln Ala Gln Asp
    1175            1180            1185

Arg Ala His Arg Ile Gly Gln Gln Asn Glu Val Arg Val Leu Arg
    1190            1195            1200

Leu Cys Thr Val Asn Ser Val Glu Glu Lys Ile Leu Ala Ala Ala
    1205            1210            1215

Lys Tyr Lys Leu Asn Val Asp Gln Lys Val Ile Gln Ala Gly Met
    1220            1225            1230

Phe Asp Gln Lys Ser Ser Ser His Glu Arg Arg Ala Phe Leu Gln
    1235            1240            1245

Ala Ile Leu Glu His Glu Glu Gln Asp Glu Ser Arg His Cys Ser
    1250            1255            1260

Thr Gly Ser Gly Ser Ala Ser Phe Ala His Thr Ala Pro Pro Pro
    1265            1270            1275

Ala Gly Val Asn Pro Asp Leu Glu Glu Pro Pro Leu Lys Glu Glu
    1280            1285            1290

Asp Glu Val Pro Asp Asp Glu Thr Val Asn Gln Met Ile Ala Arg
    1295            1300            1305

His Glu Glu Glu Phe Asp Leu Phe Met Arg Met Asp Leu Asp Arg
    1310            1315            1320

Arg Arg Glu Glu Ala Arg Asn Pro Lys Arg Lys Pro Arg Leu Met
    1325            1330            1335

Glu Glu Asp Glu Leu Pro Ser Trp Ile Ile Lys Asp Asp Ala Glu
    1340            1345            1350

Val Glu Arg Leu Thr Cys Glu Glu Glu Glu Lys Met Phe Gly
    1355            1360            1365

Arg Gly Ser Arg His Arg Lys Glu Val Asp Tyr Ser Asp Ser Leu
    1370            1375            1380

Thr Glu Lys Gln Trp Leu Lys Ala Ile Glu Glu Gly Thr Leu Glu
    1385            1390            1395

Glu Ile Glu Glu Glu Val Arg Gln Lys Lys Ser Ser Arg Lys Arg
    1400            1405            1410
```

```
Lys Arg Asp Ser Asp Ala Gly Ser Ser Thr Pro Thr Thr Ser Thr
    1415            1420                1425

Arg Ser Arg Asp Lys Asp Glu Ser Lys Lys Gln Lys Lys Arg
1430            1435                1440

Gly Arg Pro Pro Ala Glu Lys Leu Ser Pro Asn Pro Pro Asn Leu
    1445            1450                1455

Thr Lys Lys Met Lys Lys Ile Val Asp Ala Val Ile Lys Tyr Lys
    1460            1465                1470

Asp Ser Ser Ser Gly Arg Gln Leu Ser Glu Val Phe Ile Gln Leu
    1475            1480                1485

Pro Ser Arg Lys Glu Leu Pro Glu Tyr Tyr Glu Leu Ile Arg Lys
    1490            1495                1500

Pro Val Asp Phe Lys Lys Ile Lys Glu Arg Ile Arg Asn His Lys
    1505            1510                1515

Tyr Arg Ser Leu Asn Asp Leu Glu Lys Asp Val Met Leu Leu Cys
    1520            1525                1530

Gln Asn Ala Gln Thr Phe Asn Leu Glu Gly Ser Leu Ile Tyr Glu
    1535            1540                1545

Asp Ser Ile Val Leu Gln Ser Val Phe Thr Ser Val Arg Gln Lys
    1550            1555                1560

Ile Glu Lys Glu Asp Asp Ser Glu Gly Glu Ser Glu Glu Glu
    1565            1570                1575

Glu Glu Gly Glu Glu Gly Ser Glu Ser Glu Ser Arg Ser Val
    1580            1585                1590

Lys Val Lys Ile Lys Leu Gly Arg Lys Glu Lys Ala Gln Asp Arg
    1595            1600                1605

Leu Lys Gly Gly Arg Arg Pro Ser Arg Gly Ser Arg Ala Lys
    1610            1615                1620

Pro Val Val Ser Asp Asp Asp Ser Glu Glu Glu Gln Glu Glu Asp
    1625            1630                1635

Arg Ser Gly Ser Gly Ser Glu Glu Asp
    1640            1645

<210> SEQ ID NO 15
<211> LENGTH: 8779
<212> TYPE: DNA
<213> ORGANISM: Homo sapiens

<400> SEQUENCE: 15
cgcagcctgc agcccgagac ttctgtaaag gactggggcc ccgcaactgg cctctcctgc      60
cctcttaagc gcagcgccat tttagcaacg cagaagcccg gcgccgggaa gcctcagctc     120
gcctgaaggc aggtccccctc tgacgcctcc gggagcccag gtttcccaga gtccttggga    180
cgcagcgacg agttgtgctg ctatcttagc tgtccttata ggctggccat tccaggtggt     240
ggtatttaga taaaaccact caaactctgc agtttggtct tggggtttgg aggaaagctt     300 ttattttct tcctgctccg gttcagaagg tctgaagctc atacctaacc aggcataaca      360
cagaatctgc aaaacaaaaa cccctaaaaa agcagaccca gagcagtgta aacacttctg     420
ggtgtgtccc tgactggctg cccaaggtct ctgtgtcttc ggagacaaag ccattcgctt     480
agttggtcta ctttaaaagg ccacttgaac tcgctttcca tggcgatttg ccttgtgagc     540
actttcagga gagcctggaa gctgaaaaac ggtagaaaaa tttccgtgcg ggccgtgggg     600
ggctggcggc aactgggggg ccgcagatca gagtgggcca ctggcagcca acggcccccg     660
```

```
gggctcaggc ggggagcagc tctgtggtgt gggattgagg cgttttccaa gagtgggttt    720
tcacgtttct aagatttccc aagcagacag cccgtgctgc tccgatttct cgaacaaaaa    780
agcaaaacgt gtggctgtct tgggagcaag tcgcaggact gcaagcagtt gggggagaaa    840
gtccgccatt ttgccacttc tcaaccgtcc ctgcaaggct ggggctcagt tgcgtaatgg    900
aaagtaaagc cctgaactat cacactttaa tcttccttca aaaggtggta aactatacct    960
actgtccctc aagagaacac aagaagtgct ttaagaggta ttttaaaagt tccgggggtt   1020
ttgtgaggtg tttgatgacc cgtttaaaat atgatttcca tgtttctttt gtctaaagtt   1080
tgcagctcaa atcttccac acgctagtaa tttaagtatt tctgcatgtg tagtttgcat    1140
tcaagttcca taagctgtta agaaaaatct agaaaagtaa aactagaacc tatttttaac   1200
cgaagaacta cttttttgcct ccctcacaaa ggcggcggaa ggtgatcgaa ttccggtgat   1260
gcgagttgtt ctccgtctat aaatacgcct cgcccgagct gtgcggtagg cattgaggca   1320
gccagcgcag gggcttctgc tgaggggggca ggcggagctt gaggaaaccg cagataagtt   1380
tttttctctt tgaaagatag agattaatac aactacttaa aaaatatagt caataggtta   1440
ctaagatatt gcttagcgtt aagtttttaa cgtaatttta atagcttaag attttaagag   1500
aaaatatgaa gacttagaag agtagcatga ggaaggaaaa gataaaaggt ttctaaaaca   1560
tgacggaggt tgagatgaag cttcttcatg gagtaaaaaa tgtatttaaa agaaaattga   1620
gagaaaggac tacagagccc cgaattaata ccaatagaag ggcaatgctt ttagattaaa   1680
atgaaggtga cttaaacagc ttaaagttta gtttaaaagt tgtaggtgat taaaataatt   1740
tgaaggcgat cttttaaaaa gagattaaac cgaaggtgat taaagacct tgaaatccat    1800 gacgcaggga gaattgcgtc atttaaagcc tagttaacgc atttactaaa cgcagacgaa   1860
aatgaaagaa ttaattggga gtggtaggat gaaacaattt ggagaagata gaagtttgaa   1920
gtggaaaact ggaagacaga agtacgggaa ggcgaagaaa agaatagaga agataggggaa   1980 attagaagat aaaacatac ttttagaaga aaaaagataa atttaaacct gaaaagtagg    2040
aagcagaaga aaaaagacaa gctaggaaac aaaaagctaa gggcaaaatg tacaaactta   2100
gaagaaaatt ggaagataga aacaagatag aaaatgaaaa tattgtcaag agtttcagat   2160
agaaaatgaa aaacaagcta agacaagtat tggagaagta tagaagatag aaaaatataa   2220
agccaaaaat tggataaaat agcactgaaa aaatgaggaa attattggta accaatttat   2280
tttaaaagcc catcaattta atttctggtg gtgcagaagt tagaaggtaa agcttgagaa   2340
gatgagggtg tttacgtaga ccagaaccaa tttagaagaa tacttgaagc tagaagggga   2400
agttggttaa aaatcacatc aaaaagctac taaaaggact ggtgtaattt aaaaaaaact   2460
aaggcagaag gcttttggaa gagttagaag aatttggaag gccttaaata tagtagctta   2520
gtttgaaaaa tgtgaaggac tttcgtaacg gaagtaattc aagatcaaga gtaattacca   2580
acttaatgtt tttgcattgg actttgagtt aagattattt tttaaatcct gaggactagc   2640
attaattgac agctgaccca ggtgctacac agaagtggat tcagtgaatc taggaagaca   2700
gcagcagaca ggattccagg aaccagtgtt tgatgaagct aggactgagg agcaagcgag   2760
caagcagcag ttcgtggtga agataggaaa agagtccagg agccagtgcg atttggtgaa   2820
ggaagctagg aagaaggaag gagcgctaac gatttggtgg tgaagctagg aaaaaggatt   2880
ccaggaagga gcgagtgcaa tttggtgatg aaggtagcag gcggcttggc ttggcaacca   2940
cacggaggag gcgagcaggc gttgtgcgta gaggatccta gaccagcatg ccagtgtgcc   3000
aaggccacag ggaaagcgag tggttggtaa aaatccgtga ggtcggcaat atgttgtttt   3060
```

```
tctggaactt acttatggta acctttatt tattttctaa tataatgggg gagtttcgta    3120
ctgaggtgta aagggattta tatggggacg taggccgatt tccgggtgtt gtaggtttct    3180
cttttttcagg cttatactca tgaatcttgt ctgaagcttt tgagggcaga ctgccaagtc   3240
ctggagaaat agtagatggc aagtttgtgg gtttttttt tttacacgaa tttgaggaaa     3300
accaaatgaa tttgatagcc aaattgagac aatttcagca aatctgtaag cagtttgtat    3360
gtttagttgg ggtaatgaag tatttcagtt ttgtgaatag atgacctgtt tttacttcct    3420
caccctgaat tcgttttgta aatgtagagt ttggatgtgt aactgaggcg gggggagtt     3480
ttcagtattt ttttttgtgg gggtgggggc aaaatatgtt ttcagttctt tttcccttag    3540
gtctgtctag aatcctaaag gcaaatgact caaggtgtaa cagaaaacaa gaaaatccaa    3600
tatcaggata atcagaccac cacaggttta cagtttatag aaactagagc agttctcacg    3660
ttgaggtctg tggaagagat gtccattgga gaaatggctg gtagttactc ttttttcccc    3720
ccaccccctt aatcagactt taaaagtgct taacccctta aacttgttat ttttacttg     3780
aagcattttg ggatggtctt aacagggaag agagagggtg ggggagaaaa tgttttttc     3840
taagattttc cacagatgct atagtactat tgacaaactg ggttagagaa ggagtgtacc    3900
gctgtgctgt tggcacgaac accttcaggg actggagctg cttttatcct tggaagagta    3960
ttcccagttg aagctgaaaa gtacagcaca gtgcagcttt ggttcatatt cagtcatctc    4020
aggagaactt cagaagagct tgagtaggcc aaatgttgaa gttaagtttt ccaataatgt    4080
gacttcttaa aagttttatt aaaggggagg ggcaaatatt ggcaattagt tggcagtggc    4140
ctgttacggt tgggattggt ggggtgggtt taggtaattg tttagtttat gattgcagat    4200
aaactcatgc cagagaactt aaagtcttag aatggaaaaa gtaaagaaat atcaacttcc    4260
aagttggcaa gtaactccca atgatttagt tttttttcccc ccagtttgaa ttgggaagct   4320
gggggaagtt aaatatgagc cactgggtgt accagtgcat taatttgggc aaggaaagtg    4380
tcataatttg atactgtatc tgttttcctt caaagtatag agcttttggg gaaggaaagt    4440
attgaactgg gggttggtct ggcctactgg gctgacatta actacaatta tgggaaatgc    4500
aaaagttgtt tggatatggt agtgtgtggt tctcttttgg aattttttttc aggtgattta   4560
ataataattt aaaactacta tagaaactgc agagcaaagg aagtggctta atgatcctga    4620
agggatttct tctgatggta gcttttgtat tatcaagtaa gattctattt tcagttgtgt    4680
gtaagcaagt ttttttttag tgtaggagaa atacttttcc attgtttaac tgcaaaacaa    4740
gatgttaagg tatgcttcaa aaattttgta aattgtttat tttaaactta tctgtttgta   4800
aattgtaact gattaagaat tgtgatagtt cagcttgaat gtctcttaga gggtgggctt    4860
ttgttgatga gggaggggaa acttttttt tttctataga cttttttcag ataacatctt     4920
ctgagtcata accagcctgg cagtatgatg gcctagatgc agagaaaaca gctccttggt    4980
gaattgataa gtaaaggcag aaaagattat atgtcatacc tccattgggg aataagcata    5040
accctgagat tcttactact gatgagaaca ttatctgcat atgccaaaaa attttaagca    5100
aatgaaagct accaatttaa agttacggaa tctaccattt taaagttaat tgcttgtcaa    5160
gctataacca caaaataat gaattgatga gaaatacaat gaagaggcaa tgtccatctc     5220
aaaatactgc ttttacaaaa gcagaataaa agcgaaaaga aatgaaaatg ttacactaca    5280
ttaatcctgg aataaaagaa gccgaaataa atgagagatg agttgggatc aagtggattg    5340
aggaggctgt gctgtgtgcc aatgtttcgt ttgcctcaga caggtatctc ttcgttatca    5400
```

-continued

```
gaagagttgc ttcatttcat ctgggagcag aaaacagcag gcagctgtta acagataagt    5460
ttaacttgca tctgcagtat tgcatgttag ggataagtgc ttatttttaa gagctgtgga    5520
gttcttaaat atcaaccatg gcactttctc ctgacccctt ccctagggga tttcaggatt    5580
gagaaatttt tccatcgagc ctttttaaaa ttgtaggact tgttcctgtg ggcttcagtg    5640
atgggatagt acacttcact cagaggcatt tgcatcttta ataaatttct taaaagcctc    5700
taaagtgatc agtgccttga tgccaactaa ggaaatttgt ttagcattga atctctgaag    5760
gctctatgaa aggaatagca tgatgtgctg ttagaatcag atgttactgc taaaatttac    5820
atgttgtgat gtaaattgtg tagaaaacca ttaaatcatt caaaataata aactattttt    5880
attagagaat gtatactttt agaaagctgt ctccttattt aaataaaata gtgtttgtct    5940
gtagttcagt gttggggcaa tcttgggggg gattcttctc taatctttca gaaactttgt    6000
ctgcgaacac tctttaatgg accagatcag gatttgagcg gaagaacgaa tgtaacttta    6060
aggcaggaaa gacaaatttt attcttcata aagtgatgag catataataa ttccaggcac    6120
atggcaatag aggccctcta aataaggaat aaataaccte ttagacaggt gggagattat    6180
gatcagagta aaaggtaatt acacatttta tttccagaaa gtcagggggtc tataaattga    6240 cagtgattag agtaatactt tttcacattt ccaaagtttg catgttaact ttaaatgctt    6300
acaatcttag agtggtaggc aatgttttac actattgacc ttatataggg aagggaggg    6360 gtgcctgtgg ggttttaaag aattttcctt tgcagaggca tttcatcctt catgaagcca    6420
ttcaggattt tgaattgcat atgagtgctt ggctcttcct tctgttctag tgagtgtatg    6480
agaccttgca gtgagtttat cagcatactc aaaattttt tcctggaatt tggagggatg    6540
ggaggagggg gtgggcctta cttgttgtag cttttttttt ttttacagac ttcacagaga    6600
atgcagttgt cttgacttca ggtctgtctg ttctgttggc aagtaaatgc agtactgttc    6660
tgatcccgct gctattagaa tgcattgtga aacgactgga gtatgattaa aagttgtgtt    6720
ccccaatgct tggagtagtg attgttgaag gaaaaaatcc agctgagtga taaaggctga    6780
gtgttgagga aatttctgca gttttaagca gtcgtatttg tgattgaagc tgagtacatt    6840
ttgctggtgt attttaggt aaaatgcttt ttgttcattt ctggtggtgg gaggggactg    6900
aagcctttag tctttttccag atgcaacctt aaaatcagtg acaagaaaca ttccaaacaa    6960
gcaacagtct tcaagaaatt aaactggcaa gtggaaatgt ttaaacagtt cagtgatctt    7020
tagtgcattg tttatgtgtg ggtttctctc tcccctccct tggtcttaat tcttacatgc    7080
aggaacactc agcagacaca cgtatgcgaa gggccagaga agccagaccc agtaagaaaa    7140
aatagcctat ttactttaaa taaaccaaac attccatttt aaatgtgggg attgggaacc    7200
actagttctt tcagatggta ttcttcagac tatagaagga gcttccagtt gaattcacca    7260
gtggacaaaa tgaggaaaac aggtgaacaa gcttttctg tatttacata caaagtcaga    7320
tcagttatgg gacaatagta ttgaatagat ttcagcttta tgctgagta actggcatgt    7380 gagcaaactg tgttggcgtg ggggtggagg ggtgaggtgg gcgctaagcc ttttttttaag    7440 atttttcagg tacccctcac taaaggcacc gaaggcttaa agtaggacaa ccatggagcc    7500
ttcctgtggc aggagagaca acaaagcgct attatcctaa ggtcaagaga agtgtcagcc    7560
tcacctgatt tttattagta atgaggactt gcctcaactc cctctttctg gagtgaagca    7620
tccgaaggaa tgcttgaagt acccctgggc ttctcttaac atttaagcaa gctgttttta    7680
tagcagctct taataataaa gcccaaatct caagcggtgc ttgaagggga gggaaggggg    7740
gaaagcgggc aaccactttt ccctagcttt tccagaagcc tgttaaaagc aaggtctccc    7800
```

```
cacaagcaac ttctctgcca catcgccacc ccgtgccttt tgatctagca cagacccttc    7860
acccctcacc tcgatgcagc cagtagcttg gatccttgtg ggcatgatcc ataatcggtt    7920
tcaaggtaac gatggtgtcg aggtctttgg tgggttgaac tatgttagaa aaggccatta    7980
atttgcctgc aaattgttaa cagaagggta ttaaaaccac agctaagtag ctctattata    8040
atacttatcc agtgactaaa accaacttaa accagtaagt ggagaaataa catgttcaag    8100
aactgtaatg ctgggtggga acatgtaact tgtagactgg agaagatagg catttgagtg    8160
gctgagaggg cttttgggtg ggaatgcaaa aattctctgc taagacttt tcaggtgaac     8220 ataacagact tggccaagct agcatcttag cggaagctga tctccaatgc tcttcagtag    8280
ggtcatgaag gttttctttt tcctgagaaa acaacacgta ttgttttctc aggttttgct    8340
ttttggcctt tttctagctt aaaaaaaaaa aaagcaaaag atgctggtgg ttggcactcc    8400
tggtttccag gacggggttc aaatccctgc ggcgtctttg ctttgactac taatctgtct    8460
tcaggactct ttctgtattt ctccttttct ctgcaggtgc tagttcttgg agttttgggg    8520
aggtgggagg taacagcaca atatctttga actatataca tccttgatgt ataatttgtc    8580
aggagcttga cttgattgta tattcatatt tacacgagaa cctaatataa ctgccttgtc    8640
tttttcaggt aatagcctgc agctggtgtt ttgagaagcc ctactgctga aaacttaaca    8700
attttgtgta ataaaaatgg agaagctcta aattgttgtg gttcttttgt gaataaaaaa    8760
atcttgattg gggaaaaaa                                                 8779

<210> SEQ ID NO 16
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccgggctagg ttaattggga ccaaactcga gtttggtccc aattaaccta gcttttg         58

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccggccaaca caagtcatcc cattactcga gtaatgggat gacttgtgtt ggttttg         58

<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccggcccaac atagatggac caaatctcga gatttggtcc atctatgttg ggttttg         58

<210> SEQ ID NO 19
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19
gctcctctta ggggccact                                                      19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgtaacatg gaaactgggg aaa                                                 23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acaaggtcca agcctactcc a                                                   21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtcatcttcg agtggtgcag t                                                   21

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtctcaagag cgtgaagttt ggaag                                               25

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcctggaac agtcttggc                                                      19

<210> SEQ ID NO 25
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 25
gcagaggcat acttgtaccg                                              20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acccacacac aacgctcac                                               19

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caccttgtgg agtacatgga ac                                           22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaagttggt atgggtgcct t                                            21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcccgagagg tatctctttg tg                                           22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tccacaaata ctcaggcaaa gag                                          23

<210> SEQ ID NO 31
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 31
cccagacatc agggagtaat gg                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tctgcacatt ttaaccgagg tc                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cctggagcgc agaatcgaat                                                 20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgtcccactg ggttatccca t                                               21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgaggtggt cgtggagttg                                                 20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccaacaaggg tccatcctac g                                               21

<210> SEQ ID NO 37
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 37
gagcggcaag acaacaagga                                               20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctcgcacct ggtgattatg c                                             21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agcacaagtc atcccgttaa ag                                            22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agtgacttgg attttccagc ac                                            22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
accaagcaga aatcaccatg                                               20

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtgtaatct ggatatcaga tg                                            22

<210> SEQ ID NO 43
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 43
attggggacc cttaggccat                                                    20

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccatagctga actgaaaacc acc                                                23

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgggttgtt gagtgttaca g                                                  21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caaggttgtg tcgggtggaa a                                                  21

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcagcacctt tctttgggca ca                                                 22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgtccatcgt tcatcatcgt ca                                                 22

<210> SEQ ID NO 49
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 49
tgatgttatg atggtcccac ttg                                           23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcctgtcact tgtaaaccat aga                                           23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctacctccct ttcaagacgg t                                             21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccctgagtag tatcgctcct tg                                            22

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcgttccgat ggaatccac                                                19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcagctccct ggtcagtag                                                19

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tctatcggat acttcagcgt ca                                          22

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gccagcttgt tctttacttc agc                                         23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgagtcaagt ctgaaacctt gga                                         23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cagctactcc atagggcaat ttc                                         23

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcctgagaag tatcgctccc                                             20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atctgggcgg cctacatca                                              19

<210> SEQ ID NO 61
<211> LENGTH: 19
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 61
cagtctccct gccaatcgt                                                      19

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgaacagtct cttttccaac cc                                                  22

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aattctgttg taagggcgac c                                                   21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gaagcagtgg ttaagccgga g                                                   21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
atcaaagaga cgtggatcca g                                                   21
```

METHODS AND COMPOSITIONS FOR THE TREATMENT OF VASCULAR DISEASE

CROSS-REFERENCE TO RELATED APPLICATIONS

This application is a 35 U.S.C. § 371 National Phase Entry Application of International Application No. PCT/US2019/018501 filed Feb. 19, 2019, which designates the U.S., and which claims benefit under 35 U.S.C. § 119(e) of U.S. Provisional Application No. 62/632,105 filed Feb. 19, 2018 and 62/793,614 filed Jan. 17, 2019 the contents of all of which are incorporated herein by reference in their entireties.

GOVERNMENT SUPPORT

This invention was made with government support under under Grant Nos. HL130113 and HL142809 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 15, 2019 is named 030258-091670WOPT_SL.txt and is 81,924 bytes in size.

TECHNICAL FIELD

The technology described herein relates to methods and compositions to prevent or treat vascular disease by targeting the epigenetic regulation of gene expression of vascular smooth muscle cell cytoskeletal proteins.

BACKGROUND

The vascular system is the body's network of blood vessels. It includes the arteries, veins and capillaries that carry blood to and from the heart. Cardiovascular diseases (CVDs) are a group of vascular diseases of the heart and blood vessels. Cardiovascular diseases are the leading cause of death globally: more people die annually from CVDs than from any other cause. The World Health Organization estimates that 17.9 million people died from CVDs in 2016, representing 31% of all global deaths. Of these deaths, 85% are due to heart attack and stroke.

Heart attacks and strokes are usually acute events and are mainly caused by a blockage that prevents blood from flowing to the heart or brain. The most common reason for this is a build-up of fatty deposits on the inner walls of the blood vessels that supply the heart or brain. Strokes can also be caused by bleeding from a blood vessel in the brain or from blood clots. The cause of heart attacks and strokes are usually the presence of a combination of risk factors, such as tobacco use, unhealthy diet and obesity, physical inactivity and harmful use of alcohol, hypertension, diabetes and hyperlipidaemia. Other CVDs include: atherosclerosis, coronary heart disease; cerebrovascular disease; peripheral arterial disease; rheumatic heart disease; congenital heart disease; deep vein thrombosis and pulmonary embolism. Current treatment is limited to ameliorating symptoms and slowing the natural progression of the disease but fails to address the cause of CVDs.

SUMMARY

As described herein, the inventors have discovered that in various vascular diseases, two protein complexes (i.e. PRC2 and the HDAC9 complex) inappropriately downregulate the expression of a number of genes which are responsible for providing the contractility of the smooth muscle cells of the vascular system. This results in stiffening and scarring of the vascular system. Accordingly, provided herein are compositions and methods for the prevention and/or treatment of a vascular disease, including but not limited to, atherosclerosis, ischemia/reperfusion, hypertension, restenosis, and arterial inflammation, can be prevented and/or treated by targeting the epigenetic regulation of vascular smooth muscle cell cytoskeletal proteins. The compositions and methods relate to inhibition of the PRC2 and HDAC9 complexes, resulting in restoration of those vascular smooth muscle cell cytoskeletal proteins which contribute to contractility (e.g., including but not limited to SM22a, a-SMA and/or sMHC).

Accordingly, provided herein, in some aspects, are methods to prevent or treat a thoracic aortic aneurysm in a patient comprised of administering to said patient a therapeutically effective dose of a compound or drug (or combination of said compounds or drugs) which targets the epigenetic regulation of gene expression of vascular smooth muscle cell cytoskeletal proteins.

In some embodiments of these methods and all such methods described herein, the cytoskeletal protein is SM22a encoded by the TAGLN gene.

In some embodiments of these methods and all such methods described herein, the epigenetic regulatory target is a multiprotein complex (PRC2, Polycomb repressive complex 2) responsible for gene silencing through its catalytic activity or hypermethylation of chromatin at vascular smooth muscle gene loci.

In some embodiments of these methods and all such methods described herein, the chromatin or chromosomal protein is H3.

In some embodiments of these methods and all such methods described herein, the enzyme responsible for hypermethylation is a multiprotein complex (PRC2, Polycomb repressive complex 2) and its catalytic domain the methyltransferase EZH2.

In some embodiments of these methods and all such methods described herein, the compound or drug (or combination of said compounds or drugs) inhibits PRC2 complex methyltransferase catalytic activity.

In some embodiments of these methods and all such methods described herein, the compound or drug that inhibits methyltransferase EZH2 is GSK343.

In some embodiments of these methods and all such methods described herein, the combination of compounds or drugs is GSK343 and Losartan.

In some embodiments of these methods and all such methods described herein, the method comprising administering to a subject in need thereof, a therapeutically effective amount of at least one agent that inhibits the activity of the HDAC9 complex or PRC2 complex.

In some embodiments of these methods and all such methods described herein, the vascular disease is a cardiovascular disease (CVD).

In some embodiments of these methods and all such methods described herein, the CVD is selected from the group consisting of atherosclerosis, vascular calcification, calciphylaxis, neointimal stenosis, and arterial aneurism.

In some embodiments of these methods and all such methods described herein, the at least one agent inhibits the activity of Polycomb repressive complex 2 (PRC2).

In some embodiments of these methods and all such methods described herein, the at least one agent inhibits the Histone Deacetylase 9 (HDAC9) complex.

In some embodiments of these methods and all such methods described herein, the at least one agent is an inhibitor of EZH2.

In some embodiments of these methods and all such methods described herein, the at least one agent is an inhibitor of an enzyme of Enzyme Comission (E.C.) number 2.1.1.43.

In some embodiments of these methods and all such methods described herein, the at least one agent is an inhibitor of HDAC9.

In some embodiments of these methods and all such methods described herein, the at least one agent is an inhibitor of MALAT1.

In some embodiments of these methods and all such methods described herein, the enzyme is an enzyme of Enzyme Comission (E.C.) number 3.5.1.98.

In some embodiments of these methods and all such methods described herein, the inhibitor is an inhibitory nucleic acid or a small molecule inhibitor.

Also provided here, in some aspects, are compositions to prevent or treat a thoracic aortic aneurysm in a patient comprised of administering to said patient a therapeutically effective dose of a compound or drug (or combination of said compounds or drugs) which targets the epigenetic regulation of gene expression of vascular smooth muscle cell cytoskeletal proteins.

In some embodiments of these compositions and all such compositions described herein, the cytoskeletal protein is SM22a encoded by the TAGLN gene.

In some embodiments of these compositions and all such compositions described herein, the epigenetic regulatory target is a multiprotein complex (PRC2, Polycomb repressive complex 2) responsible for gene silencing through its catalytic activity or hypermethylation of chromatin at vascular smooth muscle gene loci.

In some embodiments of these compositions and all such compositions described herein, the chromatin or chromosomal protein is H3.

In some embodiments of these compositions and all such compositions described herein, the enzyme responsible for hypermethylation is a multiprotein complex (PRC2, Polycomb repressive complex 2) and its catalytic domain the methyltransferase EZH2.

In some embodiments of these compositions and all such compositions described herein, the compound or drug (or combination of said compounds or drugs) inhibits PRC2 complex methyltransferase catalytic activity.

In some embodiments of these compositions and all such compositions described herein, the compound or drug that inhibits methyltransferase EZH2 is GSK343.

In some embodiments of these compositions and all such compositions described herein, the combination of compounds or drugs is GSK343 and Losartan.

In some embodiments of these compositions and all such compositions described herein, comprising administering to a subject in need thereof, a therapeutically effective amount of at least one agent that inhibits the activity of the HDAC9 complex or PRC2 complex.

In some embodiments of these compositions and all such compositions described herein, the vascular disease is a cardiovascular disease (CVD).

In some embodiments of these compositions and all such compositions described herein, the CVD is selected from the group consisting of atherosclerosis, vascular calcification, calciphylaxis, neointimal stenosis, and arterial aneurism.

In some embodiments of these compositions and all such compositions described herein, the at least one agent inhibits the activity of Polycomb repressive complex 2 (PRC2).

In some embodiments of these compositions and all such compositions described herein, the at least one agent inhibits the Histone Deacetylase 9 (HDAC9) complex.

In some embodiments of these compositions and all such compositions described herein, the at least one agent is an inhibitor of EZH2.

In some embodiments of these compositions and all such compositions described herein, the at least one agent is an inhibitor of an enzyme of Enzyme Comission (E.C.) number 2.1.1.43.

In some embodiments of these compositions and all such compositions described herein, the at least one agent is an inhibitor of HDAC9.

In some embodiments of these compositions and all such compositions described herein, the at least one agent is an inhibitor of MALAT1.

In some embodiments of these compositions and all such compositions described herein, the enzyme is an enzyme of Enzyme Comission (E.C.) number 3.5.1.98.

In some embodiments of these compositions and all such compositions described herein, the inhibitor is an inhibitory nucleic acid or a small molecule inhibitor.

In some embodiments of these compositions and all such compositions described herein, the composition comprising administering to a subject in need thereof, a therapeutically effective amount of at least one agent that targets transcriptional silencing of vascular smooth muscle cell cytoskeletal proteins, thereby preventing or treating the vascular disease.

In some embodiments of these compositions and all such compositions described herein, the vascular disease is selected from a cardiovascular disease (CVD).

In some embodiments of these compositions and all such compositions described herein, the CVD is selected from atherosclerosis, vascular calcification, calciphylaxis, neointimal stenosis, and arterial aneurism.

In some embodiments of these compositions and all such compositions described herein, the transcriptional silencing comprises a multiprotein complex.

In some embodiments of these compositions and all such compositions described herein, the multiprotein complex comprises a Polycomb repressive complex.

In some embodiments of these compositions and all such compositions described herein, the multiprotein complex comprises a Polycomb repressive complex 2 (PRC2).

In some embodiments of these compositions and all such compositions described herein, the multiprotein complex comprises a Histone Deacetylase.

In some embodiments of these compositions and all such compositions described herein, the multiprotein complex comprises Histone Deacetylase complex 9 (HDAC9).

In some embodiments of these compositions and all such compositions described herein, the multiprotein complex comprises a catalytic subunit that induces transcriptional silencing at vascular smooth muscle gene loci.

In some embodiments of these compositions and all such compositions described herein, the catalytic subunit induces gene silencing by hypermethylation.

In some embodiments of these compositions and all such compositions described herein, the catalytic subunit is an enzyme.

In some embodiments of these compositions and all such compositions described herein, the enzyme is methyltransferase EZH2.

In some embodiments of these compositions and all such compositions described herein, the enzyme is an enzyme of Enzyme Comission (E.C.) number 2.1.1.43.

In some embodiments of these compositions and all such compositions described herein, the enzyme induces transcriptional silencing by hypermethylation of chromatin at vascular smooth muscle gene loci.

In some embodiments of these compositions and all such compositions described herein, the enzyme is a Histone Deacetylase.

In some embodiments of these compositions and all such compositions described herein, the enzyme is Histone Deacetylase 9 (HDAC9).

In some embodiments of these compositions and all such compositions described herein, the enzyme is an enzyme of Enzyme Comission (E.C.) 3.5.1.98.

In some embodiments of these compositions and all such compositions described herein, the enzyme induces transcriptional silencing by hyperacetylation of chromatin at vascular smooth muscle gene loci.

In some embodiments of these compositions and all such compositions described herein, the enzyme induces transcriptional silencing at vascular smooth muscle gene loci is selected from the group consisting of: EZH2; HDAC9.

In some embodiments of these compositions and all such compositions described herein, the agent that induces transcriptional silencing at vascular smooth muscle gene loci is a EZH2 inhibitor.

In some embodiments of these compositions and all such compositions described herein, the EZH2 inhibitor is selected from the group consisting of: GSK343 and Losartan.

In some embodiments of these compositions and all such compositions described herein, the cytoskeletal protein is selected from the group consisting of SM22a; MMP-9; ACTA2, TAGLN, MYH11, SMTN.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in microbiology, molecular biology and medicine can be found, for example, in *The Merck Manual of Diagnosis and Therapy*, 19th Edition, published by Merck Sharp & Dohme Corp., 2011 (ISBN 978-0-911910-19-3); Robert S. Porter et al. (eds.), Black, Jacquelyn G. *Microbiology: Principles and Explorations*, 9th Edition: Wiley; 9th Edition, 2014, Moore, Veranus A. *Principles of Microbiology: A Treatise on Bacteria, Fungi and Protozoa*: Forgotten Books, 2012, *The Encyclopedia of Molecular Cell Biology and Molecular Medicine*, published by Blackwell Science Ltd., 1999-2012 (ISBN 9783527600908); and Robert A. Meyers (ed.), *Molecular Biology and Biotechnology: a Comprehensive Desk Reference*, published by VCH Publishers, Inc., 1995 (ISBN 1-56081-569-8); Lewin's Genes XI, published by Jones & Bartlett Publishers, 2014 (ISBN-1449659055); Michael Richard Green and Joseph Sambrook, *Molecular Cloning: A Laboratory Manual*, 4th ed., Cold Spring Harbor Laboratory Press, Cold Spring Harbor, N.Y., USA (2012) (ISBN 1936113414); Davis et al., *Basic Methods in Molecular Biology*, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); *Current Protocols in Molecular Biology* (CPMB), Frederick M. Ausubel (ed.), John Wiley and Sons, 2014 (ISBN 047150338X, 9780471503385), *Current Protocols in Protein Science* (CPPS), John E. Coligan (ed.), John Wiley and Sons, Inc., 2005; and *Current Protocols in Immunology* (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, an "agent" refers to e.g., a molecule, protein, peptide, antibody, or nucleic acid, that inhibits expression of a polypeptide or polynucleotide, or binds to, partially or totally blocks stimulation, decreases, prevents, delays activation, inactivates, desensitizes, or down regulates the activity of a target polypeptide or a polynucleotide encoding it. An "agent" can be any chemical, entity or moiety, including without limitation synthetic and naturally-occurring proteinaceous and non-proteinaceous entities. In some embodiments of any of the aspects, an agent is a nucleic acid, nucleic acid analog, protein, antibody, peptide, aptamer, oligomer of nucleic acids, amino acids, or carbohydrates including without limitation a protein, oligonucleotide, ribozyme, DNAzyme, glycoprotein, siRNAs, lipoprotein and/or a modification or combinations thereof etc. In certain embodiments, agents are small molecule chemical moieties. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "vascular disease" as used herein, refers to a class of diseases of the blood vessels. It is a subgroup of cardiovascular disease. Vascular disease is a pathological state of large and medium muscular arteries and is triggered by endothelial cell dysfunction. Under physiological conditions, the arterial endothelium exerts a powerful protective influence to maintain vascular homeostasis. However, during the development of vascular disease, these protective activities are lost and dysfunctional endothelial cells actually promote disease pathogenesis. Normal endothelial function is crucial for maintaining vascular and organismal health. Endothelial cells are key regulators of blood vessel constriction, thrombogenicity, inflammation, permeability, and vascular remodeling. Under normal conditions, the endothelium exerts a protective influence to inhibit these processes and maintain vascular stability and homeostasis. However, during the development of vascular disease, endothelial cells with an altered phenotype, namely 'dysfunctional' endothelium, promote these same processes and contribute to pathological changes in vascular structure and reactivity. Exemplary vascular diseases include but are not limited to Erythromelalgia, Peripheral artery disease, Buerger's disease, Raynaud's disease, and Cerebrovascular disease.

The term "Cardiovascular disease", "CVD" as used herein, refers to a class of diseases that involve the heart or blood vessels. CVD include but are not limited to coronary artery diseases (CAD) such as angina and myocardial infarction, stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, the terms "treat," "treatment," "treating," or "amelioration" refer to therapeutic treatments, wherein the object is to reverse, alleviate, ameliorate, inhibit, slow down or stop the progression or severity of a vascular disease or syndrome, e.g., epigenetic mysregulation or smooth muscle cell changes. The term "treating" includes reducing or alleviating at least one adverse effect or symptom of a vascular disease. Treatment is generally "effective" if one or more symptoms or clinical markers are reduced. Treatments described herein can reduce vascular disease symptoms for at least two weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, or more, e.g, at least 20 weeks (or 5 months), 6 months or more. Alternatively, or in addition, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized. The term "treatment" of a disease also includes providing relief from the symptoms or side-effects of the disease (including palliative treatment).

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. A subject can be male or female.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with vascular diseases. Non-limiting examples include the Fbn1$^{c1° 39Gi+}$ murine model, the apoB or apoR deficient pigs (Rapacz, et al., 1986, Science 234:1573-1577) and Watanabe heritable hyperlipidemic (WHHL) rabbits (Kita et al., 1987, Proc. Natl. Acad. Sci U.S.A. 84: 5928-5931). In addition, the compositions and methods described herein can be used to treat domesticated animals and/or pets.

As used herein, the terms "protein," "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

As used herein, the term "smooth muscle cells" (SMC) refers to an involuntary non-striated muscle. In diverse forms of vascular disease, smooth muscle cells (SMCs) are known to modulate cellular phenotype typified by down regulation of SMC-restricted contractile genes, and up regulate groups of genes involved in secretion of extracellular matrix, proliferation, and migration. This cellular behavior is important in vascular diseases including but not limited to atherosclerosis, pulmonary hypertension, aortic and peripheral aneurysms, and restenosis after percutaneous arterial intervention.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically acceptable carrier" means a pharmaceutically-acceptable material, composition or vehicle, such as a liquid or solid filler, diluent, excipient, manufacturing aid or solvent encapsulating material necessary or used in formulating an active ingredient or agent for delivery to a subject. Each carrier must be "acceptable" in the sense of being compatible with the other ingredients of the formulation and not injurious to the patient.

The term "therapeutically effective amount" as used herein refers to an amount sufficient to effect a beneficial or desired clinical result upon treatment. Specifically, the term "therapeutically effective amount" means an amount sufficient to cause a measurable improvement in an animal model of vascular disease. Improvements may include, for example, decreased prevalence and size of fatty streaks and/or cardiovascular disease plaques.

The term "unit dose" described herein is defined as a unit containing a predetermined quantity of active material calculated to produce the desired therapeutic effect in association with the required diluent i.e. a carrier or vehicle. For example, the unit dose of an inhibitor enzyme administered for example, contains the principal active ingredient, e.g., enzyme or a combination thereof, in amounts ranging from 250 μg to 5 μg. The unit dose is further defined as the dose, containing the principal active ingredient, e.g. agents that inhibit inhibit EZH2 and/or any enzyme with the biological activity of Enzyme Comission (E.C.) number 2.1.1.43 and/or Enzyme Comission (E.C.) number 3.5.1.98, may be tested for the ability to ameliorate, prevent and/or treat cardiovascular disease symptoms.

The term "gene expression" as used herein refers to the process by which information from a gene is used in the synthesis of a functional gene product. "Differential expression", as used herein, refers to both quantitative as well as qualitative differences in the genes' temporal and/or tissue expression patterns. Differentially expressed genes may represent "fingerprint genes," and/or "target genes." "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of vascular and/or cardiovascular disease. "Target gene", as used herein, refers to a differentially expressed gene involved in cardiovascular disease such that modulation of the level of target gene expression or of target gene product activity may act to ameliorate a cardiovascular disease condition. Compounds that modulate target gene expression or activity of the target gene product can be used in the prevention and/or treatment of vascular and/or cardiovascular disease. "Differential expression" as used herein refers to both quantitative as well as qualitative differences in the genes' temporal and/or tissue expression patterns. Thus, a differentially expressed gene may have its expression activated or completely inactivated in normal versus cardiovascular disease conditions, or under control versus experimental conditions. Such a qualitatively regulated gene will exhibit an expression pattern within a given tissue or cell type which is detectable in either control or cardiovascular disease subjects, but is not detectable in both. Alternatively, such a qualitatively regulated gene will exhibit an expression pattern within a given tissue or cell type which is detectable in either control or experimental subjects, but is not detectable in both. "Detectable", as used herein, refers to an RNA expression pattern which is detectable via the standard techniques of differential display, reverse transcriptase-(RT-) PCR and/or Northern analyses, which are well known to those of skill in the art.

"Target gene", as used herein, refers to a differentially expressed gene involved in vascular and/or cardiovascular disease in a manner by which modulation of the level of target gene expression or of target gene product activity may act to ameliorate symptoms of cardiovascular disease.

Other than in the operating examples, or where otherwise indicated, all numbers expressing quantities of ingredients or reaction conditions used herein should be understood as modified in all instances by the term "about." The term "about" when used in connection with percentages means ±1% of the value being referred to. For example, about 100 means from 99 to 101.

Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example."

As used in this specification and appended claims, the singular forms "a," "an", and "the" include plural references unless the context clearly dictates otherwise. Thus for example, reference to "the method" included one or more methods, and/or steps of the type described herein and/or which will become apparent to those persons skilled in the art upon reading this disclosure and so forth.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

As used herein, the term "in combination" refers to the use of more than one prophylactic and/or therapeutic agent simultaneously or sequentially and in a manner such that their respective effects are additive or synergistic.

The term "statistically significant" or "significantly" refers to statistical significance and generally means a difference of two standard deviations (2SD) or more.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein the term "consisting of" refers to compositions, methods, and respective components thereof as described herein, which are exclusive of any element not recited in that description of the embodiment.

BRIEF DESCRIPTION OF THE DRAWINGS

FIG. 1A. The expression pattern of VSMC phenotypic markers in human aortic tissue from control (n=13) and TAA(D) (n=30) donors. Loss of TAGLN (SM22a) transcript were more significant in patients who have experienced dissection (TAA-FC=0.55 vs TAAD-FC=0.12). FIG. 1B. The immunoblotting analysis of SM22a protein in human aortic tissue from control (n=7) and TAA(D) (n=9) donors. FIG. 1C. The anatomical reconstruction of patient images and immunofluorescence staining of contractile proteins of human aortas from control, TAA and TAAD samples (Top row). VVG staining of aortic samples from patients demonstrates elastin fragmentation. Bar=150 µm (Second Row). Immunofluorescence from aortic samples showing SM22a, CNN, DAPI or Vinculin, Smoothelin, and DAPI. Bar=50 urn, inset zoom 3-fold magnification. FIG. 1D. Representative photomicrographs of latex-injected wild-type and Fbnicl°39w+ mice, hearts and ascending aortas. Arrows indicate the ascending portion of the aorta. Aortic elastin fibers were stained with Verhoeff-Van Gieson stain (VVG), and immunofluorescence of DAPI F-actin and Sm22a, Bar=50 um. FIG. 1E. qPCR analysis of Tag/n (Sm22a) transcript in aortic tissue and plasma from wild-type (n=7) and Fbn1C1° 39Gl+(n=7) six-month old mice. FIG. 1F. Correlation of Tagin (Sm22a) tissue expression with aortic dimensions in Fbn1ci°39G/ ±aortas (n=7), (Least squares method used for curve fit). FIG. 1G. Immunofluorescence staining of contractile proteins in aortic VMSC treated with siCtrl or siSM22a. Bar=10 um, zoom 3-fold magnification. FIG. 1H. Immunoblotting analysis of SM22a inhibition and loss of its binding partner Calponin (CNN) in aortic VMSC. Quantitation versus (-actin shown below. FIG. 1I. siSM22a treatment of healthy VSMCs induce MMP activity as assessed by in vitro gelatin zymography. ($*p<0.05$, $**p<0.01$, $'p<0.001$, student's t-test, 2 tailed). FC, fold change; TAA, Thoracic aortic aneurysm; TAAD, Thoracic aortic aneurysm and dissection; Ctrl, control; VVG, Verhoeff-Van Gieson stain; SMTN, smoothelin; CNN, calponin; VCL, vinculin.

FIG. 2A. Echocardiographic aortic root and ascending aortic quantification of wild-type and Fbni$^{cn39G1+}$ mice at four months of age. FIG. 2B. Quantification of aortic dimension of Sm22$^{+1+}$ (n=8), Sm22$^{-/-}$ (n=10), Fbni$^{cl°39G+}$:Sm22$^{+1+}$ (n=10) and Fbn1$^{ci°39G1+}$:Sm22$^{1-}$ (n=5) at four months of age. (1-way Anova, posthoc tukey's test) FIG. 2C. Histologic analysis shows abnormal aortic architecture and increased collagen deposition in four-month old Sm22 deficient mice, H&E Bar=250 pm; Masson's trichrome Bar=250 psn, Zoom 5×; VVG Bar=50 pm. FIG. 2D. Increased MMP activity in four-month old Sm22a-deficient mice. FIG. 2E. Post mortem examination of pregnant mouse shows hemothorax. FIG. 2F. Kaplan-Meier plot of Sm22a survival during pregnancy (Sm22$^{+/+}$ n=10 and Sm22$^{/-}$, n=5, log-rank test) FIG. 2G. Trichrome and VVG staining of aortas from pregnant Sm22$^{+/+}$ and Sm22$^{4-}$ mice, Bar=50 pm, VVG, Verhoeff-Van Gieson stain.

FIG. 3A. ChIP-qPCR assays in human aortic tissue shows increased interaction of EZH2 protein and H3K27me3 modifications in TAA tissue (n=8) when compared to control aortas (n=7) at the TAGLN gene locus. Lower panel shows map of H3K27me3 modifications. ($*p<0.05$, $''p<0.01$, $*p<0.001$, student's t-test versus wild type, 2 tailed) FIG. 3B. Identification of transcription factor binding sides in hypermethylated region within intron 1 using Genomatix. FIG. 3C. VSMCs treated with siSMAD3 demonstrate inhibition of basal and TGF-3 induced SM22a expression. FIG. 3D. SMAD3 ChIP-qPCR assays in VSMCs cultured from TAA (n=8) and treated with TGF-31 (10 ng/mL) demonstrate decreased SMAD3 binding at TAGLN locus when compared to controlled VSMC cultures (n=4), ($p<0.01$, $*p<0.001$, student's t-test versus wild type, 2 tailed). FIG. 3E. qPCR analysis of SM22a transcript in control (n=4) or TAA (n=8) isolated VSMC cultures treated with recombinant TGF-31 (10 ng/mL), ("$p<0.01$, '$p<0.001$, 1-way Anova). FIG. 3F. Immunofluorescent staining of H3K27me3 modifications in human tissue from control and TAA aortas Bar=20 pm. FIG. 3G. Immunoblotting analysis of SM22a in isolated VSMCs from control and TAA VSMC cultures treated with EZH2 inhibitor (GSK343 10 pM) and/or TGF-31 (10 ng/mL). FIG. 3H. Immunofluorescent staining of Ezh2 (yellow) and H3K27me3 (red) in six-month old Fbn1$^{cl°39G1+}$ and wild type mouse aortas, Bar=40 p.m. FIG. 3C. qPCR analysis of Ezh2 and TagIn (Sm22a) transcripts in mouse VSMCs isolated from wild type, Ezh2-, $^{FbniCl039G/+}$ and Fbn 1$^{Cl°39Gt}$: EZh2$^-$ cells. ($p<0.01$, '$p<0.001$, 1-way Anova) FIG. 3J. Immunoblotting analysis of Sm22a in mouse VSMCs isolated from wild type, EzhZ$^A$, Fbni$^{cl°39G/+}$, and Fbni$^{cl°39G/+}$:Ezh2$^{-/-}$ cells treated with or without TGF-31 (10 ng/mL). FIG. 3K. Immunofluorescent staining of Sm22a (magenta) and F-actin (grey) in Fbn1$^{cl°39w+}$ and wild type mouse VSMCs treated with EZH2 inhibitor (GSK343 10 pM) and TGF-31 (10 ng/mL), Bar=10 TAA, Thoracic aortic aneurysm; Ctrl, control; H3K27me3, Histone 3 lysine 27 trimethylation; H3K27ac, Histone 3 acetylated lysine 27.

FIG. 4A. Echocardiographic aortic root and ascending aortic quantification (at six months of age) of mice treated from two months to six months of age. Wild-type (PBS, n=8; Losartan, n=6; GSK343, n=6) and Fbn1C1° 39G/+ (PBS, n=8; Losartan, n=6; GSK343, n=6) mice were treated. (1-way Anova, posthoc tukey's test) FIG. 4B. Expression pattern of VSMC phenotypic markers in aortas from wild type or Fbnicl°39Gi+ mice treated with losartan or GSK343 from two to six months of age (PBS, n=8; Losartan, n=6; GSK343, n=6) and Fbn1C1039G/+ (PBS, n=8; Losartan, n=6; GSK343, n=6). RNA levels were normalized to wild-type mice treated with PBS. FIG. 4C. Top: CT scan and histologic analysis of wild type or Fbnil$^{clo}$39G/+ mouse aortas treated with either, PBS, losartan or GSK343. Low magnification aorta VVG Bar=250 =m, high magnification VVG, H&E, Masson's Trichrome, and immunofluorescence Bar=50 um. Bottom: Quantification of histologic parameters. (1-way Anova, posthoc tukey's test), FC, fold change; VVG, Verhoeff-Van Gieson stain.

FIG. 5A. Aortic measurements and FIG. 5B. representative echocardiographic images of murine aortas before and after treated shows regression of aortic dimension in Fbni$^{ci°39G/+}$ mice treated with a combination of Losartan/ GSK343 (n=5) from four to six months of age, when compared to untreated (n=8), losartan (n=6), and GSK343 treated (n=5) mice. (1-way Anova, posthoc tukey's test) FIG. 5C. Immunohistochemical and immunofluorescent staining of Sm22a, Myh11, and Cnn in FbnI$^{ci°39G/+}$ aortic tissue. Bar=50 Rm. (1-way Anova, posthoc tukey's test), VVG, Verhoeff-Van Gieson stain.

FIG. 6A. Contractile genes (eg. TAGLN, MYH11, SMTN) responsible for aortic homeostasis are actively transcribed in VSMCs through the action of transcription factors such as SMAD3, amongst others.

FIG. 6B. In thoracic aortic aneurysm the EZH2-containing polycomb repressive complex 2 (PRC2) mediates addition of histone 3 lysine 27 trimethylation marks to the promoter and gene body of aortic genes, preventing transcription factor access to chromatin. FIG. 6C. Treatment with the EZH2 inhibitor GSK343 derepresses contractile protein expression by allowing transcription factors (such as SMAD3) access to chromatin.

FIG. 7A. Lateral view of left-sided intracranial arterial system in patient with ACTA2$^{R179H}$ (Ao_562) mutation. Cavernous internal carotid dilatation (white arrows) with abrupt tapering and obstructive lesion at terminus (red arrows). FIG. 7B. Venn diagram describing ChIP-Seq experiment in human VSMCs under conditions of with ACTA2R179H expression shows overlapping enrichment of HDAC9, BRGI and H3K27me3 modification at 1141 gene loci versus wild-type cells. Pathway analysis demonstrates multiple cellular functions involving contraction. FIG. 7C. Box plots show fold change enrichment of HDAC9, BRGI and H3K27me3 at locus of SMCs contractile elements in ACTA2$^{R179H}$ mutant versus wild-type cells. Color coded nominal P-values of individual genomic sites within loci are demonstrated. P value annotation of the peaks from macs2 was performed using the ChipSeeker package in R. FIG. 7D depicts inhibition of MALAT1 in ACTA2$^{R179"}$ mutant cells decreased levels of the repression mark H3K27me3 at the ACTA2 promoter. Statistical significance was determined by 1-way ANOVA with a Tukey's post hoc test (vs. wild type cells). (P<0.001, *P<0.0001).

FIG. 8A. Histological and immunofluorescence analysis of ligated and unligated carotids demonstrates neointimal formation and lumen obstruction (Male, n=2 and female, n=2). Ligated carotids show significant reduction in Acta2 (a-Sma), Sm22a and increased expression of Mmp9. Significance was calculated using an unpaired t-test (two tailed, vs unligated carotid). The red asterisk indicates the most downregulated gene in ligated carotid samples when compared with the contralateral unligated carotid. FIG. 8B. Heat map of contractile and synthetic SMC markers from ligated carotids (Male, n=3 and female, n=3) versus unligated carotids (Male, n=3 and female, n=3) of wild-type mice. FIG. 8C. RT-QPCR analysis demonstrates up regulation of Hdac9 and Malatl mRNAs in ligated carotids of wild-type mice. Significance was calculated using an unpaired t-test (two tailed, vs unligated carotid). FIG. 8D. Imnnunofluorescence (Hdac9 and Brgl) and in situ hybridization (Malatl) staining of ligated carotid localizes robust expression to the newly formed neointima. FIG. 8E. 3D sequential immunofluorescence and in situ hybridization microscopy of ligated carotids show colocalization of Hdac9, Brgl and Malatl in neointimal cells. Global Pearson's colocalization (GPC) of spatial overlap between Malatl-Hdac9 and Malatl-Brgl is shown. Scale bar: 50 pm.

FIG. 9A. Histological quantification of neointimal hyperplasia in ligated carotid from wild type (Male, n=6 and Female, n=6), Malatfl− (Male, n=6 and Female, n=6) and Hdac9fin:TagIn-cre (Male, n=6 and Female, n=6) mice. Fifteen horizontal cross-section slides (10 pm) per carotid were analyzed. FIG. 9B. Histological and immunofluorescence analysis of ligated carotids shows strong inhibition of neointimal hyperplasia is observed in horizontal and vertical cross-sections of Malatfl- and Hdac9flni:TagIn-cre mice. Genetic ablation of Hdac9 or Malatl restored protein levels of Acta2, Cnn1 and Sm22a in carotid artery media. FIG. 9C. Immunofluorescence analysis of ligated carotids shows preservation of the endothelial layer in ligated carotid of Ma'atoll- and Hdac9fl111:TagIn-cre mice mice. Endothelial layer is indicated by CD31 staining, artery media is indicated by Acta2 staining and Mmp9. Significance was calculated using 1-way ANOVA with a Tukey's test. FIG. 9D. Heat map of contractile and synthetic SMC markers from ligated carotid of Malat14− (n=7) and Hdac9finl:Tagin-cre (n=7) mice vs ligated carotid (n=7) of wild type mice. Significance was calculated using an unpaired t-test (two tailed, vs wild type-ligated carotid). Scale bar: 50 pm.

FIG. 10A. Immunofluorescence analysis of p-PDGFRp), F-actin and nucleus in ligated carotid of wild type (n=4), Malatf$^{−}$ (n=4), and Hdac9$^{fini}$:TagIn-cre mice (n=4). FIG. 10B. Immunofluorescence analysis of p-FAK, F-actin and nucleus in ligated carotid of wild type (n=4), Malat$^{4−}$ (n=4) and Hdac9$^{fini}$:TagIn-cre mice (n=4). Significance was calculated using 1-way ANOVA with a Tukey's test. Dashed lines indicated arterial media, M=media, L=Lumen. Scale bar: 50 pm.

FIG. 11A. Upper panel, treatment strategy of experimental carotid artery stenosis with GapmeR-Malatl or GSK343. Lower panel, qPCR analysis demonstrates Malatl mRNA levels in aortic and liver tissues from vehicle (n=5) and GapmeR-Malatl (n=4) treated mice. FIG. 11B. Histological and immunofluorescence analysis of ligated carotids of vehicle, GapmeR-Malatl and GSK343 treated mice. FIG. 11C. Quantification plot of vehicle (Male, n=6 and Female, n=6), GapmeR-Malatl (Male, n=3 and Female, n=3) and GSK343 (Male, n=6 and Female, n=6) treatment groups show significant inhibition of neointimal formation FIG. 11D. Detection of GapmeR-Malatl molecule conjugated with 3'-FAM-Fluorphore in ligated carotid of GapmeR-Malatl treated mice but not in vehicle and GSK343 treated mice. FIG. 11E. Inhibition of Mmp activity in ligated aortas of GapmeR-Malatl and GSK343 treated mice. Mice were tail vein injected with MMPSense 750 FAST, a near-infrared fluorescence sensor for MMP2 and MMP9 activity twenty fours hours to sacrifice, dissection, and imaging. Significance was calculated using 1-way ANOVA with a Tukey's multi comparisons test.

FIG. 12A. Immunofluorescence analysis of p-PDGFRI3, F-actin and nucleus in ligated carotid of vehicle (n=4), GapmeR-Malatl (n=4), or GSK343 (n=4). FIG. 12B. Immunofluorescence analysis of p-FAK F-actin and nucleus in ligated carotid of vehicle (n=4), GapmeR-Malatl (n=4) or GSK343 (n=4). FIG. 12C.) Immunofluorescence analysis of CD31, Hdac9 and Mmp9 in ligated carotid of ligated carotid of vehicle (n=4), GapmeR-Malatl (n=4), or GSK343 (n=4). Significance was calculated using 1-way ANOVA with a Tukey's multi comparisons test. Dashed lines indicated arterial media, M=media, L=Lumen. Scale bar: 50 pm.

FIG. 13A. Venn diagram describing ChIP-Seq experiment in human VSMCs under conditions of with TGFR2$^{G357w}$ expression shows overlapping enrichment of HDAC9, BRGI and H3K27me3 modification at 663 gene loci versus wild-type cells. Pathway analysis demonstrates multiple cellular functions involving smooth muscle cell contraction. FIG. 13B. Box plots show fold change enrichment of HDAC9, BRGI and H3K27me3 at locus of SMCs contractile elements in TGFR2$^{G357w}$ mutant versus wild-type cells. Color coded nominal p-values of individual genomic site within locus. P value annotation of the peaks from macs2 was performed using the ChipSeeker™ package in R. FIG. 13C. p-values of selected genomic sites in the promoters of listed genes after Benjamini-Hochberg correction for multiple testing of with ACTA2$^{R179n}$ expressing cells.

FIGS. 14A-14E demonstrate that deletion of Ezh2 in vascular smooth muscle compartment in carotid ligation. FIG. 14A. Detection of Myh11-cre-GFP positive in lung and aorta tissues. FIG. 14B. Gel image of PCR genotyping. FIG. 14C. Immunoblot assays shows protein levels of Ezh2 in male and female Myh11-cre mice compared with not cre mouse. FIG. 14D. Histological and immunofluorescence analysis of ligated carotids of GapmeR-Malat1-3'FAM (n=3) and Ezh2fl/fl:Myh11-cre-GFP (n=6). Acta2, Mmp9, Sm22a and nucleus. FIG. 14E. Ratio of neointima vs media of ligated carotids of wild type (n=6) and Ezh2fl/fl/Myh11-cre-GFP (n=6) mice. Significance was calculated using 1-way ANOVA with a Tukey's multi comparisons test.

DETAILED DESCRIPTION

Figure 1A:
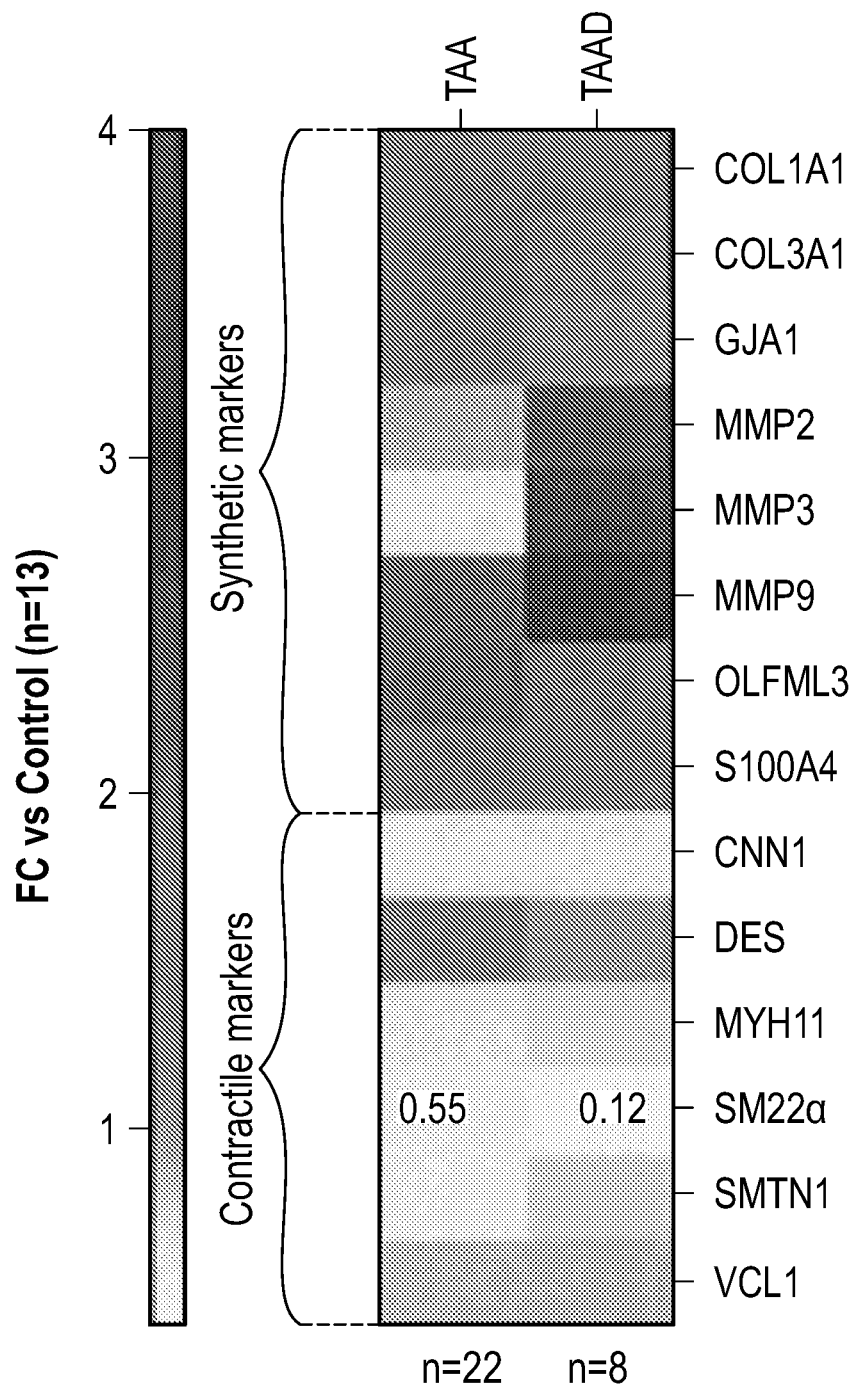
FIGS. 1A-1I demonstrate the decrement of members of the VSMC contractile apparatus in patients with TAA.

Methods and compositions for the diagnosis and treatment of cardiovascular disease, including but not limited to atherosclerosis, ischemia/reperfusion, hypertension, restenosis, and arterial inflammation, are described herein. The compositions and methods described herein are based, in part, on the surprising discovery that a vascular disease can be prevented and/or treated by inhibiting the HDCA9 and/or PRC2 complexes.

Vascular disease is a class of diseases of the blood vessels, the arteries and veins of the circulatory system of the body. It is a subgroup of cardiovascular disease. Disorders in this vast network of blood vessels can cause a range of health problems which can be severe or prove fatal.

Vascular disease is a pathological state of large and medium muscular arteries and is triggered by endothelial cell dysfunction. Under physiological conditions, the arterial endothelium exerts a powerful protective influence to maintain vascular homeostasis. However, during the development of vascular disease, these protective activities are lost and dysfunctional endothelial cells actually promote disease pathogenesis. Normal endothelial function is crucial for maintaining vascular and organismal health. Endothelial cells are key regulators of blood vessel constriction, thrombogenicity, inflammation, permeability, and vascular remodeling. Under normal conditions, the endothelium exerts a protective influence to inhibit these processes and maintain vascular stability and homeostasis. However, during the development of vascular disease, endothelial cells with an altered phenotype, namely 'dysfunctional' endothelium, promote these same processes and contribute to pathological changes in vascular structure and reactivity.

Because of factors like pathogens, oxidized LDL particles and other inflammatory stimuli endothelial cells become active. The process causes thickening of the vessel wall, forming a plaque that consists of proliferating smooth muscle cells, macrophages and lymphocytes. The plaque results in a restricted blood flow which will decrease the amount of oxygen and nutrients that reach certain organs, the plaque might rupture causing the formation of clots.

There are several types of vascular disease, the signs and symptoms depend on which type, among them are: Erythromelalgia is a rare peripheral vascular disease where syndromes include burning pain, increased temperature, erythema and swelling, of mainly the hands and feet are affected. Peripheral artery disease is the narrowing of renal arteries that carry blood to the kidneys from the aorta. Buerger's disease is due to small blood vessels that inflame and swell, vessels then narrow or are blocked by blood clots. Raynaud's disease is a rare peripheral vascular disorder of constriction of the peripheral blood vessels, in the fingers and toes when the person is cold. Disseminated intravascular coagulation is a widespread activation of clotting in the smaller blood vessels. Cerebrovascular disease is a group of vascular diseases that affect brain function.

Animal-based model systems of cardiovascular disease may include, but are not limited to, non-recombinant and engineered transgenic animals. Non-recombinant animal models for cardiovascular disease may include, for example, genetic models. Such genetic cardiovascular disease models may include, for example, apoB or apoR deficient pigs (Rapacz, et al., 1986, Science 234:1573-1577) and Watanabe heritable hyperlipidemic (WHHL) rabbits (Kita et al., 1987, Proc. Natl. Acad. Sci U.S.A. 84: 5928-5931).

Smooth muscle is an involuntary non-striated muscle. It is divided into two subgroups; the single-unit (unitary) and multiunit smooth muscle. Within single-unit cells, the whole bundle or sheet contracts as a syncytium. Smooth muscle cells are found in the walls of hollow organs, including the stomach, intestines, urinary bladder and uterus, and in the walls of passageways, such as the arteries and veins of the circulatory system, and the tracts of the respiratory, urinary, and reproductive systems. These cells are also present in the eyes and are able to change the size of the iris and alter the shape of the lens. In the skin, smooth muscle cells cause hair to stand erect in response to cold temperature or fear.

Most smooth muscle is of the single-unit variety, that is, either the whole muscle contracts or the whole muscle relaxes, but there is multiunit smooth muscle in the trachea, the large elastic arteries, and the iris of the eye. Single unit smooth muscle, however, is most common and lines blood vessels (except large elastic arteries), the urinary tract, and the digestive tract.

Smooth muscle is fundamentally different from skeletal muscle and cardiac muscle in terms of structure, function, regulation of contraction, and excitation-contraction coupling. Smooth muscle cells known as myocytes, have a fusiform shape and, like striated muscle, can tense and relax. However, smooth muscle tissue tends to demonstrate greater elasticity and function within a larger length-tension curve than striated muscle. This ability to stretch and still maintain contractility is important in organs like the intestines and urinary bladder. In the relaxed state, each cell is spindle-shaped, 20-500 micrometers in length.

In VD or CVD, the phenotype of SMC can be modulated. These modulated phenotypes are characterized by down regulation of SMC-restricted contractile genes, and up regulation of groups of genes involved in secretion of extracellular matrix, proliferation, and migration. Such down regulation of SMC-restricted contractile genes, and up regulation of groups of genes involved in secretion of extracellular matrix, proliferation, and migration is important in vascular diseases such as atherosclerosis, pulmonary hypertension, aortic and peripheral aneurysms, and restenosis after percutaneous arterial intervention.

In some embodiments of any of the aspects, described herein are human mutations in genes encoding these same SMC-restricted contractile genes. For instance, mutations in ACTA2, the gene encoding alpha-smooth muscle actin (a-SMA) are a major cause of nonsyndromic thoracic aortic aneurysm. Similarly, mutations in the gene MYH/1, encoding smooth muscle myosin heavy chain (smMHC), the binding partner of this actin isoform, causes a combined presentation of Thoracic Aortic Aneurysm (TAA) and patent ductus arteriosis. Disruption of SMC contraction can be an underlying mechanism of TAA pathogenesis.

Arterial stenosis is a common human condition and the health impact is staggering. While the majority of arterial stenosis is associated with atherosclerosis, stenosis can also occur in the context of restenosis after percutaneous intervention, or congenital stenoses such aortic or pulmonary obstruction.

Pulmonary obstruction is thought to be caused by excessive medial or intimal expansion of SMCs. Arterial SMCs undergo profound phenotypic changes during these disease processes, having the ability to acquire characteristics of chondrocytes, osteocytes, and macrophages. However, one of the most common forms is a less differentiated cellular form known as the proliferative phenotype. This phenotype is characterized by cellular proliferation, loss of definitive markers of the smooth muscle cell phenotype (such as cc-SMA), and increased activation of matrix degrading enzymes.

While most arterial stenosis occurs in the context of atherosclerosis, some rare forms of Mendelian vascular smooth muscle dysfunction also encompass arterial stenosis as a phenotype. One such condition is the vascular disease caused by mutations in ACTA2. Patients with particular missense mutations in ACTA2 (and to a lesser extent in MYHI I) show intracranial and coronary arterial stenosis thought to be caused by excessive medial hyperplasia.

In some embodiments of any of the aspects, described herein is a method to prevent or treat a thoracic aortic aneurysm in a patient comprised of administering to said patient a therapeutically effective dose of a compound or drug (or combination of said compounds or drugs) which targets the epigenetic regulation of gene expression of vascular smooth muscle cell cytoskeletal proteins.

In some embodiments of any of the aspects, targeting the epigenetic regulation of gene expression of vascular smooth muscle cell cytoskeletal proteins can comprise inhibiting the PRC2 complex and/or the HDAC9 complex.

In some embodiments of any of the aspects, the epigenetic regulatory target is a multiprotein complex (PRC2, Polycomb repressive complex 2) responsible for gene silencing through its catalytic activity or hypermethylation of chromatin at vascular smooth muscle gene loci.

The polycombine repressive complex (PRC2) is a key epigenetic regulator of the SMC cytoskeletal genes described herein. Accordingly, in some embodiments of any of the aspects, the method and compostions described herein can modulate one or more components of the polycomb repressive complex (PRC2), for example, Enhancer of zeste homolog 2 (EZH2).

PRC2 (polycomb repressive complex 2) is one of the two classes of polycomb-group proteins or (PcG). The PRC2 is evolutionarily conserved, and has been found in mammals, insects, and plants. The other component of this group of proteins is PRC1 (Polycomb Repressive Complex 1). This complex has histone methyltransferase activity and primarily trimethylates histone H3 on lysine 27 (i.e. H3K27me3), a mark of transcriptionally silent chromatin. PRC2 is required for initial targeting of genomic region (PRC Response Elements or PRE) to be silenced, while PRC1 is required for stabilizing this silencing and underlies cellular memory of silenced region after cellular differentiation. PRC2 is present in all multicellular organisms.

PRC2 is a multiprotein enzyme complex which comprises at least four components, EZH2, Suz12, Eeed and RbAp46/48. Enhancer of zeste homolog 2 (EZH2) is responsible for the methylation activity of PRC2. In some embodiments of any of the aspects, the inhibitor of the PRC2 complex is an inhibitor of Ezh1/2, Suz12, Eeed and RbAp46/48.

In some embodiments of any of the aspects, the inhibitor of the PRC2 complex is an inhibitor of SUZ12. As used herein, "SUZ12" or "SUZ12 polycomb repressive complex 2 subunit" is a protein that has been identified at the breakpoints of a recurrent chromosomal translocation and is encoded by the SUZ12 gene. The protein encoded by this gene contains a zinc finger domain in the C terminus of the coding region.

Sequences for SUZ12 are known for a number of species, e.g., human SUZ12 (the SUZ12 NCBI Gene ID is 23512) mRNA sequences (e.g., NM_001321207.1 and polypeptide sequences (e.g., NP_001308136.1).

These, together with any naturally occurring allelic, splice variants, and processed forms thereof that catalyze the same reaction are contemplated for use in the methods and compositions described herein.

In some embodiments of any of the aspects, the SUZ12 nucleic acid includes or is derived from human SUZ12 having the following nucleic acid sequence CCDS82101.1 (SEQ ID NO: 3):

ATGGCGCCTCAGAAGCACGGCGGTGGGGGAGGGGGCGGCTCGGGGCCCAGC

GCGGGGTCCGGGGGAGGCG

GCTTCGGGGGTTCGGCGGCGGTGGCGGCGGCGACGGCTTCGGGCGGCAAAT

CCGGCGGCGGGAGCTGTGG

AGGGGGTGGCAGTTACTCGGCCTCCTCCTCCTCCTCCGCGGCGGCAGCGGC

GGGGGCTGCGGTGTTACCG

GTGAAGAAGCCGAAAATGGAGCACGTCCAGGCTGACCACGAGCTTTTCCTC

CAGGCCTTTGAGAAGCCAA

CACAGATCTATAGATTTCTTCGAACTCGGAATCTCATAGCACCAATATTTT

TGCACAGAACTCTTACTTA

CATGTCTCATCGAAACTCCAGAACAAACATCAAAAGCTTGTCAGCTCATTT

GCAGCTTACGTTTACTGGT

TTCTTCCACAAAAATGATAAGCCATCACCAAACTCAGAAAATGAACAAAAT

TCTGTTACCCTGGAAGTCC

TGCTTGTGAAAGTTTGCCACAAAAAAAGAAAGGATGTAAGTTGTCCAATAA

GGCAAGTTCCCACAGGTAA

AAAGCAGGTGCCTTTGAATCCTGACCTCAATCAAACAAAACCCGGAAATTT

CCCGTCCCTTGCAGTTTCC

AGTAATGAATTTGAACCTAGTAACAGCCATATGGTGAAGTCTTACTCGTTG

CTATTTAGAGTGACTCGTC

-continued

```
CAGGAAGAAGAGAGTTTAATGGAATGATTAATGGAGAAACCAATGAAAATA

TTGATGTCAATGAAGAGCT

TCCAGCCAGAAGAAAACGAAATCGTGAGGATGGGGAAAAGACATTTGTTGC

ACAAATGACAGTATTTGAT

AAAAACAGGCGCTTACAGCTTTTAGATGGGGAATATGAAGTAGCCATGCAG

GAAATGGAAGAATGTCCAA

TAAGCAAGAAAAGAGCAACATGGGAGACTATTCTTGATGGGAAGAGGCTGC

CTCCATTCGAAACATTTTC

TCAGGGACCTACGTTGCAGTTCACTCTTCGTTGGACAGGAGAGACCAATGA

TAAATCTACGGCTCCTATT

GCCAAACCTCTTGCCACTAGAAATTCAGAGAGTCTCCATCAGGAAAACAAG

CCTGGTTCAGTTAAACCTA

CTCAAACTATTGCTGTTAAAGAATCATTGACTACAGATCTACAAACAAGAA

AAGAAAAGGATACTCCAAA

TGAAAACCGACAAAAATTAAGAATATTTTATCAGTTTCTCTATAACAACAA

TACAAGGCAACAAACTGAA

GCAAGAGATGACCTGCATTGCCCTTGGTGTACTCTGAACTGCCGCAAACTT

TATAGTTTACTCAAGCATC

TTAAACTCTGCCATAGCAGATTTATCTTCAACTATGTTTATCATCCAAAAG

GTGCTAGGATAGATGTTTC
```

```
TATCAATGAGTGTTATGATGGCTCCTATGCAGGAAATCCTCAGGATATTCA

TCGCCAACCTGGATTTGCT

TTTAGTCGCAACGGACCAGTTAAGAGAACACCTATCACACATATTCTTGTG

TGCAGGCCAAAACGAACAA

AAGCAAGCATGTCTGAATTTCTTGAATCTGAAGATGGGGAAGTAGAACAGC

AAAGAACATATAGTAGTGG

CCACAATCGTCTGTATTTCCATAGTGATACCTGCTTACCTCTCCGTCCACA

AGAAATGGAAGTAGATAGT

GAAGATGAAAGGATCCTGAATGGCTAAGAGAAAAAACCATTACACAAATT

GAAGAGTTTTCTGATGTTA

ATGAAGGAGAGAAAGAAGTGATGAAACTCTGGAATCTCCATGTCATGAAGC

ATGGGTTTATTGCTGACAA

TCAAATGAATCATGCCTGTATGCTGTTTGTAGAAAATTATGGACAGAAAAT

AATTAAGAAGAATTTATGT

CGAAACTTCATGCTTCATCTAGTCAGCATGCATGACTTTAATCTTATTAGC

ATAATGTCAATAGATAAAG

CTGTTACCAAGCTCCGTGAAATGCAGCAAAAATTAGAAAAGGGGGAATCTG

CTTCCCCTGCAAACGAAGA

AATAACTGAAGAACAAAATGGGACAGCAAATGGATTTAGTGAAATTAACTC

AAAAGAGAAAGCTTTGGAA

ACAGATAGTGTCTCAGGGGTTTCAAAACAGAGCAAAAAACAAAAACTCTGA
```

In some embodiments of any of the aspects, the SUZ12 polypeptide includes or is derived from human SUZ12 having the following amino acid sequence NP_001308136.1 (SEQ ID NO: 4):

```
  1 mapqkhgggg gggsgpsags ggggfggsaa vaaatasggk sgggscgggg sysasssssa 61 aaaagaavlp vkkpkmehvq adhelflqaf ekptqiyrfl rtrnliapif lhrtltymsh 121 rnsrtniksl sahlqltftg ffhkndkpsp nseneqnsvt levllvkvch kkrkdvscpi 181 rqvptgkkqv plnpdlnqtk pgnfpslavs snefepsnsh mvksysllfr vtrpgrrefn 241 gmingetnen idvneelpar rkrnredgek tfvaqmtvfd knrrlqlldg eyevamqeme 301 ecpiskkrat wetildgkrl ppfetfsqgp tlqftlrwtg etndkstapi akplatrnse 361 slhqenkpgs vkptqtiavk eslttdlqtr kekdtpnenr qklrifyqfl ynnntrqqte 421 arddlhcpwc tlncrklysl lkhlklchsr fifnyvyhpk garidvsine cydgsyagnp 481 qdihrqpgfa fsrngpvkrt pithilvcrp krtkasmsef lesedgeveq qrtyssghnr 541 lyfhsdtclp lrpqemevds edekdpewlr ektitqieef sdvnegekev mklwnlhvmk 601 hgfiadnqmn hacmlfveny gqkiikknlc rnfmlhlvsm hdfnlisims idkavtklre 661 mqqklekges aspaneeite eqngtangfs einskekale tdsvsgvskq skkqkl
```

In some embodiments of any of the aspects, the inhibitor of the PRC2 complex is an inhibitor of EED.

As used herein, "EED" or "Embryonic ectoderm development" is a Polycomb protein and a member of the Polycomb-group (PcG) family is encoded by the EED gene.

Sequences for EED are known for a number of species, e.g., human EED (the EED NCBI Gene ID is 8726) mRNA sequences (e.g., NM_001308007.1 and polypeptide sequences (e.g., NP_001294936.1).

These, together with any naturally occurring allelic, splice variants, and processed forms thereof that catalyze the same reaction are contemplated for use in the methods and compositions described herein.

In some embodiments of any of the aspects, the EED nucleic acid includes or is derived from human EED having the following nucleic acid sequence CCDS76463.1 (SEQ ID NO: 5):

```
ATGTCCGAGAGGGAAGTGTCGACTGCGCCGGCGGGAACAGACATGCCTGC

GGCCAAGAAGCAGAAGCTGA

GCAGTGACGAGAACAGCAATCCAGACCTCTCTGGAGACGAGAATGATGAC

GCTGTCAGTATAGAAAGTGG

TACAAACACTGAACGCCCTGATACACCTACAAACACGCCAAATGCACCTG

GAAGGAAAAGTTGGGGAAAG

GGAAAATGGAAGTCAAAGAAATGCAAATATTCTTTCAAATGTGTAAATAG

TCTCAAGGAAGATCATAACC

AACCATTGTTTGGAGTTCAGTTTAACTGGCACAGTAAAGAAGGAGATCCA

TTAGTGTTTGCAACTGTAGG

AAGCAACAGAGTTACCTTGTATGAATGTCATTCACAAGGAGAAATCCGGT

TGTTGCAATCTTACGTGGAT

GCTGATGCTGATGAAAACTTTTACACTTGTGCATGGACCTATGATAGCAA

TACGAGCCATCCTCTGCTGG
```

```
CTGTAGCTGGATCTAGAGGCATAATTAGGATAATAAATCCTATAACAATG

CAGTGTATAAAGCACTATGT

TGGCCATGGAAATGCTATCAATGAGCTGAAATTCCATCCAAGAGATCCAA

ATCTTCTCCTGTCAGTAAGT

AAAGATCATGCTTTACGATTATGGAATATCCAGACGGACACTCTGGTGGC

AATATTTGGAGGCGTAGAAG

GGCACAGAGATGAAGTTCTAAGTGCTGATTATGATCTTTTGGGTGAAAAA

ATAATGTCCTGTGGTATGGA

TCATTCTCTTAAACTTTGGAGGATCAATTCAAAGAGAATGATGAATGCAA

TTAAGGAATCTTATGATTAT

AATCCAAATAAAACTAACAGGCCATTTATTTCTCAGAAAATCCATTTTCC

TGATTTTTCTACCAGAGACA

TACATAGGAATTATGTTGATTGTGTGCGATGGTTAGGCGATTTGATACTT

TCTAAGAGTGGCCGTGCCAT

TTTACATTCCCACCAGCAATGTATGAGAGATCCAGTGTCTCCGAATCTTC

GCCAGCATTTGTCTTGTGAA

AATGCCATTGTGTGCTGGAAACCTGGCAAGATGGAAGATGATATAGATAA

AATTAAACCCAGTGAATCTA

ATGTGACTATTCTTGGGCGATTTGATTACAGCCAGTGTGACATTTGGTAC

ATGAGGTTTTCTATGGATTT

CTGGCAAAAGATGCTTGCATTGGGCAATCAAGTTGGCAAACTTTATGTTT

GGGATTTAGAAGTAGAAGAT

CCTCATAAAGCCAAATGTACAACACTGACTCATCATAAATGTGGTGCTGC

TATTCGACAAACCAGTTTTA

GCAGGGATAGCAGCATTCTTATAGCTGTTTGTGATGATGCCAGTATTTGG

CGCTGGGATCGACTTCGATAA
```

In some embodiments of any of the aspects, the EED polypeptide includes or is derived from human EED having the following amino acid sequence NP_001294936.1 (SEQ ID NO: 6):

```
  1  mserevstap agtdmpaakk qklssdensn pdlsgdendd avsiesgtnt erpdtptntp 61  napgrkswgk gkwkskkcky sfkcvnslke dhnqplfgvq fnwhskegdp lvfatvgsnr 121  ytlyechsqg eirllqsyvd adadenfytc awtydsntsh pllavagsrg iiriinpitm 181  qcikhyvghg nainelkfhp rdpnlllsvs kdhalrlwni qtdtlvaifg gveghrdevl 241  sadydllgek imscgmdhsl klwrinskrm mnaikesydy npnktnrpfi sqkihfpdfs 301  trdihrnyvd cyrwlgdlil sksgrailhs hqqcmrdpvs pnlrqhlsce naivcwkpgk 361  meddidkikp sesnvtilgr fdysqcdiwy mrfsmdfwqk mlalgnqvgk lyvwdleved 421  phkakcttlt hhkcgaairq tsfsrdssil iavcddasiw rwdrlr
```

In some embodiments of any of the aspects, the inhibitor of the PRC2 complex is an inhibitor of RbAp46/48.

As used herein, "RbAp46/48" or "Histone-binding protein RBBP4" is a Histone-binding protein encoded by the RbAp46/48 gene.

Sequences for RbAp46/48 are known for a number of species, e.g., human RbAp46/48 (the RbAp46/48 NCBI Gene ID is 5928) and polypeptide sequences (e.g., NP_001128727.1).

RbAp46/48 is assigned Enzyme Comission (E.C.) 2.1.1.43. An enzyme of this EC number would be anticipated to perform similarily in methods and compositions as described herein.

These, together with any naturally occurring allelic, splice variants, and processed forms thereof that catalyze the same reaction are contemplated for use in the methods and compositions described herein.

In some embodiments of any of the aspects, the RbAp46/48 nucleic acid includes or is derived from human RbAp46/48 having the following nucleic acid sequence CCDS44105.1 (SEQ ID NO: 7):

ATGGCCGACAAGGAAGCCTTCGACGACGCAGTGGAAGAACGAGTGATCAAC

GAGGAATACAAAATATGGA

AAAAGAACACCCCTTTTCTTTATGATTTGGTGATGACCCATGCTCTGGAGT

GGCCCAGCCTAACTGCCCA

GTGGCTTCCAGATGTAACCAGACCAGAAGGGAAAGATTTCAGCATTCATCG

ACTTGTCCTGGGGACACAC

ACATCGGATGAACAAAACCATCTTGTTATAGCCAGTGTGCAGCTCCCTAAT

GATGATGCTCAGTTTGATG

CGTCACACTACGACAGTGAGAAAGGAGAATTTGGAGGTTTTGGTTCAGTTA

GTGGAAAAATTGAAATAGA

AATCAAGATCAACCATGAAGGAGAAGTAAACAGGGCCCGTTATATGCCCCA

GAACCCTTGTATCATCGCA

ACAAAGACTCCTTCCAGTGATGTTCTTGTTTTTGACTATACAAAACATCCT

TCTAAACCAGATCCTTCTG

GAGAGTGCAACCCAGACTTGCGTCTCCGTGGACATCAGAAGGAAGGCTATG

GGCTTTCTTGGAACCCAAA

TCTCAGTGGGCACTTACTTAGTGCTTCAGATGACCATACCATCTGCCTGTG

GGACATCAGTGCCGTTCCA

AAGGAGGGAAAAGTGGTAGATGCGAAGACCATCTTTACAGGGCATACGGCA

GTAGTAGAAGATGTTTCCT

GGCATCTACTCCATGAGTCTCTGTTTGGGTCAGTTGCTGATGATCAGAAAC

TTATGATTTGGGATACTCG

TTCAAACAATACTTCCAAACCAAGCCACTCAGTTGATGCTCACACTGCTGA

AGTGAACTGCCTTTCTTTC

AATCCTTATAGTGAGTTCATTCTTGCCACAGGATCAGCTGACAAGACTGTT

GCCTTGTGGGATCTGAGAA

ATCTGAAACTTAAGTTGCATTCCTTTGAGTCACATAAGGATGAAATATTCC

AGGTTCAGTGGTCACCTCA

CAATGAGACTATTTTAGCTTCCAGTGGTACTGATCGCAGACTGAATGTCTG

GGATTTAAGTAAAATTGGA

GAGGAACAATCCCCAGAAGATGCAGAAGACGGGCCACCAGAGTTGTTGTTT

ATTCATGGTGGTCATACTG

CCAAGATATCTGATTTCTCCTGGAATCCCAATGAACCTTGGGTGATTTGTT

CTGTATCAGAAGACAATAT

CATGCAAGTGTGGCAAATGGCAGAGAACATTTATAATGATGAAGACCCTGA

AGGAAGCGTGGATCCAGAA

GGACAAGGGTCCTAG

In some embodiments of any of the aspects, the RbAp46/48 polypeptide includes or is derived from human RbAp46/48 having the following amino acid sequence NP_001128727.1 (SEQ ID NO: 8):

```
  1 madkeafdda veervineey kiwkkntpfl ydlvmthale wpsltaqwlp dvtrpegkdf 61 sihrlvlgth tsdeqnhlvi asvqlpndda qfdashydse kgefggfgsv sgkieieiki 121 nhegevnrar ympqnpciia tktpssdvlv fdytkhpskp dpsgecnpdl rlrghqkegy 181 glswnpnlsg hllsasddht iclwdisavp kegkvvdakt iftghtavve dvswhllhes 241 lfgsvaddqk lmiwdtrsnn tskpshsvda htaevnclsf npysefilat gsadktvalw 301 dlrnlklklh sfeshkdeif qvqwsphnet ilassgtdrr lnvwdlskig eeqspedaed 361 gppellfihg ghtakisdfs wnpnepwvic svsednimqv wqmaeniynd edpegsvdpe 421 gqgs
```

In some embodiments of any of the aspects, PRC2 can be inhibited by inhibition of EZH2, which is the catalytic subunit of PRC2. As used herein, "EZH2" or "Enhancer of zeste homolog 2" refers to an enzyme of the histone-lysine N-methyltransferase enzyme encoded by the EZH2 gene. EZH2 catalyzes the addition of methyl groups to histone H3 at lysine 27 by using the cofactor S-adenosyl-L-methionine. Methylation activity of EZH2 facilitates heterochromatin formation thereby silencing gene function.

EZH2 inhibition allows for more efficient expression of contractile protein expression including but not limited to SM22a, a-SMA, smMHC. The increased expression of such contractile proteins can result in the prevention and/or treatment of vascular diseases including but not limited to aortic aneurysm treat aortic aneurysm.

EZH2 is assigned Enzyme Comission (E.C.) 2.1.1.43. An enzyme of this EC number would be anticipated to perform similarly in methods and compositions as described herein.

Sequences for EZH2 are known for a number of species, e.g., human EZH2 (the EZH2 NCBI Gene ID is 2146) mRNA sequences (e.g., NM_001203247.1) and polypeptide sequences (e.g., NP_001190176.1).

These, together with any naturally occurring allelic, splice variants, and processed forms thereof that catalyze the same reaction are contemplated for use in the methods and compositions described herein.

In some embodiments of any of the aspects, the EZH2 nucleic acid includes or is derived from human EZH2 having the following nucleic acid sequence CCDS56516.1 (SEQ ID NO: 9):

ATGGGCCAGACTGGGAAGAAATCTGAGAAGGGACCAGTTTGTTGGCGGAA

GCGTGTAAAATCAGAGTACA

TGCGACTGAGACAGCTCAAGAGGTTCAGACGAGCTGATGAAGTAAAGAGT

ATGTTTAGTTCCAATCGTCA

GAAAATTTTGGAAAGAACGGAAATCTTAAACCAAGAATGGAAACAGCGAA

GGATACAGCCTGTGCACATC

CTGACTTCTGTGAGCTCATTGCGCGGGACTAGGGAGTGTTCGGTGACCAG

TGACTTGGATTTTCCAACAC

AAGTCATCCCATTAAAGACTCTGAATGCAGTTGCTTCAGTACCCATAATG

TATTCTTGGTCTCCCCTACA

GCAGAATTTTATGGTGGAAGATGAAACTGTTTTACATAACATTCCTTATA

TGGGAGATGAAGTTTTAGAT

CAGGATGGTACTTTCATTGAAGAACTAATAAAAAATTATGATGGGAAAGT

ACACGGGGATAGAGAATGTG

GGTTTATAAATGATGAAATTTTTGTGGAGTTGGTGAATGCCCTTGGTCAA

TATAATGATGATGACGATGA

TGATGATGGAGACGATCCTGAAGAAAGAGAAGAAAAGCAGAAAGATCTGG

AGGATCACCGAGATGATAAA

GAAAGCCGCCCACCTCGGAAATTTCCTTCTGATAAAATTTTTGAAGCCAT

TTCCTCAATGTTTCCAGATA

AGGGCACAGCAGAAGAACTAAAGGAAAAATATAAAGAACTCACCGAACAG

CAGCTCCCAGGCGCACTTCC

TCCTGAATGTACCCCCAACATAGATGGACCAAATGCTAAATCTGTTCAGA

GAGAGCAAAGCTTACACTCC

TTTCATACGCTTTTCTGTAGGCGATGTTTTAAATATGACTGCTTCCTACA

TCCTTTTCATGCAACACCCA

ACACTTATAAGCGGAAGAACACAGAAACAGCTCTAGACAACAAACCTTGT

GGACCACAGTGTTACCAGCA

TTTGGAGGGAGCAAAGGAGTTTGCTGCTGCTCTCACCGCTGAGCGGATAA

AGACCCCACCAAAACGTCCA

GGAGGCCGCAGAAGAGGACGGCTTCCCAATAACAGTAGCAGGCCCAGCAC

CCCCACCATTAATGTGCTGG

AATCAAAGGATACAGACAGTGATAGGGAAGCAGGGACTGAAACGGGGGGA

GAGAACAATGATAAAGAAGA

AGAAGAGAAGAAAGATGAAACTTCGAGCTCCTCTGAAGCAAATTCTCGGT

GTCAAACACCAATAAAGATG

AAGCCAAATATTGAACCTCCTGAGAATGTGGAGTGGAGTGGTGCTGAAGC

CTCAATGTTTAGAGTCCTCA

TTGGCACTTACTATGACAATTTCTGTGCCATTGCTAGGTTAATTGGGACC

AAAAACATGTAGACAGGTGTA

TGAGTTTAGAGTCAAAGAATCTAGCATCATAGCTCCAGCTCCCGCTGAGG

ATGTGGATACTCCTCCAAGG

AAAAAGAAGAGGAAACACCGGTTGTGGGCTGCACACTGCAGAAAGATACA

GCTGAAAAAGGACGGCTCCT

CTAACCATGTTTACAACTATCAACCCTGTGATCATCCACGGCAGCCTTGT

GACAGTTCGTGCCCTTGTGT

GATAGCACAAAATTTTTGTGAAAAGTTTTGTCAATGTAGTTCAGAGTGTC

AAAACCGCTTTCCGGGATGC

CGCTGCAAAGCACAGTGCAACACCAAGCAGTGCCCGTGCTACCTGGCTGT

CCGAGAGTGTGACCCTGACC

TCTGTCTTACTTGTGGAGCCGCTGACCATTGGGACAGTAAAAATGTGTCC

TGCAAGAACTGCAGTATTCA

GCGGGGCTCCAAAAAGCATCTATTGCTGGCACCATCTGACGTGGCAGGCT

GGGGGATTTTTATCAAAGAT

CCTGTGCAGAAAAATGAATTCATCTCAGAATACTGTGGAGAGATTATTTC

TCAAGATGAAGCTGACAGAA

GAGGGAAAGTGTATGATAAATACATGTGCAGCTTTCTGTTCAACTTGAAC

AATGATTTTGTGGTGGATGC

AACCCGCAAGGGTAACAAAATTCGTTTTGCAAATCATTCGGTAAATCCAA

ACTGCTATGCAAAAGTTATG

-continued
ATGGTTAACGGTGATCACAGGATAGGTATTTTTGCCAAGAGAGCCATCCA

GACTGGCGAAGAGCTGTTTT

TTGATTACAGATACAGCCAGGCTGATGCCCTGAAGTATGTCGGCATCGAA

AGAGAAATGGAAATCCCTTG

A

In some embodiments of any of the aspects, the EZH2 polypeptide includes or is derived from human EZH2 having the following amino acid sequence NP_001190176.1 (SEQ ID NO: 10):

| | | | | | |
|---|---|---|---|---|---|
| 1 | mgqtgkksek | gpvcwrkrvk | seymrlrqlk | rfrradevks | mfssnrqkil erteilnqew |
| 61 | kqrriqpvhi | ltsvsslrgt | recsvtsdld | fptqviplkt | lnavasvpim yswsplqqnf |
| 121 | mvedetvlhn | ipymgdevld | qdgtfieeli | knydgkvhgd | recgfindei fvelvnalgq |
| 181 | yndddddddg | ddpeereekq | kdledhrddk | esrpprkfps | dkifeaissm fpdkgtaeel |
| 241 | kekykelteq | qlpgalppec | tpnidgpnak | svqreqslhs | fhtlfcrrcf kydcflhpfh |
| 301 | atpntykrkn | tetaldnkpc | gpqcyqhleg | akefaaalta | eriktppkrp ggrrrgrlpn |
| 361 | nssrpstpti | nvleskdtds | dreagtetgg | enndkeeeek | kdetssssea nsrcqtpikm |
| 421 | kpnieppenv | ewsgaeasmf | rvligtyydn | fcaiarligt | ktcrqvyefr vkessiiapa |
| 481 | paedvdtppr | kkkrkhrlwa | ahcrkiqlkk | dgssnhvyny | qpcdhprqpc dsscpcviaq |
| 541 | nfcekfcqcs | secqnrfpgc | rckaqcntkq | cpcylavrec | dpdlcltcga adhwdsknvs |
| 601 | ckncsiqrgs | kkhlllapsd | vagwgifikd | pvqknefise | ycgeiisqde adrrgkvydk |
| 661 | ymcsflfnln | ndfvvdatrk | gnkirfanhs | vnpncyakvm | mvngdhrigi fakraiqtge |
| 721 | elffdyrysq | adalkyvgie | remeip | | |

EZH2 inhibitors can include inhibitory nucleic acids and small molecules, e.g., GSK343, LosartanTazemetostat, CPI-1205 and/or PF-06821497.

HDAC9 is a component of a multiprotein enzyme complex which comprises at least two components, BRG1 and MALAT1. In some embodiments of any of the aspects, the inhibitor of the HDAC9-BRG1-MALAT1 complex is an inhibitor of BRG1 and/or MALAT1.

The HDAC9-BRG1-MALAT1 chromatin-modifying complex is recruited to the promoters of vascular smooth muscle cell (VSMC)-specific genes in the presence of gene products modified with thoracic aortic aneurysm (TAA)-associated mutations. Amongst other functions, the HDAC9 complex recruits PRC2 (Polycomb repressive complex 2) to catalyze the trimethylation of Histone 3 on lysine 27 (H3K27) through EZH2, its enzymatic subunit.

As used herein, "HDAC9" or "Histone Deeacetylase 9" refers to an enzyme of the Histone Deacetylase family encoded by the HDAC9 gene. HDAC9 catalyzes the the deacetylation of lysine residues on the N-terminal part of the core histones (H2A, H2B, H3 and H4). Multiple transcript variants encoding different isoforms have been found for this gene.

As described herein, the HDAC9 complex that is involved in transcriptional silencing of contractile associated gene products and undergoes downregulation in stenotic lesions. Accordingly, inhibition of the HDAC9 complex can prevent or treat vascular disease, e.g., stenotic disease and ameliorate arterial obstruction.

In some embodiments of any of the aspects, described herein are methods and compositions related to HDAC9 complex inhibition for the improvement of smooth muscle dependent stenotic vascular disease.

In some embodiments of any of the aspects, an inhibitor of the HDAC9 complex can be an inhibitor of MALAT1, BRG1, HDAC9, and/or EZH2.

HDAC9 is assigned Enzyme Comission (E.C.) 3.5.1.98. An enzyme of this EC number would be anticipated to perform similarily in methods and compositions as described herein.

Sequences for HDAC9 are known for a number of species, e.g., human HDAC9 (the HDAC9 NCBI Gene ID is 9734) mRNA sequences (e.g., NM_001204144.2 and polypeptide sequences (e.g., NP_001191073.1).

These, together with any naturally occurring allelic, splice variants, and processed forms thereof that catalyze the same reaction are contemplated for use in the methods and compositions described herein.

In some embodiments of any of the aspects, the HDAC9 nucleic acid includes or is derived from human HDAC9 having the following nucleic acid sequence CCDS56465.1 (SEQ ID NO: 11):

ATGATGAGCTCACCTGCACAGCCTGACCTCATGTGGAACCTTGTACCATG

GGTGCTATTCTGTGGCTGCT

GTAGGATCTTCCCAGATGGGGTGGCTGGACGAGAGCAGCTCTTGGCTCAG

CAAAGAATGCACAGTATGAT

CAGCTCAGTGGATGTGAAGTCAGAAGTTCCTGTGGGCCTGGAGCCCATCT

CACCTTTAGACCTAAGGACA

GACCTCAGGATGATGATGCCCGTGGTGGACCCTGTTGTCCGTGAGAAGCA

ATTGCAGCAGGAATTACTTC

TTATCCAGCAGCAGCAACAAATCCAGAAGCAGCTTCTGATAGCAGAGTTT

CAGAAACAGCATGAGAACTT

GACACGGCAGCACCAGGCTCAGCTTCAGGAGCATATCAAGGAACTTCTAG

CCATAAAACAGCAACAAGAA

-continued

```
CTCCTAGAAAAGGAGCAGAAACTGGAGCAGCAGAGGCAAGAACAGGAAGT

AGAGAGGCATCGCAGAGAAC

AGCAGCTTCCTCCTCTCAGAGGCAAAGATAGAGGACGAGAAAGGGCAGTG

GCAAGTACAGAAGTAAAGCA

GAAGCTTCAAGAGTTCCTACTGAGTAAATCAGCAACGAAAGACACTCCAA

CTAATGGAAAAAATCATTCC

GTGAGCCGCCATCCCAAGCTCTGGTACACGGCTGCCCACCACACATCATT

GGATCAAAGCTCTCCACCCC

TTAGTGGAACATCTCCATCCTACAAGTACACATTACCAGGAGCACAAGAT

GCAAGGATGATTTCCCCCT

TCGAAAAACTGAATCCTCAGTCAGTAGCAGTTCTCCAGGCTCTGGTCCCA

GTTCACCAAACAATGGGCCA

ACTGGAAGTGTTACTGAAAATGAGACTTCGGTTTTGCCCCCTACCCCTCA

TGCCGAGCAAATGGTTTCAC

AGCAACGCATTCTAATTCATGAAGATTCCATGAACCTGCTAAGTCTTTAT

ACCTCTCCTTCTTTGCCCAA

CATTACCTTGGGGCTTCCCGCAGTGCCATCCCAGCTCAATGCTTCGAATT

CACTCAAAGAAAAGCAGAAG

TGTGAGACGCAGACGCTTAGGCAAGGTGTTCCTCTGCCTGGGCAGTATGG

AGGCAGCATCCCGGCATCTT

CCAGCCACCCTCATGTTACTTTAGAGGGAAAGCCACCCAACAGCAGCCAC

CAGGCTCTCCTGCAGCATTT

ATTATTGAAAGAACAAATGCGACAGCAAAAGCTTCTTGTAGCTGGTGGAG

TTCCCTTACATCCTCAGTCT

CCCTTGGCAACAAAAGAGAGAATTTCACCTGGCATTAGAGGTACCCACAA

ATTGCCCCGTCACAGACCCC

TGAACCGAACCCAGTCTGCACCTTTGCCTCAGAGCACGTTGGCTCAGCTG

GTCATTCAACAGCAACACCA

GCAATTCTTGGAGAAGCAGAAGCAATACCAGCAGCAGATCCACATGAACA

AACTGCTTTCGAAATCTATT

GAACAACTGAAGCAACCAGGCAGTCACCTTGAGGAAGCAGAGGAAGAGCT

TCAGGGGGACCAGGCGATGC

AGGAAGACAGAGCGCCCTCTAGTGGCAACAGCACTAGGAGCGACAGCAGT

GCTTGTGTGGATGACACACT

GGGACAAGTTGGGGCTGTGAAGGTCAAGGAGGAACCAGTGGACAGTGATG

AAGATGCTCAGATCCAGGAA

ATGGAATCTGGGGAGCAGGCTGCTTTTATGCAACAGGTAATAGGCAAAGA

TTTAGCTCCAGGATTTGTAA

TTAAAGTCATTATCTGA
```

In some embodiments of any of the aspects, the HDAC9 polypeptide includes or is derived from human HDAC9 having the following amino acid sequence NP_001191073.1 (SEQ ID NO: 12):

```
MMSSPAQPDLMWNLVPWVLFCGCCRIFPDGVAGREQLLAQQRMHSMISSV

DVKSEVPVGLEPISPLDLRT

DLRMMMPVVDPVVREKQLQQELLLIQQQQQIQKQLLIAEFQKQHENLTRQ

HQAQLQEHIKELLAIKQQQE

LLEKEQKLEQQRQEQEVERHRREQQLPPLRGKDRGRERAVASTEVKQKLQ

EFLLSKSATKDTPTNGKNHS

VSRHPKLWYTAAHHTSLDQSSPPLSGTSPSYKYTLPGAQDAKDDFPLRKT

ESSVSSSSPGSGPSSPNNGP

TGSVTENETSVLPPTPHAEQMVSQQRILIHEDSMNLLSLYTSPSLPNITL

GLPAVPSQLNASNSLKEKQK

CETQTLRQGVPLPGQYGGSIPASSSHPHVTLEGKPPNSSHQALLQHLLLK

EQMRQQKLLVAGGVPLHPQS

PLATKERISPGIRGTHKLPRHRPLNRTQSAPLPQSTLAQLVIQQQHQQFL

EKQKQYQQQIHMNKLLSKSI

EQLKQPGSHLEEAEEELQGDQAMQEDRAPSSGNSTRSDSSACVDDTLGQV

GAVKVKEEPVDSDEDAQIQE

MESGEQAAFMQQVIGKDLAPGFVIKVII
```

As used herein, "BRG1" or "Brahma-related gene 1 protein" refers to a member of the SWI/SNF family of proteins encoded by the BRG1 gene. As described above herein, BRG11 is a component of the epigenetic remodeling complex HDAC9-BRG1-MALAT1 and in some embodiments of any of the aspects, an inhibitor of the HDAC9 complex can be an inhibitor of BRG1. In some embodiments of any of the aspects, and BRG1 inhibitor can be an inhibitory nucleic acid.

Sequences for BRG1 are known for a number of species, e.g., human BRG1 (the BRG1 NCBI Gene ID is 6597), RNA sequences (e.g., NM_001128844.1 and polypeptide sequences (e.g., NP_001122316.1).

These, together with any naturally occurring allelic, splice variants, and processed forms thereof that catalyze the same reaction are contemplated for use in the methods and compositions described herein.

In some embodiments of any of the aspects, the BRG1 nucleic acid includes or is derived from human BRG1 having the following nucleic acid sequence CCDS12253.1 (SEQ ID NO: 13):

```
ATGTCCACTCCAGACCCACCCCTGGGCGGAACTCCTCGGCCAGGTCCTTC

CCCGGGCCCTGGCCCTTCCC

CTGGAGCCATGCTGGGCCCTAGCCCGGGTCCCTCGCCGGGCTCCGCCCAC

AGCATGATGGGCCCAGCCC

AGGGCCGCCCTCAGCAGGACACCCCATCCCCACCCAGGGGCCTGGAGGGT

ACCCTCAGGACAACATGCAC
```

-continued

```
CAGATGCACAAGCCCATGGAGTCCATGCATGAGAAGGGCATGTCGGACGA

CCCGCGCTACAACCAGATGA

AAGGAATGGGGATGCGGTCAGGGGGCCATGCTGGGATGGGGCCCCCGCCC

AGCCCCATGGACCAGCACTC

CCAAGGTTACCCCTCGCCCCTGGGTGGCTCTGAGCATGCCTCTAGTCCAG

TTCCAGCCAGTGGCCCGTCT

TCGGGGCCCCAGATGTCTTCCGGGCCAGGAGGTGCCCCGCTGGATGGTGC

TGACCCCCAGGCCTTGGGGC

AGCAGAACCGGGGCCCAACCCCATTTAACCAGAACCAGCTGCACCAGCTC

AGAGCTCAGATCATGGCCTA

CAAGATGCTGGCCAGGGGGCAGCCCCTCCCCGACCACCTGCAGATGGCGG

TGCAGGGCAAGCGGCCGATG

CCCGGGATGCAGCAGCAGATGCCAACGCTACCTCCACCCTCGGTGTCCGC

AACAGGACCCGGCCCTGGCC

CTGGCCCTGGCCCCGGCCCGGGTCCCGGCCCGGCACCTCCAAATTACAGC

AGGCCTCATGGTATGGGAGG

GCCCAACATGCCTCCCCAGGACCCTCGGGCGTGCCCCCCGGGATGCCAG

GCCAGCCTCCTGGAGGGCCT

CCCAAGCCCTGGCCTGAAGGACCCATGGCGAATGCTGCTGCCCCCACGAG

CACCCCTCAGAAGCTGATTC

CCCCGCAGCCAACGGGCCGCCCTTCCCCCGCGCCCCCTGCCGTCCCACCC

GCCGCCTCGCCCGTGATGCC

ACCGCAGACCCAGTCCCCCGGGCAGCCGGCCCAGCCCGCGCCCATGGTGC

CACTGCACCAGAAGCAGAGC

CGCATCACCCCCATCCAGAAGCCGCGGGGCCTCGACCCTGTGGAGATCCT

GCAGGAGCGCGAGTACAGGC

TGCAGGCTCGCATCGCACACCGAATTCAGGAACTTGAAAACCTTCCCGGG

TCCCTGGCCGGGGATTTGCG

AACCAAAGCGACCATTGAGCTCAAGGCCCTCAGGCTGCTGAACTTCCAGA

GGCAGCTGCGCCAGGAGGTG

GTGGTGTGCATGCGGAGGGACACAGCGCTGGAGACAGCCCTCAATGCTAA

GGCCTACAAGCGCAGCAAGC

GCCAGTCCCTGCGCGAGGCCCGCATCACTGAGAAGCTGGAGAAGCAGCAG

AAGATCGAGCAGGAGCGCAA

GCGCCGGCAGAAGCACCAGGAATACCTCAATAGCATTCTCCAGCATGCCA

AGGATTTCAAGGAATATCAC

AGATCCGTCACAGGCAAAATCCAGAAGCTGACCAAGGCAGTGGCCACGTA

CCATGCCAACACGGAGCGGG

AGCAGAAGAAAGAGAACGAGCGGATCGAGAAGGAGCGCATGCGGAGGCTC

ATGGCTGAAGATGAGGAGGG
```

-continued

```
GTACCGCAAGCTCATCGACCAGAAGAAGGACAAGCGCCTGGCCTACCTCT

TGCAGCAGACAGACGAGTAC

GTGGCTAACCTCACGGAGCTGGTGCGGCAGCACAAGGCTGCCCAGGTCGC

CAAGGAGAAAAAGAAGAAAA

AGAAAAAGAAGAAGGCAGAAAATGCAGAAGGACAGACGCCTGCCATTGGG

CCGGATGGCGAGCCTCTGGA

CGAGACCAGCCAGATGAGCGACCTCCCGGTGAAGGTGATCCACGTGGAGA

GTGGGAAGATCCTCACAGGC

ACAGATGCCCCCAAAGCCGGGCAGCTGGAGGCCTGGCTCGAGATGAACCC

GGGGTATGAAGTAGCTCCGA

GGTCTGATAGTGAAGAAAGTGGCTCAGAAGAAGAGGAAGAGGAGGAGGAG

GAAGAGCAGCCGCAGGCAGC

ACAGCCTCCCACCCTGCCCGTGGAGGAGAAGAAGAAGATTCCAGATCCAG

ACAGCGATGACGTCTCTGAG

GTGGACGCGCGGCACATCATTGAGAATGCCAAGCAAGATGTCGATGATGA

ATATGGCGTGTCCCAGGCCC

TTGCACGTGGCCTGCAGTCCTACTATGCCGTGGCCCATGCTGTCACTGAG

AGAGTGGACAAGCAGTCAGC

GCTTATGGTCAATGGTGTCCTCAAACAGTACCAGATCAAAGGTTTGGAGT

GGCTGGTGTCCCTGTACAAC

AACAACCTGAACGGCATCCTGGCCGACGAGATGGGCCTGGGGAAGACCAT

CCAGACCATCGCGCTCATCA

CGTACCTCATGGAGCACAAACGCATCAATGGGCCCTTCCTCATCATCGTG

CCTCTCTCAACGCTGTCCAA

CTGGGCGTACGAGTTTGACAAGTGGGCCCCCTCCGTGGTGAAGGTGTCTT

ACAAGGGATCCCCAGCAGCA

AGACGGGCCTTTGTCCCCCAGCTCCGGAGTGGGAAGTTCAACGTCTTGCT

GACGACGTACGAGTACATCA

TCAAAGACAAGCACATCCTCGCCAAGATCCGTTGGAAGTACATGATTGTG

GACGAAGGTCACCGCATGAA

GAACCACCACTGCAAGCTGACGCAGGTGCTCAACACGCACTATGTGGCAC

CCCGCCGCCTGCTGCTGACG

GGCACACCGCTGCAGAACAAGCTTCCCGAGCTCTGGGCGCTGCTCAACTT

CCTGCTGCCCACCATCTTCA

AGAGCTGCAGCACCTTCGAGCAGTGGTTTAACGCACCCTTTGCCATGACC

GGGGAAAAGGTGGACCTGAA

TGAGGAGGAAACCATTCTCATCATCCGGCGTCTCCACAAAGTGCTGCGGC

CCTTCTTGCTCCGACGACTC

AAGAAGGAAGTCGAGGCCCAGTTGCCCGAAAAGGTGGAGTACGTCATCAA

GTGCGACATGTCTGCGCTGC
```

```
AGCGAGTGCTCTACCGCCACATGCAGGCCAAGGGCGTGCTGCTGACTGAT

GGCTCCGAGAAGGACAAGAA

GGGCAAAGGCGGCACCAAGACCCTGATGAACACCATCATGCAGCTGCGGA

AGATCTGCAACCACCCCTAC

ATGTTCCAGCACATCGAGGAGTCCTTTTCCGAGCACTTGGGGTTCACTGG

CGGCATTGTCCAAGGGCTGG

ACCTGTACCGAGCCTCGGGTAAATTTGAGCTTCTTGATAGAATTCTTCCC

AAACTCCGAGCAACCAACCA

CAAAGTGCTGCTGTTCTGCCAAATGACCTCCCTCATGACCATCATGGAAG

ATTACTTTGCGTATCGCGGC

TTTAAATACCTCAGGCTTGATGGAACCACGAAGGCGGAGGACCGGGGCAT

GCTGCTGAAAACCTTCAACG

AGCCCGGCTCTGAGTACTTCATCTTCCTGCTCAGCACCCGGGCTGGGGGG

CTCGGCCTGAACCTCCAGTC

GGCAGACACTGTGATCATTTTTGACAGCGACTGGAATCCTCACCAGGACC

TGCAAGCGCAGGACCGAGCC

CACCGCATCGGGCAGCAGAACGAGGTGCGTGTGCTCCGCCTCTGCACCGT

CAACAGCGTGGAGGAGAAGA

TCCTAGCTGCAGCCAAGTACAAGCTCAACGTGGACCAGAAGGTGATCCAG

GCCGGCATGTTCGACCAGAA

GTCCTCCAGCCATGAGCGGCGCGCCTTCCTGCAGGCCATCCTGGAGCACG

AGGAGCAGGATGAGAGCAGA

CACTGCAGCACGGGCAGCGGCAGTGCCAGCTTCGCCCACACTGCCCCTCC

GCCAGCGGGCGTCAACCCCG

ACTTGGAGGAGCCACCTCTAAAGGAGGAAGACGAGGTGCCCGACGACGAG

ACCGTCAACCAGATGATCGC

CCGGCACGAGGAGGAGTTTGATCTGTTCATGCGCATGGACCTGGACCGCA

GGCGCGAGGAGGCCCGCAAC

CCCAAGCGGAAGCCGCGCCTCATGGAGGAGGACGAGCTCCCCTCGTGGAT

CATCAAGGACGACGCGGAGG

TGGAGCGGCTGACCTGTGAGGAGGAGGAGGAGAAGATGTTCGGCCGTGGC

TCCCGCCACCGCAAGGAGGT

GGACTACAGCGACTCACTGACGGAGAAGCAGTGGCTCAAGGCCATCGAGG

AGGGCACGCTGGAGGAGATC

GAAGAGGAGGTCCGGCAGAAGAAATCATCACGGAAGCGCAAGCGAGACAG

CGACGCCGGCTCCTCCACCC

CGACCACCAGCACCCGCAGCCGCGACAAGGACGACGAGAGCAAGAAGCAG

AAGAAGCGCGGCGGCCGCC

TGCCGAGAAACTCTCCCCTAACCCACCCAACCTCACCAAGAAGATGAAGA

AGATTGTGGATGCCGTGATC

AAGTACAAGGACAGCAGCAGTGGACGTCAGCTCAGCGAGGTCTTCATCCA

GCTGCCCTCGCGAAAGGAGC

TGCCCGAGTACTACGAGCTCATCCGCAAGCCCGTGGACTTCAAGAAGATA

AAGGAGCGCATTCGCAACCA

CAAGTACCGCAGCCTCAACGACCTAGAGAAGGACGTCATGCTCCTGTGCC

AGAACGCACAGACCTTCAAC

CTGGAGGGCTCCCTGATCTATGAAGACTCCATCGTCTTGCAGTCGGTCTT

CACCAGCGTGCGGCAGAAAA

TCGAGAAGGAGGATGACAGTGAAGGCGAGGAGAGTGAGGAGGAGGAAGAG

GGCGAGGAGGAAGGCTCCGA

ATCCGAATCTCGGTCCGTCAAAGTGAAGATCAAGCTTGGCCGGAAGGAGA

AGGCACAGGACCGGCTGAAG

GGCGGCCGGCGGCGGCCGAGCCGAGGGTCCCGAGCCAAGCCGGTCGTGAG

TGACGATGACAGTGAGGAGG

AACAAGAGGAGGACCGCTCAGGAAGTGGCAGCGAAGAAGACTGA
```

In some embodiments of any of the aspects, the BRG1 polypeptide includes or is derived from human BRG1 having the following amino acid sequence NP_001122316.1 (SEQ ID NO: 14):

```
  1  mstpdpplgg tprpgpspgp gpspgamlgp spgpspgsah smmgpspgpp saghpiptqg
 61  pggypqdnmh qmhkpmesmh ekgmsddpry nqmkgmgmrs gghagmgppp spmdqhsqgy
121  psplggseha sspvpasgps sgpqmssgpg gapldgadpq algqqnrgpt pfnqnqlhql
181  raqimaykml argqplpdhl qmavqgkrpm pgmqqqmptl pppsysatgp gpgpgpgpgp
241  gpgpappnys rphgmggpnm pppgpsgvpp gmpgqppggp pkpwpegpma naaaptstpq
301  klippqptgr pspappavpp aaspvmppqt qspgqpaqpa pmvplhqkqs ritpiqkprg
361  ldpveilqer eyrlqariah riqelenlpg slagdlrtka tielkalrll nfqrqlrqev
421  vvcmrrdtal etalnakayk rskrqslrea riteklekqq kieqerkrrq khqeylnsil
481  qhakdfkeyh rsvtgkiqkl tkavatyhan tereqkkene riekermrrl maedeegyrk
541  lidqkkdkrl ayllqqtdey vanltelvrq hkaaqvakek kkkkkkkkae naegqtpaig
```

```
 601   pdgepldets  qmsdlpvkvi  hvesgkiltg  tdapkagqle  awlemnpgye  vaprsdsees
 661   gseeeeeeee  eeqpqaaqpp  tlpveekkki  pdpdsddvse  vdarhiiena  kqdvddeygv
 721   sqalarglqs  yyavahavte  rvdkqsalmv  ngvlkqyqik  glewlvslyn  nnlngilade
 781   mglgktiqti  alitylmehk  ringpfliiv  plstlsnway  efdkwapsvv  kvsykgspaa
 841   rrafvpqlrs  gkfnvlltty  eyiikdkhil  akirwkymiv  deghrmknhh  ckltqvlnth
 901   yvaprrlllt  gtplqnklpe  lwallnfllp  tifkscstfe  qwfnapfamt  gekvdlneee
 961   tiliirrlhk  vlrpfllrrl  kkeveaqlpe  kveyvikcdm  salqrvlyrh  mqakgvlltd
1021   gsekdkkgkg  gtktlmntim  qlrkicnhpy  mfqhieesfs  ehlgftggiv  qgldlyrasg
1081   kfelldrilp  klratnhkvl  lfcqmtslmt  imedyfayrg  fkylrldgtt  kaedrgmllk
1141   tfnepgseyf  ifllstragg  lglnlqsadt  viifdsdwnp  hqdlqaqdra  hrigqqnevr
1201   vlrlctvnsv  eekilaaaky  klnvdqkviq  agmfdqksss  herraflqai  leheeqdesr
1261   hcstgsgsas  fahtapppag  vnpdleeppl  keedevpdde  tvnqmiarhe  eefdlfmrmd
1321   ldrrreearn  pkrkprlmee  delpswiikd  daeverltce  eeeekmfgrg  srhrkevdys
1381   dsltekqwlk  aieegtleei  eeevrqkkss  rkrkrdsdag  sstpttstrs  rdkddeskkq
1441   kkrgrppaek  lspnppnltk  kmkkivdavi  kykdsssgrq  lsevfiqlps  rkelpeyyel
1501   irkpvdfkki  kefirnhkyr  slndlekdvm  llcqnaqtfn  legsliyeds  ivlqsvftsv
1561   rqkiekedds  egeeseeeee  geeegseses  rsvkvkiklg  rkekaqdrlk  ggnipsrgs
1621   rakpvvsddd  seeeqeedrs  gsgseed
```

As used herein, "MALAT1" or "metastasis associated lung adenocarcinoma transcript 1" refers to long non-coding RNA derived by RNase P cleavage of a tRNA-like small ncRNA from its 3' end. The resultant mature transcript lacks a canonical poly(A) tail but is instead stabilized by a 3' triple helical structure. This transcript is retained in the nucleus where it forms molecular scaffolds for ribonucleoprotein complexes.

As described above herein, MALAT1 is a component of the epigenetic remodeling complex HDAC9-BRG1-MALAT1 and in some embodiments of any of the aspects, an inhibitor of the HDAC9 complex can be an inhibitor of MALAT1. In some embodiments of any of the aspects, and MALAT1 inhibitor can be an inhibitory nucleic acid.

Sequences for MALAT1 are known for a number of species, e.g., human MALAT1 (the MALAT1 NCBI Gene ID is 378938) and RNA sequences (e.g., NR_002819.4).

In some embodiments of any of the aspects, the MALAT1 RNA includes or is derived from human RNA having the following amino acid sequence NR_002819.4 (SEQ ID NO: 15):

```
  1   cgcagcctgc  agcccgagac  ttctgtaaag  gactggggcc  ccgcaactgg  cctctcctgc
 61   cctcttaagc  gcagcgccat  tttagcaacg  cagaagcccg  gcgccgggaa  gcctcagctc
121   gcctgaaggc  aggtcccctc  tgacgcctcc  gggagcccag  gtttcccaga  gtccttggga
181   cgcagcgacg  agttgtgctg  ctatcttagc  tgtccttata  ggctggccat  tccaggtggt
241   ggtatttaga  taaaaccact  caaactctgc  agtttggtct  tggggtttgg  aggaaagctt
301   ttatttttct  tcctgctccg  gttcagaagg  tctgaagctc  atacctaacc  aggcataaca
361   cagaatctgc  aaaacaaaaa  cccctaaaaa  agcagaccca  gagcagtgta  aacacttctg
421   ggtgtgtccc  tgactggctg  cccaaggtct  ctgtgtcttc  ggagacaaag  ccattcgctt
481   agttggtcta  ctttaaaagg  ccacttgaac  tcgctttcca  tggcgatttg  ccttgtgagc
541   actttcagga  gagcctggaa  gctgaaaaac  ggtagaaaaa  tttccgtgcg  ggccgtgggg
601   ggctggcggc  aactggggg   ccgcagatca  gagtgggcca  ctggcagcca  acggcccccg
661   gggctcaggc  ggggagcagc  tctgtggtgt  gggattgagg  cgttttccaa  gagtgggttt
721   tcacgtttct  aagatttccc  aagcagacag  cccgtgctgc  tccgatttct  cgaacaaaaa
781   agcaaaacgt  gtggctgtct  tgggagcaag  tcgcaggact  gcaagcagtt  gggggagaaa
```

-continued

```
 841   gtccgccatt ttgccacttc tcaaccgtcc ctgcaaggct ggggctcagt tgcgtaatgg
 901   aaagtaaagc cctgaactat cacactttaa tcttccttca aaaggtggta aactatacct
 961   actgtccctc aagagaacac aagaagtgct ttaagaggta ttttaaaagt tccgggggtt
1021   ttgtgaggtg tttgatgacc cgtttaaaat atgatttcca tgtttctttt gtctaaagtt
1081   tgcagctcaa atctttccac acgctagtaa tttaagtatt tctgcatgtg tagtttgcat
1141   tcaagttcca taagctgtta agaaaaatct agaaagtaa aactagaacc tattttaac
1201   cgaagaacta cttttttgcct ccctcacaaa ggcggcggaa ggtgatcgaa ttccggtgat
1261   gcgagttgtt ctccgtctat aaatacgcct cgcccgagct gtgcggtagg cattgaggca
1321   gccagcgcag gggcttctgc tgaggggca ggcggagctt gaggaaaccg cagataagtt
1381   tttttctctt tgaaagatag agattaatac aactacttaa aaaatatagt caataggtta
1441   ctaagatatt gcttagcgtt aagtttttaa cgtaatttta atagcttaag attttaagag
1501   aaaatatgaa gacttagaag agtagcatga ggaaggaaaa gataaaaggt ttctaaaaca
1561   tgacggaggt tgagatgaag cttcttcatg gagtaaaaaa tgtatttaaa agaaaattga
1621   gagaaaggac tacagagccc cgaattaata ccaatagaag ggcaatgctt ttagattaaa
1681   atgaaggtga cttaaacagc ttaaagttta gtttaaaagt tgtaggtgat taaaataatt
1741   tgaaggcgat cttttaaaaa gagattaaac cgaaggtgat taaaagacct tgaaatccat
1801   gacgcaggga gaattgcgtc atttaaagcc tagttaacgc atttactaaa cgcagacgaa
1861   aatggaaaga ttaattggga gtggtaggat gaaacaattt ggagaagata gaagtttgaa
1921   gtggaaaact ggaagacaga agtacgggaa ggcgaagaaa agaatagaga agatagggaa
1981   attagaagat aaaaacatac ttttagaaga aaaaagataa attttaaacct gaaaagtagg
2041   aagcagaaga aaaaagacaa gctaggaaac aaaaagctaa gggcaaaatg tacaaactta
2101   gaagaaaatt ggaagataga aacaagatag aaaatgaaaa tattgtcaag agtttcagat
2161   agaaaatgaa aaacaagcta agacaagtat tggagaagta tagaagatag aaaaatataa
2221   agccaaaaat tggataaaat agcactgaaa aaatgaggaa attattggta accaatttat
2281   tttaaaagcc catcaatta atttctggtg gtgcagaagt tagaaggtaa agcttgagaa
2341   gatgagggtg tttacgtaga ccagaaccaa tttagaagaa tacttgaagc tagaaggga
2401   agttggttaa aaatcacatc aaaaagctac taaaaggact ggtgtaattt aaaaaaaact
2461   aaggcagaag gcttttggaa gagttagaag aatttggaag gccttaaata tagtagctta
2521   gtttgaaaaa tgtgaaggac tttcgtaacg gaagtaattc aagatcaaga gtaattacca
2581   acttaatgtt tttgcattgg actttgagtt aagattattt tttaaatcct gaggactagc
2641   attaattgac agctgaccca ggtgctacac agaagtggat tcagtgaatc taggaagaca
2701   gcagcagaca ggattccagg aaccagtgtt tgatgaagct aggactgagg agcaagcgag
2761   caagcagcag ttcgtggtga agataggaaa agagtccagg agccagtgcg atttggtgaa
2821   ggaagctagg aagaaggaag gagcgctaac gatttggtgg tgaagctagg aaaaaggatt
2881   ccaggaagga gcgagtgcaa tttggtgatg aaggtagcag gcggcttggc ttggcaacca
2941   cacggaggag gcgagcaggc gttgtgcgta gaggatccta gaccagcatg ccagtgtgcc
3001   aaggccacag ggaaagcgag tggttggtaa aaatccgtga ggtcggcaat atgttgtttt
3061   tctggaactt acttatggta accttttatt tattttctaa tataatgggg gagtttcgta
3121   ctgaggtgta aagggattta tatggggacg taggccgatt tccgggtgtt gtaggtttct
3181   ctttttcagg cttatactca tgaatcttgt ctgaagcttt tgagggcaga ctgccaagtc
```

-continued

```
3241  ctggagaaat agtagatggc aagtttgtgg gttttttttt tttacacgaa tttgaggaaa
3301  accaaatgaa tttgatagcc aaattgagac aatttcagca aatctgtaag cagtttgtat
3361  gtttagttgg ggtaatgaag tatttcagtt ttgtgaatag atgacctgtt tttacttcct
3421  caccctgaat tcgttttgta aatgtagagt ttggatgtgt aactgaggcg gggggagtt
3481  ttcagtattt ttttttgtgg gggtgggggc aaaatatgtt ttcagttctt tttcccttag
3541  gtctgtctag aatcctaaag gcaaatgact caaggtgtaa cagaaaacaa gaaaatccaa
3601  tatcaggata atcagaccac cacaggttta cagtttatag aaactagagc agttctcacg
3661  ttgaggtctg tggaagagat gtccattgga gaaatggctg gtagttactc ttttttcccc
3721  ccaccccctt aatcagactt taaaagtgct taacccctta aacttgttat ttttacttg
3781  aagcattttg ggatggtctt aacaggaag agagagggtg ggggagaaaa tgttttttc
3841  taagattttc cacagatgct atagtactat tgacaaactg ggttagagaa ggagtgtacc
3901  gctgtgctgt tggcacgaac accttcaggg actggagctg cttttatcct tggaagagta
3961  ttcccagttg aagctgaaaa gtacagcaca gtgcagcttt ggttcatatt cagtcatctc
4021  aggagaactt cagaagagct tgagtaggcc aaatgttgaa gttaagtttt ccaataatgt
4081  gacttcttaa aagttttatt aaaggggagg ggcaaatatt ggcaattagt tggcagtggc
4141  ctgttacggt tgggattggt ggggtgggtt taggtaattg tttagtttat gattgcagat
4201  aaactcatgc cagagaactt aaagtcttag aatggaaaaa gtaaagaaat atcaacttcc
4261  aagttggcaa gtaactccca atgatttagt ttttttcccc ccagtttgaa ttgggaagct
4321  gggggaagtt aaatatgagc cactgggtgt accagtgcat taatttgggc aaggaaagtg
4381  tcataatttg atactgtatc tgttttcctt caaagtatag agcttttggg gaaggaaagt
4441  attgaactgg gggttggtct ggcctactgg gctgacatta actacaatta tgggaaatgc
4501  aaaagttgtt tggatatggt agtgtgtggt tctcttttgg aattttttc aggtgattta
4561  ataataattt aaaactacta tagaaactgc agagcaaagg aagtggctta atgatcctga
4621  agggatttct tctgatggta gcttttgtat tatcaagtaa gattctattt tcagttgtgt
4681  gtaagcaagt ttttttttag tgtaggagaa atacttttcc attgtttaac tgcaaaacaa
4741  gatgttaagg tatgcttcaa aaattttgta aattgtttat tttaaactta tctgtttgta
4801  aattgtaact gattaagaat tgtgatagtt cagcttgaat gtctcttaga gggtgggctt
4861  ttgttgatga gggagggaa actttttttt tttctataga ctttttcag ataacatctt
4921  ctgagtcata accagcctgg cagtatgatg cctagatgc agagaaaaca gctccttggt
4981  gaattgataa gtaaaggcag aaaagattat atgtcatacc tccattgggg aataagcata
5041  accctgagat tcttactact gatgagaaca ttatctgcat atgccaaaaa attttaagca
5101  aatgaaagct accaatttaa agttacggaa tctaccattt taaagttaat tgcttgtcaa
5161  gctataacca caaaaataat gaattgatga gaaatacaat gaagaggcaa tgtccatctc
5221  aaaatactgc ttttacaaaa gcagaataaa agcgaaaaga aatgaaaatg ttacactaca
5281  ttaatcctgg aataaaagaa gccgaaataa atgagagatg agttgggatc aagtggattg
5341  aggaggctgt gctgtgtgcc aatgtttcgt ttgcctcaga caggtatctc ttcgttatca
5401  gaagagttgc ttcatttcat ctgggagcag aaaacagcag gcagctgtta acagataagt
5461  ttaacttgca tctgcagtat tgcatgttag ggataagtgc ttattttaa gagctgtgga
5521  gttcttaaat atcaaccatg gcactttctc ctgaccccctt ccctagggga tttcaggatt
5581  gagaaatttt tccatcgagc ctttttaaaa ttgtaggact tgttcctgtg ggcttcagtg
5641  atgggatagt acacttcact cagaggcatt tgcatcttta aataatttct taaaagcctc
```

-continued

```
5701  taaagtgatc agtgccttga tgccaactaa ggaaatttgt ttagcattga atctctgaag
5761  gctctatgaa aggaatagca tgatgtgctg ttagaatcag atgttactgc taaaatttac
5821  atgttgtgat gtaaattgtg tagaaaacca ttaaatcatt caaaataata aactatttt
5881  attagagaat gtactcttt agaaagctgt ctccttattt aaataaaata gtgtttgtct
5941  gtagttcagt gttggggcaa tcttgggggg gattcttctc taatctttca gaaactttgt
6001  ctgcgaacac tctttaatgg accagatcag gatttgagcg gaagaacgaa tgtaacttta
6061  aggcaggaaa gacaaatttt attcttcata aagtgatgag catataataa ttccaggcac
6121  atggcaatag aggccctcta aataaggaat aaataacctc ttagacaggt gggagattat
6181  gatcagagta aaaggtaatt acacatttta tttccagaaa gtcagggtc tataaattga
6241  cagtgattag agtaatactt tttcacattt ccaaagtttg catgttaact taaatgctt
6301  acaatcttag agtggtaggc aatgttttac actattgacc ttatataggg aagggagggg
6361  gtgcctgtgg ggttttaaag aatttccctt tgcagaggca tttcatcctt catgaagcca
6421  ttcaggattt tgaattgcat atgagtgctt ggctcttcct tctgttctag tgagtgtatg
6481  agaccttgca gtgagtttat cagcatactc aaaatttttt tcctggaatt tggagggatg
6541  ggaggagggg gtggggctta cttgttgtag cttttttttt ttttacagac ttcacagaga
6601  atgcagttgt cttgacttca ggtctgtctg ttctgttggc aagtaaatgc agtactgttc
6661  tgatcccgct gctattagaa tgcattgtga aacgactgga gtatgattaa aagttgtgtt
6721  ccccaatgct tggagtagtg attgttgaag gaaaaaatcc agctgagtga taaaggctga
6781  gtgttgagga aatttctgca gttttaagca gtcgtatttg tgattgaagc tgagtacatt
6841  ttgctggtgt attttaggt aaaatgcttt tgttcattt ctggtggtgg gaggggactg
6901  aagcctttag tcttttccag atgcaacctt aaaatcagtg acaagaaaca ttccaaacaa
6961  gcaacagtct tcaagaaatt aaactggcaa gtggaaatgt ttaaacagtt cagtgatctt
7021  tagtgcattg tttatgtgtg ggtttctctc tcccctccct tggtcttaat tcttacatgc
7081  aggaacactc agcagacaca cgtatgcgaa gggccagaga agccagaccc agtaagaaaa
7141  aatagcctat ttacttaaa taaaccaaac attccatttt aaatgtgggg attgggaacc
7201  actagttctt tcagatggta ttcttcagac tatagaagga gcttccagtt gaattcacca
7261  gtggacaaaa tgaggaaaac aggtgaacaa gcttttctg tatttacata caaagtcaga
7321  tcagttatgg gacaatagta ttgaatagat ttcagcttta tgctggagta actggcatgt
7381  gagcaaactg tgttggcgtg ggggtggagg ggtgaggtgg gcgctaagcc tttttttaag
7441  attttcagg tacccctcac taaaggcacc gaaggcttaa agtaggacaa ccatggagcc
7501  ttcctgtggc aggagagaca acaaagcgct attatcctaa ggtcaagaga agtgtcagcc
7561  tcacctgatt tttattagta atgaggactt gcctcaactc cctctttctg gagtgaagca
7621  tccgaaggaa tgcttgaagt acccctgggc ttctcttaac atttaagcaa gctgtttta
7681  tagcagctct taataataaa gcccaaatct caagcggtgc ttgaagggga gggaaagggg
7741  gaaagcgggc aaccactttt ccctagcttt tccagaagcc tgttaaaagc aaggtctccc
7801  cacaagcaac ttctctgcca catcgccacc ccgtgccttt tgatctagca cagacccttc
7861  acccctcacc tcgatgcagc cagtagcttg gatccttgtg ggcatgatcc ataatcggtt
7921  tcaaggtaac gatggtgtcg aggtctttgg tgggttgaac tatgttagaa aaggccatta
7981  atttgcctgc aaattgttaa cagaagggta ttaaaaccac agctaagtag ctctattata
8041  atacttatcc agtgactaaa accaacttaa accagtaagt ggagaaataa catgttcaag
```

```
-continued
8101   aactgtaatg ctgggtggga acatgtaact tgtagactgg agaagatagg catttgagtg 8161   gctgagaggg cttttgggtg ggaatgcaaa aattctctgc taagacttt  tcaggtgaac 8221   ataacagact tggccaagct agcatcttag cggaagctga tctccaatgc tcttcagtag 8281   ggtcatgaag gtttttcttt tcctgagaaa acaacacgta ttgttttctc aggttttgct 8341   ttttggcctt tttctagctt aaaaaaaaaa aaagcaaaag atgctggtgg ttggcactcc 8401   tggtttccag gacgggttc  aaatccctgc ggcgtctttg ctttgactac taatctgtct 8461   tcaggactct ttctgtattt ctccttttct ctgcaggtgc tagttcttgg agttttgggg 8521   aggtgggagg taacagcaca atatctttga actatataca tccttgatgt ataatttgtc 8581   aggagcttga cttgattgta tattcatatt tacacgagaa cctaatataa ctgccttgtc 8641   tttttcaggt aatagcctgc agctggtgtt ttgagaagcc ctactgctga aaacttaaca 8701   attttgtgta ataaaatgg  agaagctcta aattgttgtg gttcttttgt gaataaaaaa 8761   atcttgattg gggaaaaaa
```

In one aspect of any of the embodiments, provided herein is a composition to prevent or treat a vascular disease in a patient comprised of administering to said patient a therapeutically effective dose of a compound or drug (or combination of said compounds or drugs) which targets the epigenetic regulation of gene expression of vascular smooth muscle cell cytoskeletal proteins.

In one aspect of any of the embodiments, provided herein the cytoskeletal protein is SM22a encoded by the TAGLN gene. As described herein, contractile genes including but not limited to TAGLN, MYH11 and/or SMTN responsible for aortic homeostasis are actively transcribed in VSMCs through the action of transcription factors such as SMAD3, among others.

In one aspect of any of the embodiments, the epigenetic regulatory target is a multiprotein complex (PRC2, Polycomb repressive complex 2) responsible for gene silencing through its catalytic activity or hypermethylation of chromatin at vascular smooth muscle gene loci.

In one aspect of any of the embodiments, the enzyme responsible for hypermethylation is a multiprotein complex (PRC2, Polycomb repressive complex 2) and its catalytic domain the methyltransferase EZH2.

In one aspect of any of the embodiments, the chromatin or chromosomal protein is H3.

As described herein, in vascular diseases including thoracic aortic aneurysms, the EZH2-containing polycomb repressive complex 2 (PRC2) mediates addition of histone 3 lysine 27 trimethylation marks to the promoter and gene body of aortic genes thereby preventing transcription factor access to chromatin. As described herein, treatment with the EZH2 inhibitor GSK343 derepresses contractile protein expression by allowing transcription factors (such as SMAD3) access to chromatin.

In one aspect of any of the embodiments, the compound or drug (or combination of said compounds or drugs) inhibits PRC2 complex methyltransferase catalytic activity.

In one aspect of any of the embodiments, the compound or drug that inhibits methyltransferase EZH2 is GSK343.

In one aspect of any of the embodiments, the combination of compounds or drugs is GSK343 and Losartan.

A composition for preventing or treating a vascular disease, the composition comprising administering to a subject in need thereof, a therapeutically effective amount of at least one agent that targets transcriptional silencing of vascular smooth muscle cell cytoskeletal proteins, thereby preventing or treating the vascular disease.

In one aspect of any of the embodiments, the vascular disease is selected from a cardiovascular disease (CVD) including but not limited to atherosclerosis, vascular calcification, calciphylaxis, neointimal stenosis, and arterial aneurism.

In one aspect of any of the embodiments, provided herein is a method of preventing or treating a vascular disease, the method comprising administering to to a subject in need thereof, a therapeutically effective amount of at least one agent that inhibits the activity of the HDAC9 complex or PRC2 complex.

In one aspect of any of the embodiments, the vascular disease is a cardiovascular disease (CVD) selected from the group consisting of atherosclerosis, vascular calcification, calciphylaxis, neointimal stenosis, and arterial aneurism.

In one aspect of any of the embodiments, at least one agent inhibits the activity of Polycomb repressive complex 2 (PRC2).

In one aspect of any of the embodiments, at least one agent inhibits the Histone Deacetylase 9 (HDAC9) complex.

In one aspect of any of the embodiments, at least one agent is an inhibitor of EZH2.

In one aspect of any of the embodiments, at least one agent is an inhibitor of an enzyme of Enzyme Comission (E.C.) number 2.1.1.43.

In one aspect of any of the embodiments, at least one agent is an inhibitor of HDAC9.

In one aspect of any of the embodiments, at least one agent is an inhibitor of MALAT1

In one aspect of any of the embodiments, the enzyme is an enzyme of Enzyme Comission (E.C.) number 3.5.1.98.

In one aspect of any of the embodiments, the inhibitor is an inhibitory nucleic acid or a small molecule inhibitor.

As used herein, "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RT-PCR with primers can be used to determine the level of RNA and Western blotting with an antibody can be used to determine the level of a polypeptide. The activity of, e.g. of the HDAC9 complex or PRC2 complex, can be determined using methods known in the art. In some embodiments of any of the aspects, the inhibitor can be an inhibitory nucleic acid; an aptamer; an antibody reagent; an antibody; or a small molecule. An inhibitor of a target described herein can inhibit the activity, expression, or accumulation of the target polypeptide.

Inhibitors of, e.g., of the PRC2 complex, can include inhibitors that act directly on the target itself (e.g., that bind one of the components of the PRC2 complex, e.g. to the EZH2 protein or transcript, e.g., direct inhibitors) or inhibitors that act indirectly on the target, e.g., directly on one or more regulators of the PRC2 complex.

Inhibitors of, e.g., of the HDAC9 complex, can include inhibitors that act directly on the target itself (e.g., that bind one of the components of the HDAC9 complex, e.g. to the MALAT1 protein or transcript, e.g., direct inhibitors) or inhibitors that act indirectly on the target, e.g., directly on one or more regulators of the PRC2 complex.

In one aspect of any of the embodiments, provided herein is a method of treating a vascular disease in a subject in need thereof, the method comprising administering an inhibitor of EZH2.

In one aspect of any of the embodiments, provided herein is a method of treating a vascular disease in a subject in need thereof, the method comprising administering an inhibitor of HDAC9.

In some embodiments of any of the aspects two or more individual reagents of an inhibitor of an epigenetic regulator protein can be administered, e.g. an inhibitor of EZH2 and/or an inhibitor of an enzyme with the biological activity of Enzyme Comission (E.C.) number 2.1.1.43 and/or HDAC9 and/or an inhibitor of an enzyme with the biological activity of Enzyme Comission (E.C.) number 3.5.1.98, e.g., one or two different inhibitors of an epigenetic regulator protein.

In one aspect of any of the embodiments, provided herein is a method of treating a vascular disease in a subject in need thereof, the method comprising administering an inhibitor of EZH2.

In some embodiments of any of the aspects, the inhibitor is an inhibitory nucleic acid, an aptamer, a genome editing system, an antisense oligonucleotide, shRNA, and an siRNA, an inhibitory antibody reagent, an antibody, a peptide, or a small molecule.

The term "RNAi" or "siRNA" or "shRNA" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA. Exemplary RNAi sequences target human EZH2 (e.g. SEQ ID NOs: 9) include but are not limited to the following RNAi sequences, e.g. TRCN0000040074 (Sigma Aldrich): 5'CCGGGCTAGGTTAATTGGGAC-CAAACTCGAGTTTGGTCCCAAT-TAACCTAGCTTTTTG3' (SEQ ID NO: 16); and/or TRCN0000040075 (Sigma Aldrich): 5'CCGGC-CAACACAAGTCATCCCATTACTCGAGTAATGG-GATGACTTGTGTTGGTTTTTG3' (SEQ ID NO: 17); and/or TRCN0000040077 (Sigma Aldrich): 5'CCGGCCCAACATAGATGGACCAAATCTCGAGAT-TTGGTCCATCTATGTTGGGTTTTTG3' (SEQ ID NO: 18).

In some embodiments of any of the aspects, the agent that inhibits the activity of the HDAC9 complex or PRC2 complex is an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides as described herein are complementary nucleic acid sequences designed to hybridize under cellular conditions to a gene. Thus, oligonucleotides are chosen that are sufficiently complementary to the target, i.e., that hybridize sufficiently well and with sufficient specificity in the context of the cellular environment, to give the desired effect. For example, an antisense oligonucleotide that inhibits activity and/or levels of the HDAC9 complex and/or the PRC2 complex directly or indirectly may comprise at least 2, at least 5, at least 10, at least 15, at least 20, at least 25, at least 30, at least 40, at least 50 or more bases complementary to a portion of the coding sequence of the human EZH2, Suz12, Eeed, RbAp46/48, MALAT1, BRG1 gene (e.g., SEQ ID NOs: 3-15), respectively.

In some embodiments of any of the aspects, inhibition of the HDAC9 complex is achieved with inhibitory nucleic acids against MALAT1.

In some embodiments of any of the aspects, the inhibitory nucleic acid is directed against MALAT1 has the sequence of SEQ ID NO: 1 or 2. In some embodiments of any of the aspects, the inhibitory nucleic acid against MALAT1 is a GapmeR targeting the long non-coding RNA (lncRNA) MALAT1 to dissociate the complex which recruits PRC2 to chromatin.

As used herein, the term "GapmeRs" refers to small antisense DNAs with modified end nucleotides that recruit RNAse H for target transcript degradation. In some embodiments of any of the aspects, peripherally injected GapmeR can be used to assay repression of MALAT1 in arterial tissue.

In some embodiments of any of the aspects, inhibition of the HDAC9 complex is achieved with inhibitory nucleic acids against MALAT1 is effective at controlling vascular disease including but not limited to arterial stenosis.

As used herein, the term "small molecule" refers to a organic or inorganic molecule, either natural (i.e., found in nature) or non-natural (i.e., not found in nature), which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem. Soc. 120:8565, 1998; incorporated herein by reference). In certain other preferred embodiments, natural-product-like small molecules are utilized.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals including humans. For example, a compound, such as a test compound, such as a drug, can inhibits the activity of the HDAC9 complex or PRC2 complex as provided herein.

The term "derivative" as used herein means any chemical, conservative substitution, or structural modification of an agent. The derivative can improve characteristics of the agent or small molecule such as pharmacodynamics, pharmacokinetics, absorption, distribution, delivery, targeting to a specific receptor, or efficacy. For example, for a small molecule, the derivative can consist essentially of at least one chemical modification to about ten modifications. The derivative can also be the corresponding salt of the agent. The derivative can be the pro-drug of the small molecule as provided herein.

In one aspect of any of the embodiments, the EZH2 inhibitor is selected from the group consisting of: GSK-343; Losartan, tazemetostat, CPI-1205 and PF-06821497.

In one aspect of any of the embodiments, provided herein is a method of preventing or treating a vascular disease, the method comprising administering to to a subject in need thereof, a therapeutically effective amount of the small molecule GSK-343.

In one aspect of any of the embodiments, the small molecule GSK-343 inhibits the activity of the HDAC9 complex or PRC2 complex.

In one aspect of any of the embodiments, small molecule GSK-343 prevents PRC2-mediated transcriptional repression.

In one aspect of any of the embodiments, provided herein is a method for treating vascular disease, the method comprising administering to a subject in need thereof small molecule GSK-343, which can be found in US20170105997A1, incorporated herein by reference only.

As used herein, the term "small molecule GSK-343" is a potent, specific inhibitor of the histone H3-lysine 27 (H3K27) methyltransferase EZH2. GSK-343 inhibits EZH2 enzymatic activity with an $IC_{50}$ of 4 nM. The compound displays 60-fold selectivity for EZH2 vs. EZH1, and 1000 fold or greater selectivity against other histone methyltransferases. The $IC_{50}$ for inhibition of H3K27 methylation is <200 nM in HCC1806 cells.

The structure of small molecule EZH2 inhibitor GSK-343 is as follows:

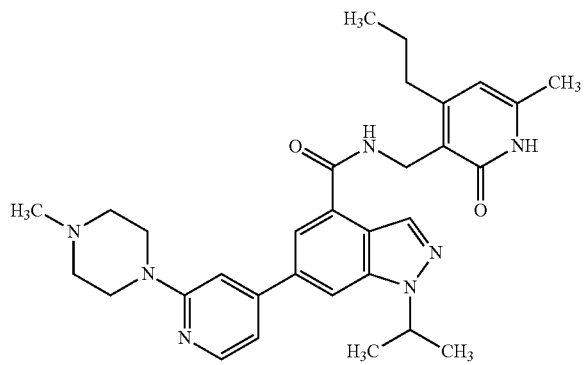

In one aspect of any of the embodiments, provided herein is a method of preventing or treating a vascular disease, the method comprising administering to to a subject in need thereof, a therapeutically effective amount of the small molecule Losartan.

In one aspect of any of the embodiments, the small molecule Losartan inhibits the activity of the HDAC9 complex or PRC2 complex.

In one aspect of any of the embodiments, small molecule Losartan prevents PRC2-mediated transcriptional repression.

As used herein, the term "Losartan" refers to an angiotensin II receptor blocker used in the therapy of hypertension and diabetic nephropathy. Losartan is associated with a low rate of transient serum aminotransferase elevations and has been linked to rare instances of acute liver injury.

The structure of small molecule EZH2 inhibitor Losartan is as follows:

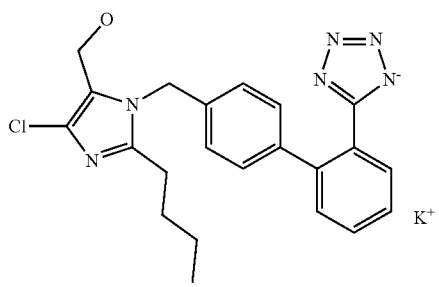 [SMILES: CCCCc1nc(Cl)c(CO)n1Cc1ccc(-c2ccccc2-c2nnn[n-]2)cc1 ; [K+]]

In one aspect of any of the embodiments, provided herein is a method of preventing or treating a vascular disease, the method comprising administering to to a subject in need thereof, a therapeutically effective amount of the small molecule Tazemetostat.

In one aspect of any of the embodiments, the small molecule Tazemetostat inhibits the activity of the HDAC9 complex or PRC2 complex.

In one aspect of any of the embodiments, small molecule Tazemetostat prevents PRC2-mediated transcriptional repression.

As used herein the term "Tazesmetostat" refers to an experimental cancer drug that acts as a potent selective EZH2 inhibitor.

The structure of the small molecule EZH2 inhibitor Tazemetostat is as follows:

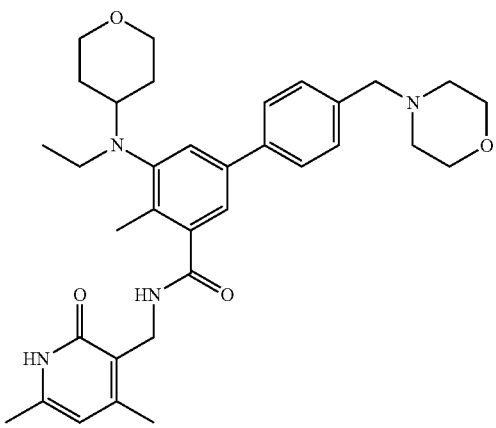 [SMILES: CCN(c1cc(-c2ccc(CN3CCOCC3)cc2)cc(C(=O)NCc2c(C)cc(C)[nH]c2=O)c1C)C1CCOCC1]

In one aspect of any of the embodiments, provided herein is a method of preventing or treating a vascular disease, the method comprising administering to to a subject in need thereof, a therapeutically effective amount of the small molecule CPI-1205.

In one aspect of any of the embodiments, provided herein is a method for treating vascular disease, the method comprising administering to a subject in need thereof small molecule CPI-1205, which can be found in WO2018081530A1, incoporated herein by reference only.

In one aspect of any of the embodiments, the small molecule CPI-1205 inhibits the activity of the HDAC9 complex or PRC2 complex.

In one aspect of any of the embodiments, small molecule CPI-1205 prevents PRC2-mediated transcriptional repression.

As used herein the term "Tazesmetostat" refers to an experimental cancer drug that acts as a potent selective EZH2 inhibitor.

The structure of small molecule EZH2 inhibitor CPI-1205 is as follows:

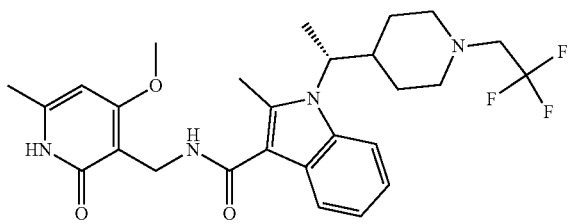 [SMILES: COc1cc(C)[nH]c(=O)c1CNC(=O)c1c(C)n([C@H](C)C2CCN(CC(F)(F)F)CC2)c2ccccc12]

In one aspect of any of the embodiments, provided herein is a method of preventing or treating a vascular disease, the method comprising administering to to a subject in need thereof, a therapeutically effective amount of the small molecule PF-06821497.

In one aspect of any of the embodiments, the small molecule PF-06821497 inhibits the activity of the HDAC9 complex or PRC2 complex.

In one aspect of any of the embodiments, small molecule PF-06821497 prevents PRC2-mediated transcriptional repression.

As used herein the term "PF-06821497" refers to an experimental cancer drug that acts as a potent selective EZH2 inhibitor.

The structure of the small molecule EZH2 inhibitor PF-06821497 is as follows:

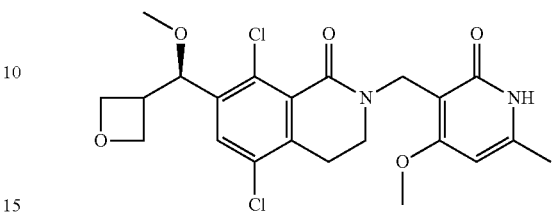

Disclosed herein are compositions for the treatment of vascular disease in a subject by administration of a unit dosage of an agent that that targets the epigenetic regulation of gene expression of vascular smooth muscle cell cytoskeletal proteins for the treatment of vascular diseases.

In some embodiments of any of the aspects, a composition comprises an inhibitor of an enzyme with the biological activity of Enzyme Comission (E.C.) number 2.1.1.43.

In another embodiment, a composition comprises an inhibitor of an enzyme with the biological activity of Enzyme Comission (E.C.) number 3.5.1.98.

Any of the compounds that inhibit EZH2 and/or any enzyme with the biological activity of Enzyme Comission (E.C.) number 2.1.1.43 including but not limited to Tazemetostat, CPI-1205, PF-06821497, Losartan and GSK343, may be tested for the ability to ameliorate cardiovascular disease symptoms. Cell-based and animal model-based assays for the identification of compounds exhibiting such an ability to ameliorate cardiovascular disease symptoms are described below.

Any of the compounds that inhibit HDAC9 and/or an enzyme with the biological activity of Enzyme Comission (E.C.) number 3.5.1.98 including but not limited to TMP269, Quisinostat, CUDC-101, Pracinostat (SB939), CUDC-907 may be tested for the ability to ameliorate cardiovascular disease symptoms. Cell-based and animal model-based assays for the identification of compounds exhibiting such an ability to ameliorate cardiovascular disease symptoms are described below.

The compositions and methods described herein can be administered to a subject having or diagnosed as having one of the conditions described herein. In some embodiments of any of the aspects, the methods described herein comprise administering an effective amount of compositions described herein, e.g. an engineered cellular composition to a subject in order to alleviate a symptom of a condition described herein. In some embodiments of any of the aspects, a therapeutically effective dose of the composition is administered. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to parenteral, intravenous, intramuscular, subcutaneous, transdermal, airway (aerosol), pulmonary, cutaneous, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g. for tumor size and/or inflammatory markers, among others. The dosage can be determined by a physician and adjusted, as necessary, to suit observed effects of the treatment.

In some embodiments of any of the aspects, a composition described herein can be a pharmaceutical composition. In some embodiments of any of the aspects, the technology described herein relates to a pharmaceutical composition comprising an engineered cellular composition as described herein, and optionally a pharmaceutically acceptable carrier. In some embodiments of any of the aspects, the active ingredients of the pharmaceutical composition comprise an engineered cellular composition as described herein. In some embodiments of any of the aspects, the active ingredients of the pharmaceutical composition consist essentially of an engineered cellular composition as described herein. In some embodiments of any of the aspects, the active ingredients of the pharmaceutical composition consist of an engineered cellular composition as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, as described herein.

In some embodiments of any of the aspects, the pharmaceutical composition comprising an engineered cellular composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry or lyophilized products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an engineered cellular composition as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, the engineered cellular composition described herein is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include beta blockers including metoprolol (Lopressor, Toprol-XL), atenolol (Tenormin) and/or bisoprolol (Zebeta); and/or angiotensin II receptor blockers include losartan (Cozaar), valsartan (Diovan) and olmesartan (Benicar); and/or statins include atorvastatin (Lipitor), lovastatin (Altoprev) and/or simvastatin (Zocor) derivatives of any of the above.

In addition, the methods of treatment can further include the use of radiation or radiation therapy. Further, the methods of treatment can further include the use of surgical treatments.

By way of non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g., endorphins, enkephalins and dynorphin), steroids, analgesics, barbiturates, oxycodone, morphine, lidocaine and the like.

In certain embodiments, an effective dose of a composition comprising an engineered cellular composition as described herein can be administered to a patient once. In certain embodiments, an effective dose of a composition can be administered to a patient repeatedly. In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an engineered cellular composition as described herein can be administered over a period of time, such as over a 5 minute, 10 minute, 15 minute, 20 minute, or 25 minute period.

The dosage ranges for the administration of the compositions described herein, according to the methods described herein depend upon, for example, the potency of the cells, and the extent to which symptoms, markers, or indicators of a condition described herein are desired to be reduced, for example the percentage reduction desired for tumor growth or the extent to which, for example, wound healing are desired to be induced. The dosage should not be so large as to cause adverse side effects, such as excessive inflammation or immunosuppression. Generally, the dosage will vary with the age, condition, and sex of the patient and can be determined by one of skill in the art. The dosage can also be adjusted by the individual physician in the event of any complication.

The efficacy of an engineered cellular composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g., tumor growth, tumor size, inflammation, wound size, etc.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In certain embodiments, cellular assays can be used for the measurement of the prevention and treatment of cardiovascular diseases symptoms. Cell systems may be exposed to a compound, suspected of exhibiting an ability to ameliorate, prevent or treat cardiovascular disease symptoms, at a sufficient concentration and for a time sufficient to elicit such an amelioration of cardiovascular disease symptoms in the exposed cells.

In another embodiment, cell systems may be exposed to a compound that inhibit EZH2 and/or any enzyme with the biological activity of Enzyme Comission (E.C.) number 2.1.1.43 including but not limited to Tazemetostat, CPI-1205, PF-06821497, Losartan and GSK343 suspected of exhibiting an ability to ameliorate cardiovascular disease symptoms, at a sufficient concentration and for a time sufficient to elicit such an amelioration of cardiovascular disease symptoms in the exposed cells.

In another embodiment, cell systems may be exposed to a compound that inhibit HDAC9 and/or an enzyme with the biological activity of Enzyme Comission (E.C.) number 3.5.1.98 including but not limited to TMP269, Quisinostat, CUDC-101, Pracinostat (SB939), CUDC-907, suspected of exhibiting an ability to ameliorate cardiovascular disease symptoms, at a sufficient concentration and for a time sufficient to elicit such an amelioration of cardiovascular disease symptoms in the exposed cells.

After exposure, the cells are examined to determine whether one or more of the cardiovascular disease cellular phenotypes has been altered to resemble a more normal or more wild type, non-cardiovascular disease phenotype. For example, and not by way of limitation, in the case of monocytes, such more normal phenotypes may include but are not limited to decreased rates of LDL uptake, adhesion to endothelial cells, transmigration, foam cell formation, fatty streak formation, and production by foam cells of growth factors such as bFGF, IGF-I, VEGF, IL-1, M-CSF, TGFO, TGFa, TNFα, HB-EGF, PDGF, IFN-γ, and GM-CSF.

One cellular system includes smooth muscle cells (Navab et al., 1988, J. Clin. Invest., 82:1853). In this system, a multilayer of human aortic smooth muscle cells is grown on a micropore filter covered with a gel layer of native collagen, and a monolayer of human aortic endothelial cells was grown on top of the collagen layer. Exposure of this coculture to human monocytes in the presence of chemotactic factor rFMLP results in monocyte attachment to the endothelial cells followed by migration across the endothelial monolayer into the collagen layer of the subendothelial space. This type of culture can also be treated with LDL to generate foam cells. The foam cells can then be harvested and their pattern of gene expression compared to that of untreated cells using methods know to those skilled in the art. Differentially expressed genes can be detected, by comparing the pattern of gene expression between the experimental and control conditions.

Additionally, gene expression patterns may be utilized to assess the ability of a compound to ameliorate cardiovascular disease symptoms. For example, the expression pattern of one or more fingerprint genes may form part of a "fingerprint profile" which may be then be used in such an assessment. "Fingerprint profile", as used herein, refers to the pattern of mRNA expression obtained for a given tissue or cell type under a given set of conditions. Such conditions may include, but are not limited to, atherosclerosis, ischemia/reperfusion, hypertension, restenosis, and arterial inflammation.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method to prevent or treat a thoracic aortic aneurysm in a patient comprised of administering to said patient a therapeutically effective dose of a compound or drug (or combination of said compounds or drugs) which targets the epigenetic regulation of gene expression of vascular smooth muscle cell cytoskeletal proteins.
2. The method of paragraph 1 wherein the cytoskeletal protein is SM22a encoded by the TAGLN gene.
3. The method of paragraph 1 wherein the epigenetic regulatory target is a multiprotein complex (PRC2, Polycomb repressive complex 2) responsible for gene silencing through its catalytic activity or hypermethylation of chromatin at vascular smooth muscle gene loci.
4. The method of paragraph 3 wherein the chromatin or chromosomal protein is H3.
5. The method of paragraph 3 or 4 wherein the enzyme responsible for hypermethylation is a multiprotein complex (PRC2, Polycomb repressive complex 2) and its catalytic domain the methyltransferase EZH2.
6. The method any of paragraphs 1-5 wherein the compound or drug (or combination of said compounds or drugs) inhibits PRC2 complex methyltransferase catalytic activity.
7. The method of paragraph 6 wherein the compound or drug that inhibits methyltransferase EZH2 is GSK343.
8. The method of paragraphs 6 or 7 wherein the combination of compounds or drugs is GSK343 and Losartan.
9. A method of preventing or treating a vascular disease, the method comprising administering to a subject in need thereof, a therapeutically effective amount of at least one agent that inhibits the activity of the HDAC9 complex or PRC2 complex.
10. The method of paragraph 9, wherein the vascular disease is a cardiovascular disease (CVD).
11. The method of paragraph 10, wherein the CVD is selected from the group consisting of atherosclerosis, vascular calcification, calciphylaxis, neointimal stenosis, and arterial aneurism.
12. The method of any of paragraphs 9-11, wherein the at least one agent inhibits the activity of Polycomb repressive complex 2 (PRC2).
13. The method of any of paragraphs 9-11, wherein the at least one agent inhibits the Histone Deacetylase 9 (HDAC9) complex.
14. The method of any of paragraphs 9-13, wherein the at least one agent is an inhibitor of EZH2.
15. The method of any of paragraphs 19-14, wherein the at least one agent is an inhibitor of an enzyme of Enzyme Comission (E.C.) number 2.1.1.43.
16. The method of any of paragraphs 9-15, wherein the at least one agent is an inhibitor of HDAC9.
17. The method of any of paragraphs 9-16, wherein the at least one agent is an inhibitor of MALAT1.
18. The method of paragraph 9, wherein the enzyme is an enzyme of Enzyme Comission (E.C.) number 3.5.1.98.
19. The method of any of paragraphs 9-18, wherein the inhibitor is an inhibitory nucleic acid or a small molecule inhibitor.
20. A composition to prevent or treat a thoracic aortic aneurysm in a patient comprised of administering to said patient a therapeutically effective dose of a compound or drug (or combination of said compounds or drugs) which targets the epigenetic regulation of gene expression of vascular smooth muscle cell cytoskeletal proteins.
21. The composition of paragraph 20 wherein the cytoskeletal protein is SM22a encoded by the TAGLN gene.
22. The composition of paragraph 20 wherein the epigenetic regulatory target is a multiprotein complex (PRC2, Polycomb repressive complex 2) responsible for gene silencing through its catalytic activity or hypermethylation of chromatin at vascular smooth muscle gene loci.
23. The composition of paragraph 20 wherein the chromatin or chromosomal protein is H3.
24. The composition of paragraph 20 or 22 wherein the enzyme responsible for hypermethylation is a multiprotein complex (PRC2, Polycomb repressive complex 2) and its catalytic domain the methyltransferase EZH2.
25. The composition any of paragraphs 20-24 wherein the compound or drug (or combination of said compounds or drugs) inhibits PRC2 complex methyltransferase catalytic activity.
26. The composition of paragraph 25 wherein the compound or drug that inhibits methyltransferase EZH2 is GSK343.
27. The composition of paragraphs 20 or 22 wherein the combination of compounds or drugs is GSK343 and Losartan.
28. A composition of preventing or treating a vascular disease, the composition comprising administering to a subject in need thereof, a therapeutically effective amount of at least one agent that inhibits the activity of the HDAC9 complex or PRC2 complex.
29. The composition of paragraph 28, wherein the vascular disease is a cardiovascular disease (CVD).
30. The composition of paragraph 28, wherein the CVD is selected from the group consisting of atherosclerosis, vascular calcification, calciphylaxis, neointimal stenosis, and arterial aneurism.
31. The composition of any of paragraphs 28-30, wherein the at least one agent inhibits the activity of Polycomb repressive complex 2 (PRC2).
32. The composition of any of paragraphs 28-31, wherein the at least one agent inhibits the Histone Deacetylase 9 (HDAC9) complex.
33. The composition of any of paragraphs 28-32, wherein the at least one agent is an inhibitor of EZH2.
34. The composition of any of paragraphs 28-33, wherein the at least one agent is an inhibitor of an enzyme of Enzyme Comission (E.C.) number 2.1.1.43.
35. The composition of any of paragraphs 28-34, wherein the at least one agent is an inhibitor of HDAC9.
36. The composition of any of paragraphs 28-35, wherein the at least one agent is an inhibitor of MALAT1.
37. The composition of paragraph 28-36, wherein the enzyme is an enzyme of Enzyme Comission (E.C.) number 3.5.1.98.
38. The composition of any of paragraphs 28-37, wherein the inhibitor is an inhibitory nucleic acid or a small molecule inhibitor.
39. A composition for preventing or treating a vascular disease, the composition comprising administering to a subject in need thereof, a therapeutically effective amount of at least one agent that targets transcriptional silencing of vascular smooth muscle cell cytoskeletal proteins, thereby preventing or treating the vascular disease.
40. The composition of paragraph 39, wherein the vascular disease is selected from a cardiovascular disease (CVD).
41. The composition of paragraph 39, wherein the CVD is selected from atherosclerosis, vascular calcification, calciphylaxis, neointimal stenosis, and arterial aneurism.
42. The composition of paragraph 39-41, wherein the transcriptional silencing comprises a multiprotein complex.
43. The composition of paragraph 42, wherein the multiprotein complex comprises a Polycomb repressive complex.
44. The composition of paragraph 42, wherein the multiprotein complex comprises a Polycomb repressive complex 2 (PRC2).
45. The composition of paragraph 42, wherein the multiprotein complex comprises a Histone Deacetylase.
46. The composition of paragraph 42, wherein the multiprotein complex comprises Histone Deacetylase complex 9 (HDAC9).

47. The composition of paragraph 42, wherein the multiprotein complex comprises a catalytic subunit that induces transcriptional silencing at vascular smooth muscle gene loci.

48. The composition of paragraph 42 wherein the catalytic subunit induces gene silencing by hypermethylation.

49. The composition of paragraph 42-48, wherein the catalytic subunit is an enzyme.

50. The composition of paragraph 39, wherein the enzyme is methyltransferase EZH2.

51. The composition of paragraph 39, wherein the enzyme is an enzyme of Enzyme Comission (E.C.) number 2.1.1.43.

52. The composition of paragraph 39, wherein the enzyme induces transcriptional silencing by hypermethylation of chromatin at vascular smooth muscle gene loci.

53. The composition of paragraph 39, wherein the enzyme is a Histone Deacetylase.

54. The composition of paragraph 39, wherein the enzyme is Histone Deacetylase 9 (HDAC9).

55. The composition of paragraph 39, wherein the enzyme is an enzyme of Enzyme Comission (E.C.) 3.5.1.98.

56. The composition of paragraph 39, wherein the enzyme induces transcriptional silencing by hyperacetylation of chromatin at vascular smooth muscle gene loci.

57. The composition of any of paragraph 39-56, wherein the enzyme induces transcriptional silencing at vascular smooth muscle gene loci is selected from the group consisting of: EZH2; HDAC9.

58. The composition of paragraph 39, wherein the agent that induces transcriptional silencing at vascular smooth muscle gene loci is a EZH2 inhibitor.

59. The composition of paragraph 39, wherein the EZH2 inhibitor is selected from the group consisting of: GSK343 and Losartan.

60. The composition of paragraph 39 wherein the cytoskeletal protein is selected from the group consisting of SM22a; MMP-9; ACTA2, TAGLN, MYH11, SMTN.

Some embodiments of the technology described herein can be defined according to any of the following numbered paragraphs:

1. A method to prevent or treat a thoracic aortic aneurysm in a patient comprised of administering to said patient a therapeutically effective dose of a compound or drug (or combination of said compounds or drugs) which targets the epigenetic regulation of gene expression of vascular smooth muscle cell cytoskeletal proteins.

2. The method of claim 1 wherein the cytoskeletal protein is SM22a encoded by the TAGLN gene.

3. The method of claim 1 wherein the epigenetic regulatory target is a multiprotein complex (PRC2, Polycomb repressive complex 2) responsible for gene silencing through its catalytic activity or hypermethylation of chromatin at vascular smooth muscle gene loci.

4. The method of claim 3 wherein the chromatin or chromosomal protein is H3.

5. The method of claim 3 or 4 wherein the enzyme responsible for hypermethylation is a multiprotein complex (PRC2, Polycomb repressive complex 2) and its catalytic domain the methyltransferase EZH2.

6. The method any of claims 1-5 wherein the compound or drug (or combination of said compounds or drugs) inhibits PRC2 complex methyltransferase catalytic activity.

7. The method of claim 6 wherein the compound or drug that inhibits methyltransferase EZH2 is GSK343.

8. The method of claim 6 or 7 wherein the combination of compounds or drugs is GSK343 and Losartan.

EXAMPLES

Example 1: HDAC9 Complex Inhibition Improves Smooth Muscle Dependent Stenotic Vascular Disease Patients with heterozygous missense mutations in the ACTA2 or MYH11 genes are known to exhibit thoracic aortic aneurysm (TAA) and a risk of early onset aortic dissection. However, less common phenotypes involving arterial obstruction are also observed, including coronary and cerebrovascular stenotic disease. Herein the inventors show that the HDAC9 complex is involved in transcriptional silencing of contractile associated gene products, known to undergo downregulation in stenotic lesions. Furthermore, neointimal formation was inhibited in HDAC9 or MALAT1 deficient mice with preservation of contractile protein expression. Pharmacologic targeting of the HDAC9 complex through either MALAT1 antisense oligonucleotides or inhibition of the methyltransferase EZH2 (catalytic mediator recruited by the HDAC9 complex) reduced neointimal formation. In conclusion, the inventors report the implication of the HDAC9 complex in stenotic disease and demonstrate that pharmacologic therapy targeting epigenetic complexes can ameliorate arterial obstruction in an experimental system.

In diverse forms of vascular disease, smooth muscle cells (SMCs) are known to modulate cellular phenotype typified by down regulation of SMC-restricted contractile genes, and up regulate groups of genes involved in secretion of extracellular matrix, proliferation, and migration. This cellular behavior has been noted in important human diseases such as atherosclerosis, pulmonary hypertension, aortic and peripheral aneurysms, and restenosis after percutaneous arterial intervention (1, 2). Interestingly, the phenotype of thoracic aortic aneurysm (TAA) has been associated with human mutations in genes encoding these same SMC-restricted contractile genes. For instance, mutations in ACTA2, the gene encoding alpha-smooth muscle actin (a-SMA) are a major cause of nonsyndromic thoracic aortic aneurysm (3). Similarly, mutations in the gene MYH/1, encoding smooth muscle myosin heavy chain (smMHC), the binding partner of this actin isoform, causes a combined presentation of TAA and patent ductus arteriosis (4). Disruption of SMC contraction has been proposed as an underlying mechanism of TAA pathogenesis (5). However, in addition to extensive implication of the smooth muscle contractile dysfunction in aneurysmal disease, SMCs have also been extensively implicated in stenotic/ischemic vascular disease. In fact, individuals with ACTA2 mutations demonstrate pathologies such as coronary, pulmonary, or intracranial arterial stenosis (6, 7). MYH1/mutations have similarly been shown to cause a moya-moya like vascular pathology implicating this gene family in stenotic as well as aneurysmal disorders in humans (8). At the center of SMC phenotype modulation observed in vascular disease is a complex network of transcriptional pathways that coordinate repression of contractile elements such as a-SMA and smMHC and upregulation of synthetic and proliferative function (2, 9).

Recently, we described one such pathway active in TAA pathogenesis consisting of the histone deacetylase, HDAC9, the chromatin remodeling protein brahma-related gene 1 (BRG1), and the long noncoding RNA (lncRNA), MALAT1

(10). This HDAC9 chromatin-modifying complex is recruited to the promoters of VSMC-specific genes in the presence of gene products modified with TAA associated mutations. Amongst other functions, the HDAC9 complex recruits PRC2 (Polycomb repressive complex 2) to catalyze the trimethylation of Histone 3 on lysine 27 (H3K27) through EZH2, its enzymatic subunit.

In this study, the inventors investigated the role of the HDAC9 complex in modulating stenotic vascular disease using the murine carotid artery ligation model. The inventors find evidence of HDAC9 activation in medial and neointimal SMCs after ligation and binding of the HDAC9-containing complex to SMC contractile promoters correlated with transcriptional down regulation of contractile elements. Non-biased chromatin immunopreciptiation sequencing assays demonstrate multiple targets of the HDAC9 complex including cGMP, angiotensin, adrenergic and oxytocin signaling pathways. Utilizing these data, the inventors investigated inhibition of this pathway as a therapeutic modality. In experimental animals, inhibition of MALAT1 or HDAC9 expression arrested neointimal hyperplasia and partially normalized the transcriptional signature of the artery. Pharmacologic targeting of the HDAC9 complex with GapmeR antisense oligonucleotides against MALAT1 or small molecule inhibitor GSK343 was effective at controlling arterial stenosis. These data illuminate a critical role in HDAC9-mediated transcriptional silencing in the process of stenotic arterial disease and validate this pathway as a target for stenotic arterial disease.

Results:

Identification of HDAC9 targets in cells exposed to the R179H mutant allele of ACTA2

Figure 7A:
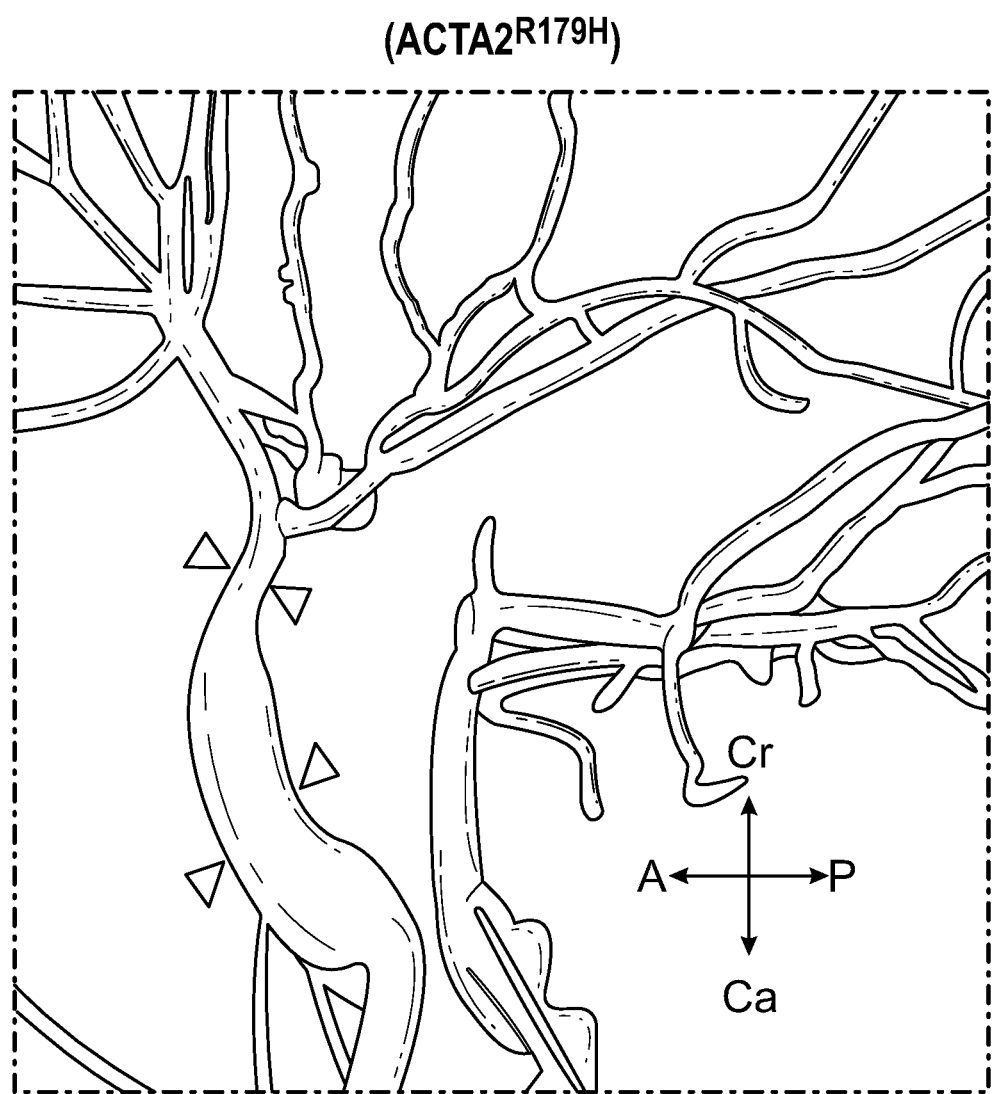
FIGS. 7A-7D demonstrates that ACTA2$^{R179H}$ mutation induces HDAC9-BRGI-MALAT1 complex interaction with genetic loci associated with VSMC contractility.
Figure 7B:
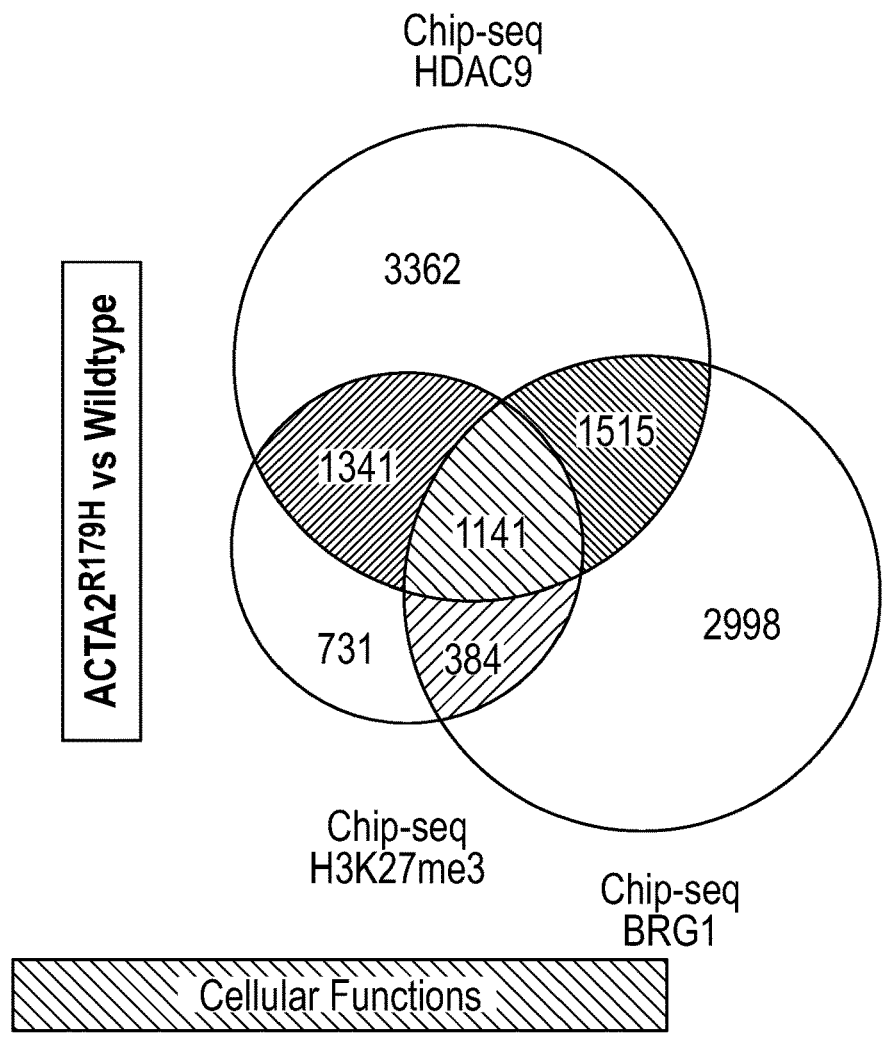
Figure 7C:
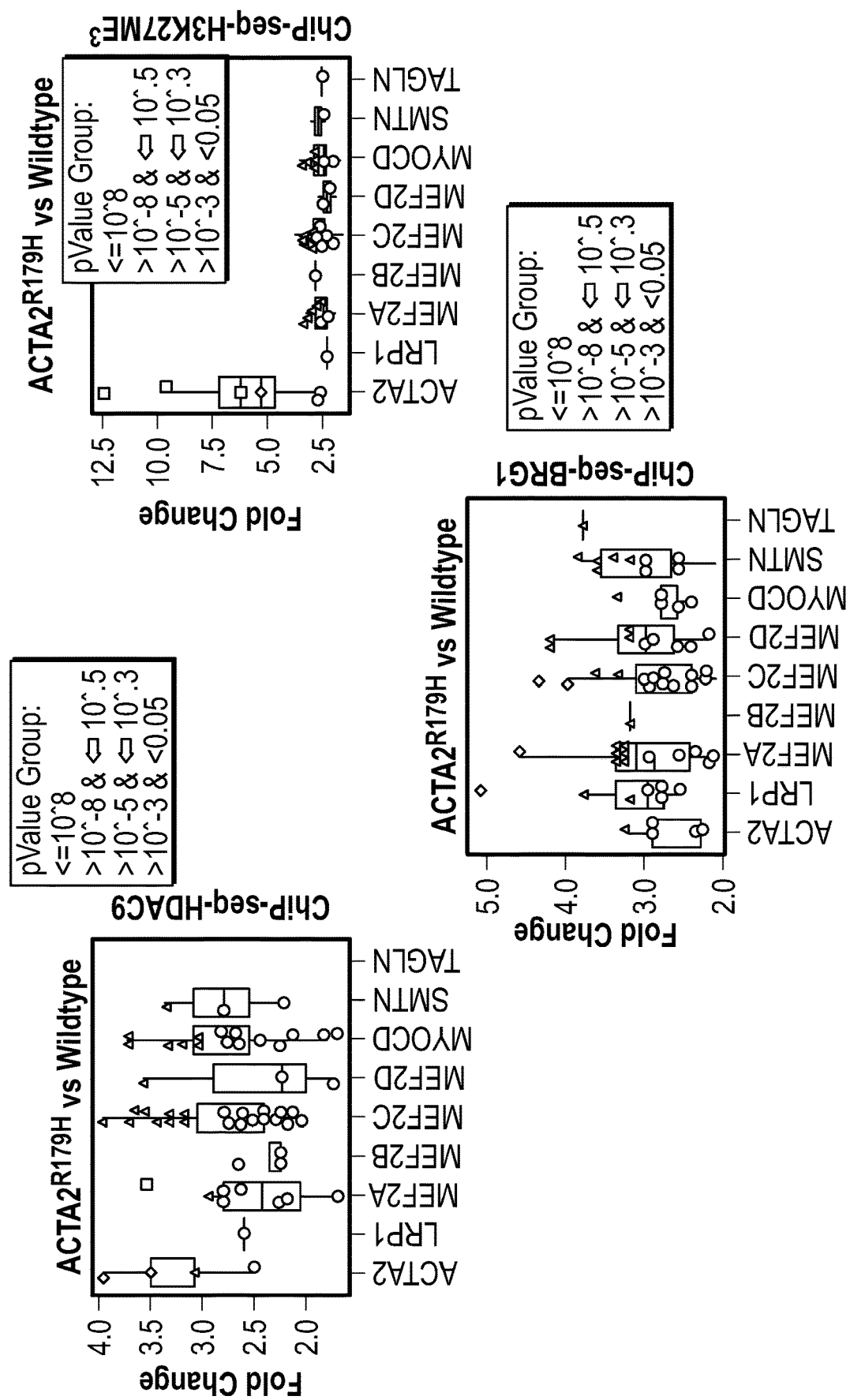
Figure 7D:
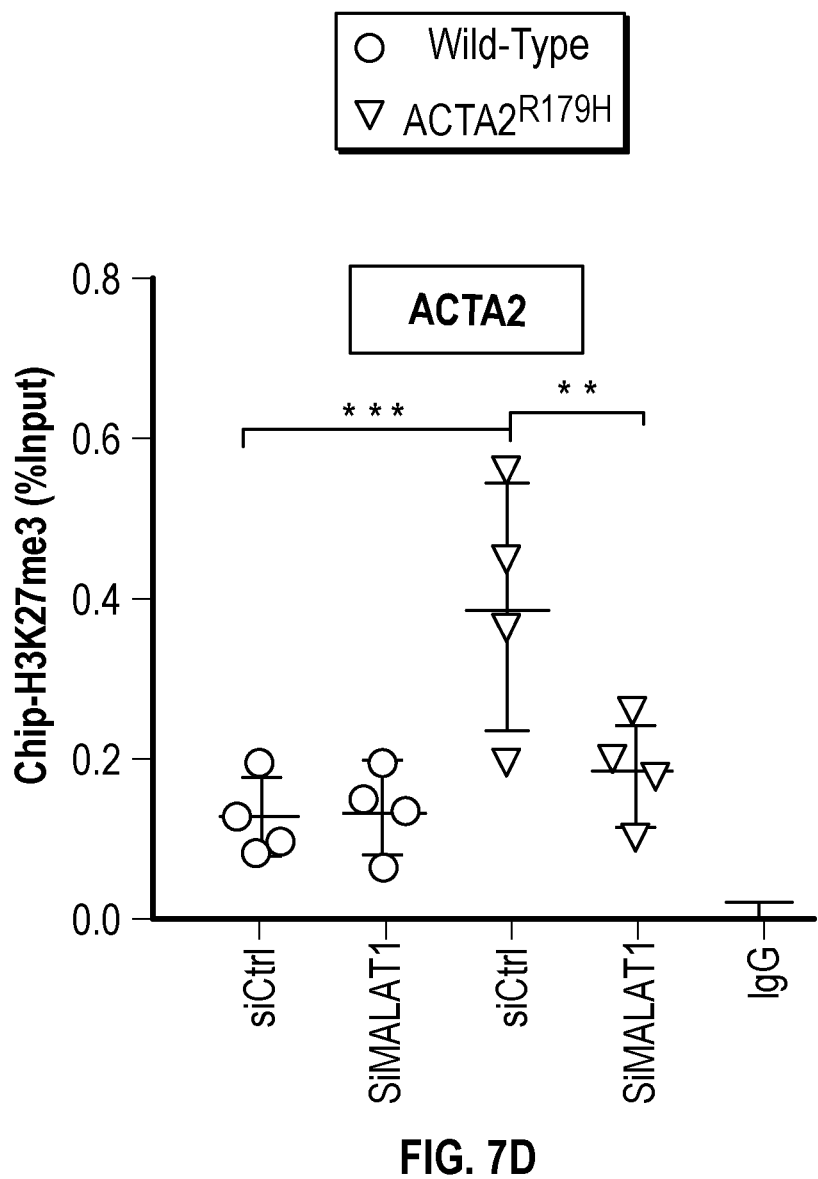

Previously the inventors have identified an epigenetic remodeling complex activated in vascular smooth muscle cells (HDAC9-BRG1-MALAT1) under the influence of genetic mutations that cause aortic aneurysm (10). However, some forms of genetically-triggered aortic disease (GTAD) such as those caused by mutations in the ACTA2 or MYI-1/'I gene also cause stenotic disease (6, 8). In particular, recurrent missense mutations in the codon for arginine 179 causes a severe form of smooth muscle dystrophy with both vascular aneurysms and stenoses (FIG. 7a) (7). To gain insight into genetic targets that may explain these phenotypic divergence, the inventors performed whole genome chromatin immunoprecipitation of HDAC9, BRG1, and the histone mark histone 3 trimethylated lysine 27 (H3K27me3) followed by next-generation sequencing analysis (ChIP-Seq) within VSMCs transduced with an ACTA2R179" allele. Analysis of genes enriched in cells expressing ACTA2R179" were sought by subtracting genes identified in baseline conditions. The results demonstrate 1141 genes identified by each of these three separate interactions (FIG. 7b and FIG. 7c and Supplemental Table 1 available on the world wide web at insight.jci.org/articles/view/124706/sd/2). In silico analysis of the core genes implicates several pathways involved in the modulation of VSMC force generation including cGMP-PKG1, renin, and adrenergic signaling in addition to genes comprising the VSMC contraction apparatus (FIG. 7c and Table 1). Interestingly, the ACTA2 locus itself demonstrated significant enrichment of H3K27me3 as well as association with HDAC9 and BRG1 (FIG. 7b). This regulation of the ACTA2 locus appears to be specific, as other alleles known to induce aneurysmal but not stenotic disease, such as TGFBR2G357W, fail to suppress the ACTA2 locus (FIG. 7). Applying multiple comparisons correction to our ChIP-seq data reveals ACTA2 as the only gene locus at genome wide significance (FIG. 7). To determine if this silencing was mediated by the HDAC9 complex we assayed for H3K27me3 modifications by targeted ChIP-qPCR at the ACTA2 promoter and found them to be MALAT1-dependent. (FIG. 7d).

TABLE 1

The KEGG pathway analysis of gene-loci enriched by HDAC9, BRG1 and H3k27me3 in ACTA2R179H cells.

| Annotation Cluster 1 | Enrichment Score: 1.38 | Count | P_Value | Benjamini |
|---|---|---|---|---|
| KEGG_PATHWAY | cGMP-PKG signaling pathway | 24 | 6.20E−06 | 1.50E−03 |
| KEGG_PATHWAY | Renin secretion | 14 | 1.10E−05 | 1.40E−03 |
| KEGG_PATHWAY | Adrenergic signaling in cardiomyocytes | 19 | 2.90E−04 | 1.40E−02 |
| KEGG_PATHWAY | Vascular smooth muscle contraction | 15 | 2.10E−03 | 5.20E−02 |
| KEGG_PATHWAY | Oxytocin signaling pathway | 16 | 1.10E−02 | 1.20E−01 |
| KEGG_PATHWAY | Aldosterone synthesis and secretion | 10 | 1.80E−02 | 1.70E−01 |
| KEGG_PATHWAY | Circadian entrainment | 11 | 1.90E−02 | 1.70E−01 |
| KEGG_PATHWAY | Cholinergic synapse | 12 | 2.10E−02 | 1.70E−01 |
| KEGG_PATHWAY | Insulin secretion | 10 | 2.40E−02 | 1.80E−01 |
| KEGG_PATHWAY | Long-term potentiation | 8 | 4.40E−02 | 2.50E−01 |
| KEGG_PATHWAY | Melanogenesis | 10 | 5.90E−02 | 3.20E−01 |
| KEGG_PATHWAY | Dopaminergic synapse | 10 | 1.80E−01 | 5.90E−01 |
| KEGG_PATHWAY | Glutamatergic synapse | 9 | 2.00E−01 | 6.10E−01 |
| KEGG_PATHWAY | Glucagon signaling pathway | 8 | 2.20E−01 | 6.10E−01 |
| KEGG_PATHWAY | Amphetamine addiction | 6 | 2.30E−01 | 6.20E−01 |
| KEGG_PATHWAY | Thyroid hormone synthesis | 6 | 2.60E−01 | 6.50E−01 |
| KEGG_PATHWAY | GnRH signaling pathway | 7 | 2.90E−01 | 6.80E−01 |
| KEGG_PATHWAY | Retrograde endocannabinoid signaling | 7 | 3.80E−01 | 7.60E−01 |
| KEGG_PATHWAY | GABAergic synapse | 6 | 4.10E−01 | 7.70E−01 |
| KEGG_PATHWAY | Cocaine addiction | 4 | 4.40E−01 | 7.80E−01 |
| KEGG_PATHWAY | Serotonergic synapse | 6 | 6.50E−01 | 8.90E−01 |
| KEGG_PATHWAY | Huntington's disease | 9 | 7.40E−01 | 9.20E−01 |
| KEGG_PATHWAY | Alcoholism | 7 | 8.80E−01 | 9.80E−01 |
| KEGG_PATHWAY | Alzheimer's disease | 5 | 9.70E−01 | 1.00E+00 |

TABLE 1-continued

The KEGG pathway analysis of gene-loci enriched
by HDAC9, BRG1 and H3k27me3 in ACTA2R179H cells.

| Annotation Cluster 2 | Enrichment Score: 1.38 | | Count | P_Value | Benjamini |
|---|---|---|---|---|---|
| KEGG_PATHWAY | Arrhythmogenic right ventricular cardiomyopathy (ARVC) | | 11 | 2.40E−03 | 5.30E−02 |
| KEGG_PATHWAY | Dilated cardiomyopathy | | 9 | 5.50E−02 | 3.10E−01 |
| KEGG_PATHWAY | Hypertrophic cardiomyopathy (HCM) | | 8 | 9.00E−02 | 4.20E−01 |
| KEGG_PATHWAY | Cardiac muscle contraction | | 5 | 5.10E−01 | 8.30E−01 |

| Annotation Cluster 3 | Enrichment Score: 1.22 | | Count | P_Value | Benjamini |
|---|---|---|---|---|---|
| KEGG_PATHWAY | Platelet activation | | 15 | 4.80E−03 | 7.70E−02 |
| KEGG_PATHWAY | Estrogen signaling pathway | | 12 | 9.40E−03 | 1.10E−01 |
| KEGG_PATHWAY | Cholinergic synapse | | 12 | 2.10E−02 | 1.70E−01 |
| KEGG_PATHWAY | Chagas disease (American trypanosomiasis) | | 10 | 7.10E−02 | 3.60E−01 |
| KEGG_PATHWAY | Amoebiasis | | 10 | 7.90E−02 | 3.80E−01 |
| KEGG_PATHWAY | Inflammatory mediator regulation of TRP channels | | 8 | 2.10E−01 | 6.00E−01 |
| KEGG_PATHWAY | Progesterone-mediated oocyte maturation | | 7 | 2.60E−01 | 6.50E−01 |
| KEGG_PATHWAY | Chemokine signaling pathway | | 10 | 5.80E−01 | 8.70E−01 |

| Annotation Cluster 4 | Enrichment Score: 1.11 | | Count | P_Value | Benjamini |
|---|---|---|---|---|---|
| KEGG_PATHWAY | AMPK signaling pathway | | 14 | 7.10E−03 | 8.50E−02 |
| KEGG_PATHWAY | Regulation of lipolysis in adipocytes | | 8 | 2.00E−02 | 1.60E−01 |
| KEGG_PATHWAY | Type II diabetes mellitus | | 7 | 3.00E−02 | 2.00E−01 |
| KEGG_PATHWAY | Insulin resistance | | 11 | 4.10E−02 | 2.40E−01 |
| KEGG_PATHWAY | Aldosterone-regulated sodium reabsorption | | 4 | 3.00E−01 | 6.80E−01 |
| KEGG_PATHWAY | Insulin signaling pathway | | 9 | 3.70E−01 | 7.60E−01 |
| KEGG_PATHWAY | Non-alcoholic fatty liver disease (NAFLD) | | 5 | 9.50E−01 | 9.90E−01 |

| Annotation Cluster 5 | Enrichment Score: 0.82 | | Count | P_Value | Benjamini |
|---|---|---|---|---|---|
| KEGG_PATHWAY | Circadian entrainment | | 11 | 1.90E−02 | 1.70E−01 |
| KEGG_PATHWAY | Salivary secretion | | 8 | 1.30E−01 | 5.20E−01 |
| KEGG_PATHWAY | Gap junction | | 8 | 1.40E−01 | 5.40E−01 |
| KEGG_PATHWAY | Long-term depression | | 6 | 1.70E−01 | 5.80E−01 |
| KEGG_PATHWAY | Gastric acid secretion | | 6 | 2.90E−01 | 6.80E−01 |
| KEGG_PATHWAY | Serotonergic synapse | | 6 | 6.50E−01 | 8.90E−01 |

| Annotation Cluster 6 | Enrichment Score: 0.53 | | Count | P_Value | Benjamini |
|---|---|---|---|---|---|
| KEGG_PATHWAY | Colorectal cancer | | 6 | 1.90E−01 | 6.00E−01 |
| KEGG_PATHWAY | Endometrial cancer | | 5 | 2.60E−01 | 6.50E−01 |
| KEGG_PATHWAY | Acute myeloid leukemia | | 4 | 5.30E−01 | 8.40E−01 |

| Annotation Cluster 7 | Enrichment Score: 0.47 | | Count | P_Value | Benjamini |
|---|---|---|---|---|---|
| KEGG_PATHWAY | Prostate cancer | | 8 | 1.40E−01 | 5.40E−01 |
| KEGG_PATHWAY | Pancreatic cancer | | 6 | 2.20E−01 | 6.10E−01 |
| KEGG_PATHWAY | Melanoma | | 6 | 2.70E−01 | 6.60E−01 |
| KEGG_PATHWAY | Chronic myeloid leukemia | | 6 | 2.80E−01 | 6.70E−01 |
| KEGG_PATHWAY | Central carbon metabolism in cancer | | 5 | 3.90E−01 | 7.60E−01 |
| KEGG_PATHWAY | Non-small cell lung cancer | | 4 | 5.30E−01 | 8.40E−01 |
| KEGG_PATHWAY | Choline metabolism in cancer | | 6 | 5.70E−01 | 8.60E−01 |
| KEGG_PATHWAY | Glioma | | 4 | 6.30E−01 | 8.80E−01 |

| Annotation Cluster 8 | Enrichment Score: 0.41 | | Count | P_Value | Benjamini |
|---|---|---|---|---|---|
| KEGG_PATHWAY | Prostate cancer | | 8 | 1.40E−01 | 5.40E−01 |
| KEGG_PATHWAY | Hepatitis B | | 8 | 5.80E−01 | 8.70E−01 |
| KEGG_PATHWAY | Viral carcinogenesis | | 10 | 6.90E−01 | 9.00E−01 |

| Annotation Cluster 9 | Enrichment Score: 0.37 | | Count | P_Value | Benjamini |
|---|---|---|---|---|---|
| KEGG_PATHWAY | Prolactin signaling pathway | | 6 | 2.70E−01 | 6.60E−01 |
| KEGG_PATHWAY | Jak-STAT signaling pathway | | 10 | 2.90E−01 | 6.80E−01 |
| KEGG_PATHWAY | Measles | | 4 | 9.60E−01 | 1.00E+00 |

TABLE 1-continued

The KEGG pathway analysis of gene-loci enriched by HDAC9, BRG1 and H3k27me3 in ACTA2R179H cells.

| Annotation Cluster 10 | Enrichment Score: 0.36 | Count | P_Value | Benjamini |
|---|---|---|---|---|
| KEGG_PATHWAY | Chagas disease (American trypanosomiasis) | 10 | 7.10E−02 | 3.60E−01 |
| KEGG_PATHWAY | Inflammatory mediator regulation of TRP channels | 8 | 2.10E−01 | 6.00E−01 |
| KEGG_PATHWAY | Renal cell carcinoma | 6 | 2.20E−01 | 6.10E−01 |
| KEGG_PATHWAY | Leukocyte transendothelial migration | 9 | 2.30E−01 | 6.20E−01 |
| KEGG_PATHWAY | Sphingolipid signaling pathway | 9 | 2.40E−01 | 6.30E−01 |
| KEGG_PATHWAY | Neurotrophin signaling pathway | 9 | 2.40E−01 | 6.30E−01 |
| KEGG PATHWAY | Progesterone-mediated oocyte maturation | 7 | 2.60E−01 | 6.50E−01 |
| KEGG_PATHWAY | Prolactin signaling pathway | 6 | 2.70E−01 | 6.60E−01 |
| KEGG_PATHWAY | HIF-1 signaling pathway | 7 | 3.60E−01 | 7.50E−01 |
| KEGG_PATHWAY | T cell receptor signaling pathway | 7 | 4.00E−01 | 7.70E−01 |
| KEGG_PATHWAY | TNF signaling pathway | 7 | 4.30E−01 | 7.80E−01 |
| KEGG_PATHWAY | VEGF signaling pathway | 4 | 5.90E−01 | 8.70E−01 |
| KEGG_PATHWAY | Osteoclast differentiation | 7 | 6.40E−01 | 8.90E−01 |
| KEGG_PATHWAY | Thyroid hormone signaling pathway | 6 | 6.70E−01 | 9.00E−01 |
| KEGG_PATHWAY | Toxoplasmosis | 6 | 7.00E−01 | 9.10E−01 |
| KEGG_PATHWAY | Fc epsilon RI signaling pathway | 3 | 8.60E−01 | 9.70E−01 |
| KEGG_PATHWAY | Pertussis | 3 | 8.90E−01 | 9.80E−01 |
| KEGG_PATHWAY | Hepatitis C | 4 | 9.60E−01 | 1.00E+00 |
| KEGG_PATHWAY | Toll-like receptor signaling pathway | 3 | 9.70E−01 | 1.00E+00 |
| KEGG_PATHWAY | Epstein-Barr virus infection | 5 | 9.90E−01 | 1.00E+00 |
| KEGG_PATHWAY | Influenza A | 4 | 9.90E−01 | 1.00E+00 |

Figure 8A:
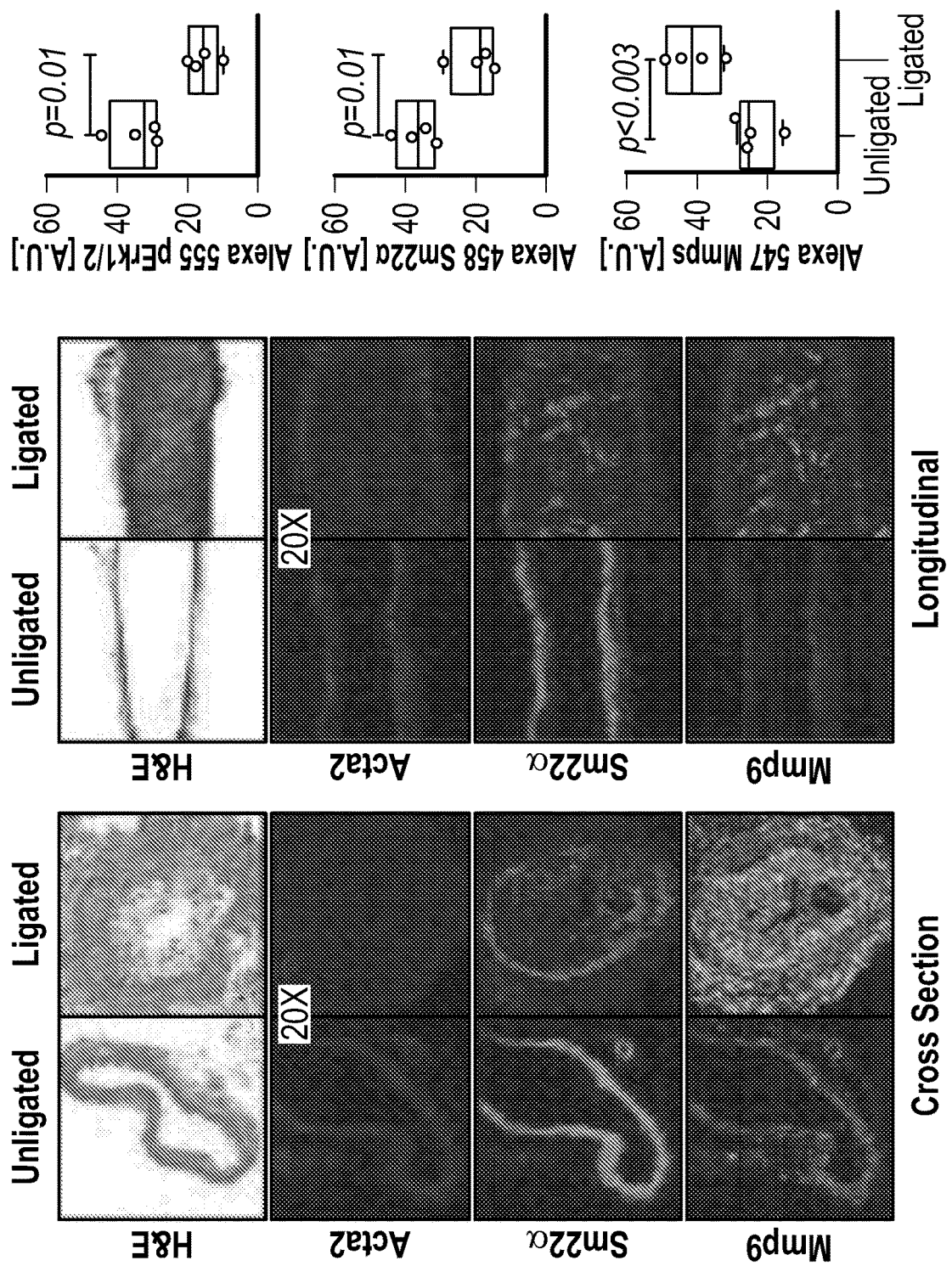
FIGS. 8A-8E demonstrates that an Experimental model of arterial stenosis induces Hdac9-Brgl-Malatl complex formation.
Figure 8B:
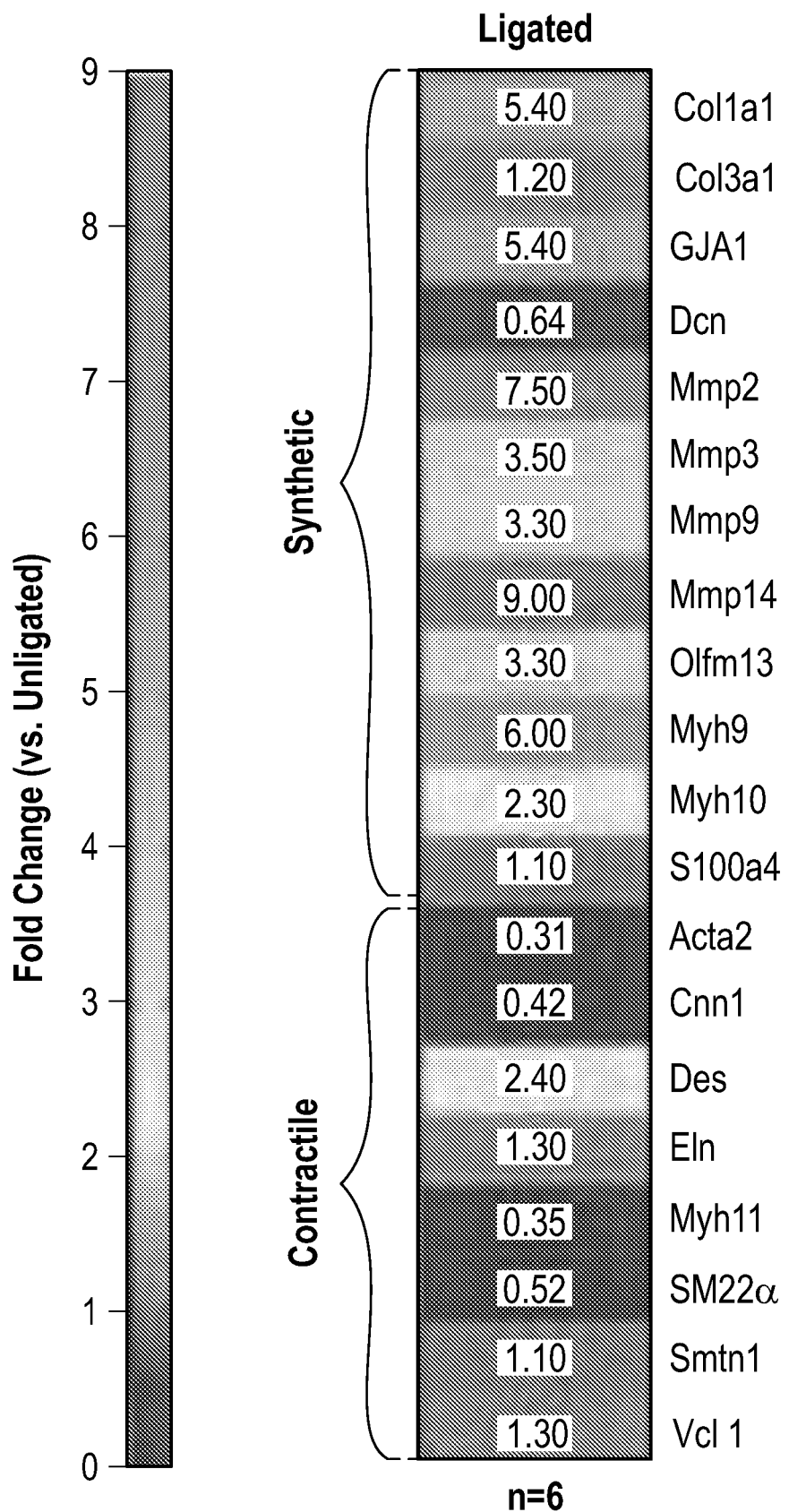
Figure 8C:
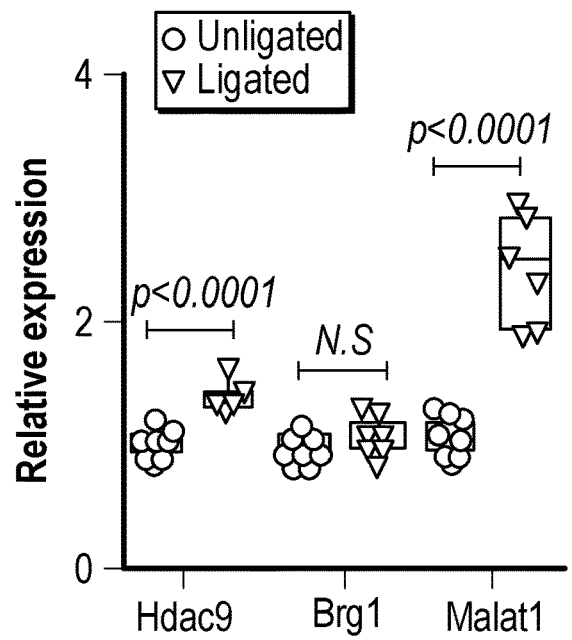
Figure 8D:
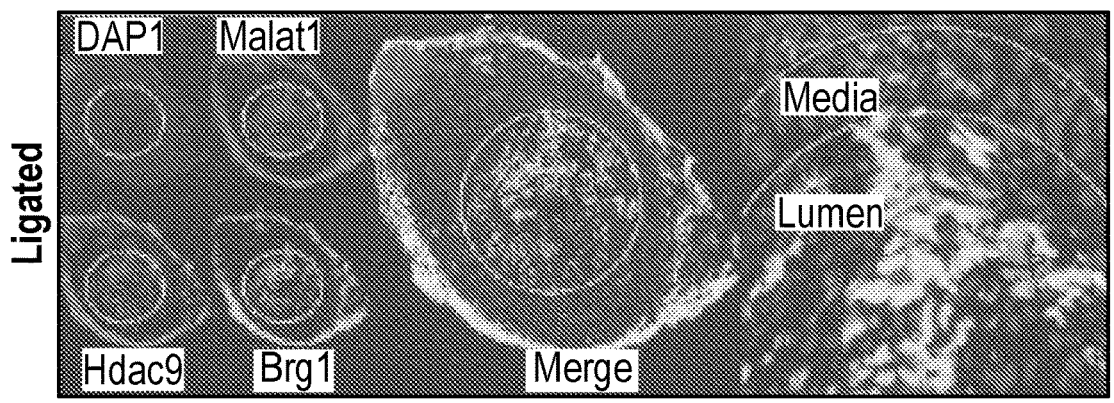
Figure 8E:
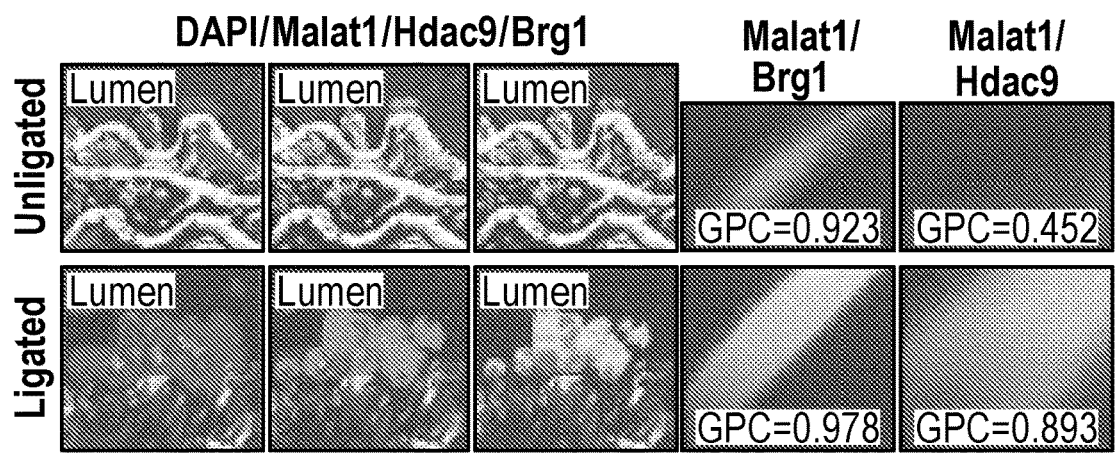

The HDAC9 complex in murine experimental neointimal hyperplasia and arterial stenosis To gain insight into the role of epigenetic silencing of gene products (such as a-SMA) in vascular stenosis the inventors performed murine carotid arterial ligation. Unilateral ligation of the carotid artery in mice induces significant transcriptional changes in the arterial media and stimulates the formation of an extensive neointima (FIG. 8a). Grossly, reactionary neointimal changes, including secretion of matrix degrading enzymes such as MMPs, smooth muscle cell proliferation and phenotypic change, and inflammation are seen. Contractile proteins such as a-SMA and 5 Sm22a are strongly downregulated within the ligated artery, while matrix degrading enzymes such as MMP9 showed increased expression (FIG. 8b). Previously, the inventors documented targeting of the HDAC9 complex to the promoters of contractile proteins in cellular models of aortic aneurysm. The inventors therefore investigated whether this complex may mediate the observed silencing during neointimal formation within the carotid ligation model. First the inventors investigated the expression level of the components of the complex HDAC9, BRG1, and MALAT1 in ligated arteries. Both HDAC9 and MALAT1 mRNA were significantly upregulated (FIG. 8c) and the components of the complex colocalized in ligated arteries within intimal nuclei (FIGS. 8d and 8e).

Inhibition of the HDAC9 Complex Improves Neointimal Hyperplasia

Figure 9A:
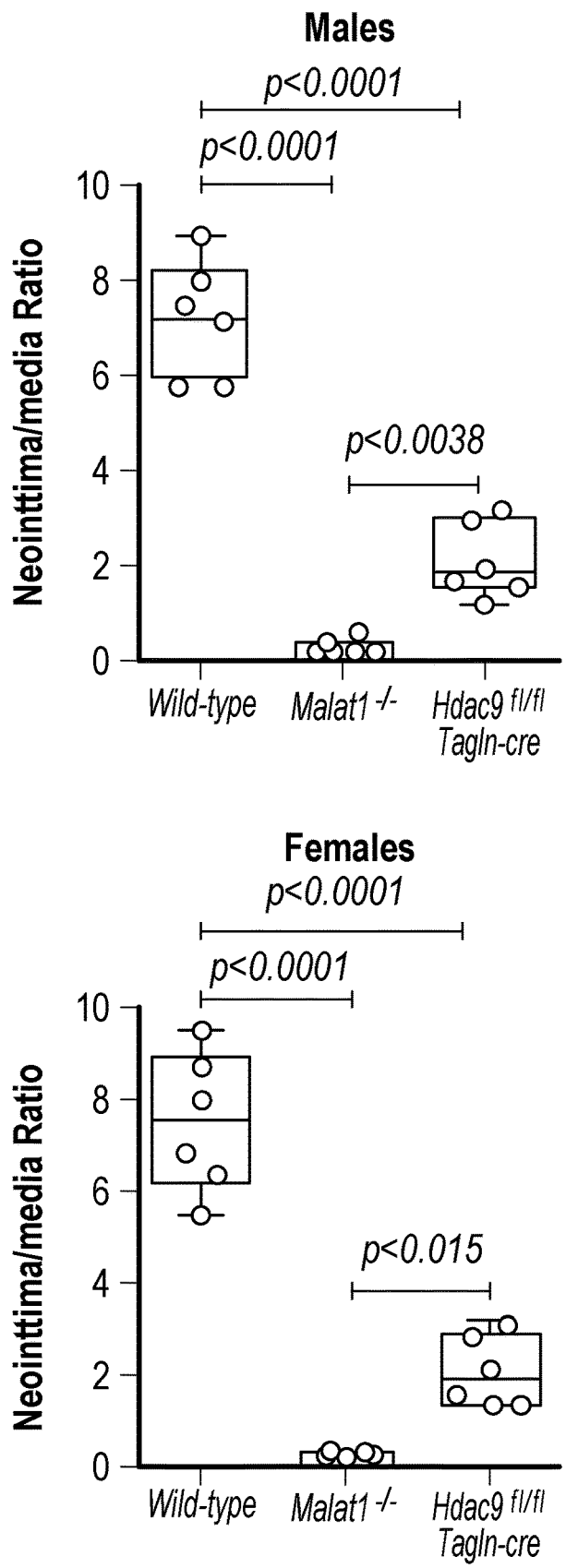
FIGS. 9A-9D demonstrate that the genetic disruption of Hdac9 or Malad inhibits neointimal formation.
Figure 9B:
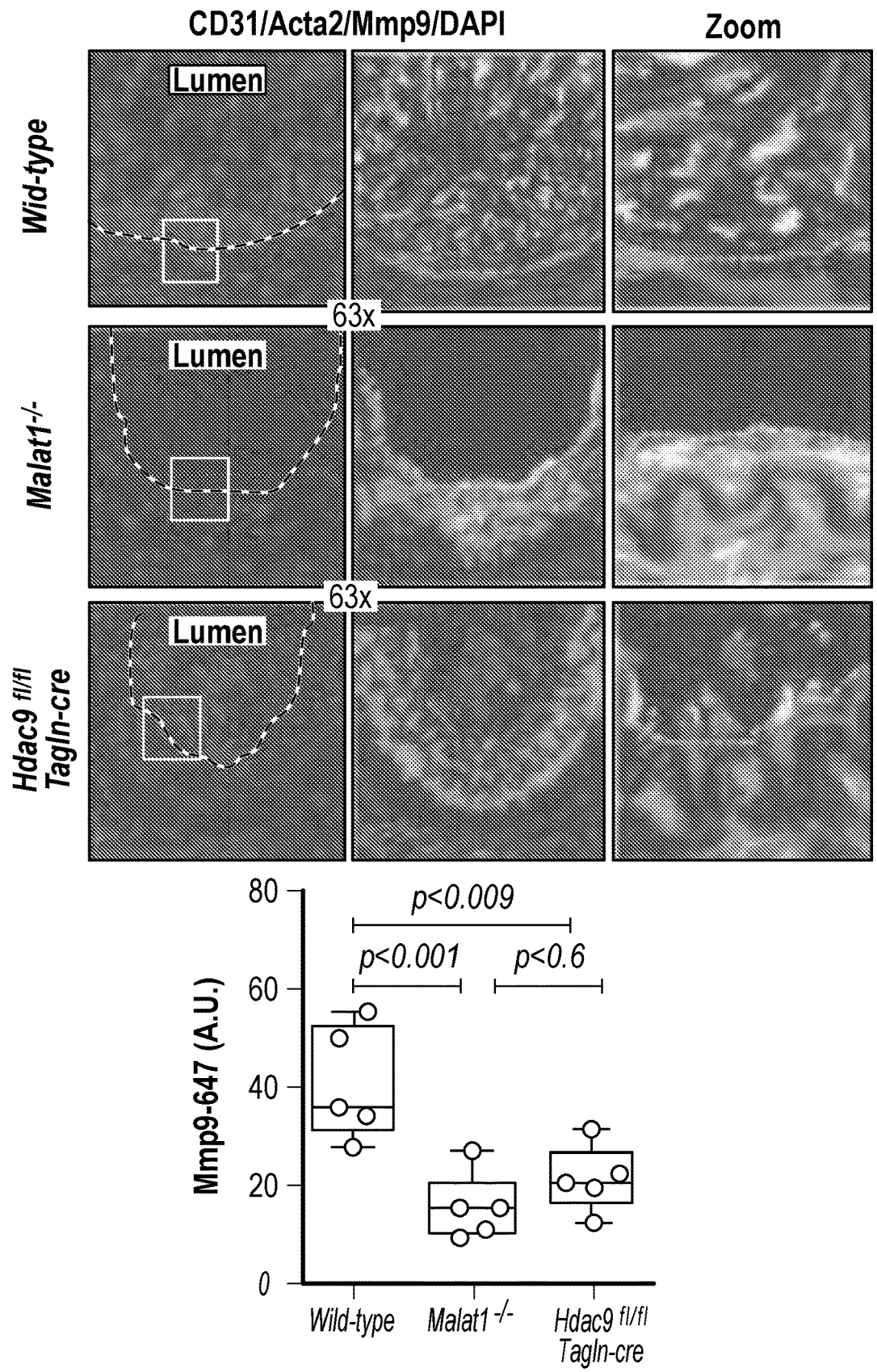
Figure 9C:
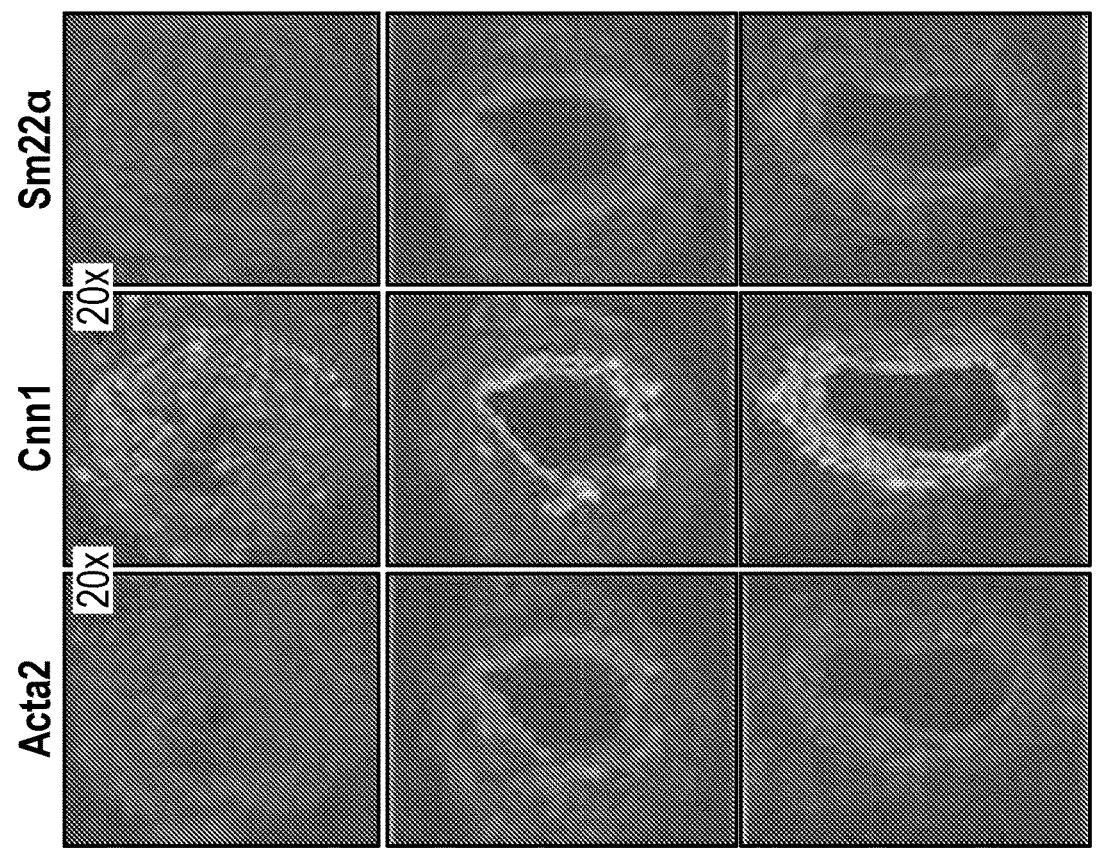
Figure 9C:
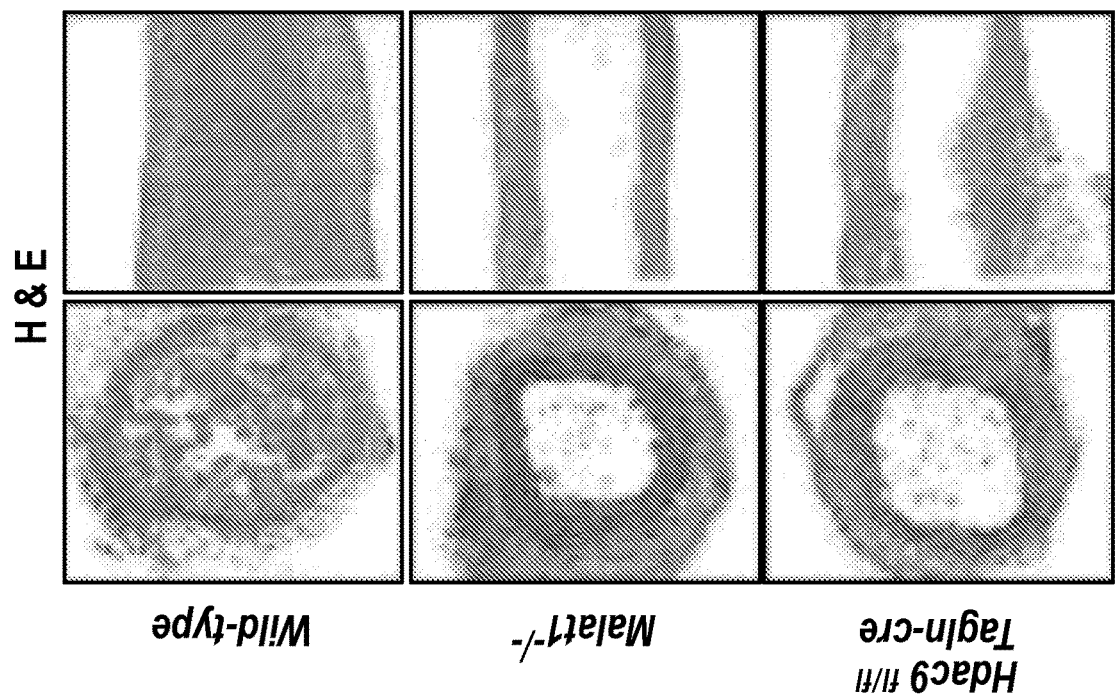
Figure 9C:
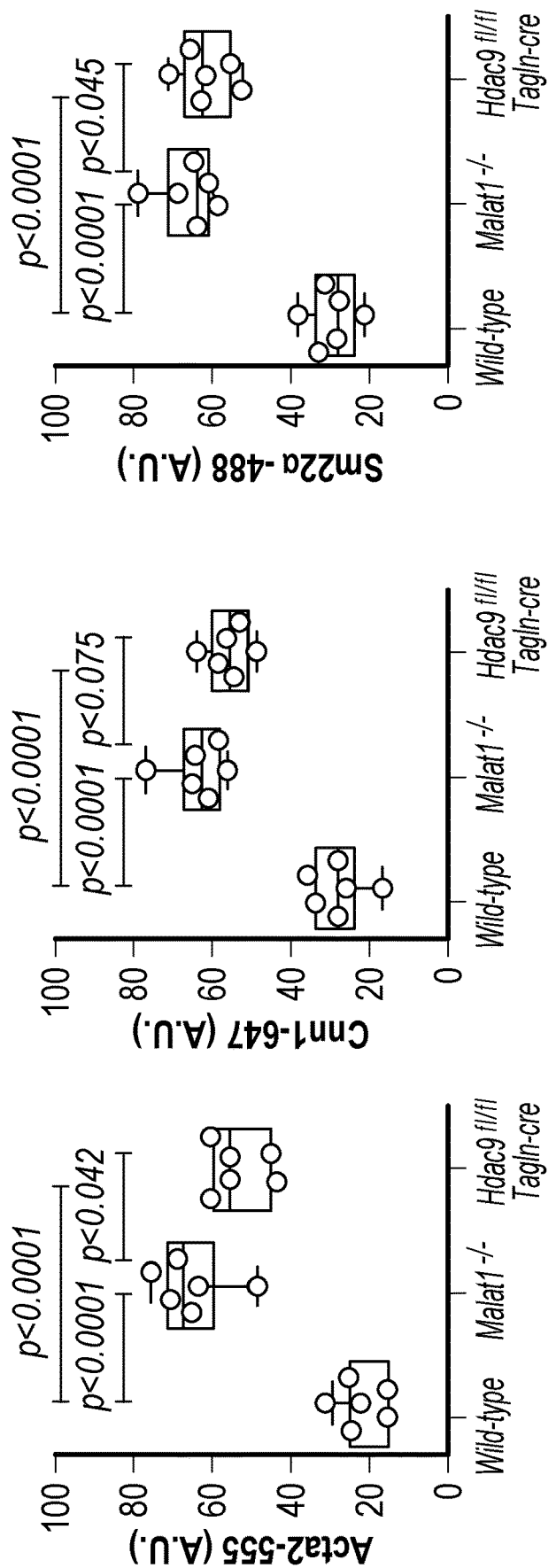
Figure 9D:
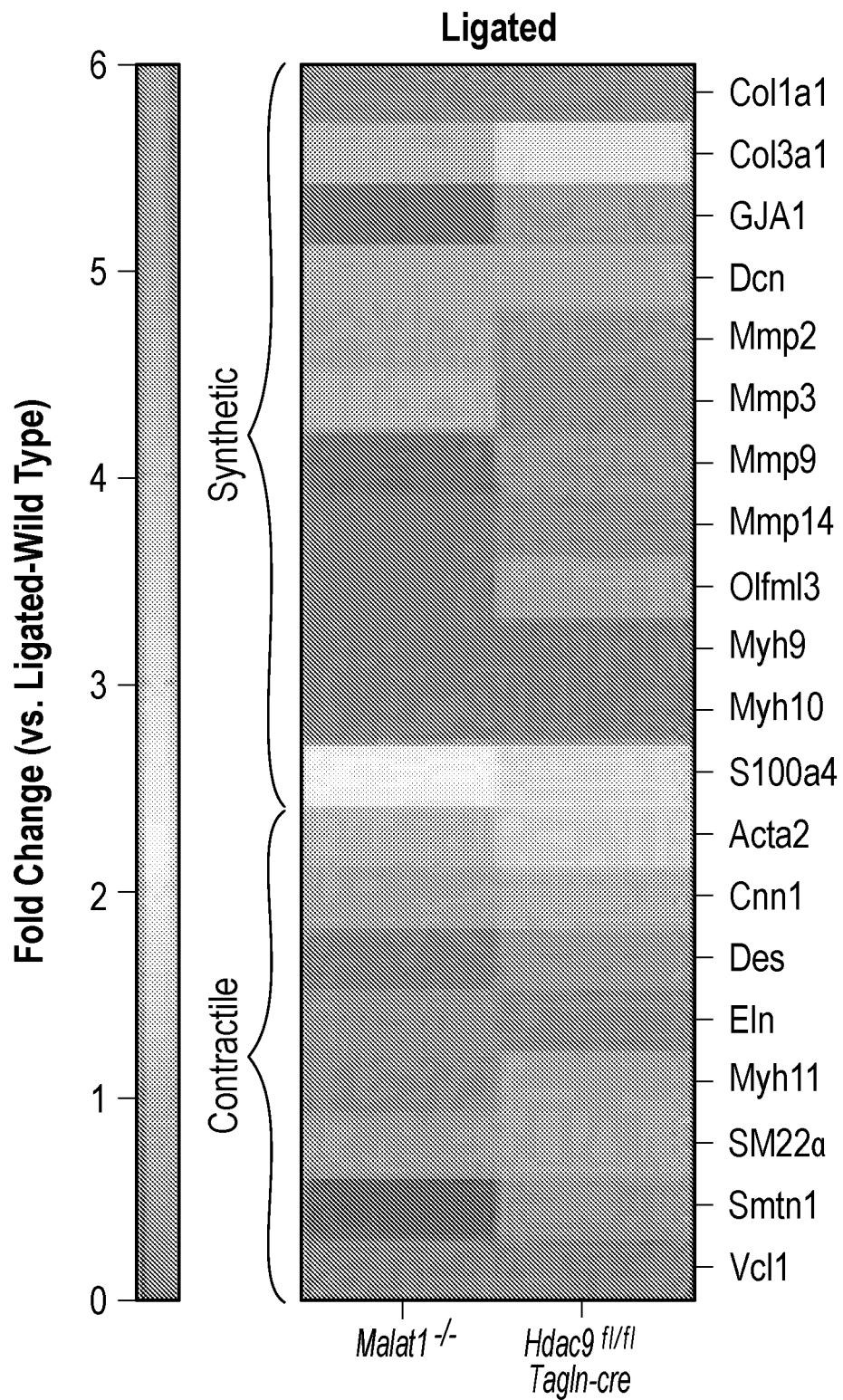

The ability of MALAT1 inhibition to prevent accumulation of H3K27me3 chromatin marks to the ACTA2 promoter (FIG. 7d) suggests that down regulation may help facilitate phenotype change necessary for neointimal hyperplasia formation. To determine if inhibition of the HDAC9 complex inhibits neointimal formation the inventors ligated the carotid arteries of mice deficient in MALAT1 or HDAC9. Carotid artery ligation was performed on Malat1-deficient (Malat1n(14) and VSMC targeted HDAC9-deficient animals (Hdac9flfl:TagIn-cre)(10). Supporting an important role in the formation of neointimal proliferation, Hdac9 and Malat deficient mice showed significantly reduced neointimal hyperplasia and stenosis 21 days after ligation (FIG. 9a and FIG. 9b). Additionally, immunostaining of contractile elements of VSMCs typically downregulated during neointimal (SM22, a-SMA, and calponin proteins) formation remained preserved in ligated carotid arteries from Malat1÷ and Hdac9flfl:TagIn-cre animals (FIG. 9b). Similarly, endothelial integrity was maintained in MalatT÷ and Hdac9fl117:TagIn-cre as assessed by CD31 staining in ligated arteries (FIG. 9c). To determine the extent of transcriptional dysregulation in the carotid arteries of targeted mice a panel of contractile and synthetic mRNAs was assayed. Amongst contractile gene products, genetic inhibition of the HDAC9 complex had the most dramatic effect on the ACTA2 gene (FIG. 9d). Consistent with both improvement in the stenotic phenotype and restoration of ACTA2 expression, expression of matrix metalloproteinase 9 (MMP9) protein is suppressed in Malati÷ and Hdac9″':TagIn-cre mice (FIG. 9c and FIG. 9d).

Figure 10A:
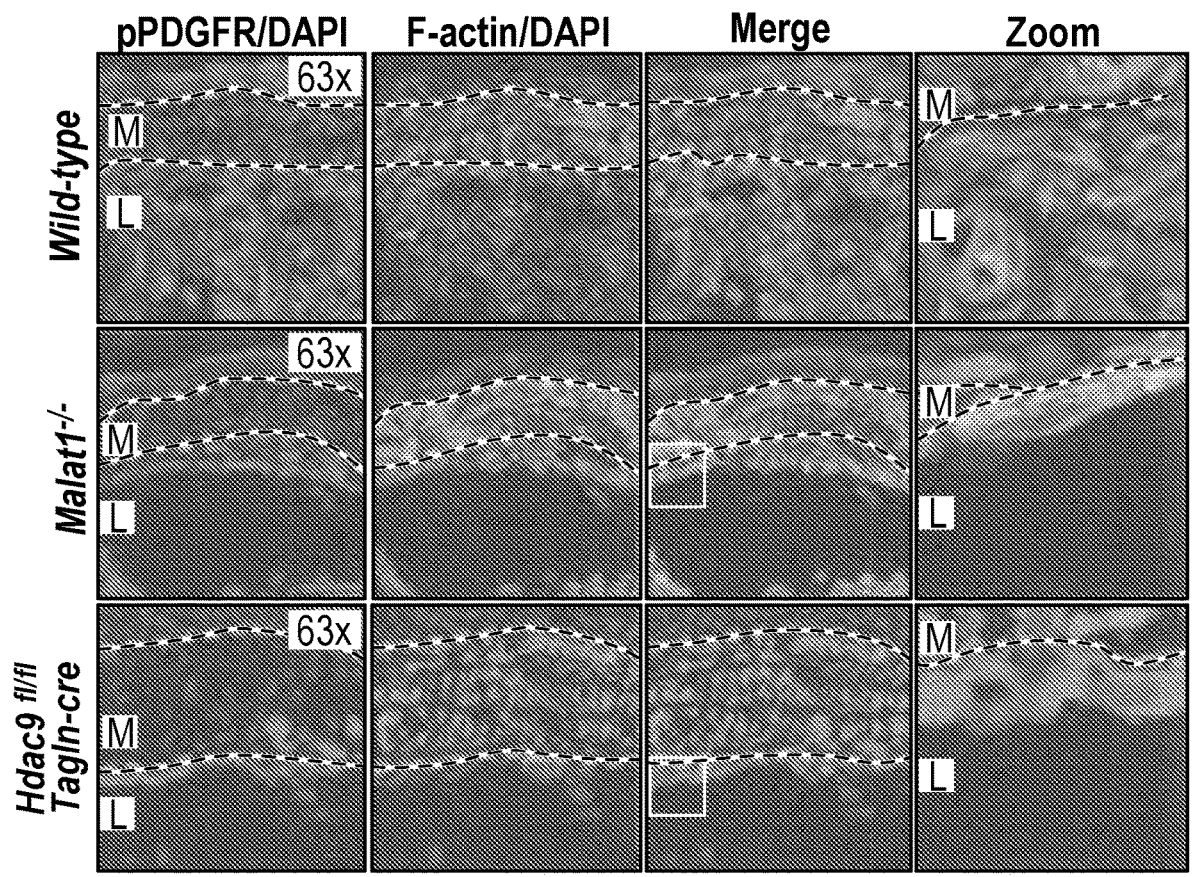
FIGS. 10A-10B demonstrate that genetic disruption of Hdac9 or Malatl inhibits activation of SMC proliferation markers.
Figure 10A:
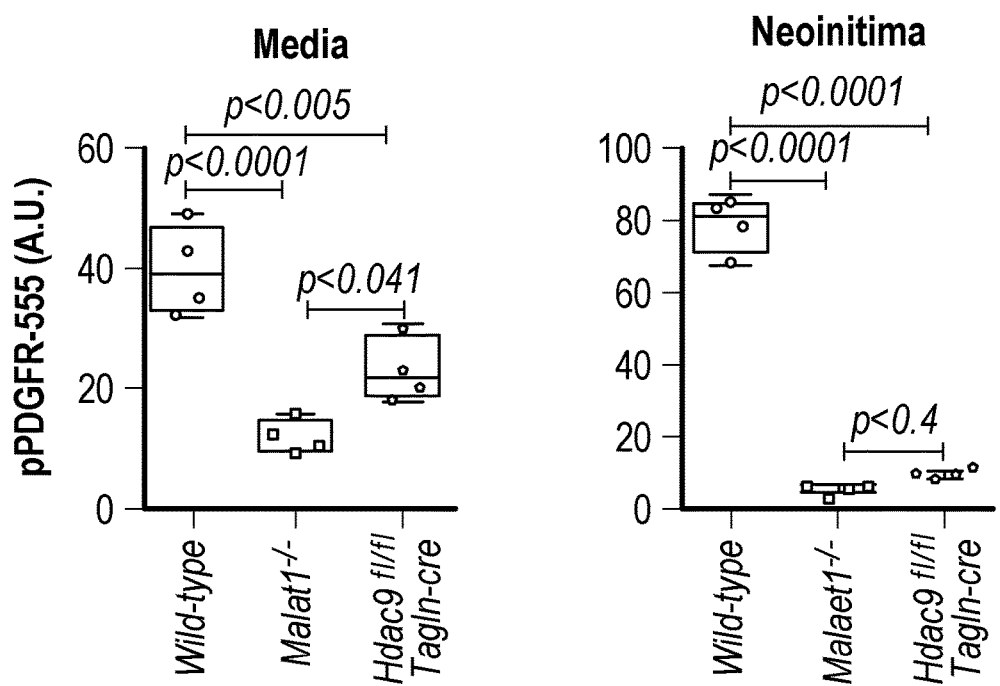
Figure 10B:
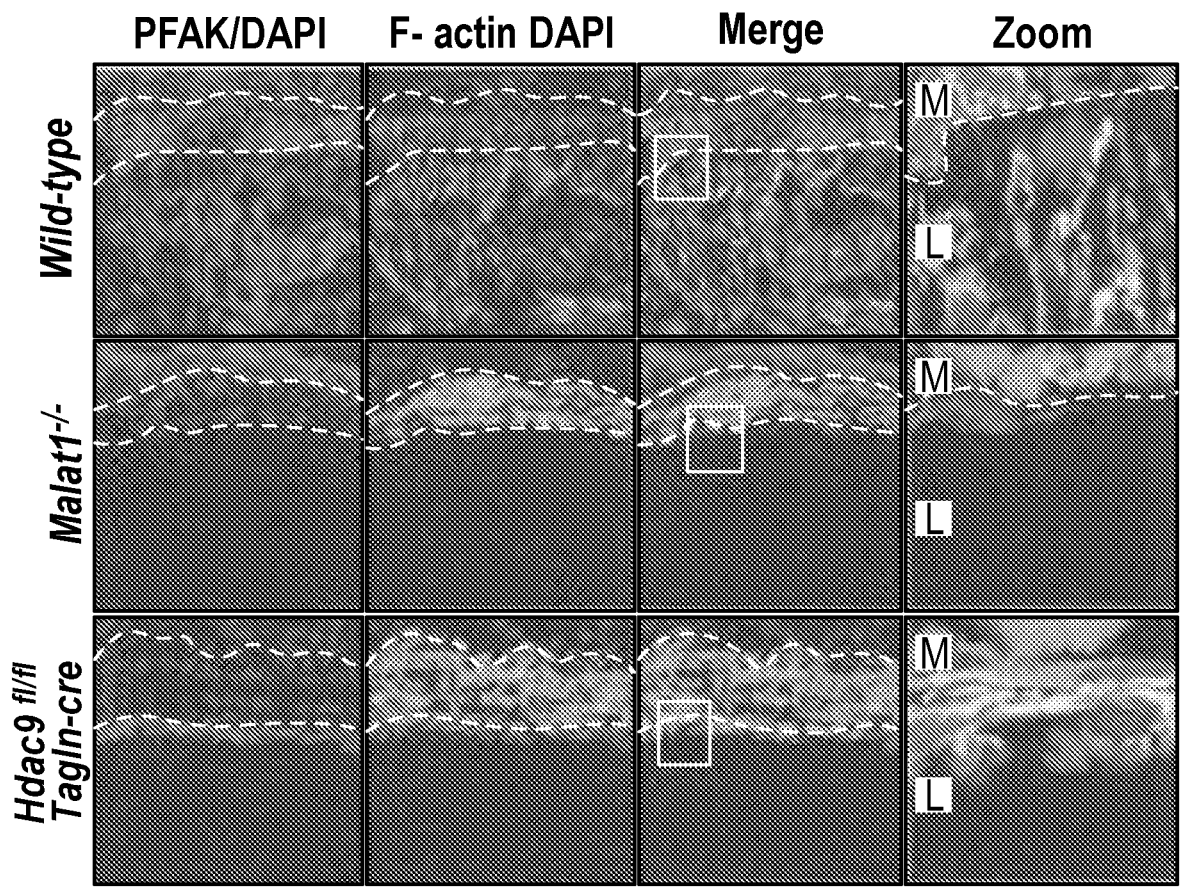
Figure 10B:
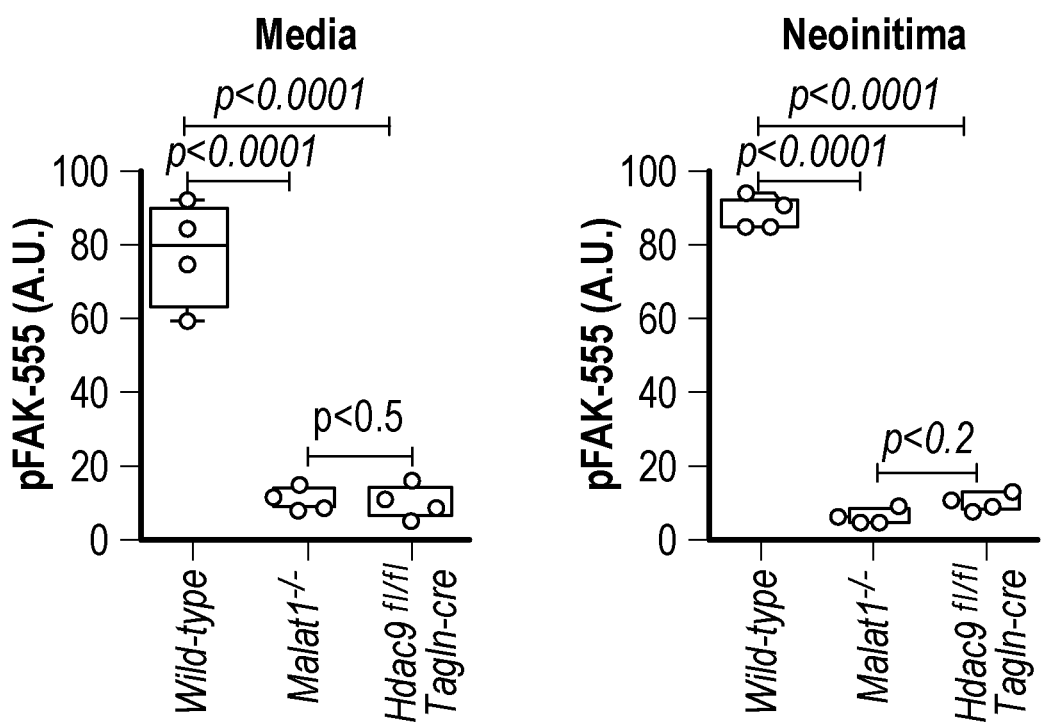

The inventors next examined proliferative and remodeling pathways known to be activated during neointimal formation (15, 16). The inventors therefore assayed activation of the platelet derived growth factor receptor (PDGFR) and focal adhesion kinase (FAK) pathways by phosphospecific antibody staining. Consistent with the observed palliation of neointimal development, dramatic reduction of phosphorylation of PDGFR and FAK was noted in the media and intima of Malati÷ and Hdac9M1:TagIn-cre mice (FIG. 10a and FIG. 10b).

Pharmacologic inhibition of the HDAC9 complex improves stenotic pathology The improvement of stenotic vascular phenotype in Malatfl- and Hdacel:TagIn-cre mice suggested that pharmacologic targeting of the complex could improve vascular performance. In previous work, the inventors demonstrated that the HDAC9 complex recruits PRC2 allowing silencing modifications of histone H3 at contractile protein promoters. Inhibition of the catalytic subunit of PRC2, an enzyme named EZH2, inhibited aortic aneurysm growth in mice (11). Therefore, the inventors explored the use of two separate treatments to inhibit transcriptional events downstream of the HDAC9 complex.

Figure 11A:
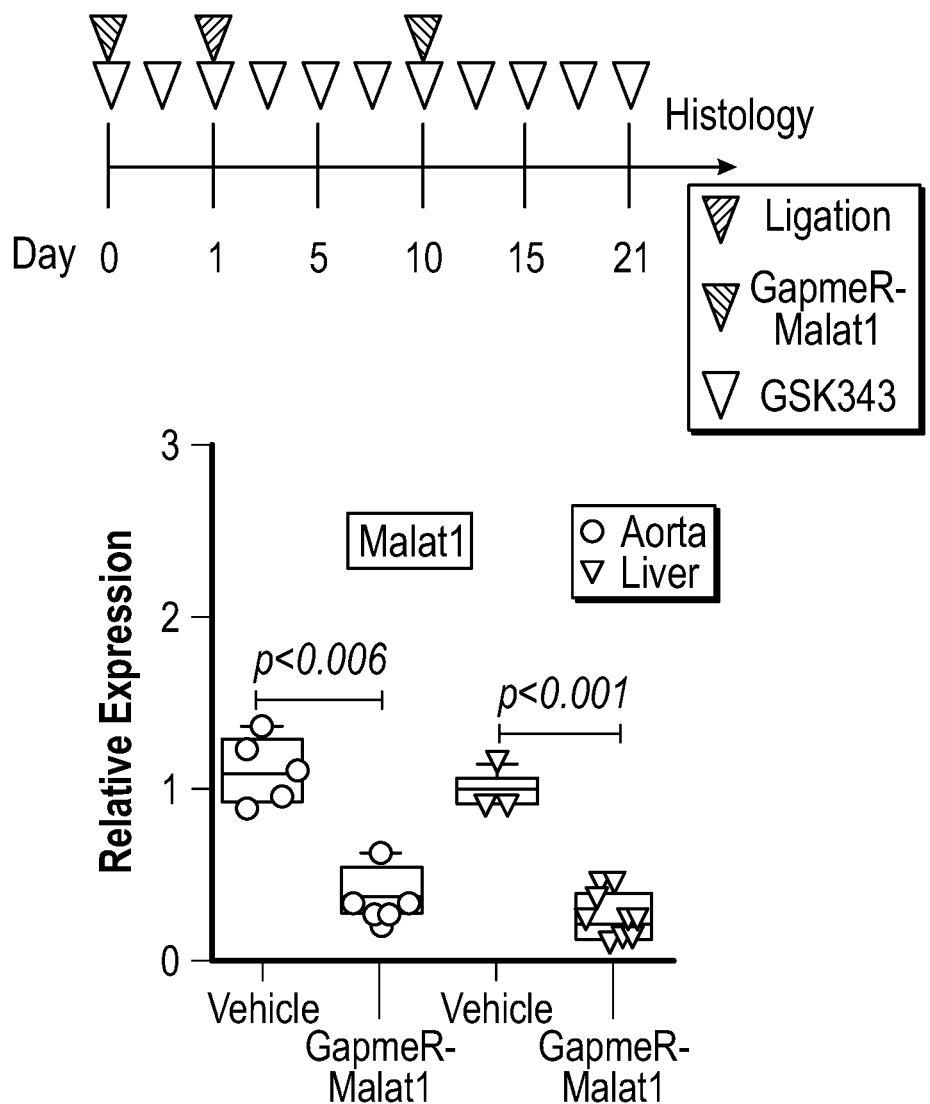
FIGS. 11A-11E demonstrate that the pharmacologic inhibition of the Hdac9-Brgl-Malatl complex inhibits neointimal formation.

In the first, the inventors used a GapmeR targeting the lncRNA MALAT1 to dissociate the complex which recruits PRC2 to chromatin. GapmeRs are small antisense DNAs with modified end nucleotides that recruit RNAse H for target transcript degradation. Using this peripherally injected GapmeR, the inventors first assayed repression of Malat1 in arterial tissue (FIG. 11a). In the second step, the inventors used a pharmacologic inhibitor of the EZH2 enzyme, GSK343, to prevent PRC2-mediated transcriptional repression.

Figure 11B:
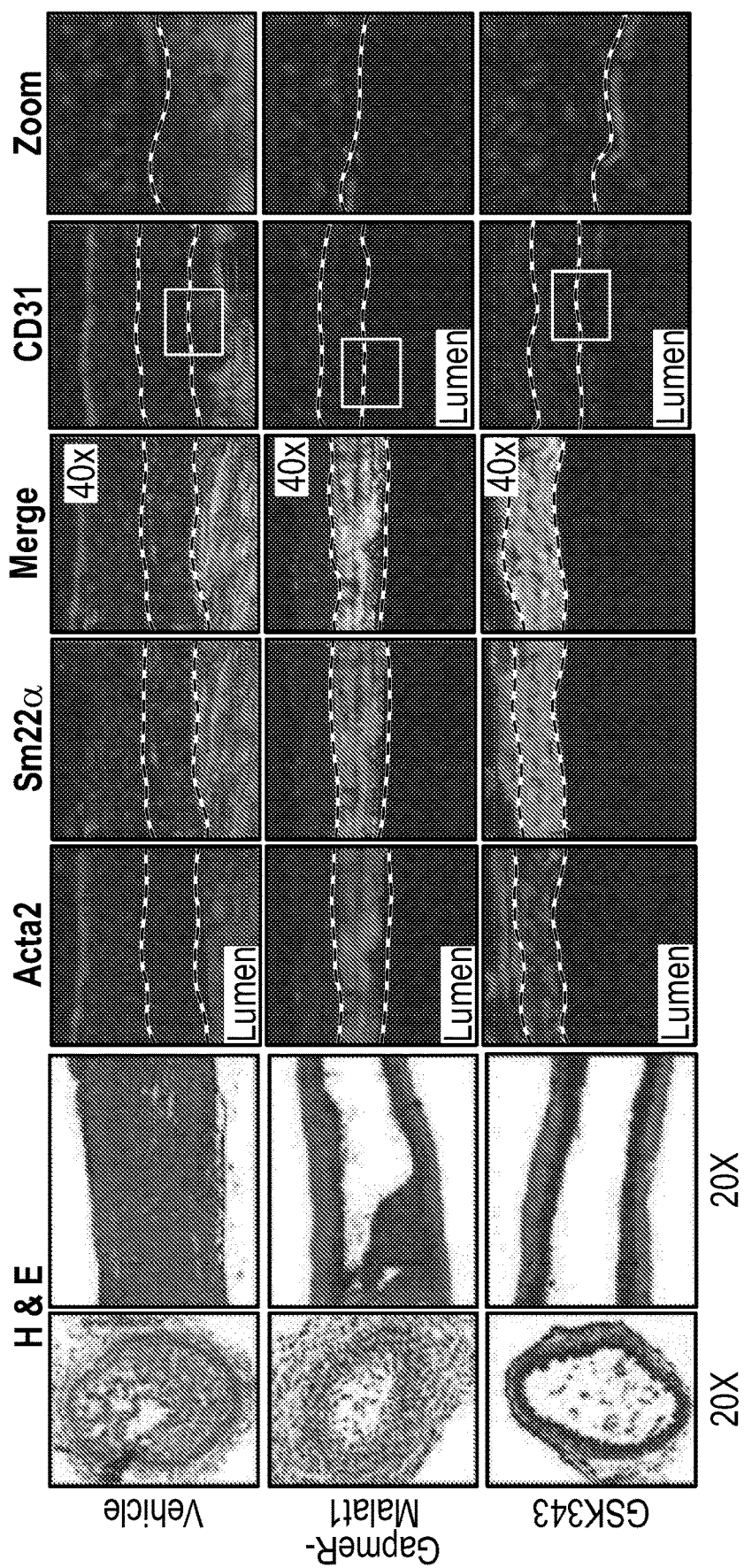
Figure 11C:
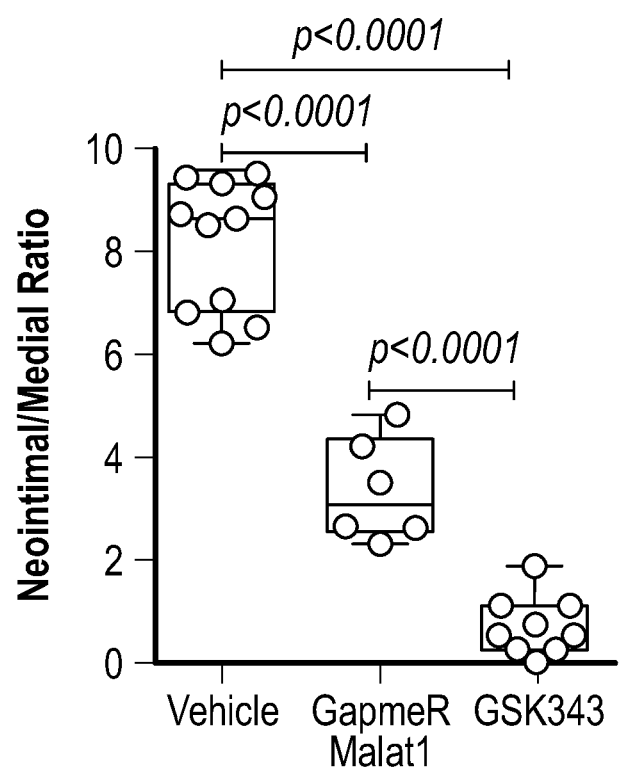
Figure 11D:
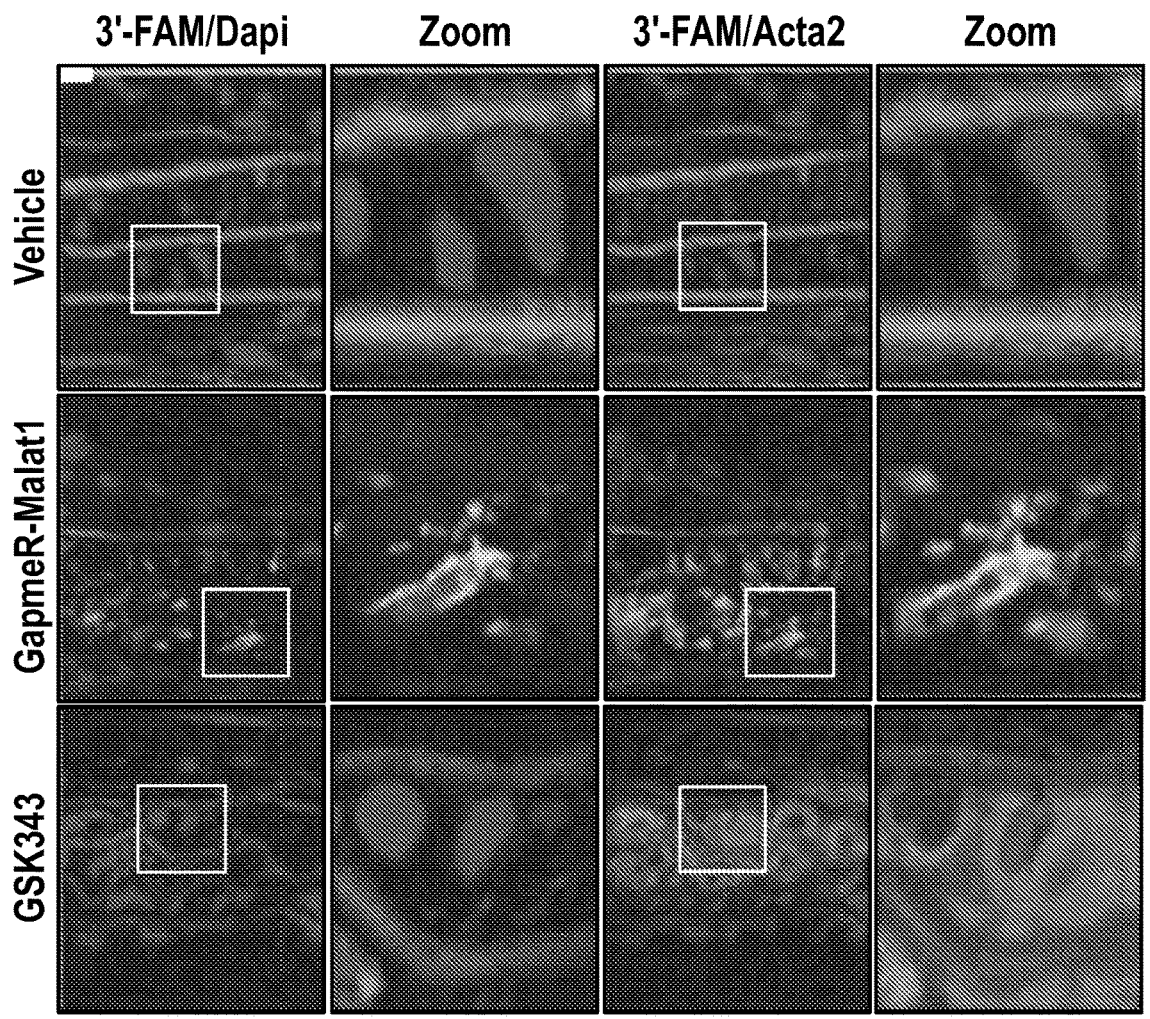
Figure 11E:
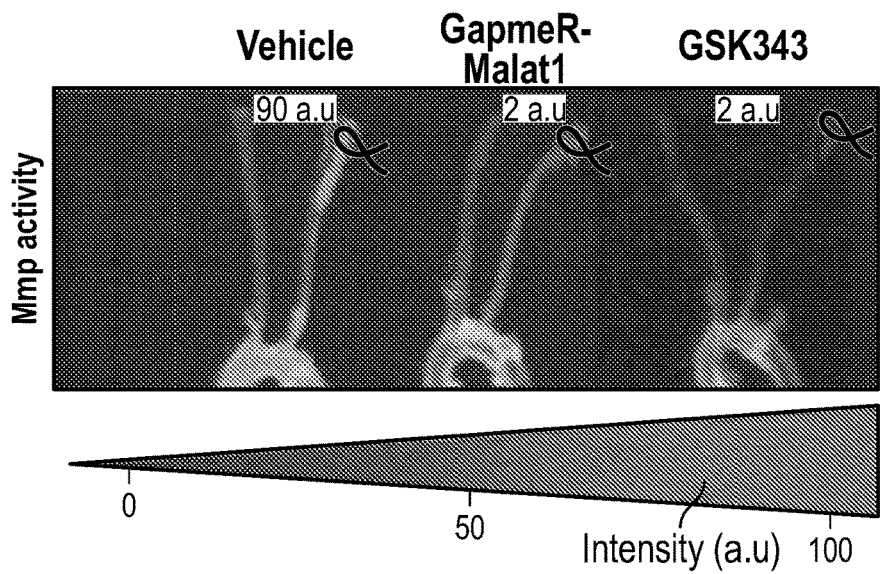

Treatment of animals with either GapmeR-Malat1 or GSK343 initiated before and continued during carotid artery ligation dramatically improved the extent of the stenotic response (FIG. 11b and FIG. 11c). Consistent with an improved gross phenotype, both GapmeR-Malat1 and GSK343 treatment improved the expression of contractile proteins such as a-SMA and SM22a, typically downregulated in neointimal hyperplasia (FIG. 11b). Supporting the concept of EZH2 being a primary therapeutic target in the arterial response, formation of a neointima was also inhibited in mice with SMC specific inactivation of the EZH2 locus (Ezh2"1:Myh11-cre)(FIGS. 8A-8E). The inventors used fluocrescently labeled GapmerR (3'-FAM-GapmeR-Malatl) to assay delivery to the vasculature. 3'-FAM-positive carotid VSMCs as well as VSMCs from GSK343-treated animals demonstrated robust expression of □□-SMA, in contrast to carotid VSMCs in wild type animals (FIG. 11d). Likewise, GapmeR-Malat1 and GSK343 treatment inhibited the activity of MMPs (FIG. 11e) known to be involved in the matrix remodeling of neointimal formation.

Figure 12A:
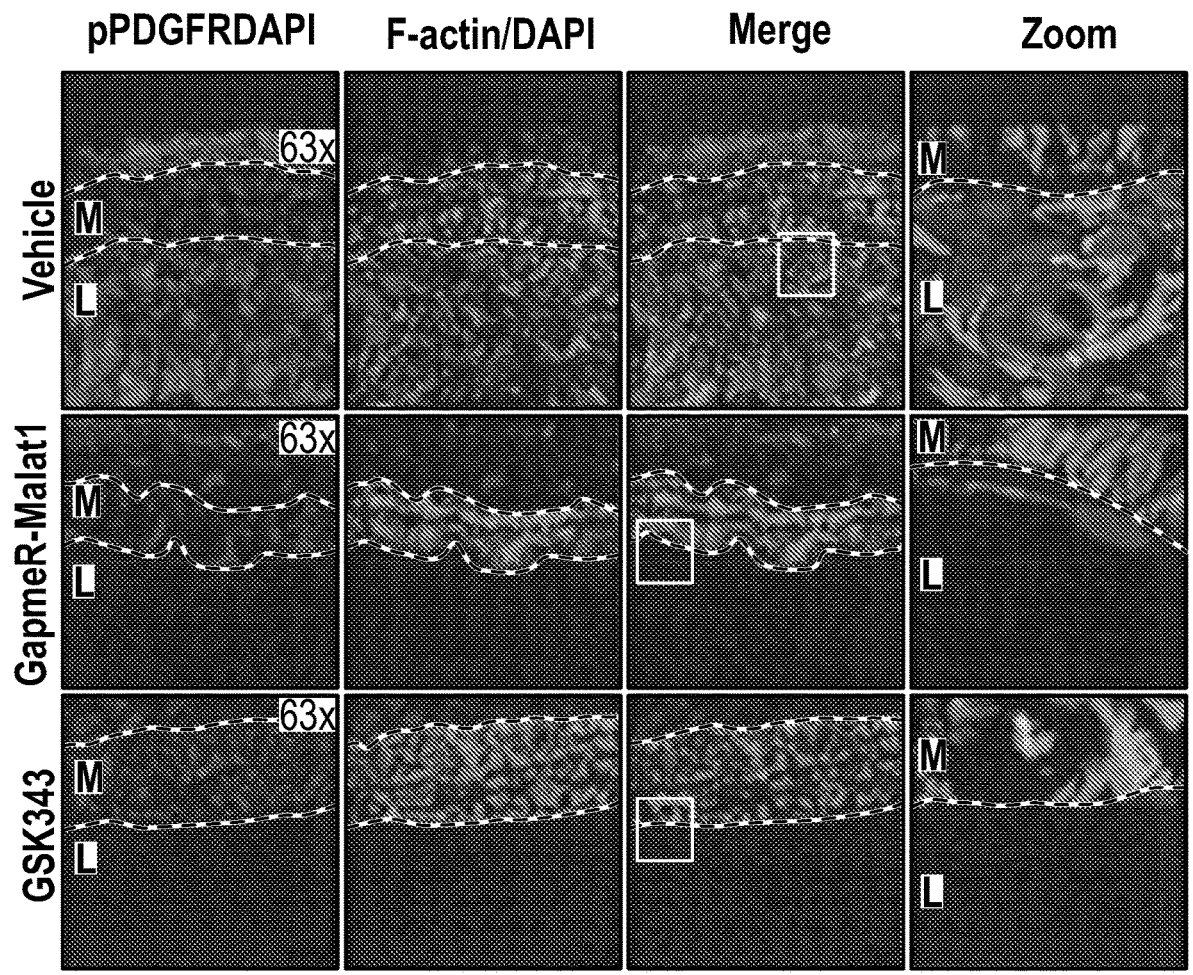
FIGS. 12A-12C demonstrate that the pharmacologic inhibition of the Hdac9-Brgl-Malatl complex inhibits SMC proliferation and downregulates Hdac9 expression.
Figure 12A:
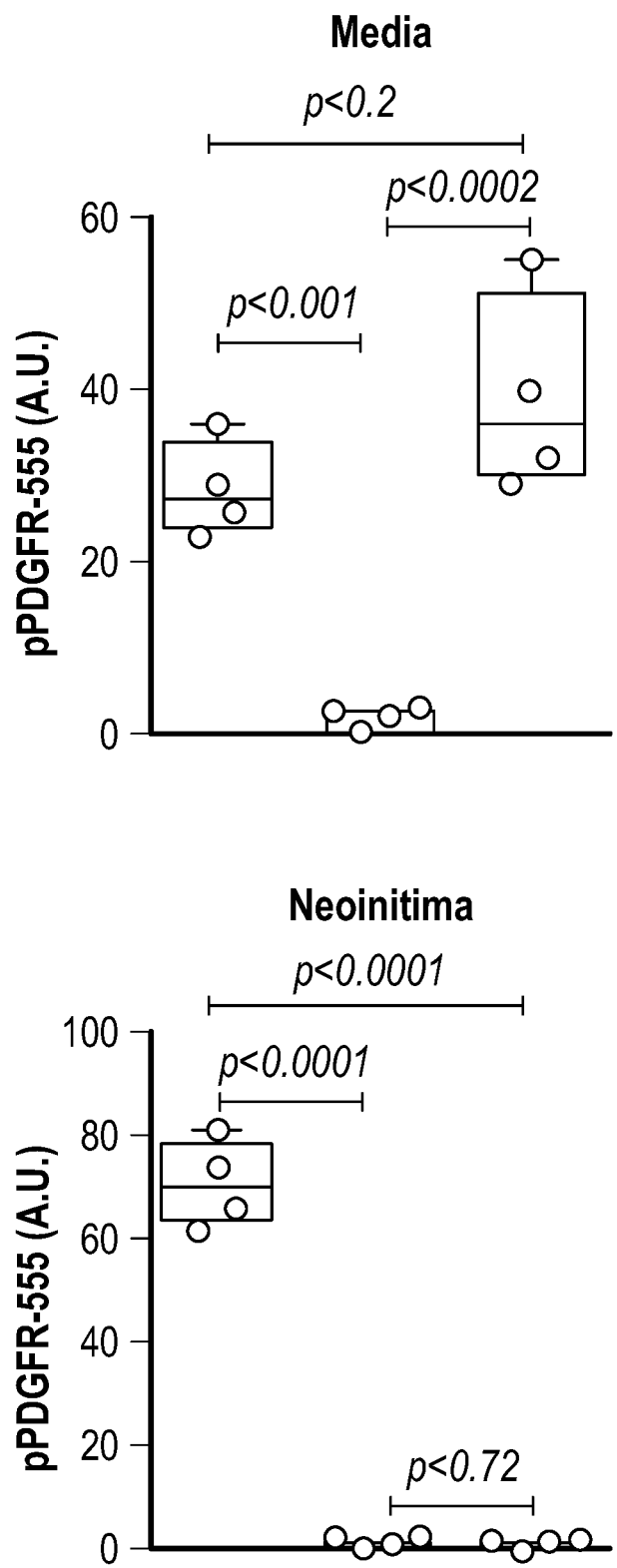
Figure 12B:
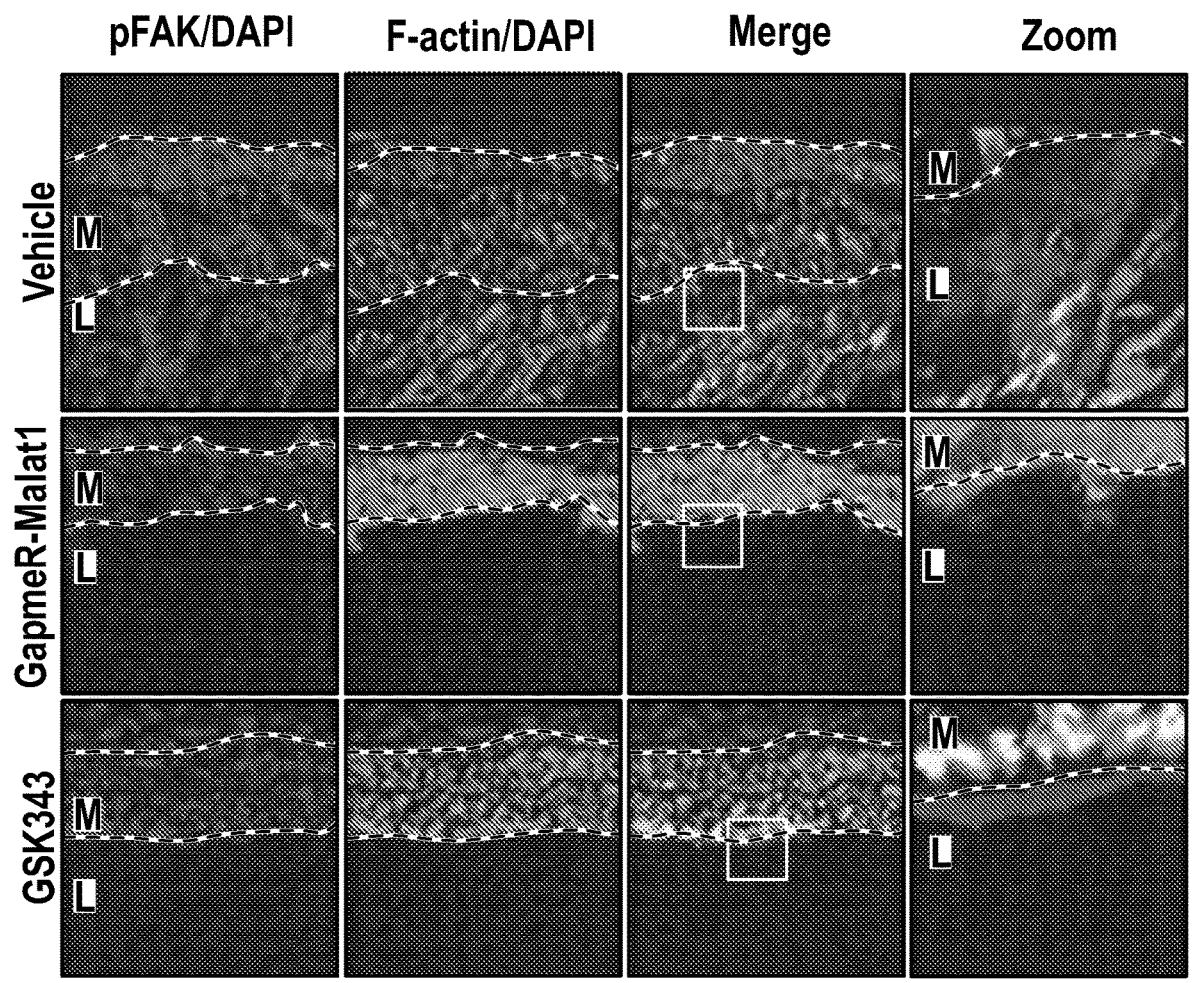
Figure 12B:
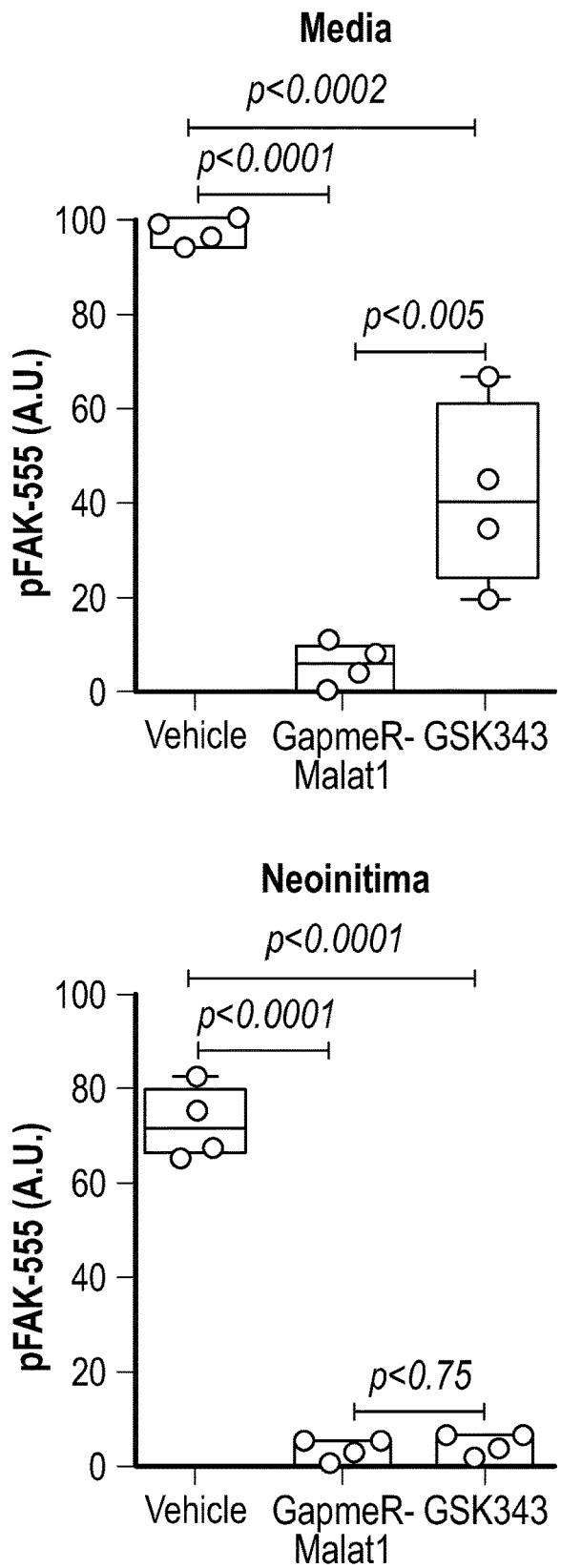
Figure 12C:
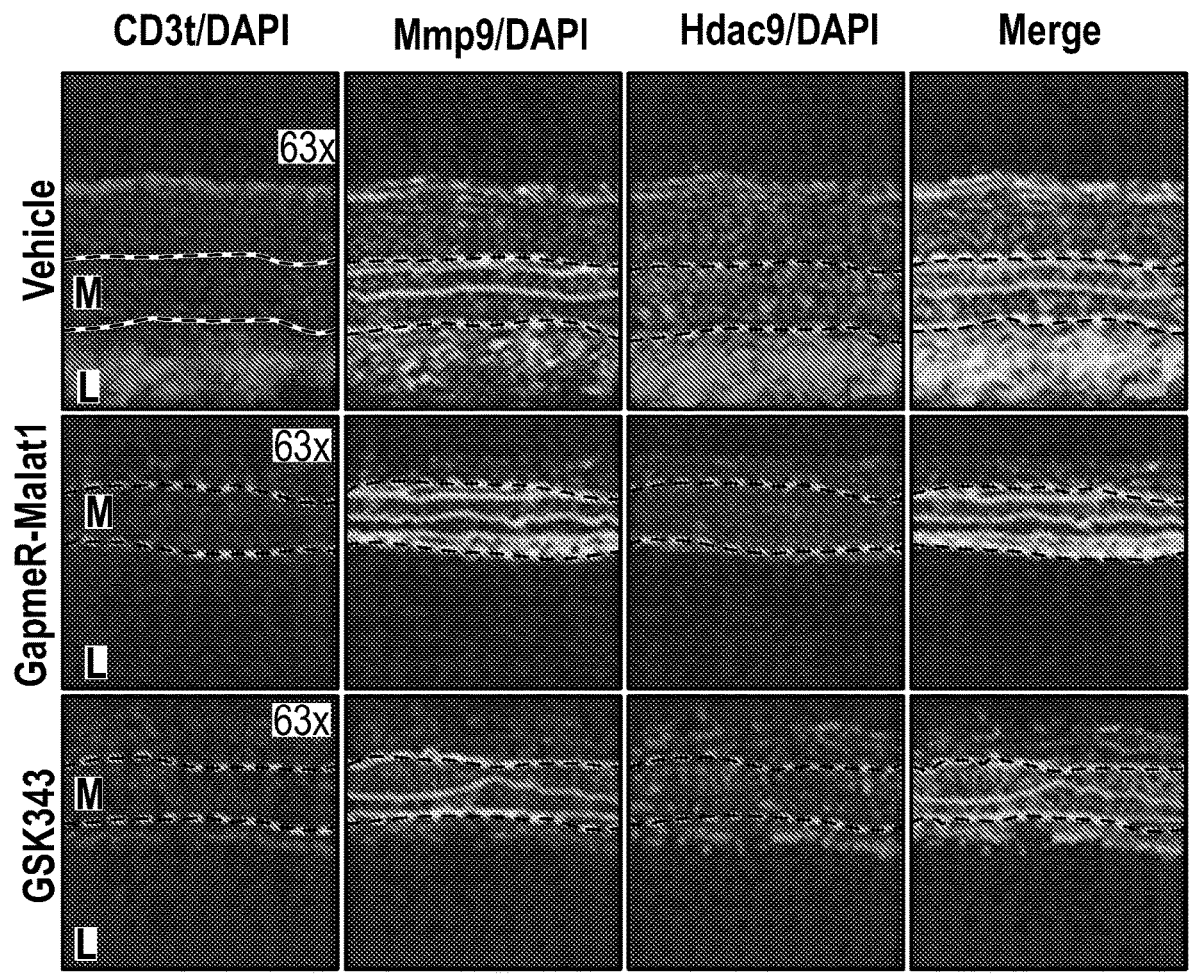
Figure 12C:
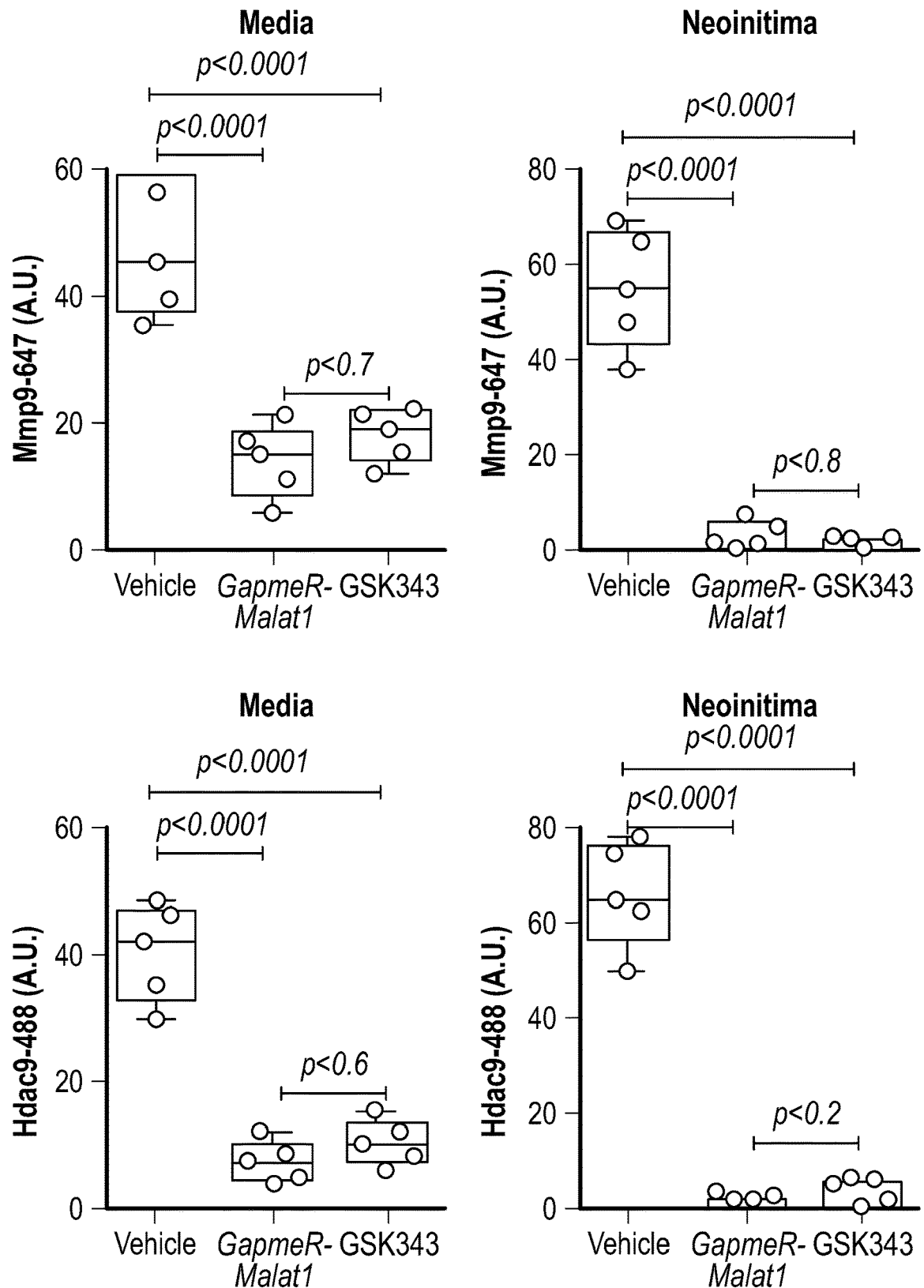
Figure 13A:
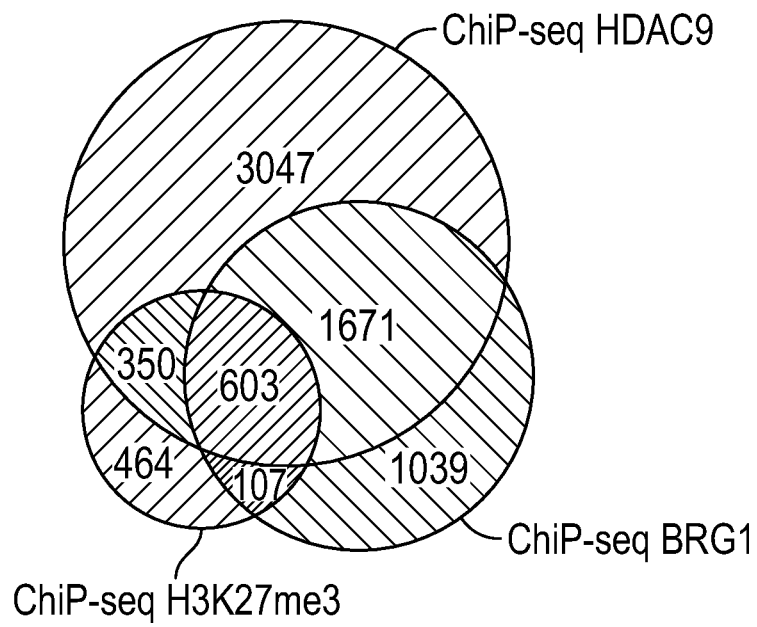
FIGS. 13A-13C demonstrate that TGFR2$^{G357w}$ mutation induces HDAC9-BRGI-MALAT1 complex interaction with genetic loci associated with VSMC contractility.
Figure 13B:
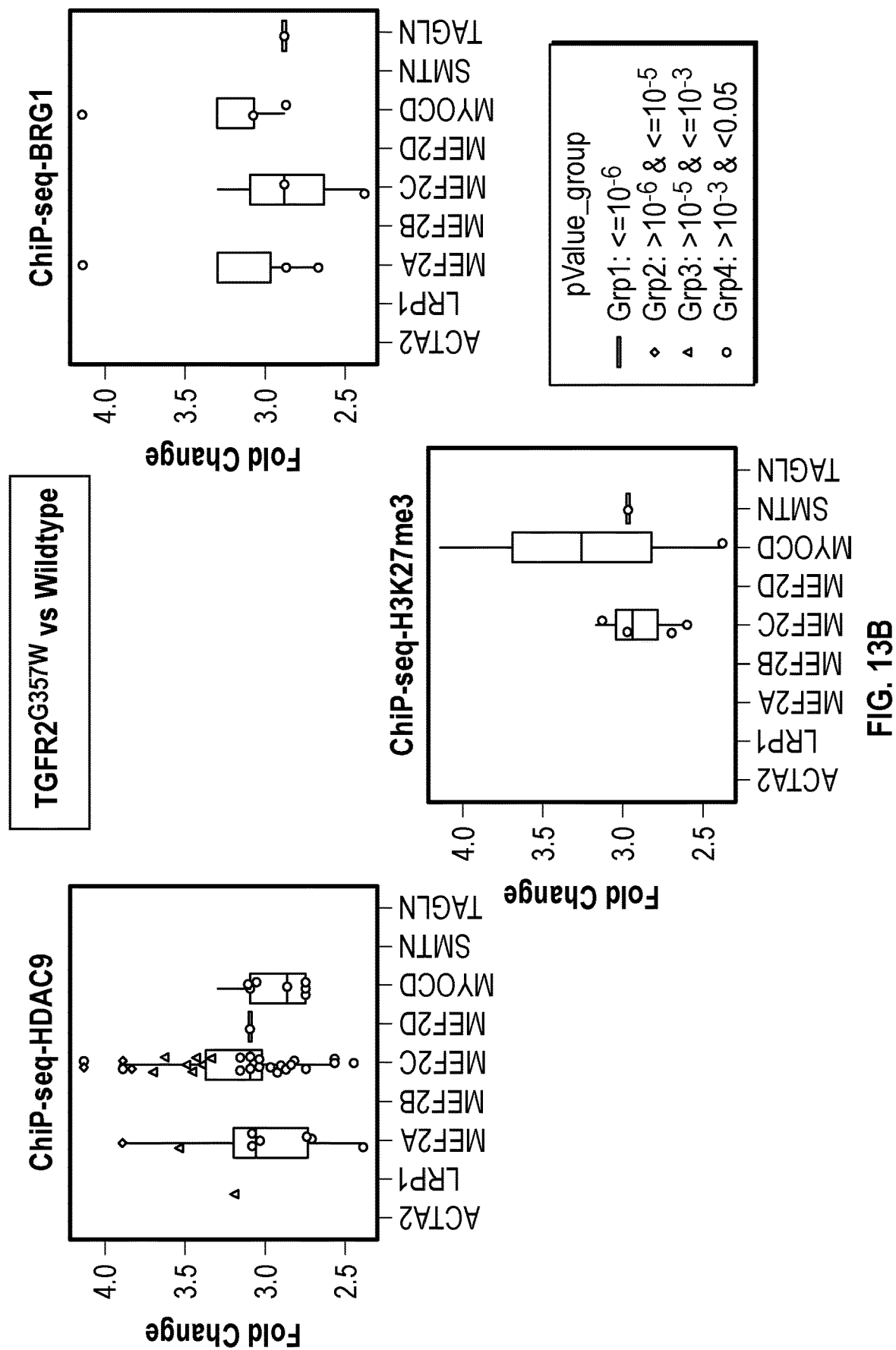
Figure 13C:
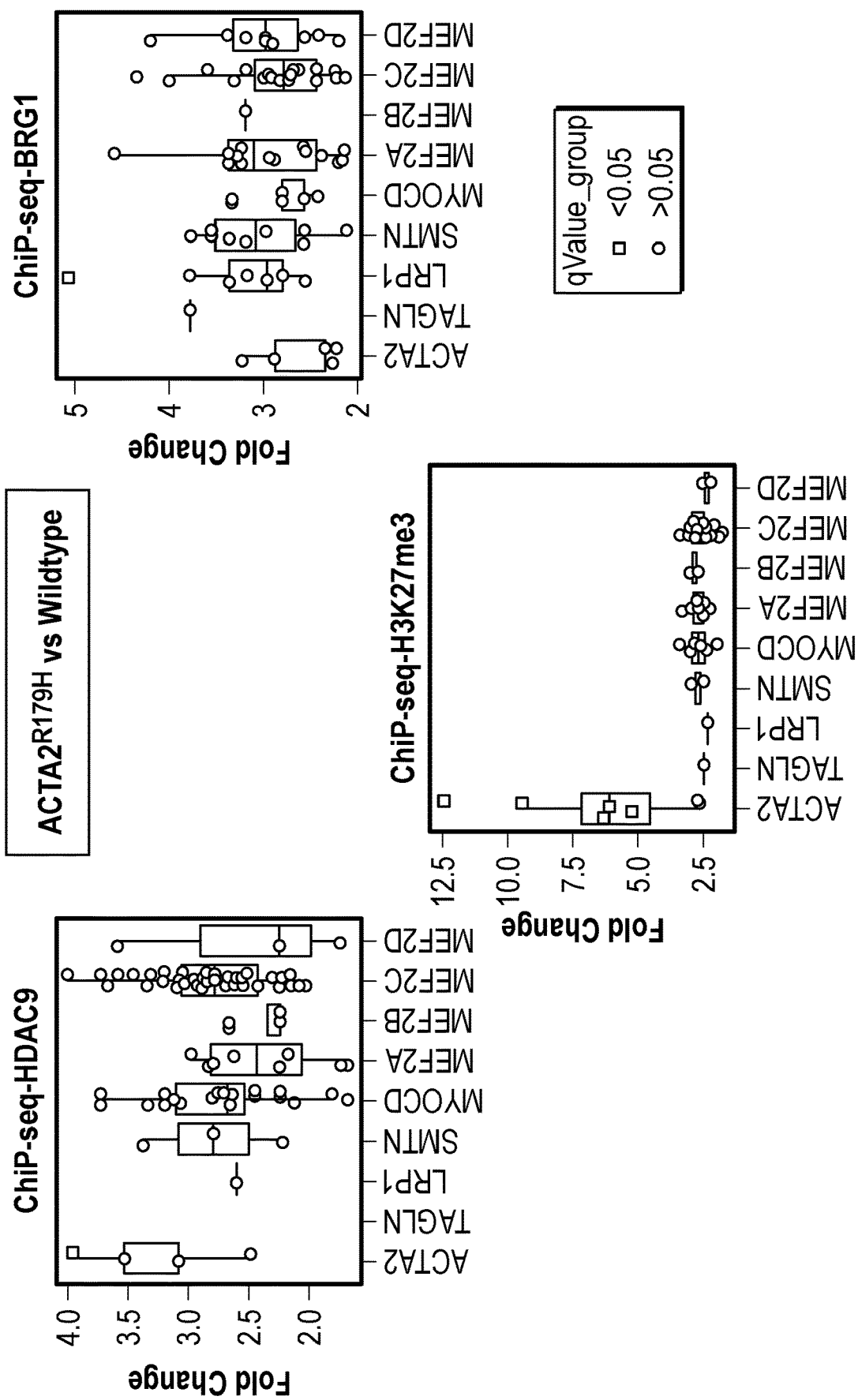
Figure 14A:
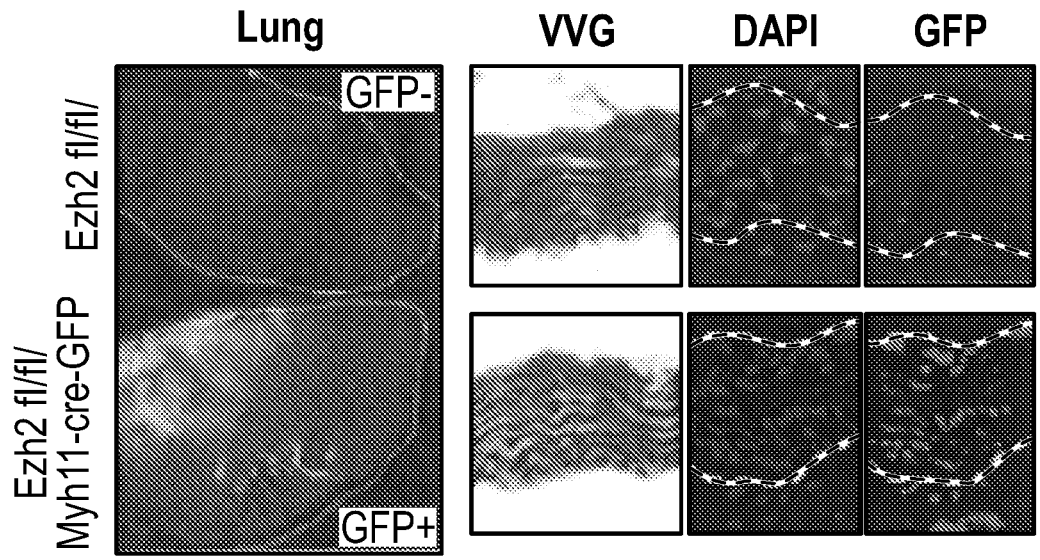
Figure 14B:
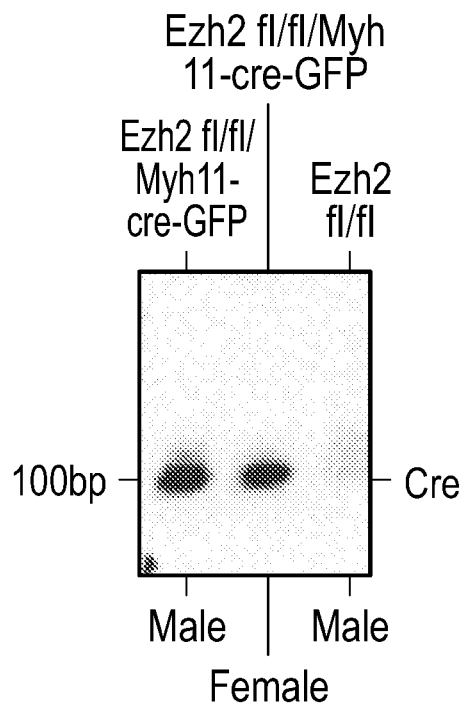

Similar to observations in in Malat1+ and Hdac9filfl: TagIn-cre mice, mice treated with GapmeR-Malat1 or GSK343 showed dramatic reduction of phosphorylation of PDGFR and FAK was in the both the media and intima of carotid arteries (FIG. 12a and FIG. 12b). Importantly, carotid arteries from mice treated with GapmeR-Malat1 or GSK343 also showed decreased accumulation of Hdac9 and Mmp9 in the arterial media and intima (FIG. 12c).

Discussion

Stenotic as well as aneurysmal lesions have been noted in individuals with mutations in members of the smooth muscle contractile apparatus. In this study the inventors used chromatin immunoprecipitation to identify targets of the HDAC9 complex in cells expressing an ACTA2R179" allele. Interestingly, multiple loci were identified interacting with the complex including vascular smooth muscle transcription factors such as MEF2A, MEF2C, and MYOCD (FIG. 7). Interestingly, one major target is the ACTA2 gene itself, consistent with previous observations of low a-SMA levels in both aneurysms and stenotic lesions. Deficiency of either MYOCD and ACTA2 are known to exacerbate neointimal stenosis after vascular injury (17, 18), implicating repressive control of these gene products as a pathogenic step in neointimal stenosis. Therefore, to further explore the HDAC9 complex activity in vascular injury the inventors used the murine carotid arterial ligation model.

Consistent with the role of the HDAC9 complex in pathogenic progression, mice deficient in either HDAC9 or MALAT1 expression, were less prone to developing neointimal hyperplasia after vascular injury and maintained contractile protein expression. The inventors therefore explored pharmacologic targeting of the complex. First, antisense oligonucleotides targeting MALAT1 were injected into wild-type mice prior to and one week after carotid ligation. GapmeR MALAT1 treated animals, similar to MALAT1 knock out mice, were resistant to neointimal development after carotid ligation. Next, the inventors treated mice with the EZH2 inhibitor, GSK343, during carotid ligation. EZH2 is the catalytic subunit of the PRC2, known to be recruited by the HDAC9 complex, to catalyze the trimethylation of histone 3 (H3K27me3) (19). Similar in effect to inhibition of MALAT1, blockage of EZH2 activity effectively inhibited neointimal formation and stenosis of the vessel with salutary effects on MMP production and contractile protein expression. These data demonstrate the feasibility of targeting epigenetic complexes necessary for neointimal development.

Arterial stenosis is a common human condition and the health impact is staggering. While the majority of arterial stenosis is associated with atherosclerosis, stenosis can also occur in the context of restenosis after percutaneous intervention, or congenital stenoses such aortic or pulmonary obstruction. In the latter cases, obstruction is thought to be caused by excessive medial or intimal expansion of SMCs. Arterial SMCs undergo profound phenotypic changes during these disease processes, having the ability to acquire characteristics of chondrocytes, osteocytes, and macrophage (20). However, one of the most common forms is a less differentiated cellular form known as the proliferative phenotype. This phenotype is characterized by cellular proliferation, loss of definitive markers of the smooth muscle cell phenotype (such as cc-SMA), and increased activation of matrix degrading enzymes (2, 20). While most arterial stenosis occurs in the context of atherosclerosis, some rare forms of Mendelian vascular smooth muscle dysfunction also encompass arterial stenosis as a phenotype. One such condition is the vascular disease caused by mutations in ACTA2. Patients with particular missense mutations in ACTA2 (and to a lesser extent in MYHI I) show intracranial and coronary arterial stenosis thought to be caused by excessive medial hyperplasia (6, 21). These data may help inform the specific pathology seen in these rare diseases.

The transcriptional changes that occur in experimental medial hyperplasia have been well documented. In the present study, the inventors observe that the HDAC9-MALAT1-BRG1 complex targets important genes such as MEF2A, MEF2C, and MYOCD, encoding regulators of smooth muscle differentiation (FIG. 7). In particular, Myocardin, the master regulator of smooth muscle differentiation has been implicated as a protective factor in neointimal stenosis (18). Mice deficient in this factor, responsible for the maintenance of VSMC identity, exhibit exacerbation of intimal reaction to arterial injury. Similarly, mice deficient in ACTA2 exhibit the same exacerbation of stenosis and intimal reaction (17). Preventing the silencing of the ACTA2 gene through inhibition of the HDAC9 complex therefore may prevent the phenotype switching necessary for neointimal proliferation. Similarly TAGLN, encoding SM22a, is associated with the transcriptional control of MMP expression and maintenance in expression of this gene, may partially account for the suppression of MMP expression noted in phenotype in Malat1÷ and Hdac91147:TagIn-cre mice.

Neointimal hyperplasia after vascular injury can occur in the context of stent placement for relief of arterial obstruction. The presence of the stent induces proliferation and expansion of the medial smooth muscle cells which can cause a secondary stenosis and reobstruct blood flow. Stents impregnated with antiproliferative agents such as rapamycin prevent neointimal proliferation. Unfortunately, the mechanism of action also prevents proper endothelialization, necessitating treatment with antiplatelet agents that increase the risk of hemorrhage (22). Agents that have the capacity to impede vascular smooth muscle cells without preventing endothelialization can improve this situation. Based on the data presented here, agents that inhibit the action of the HDAC9 complex have a comparative advantage in the treatment of such stenotic vascular disease.

Methods

Mouse Model of Carotid Stenosis

All mice used in this study were cared for under strict compliance with the Partners Institutional Animal Care and Use Committee (IACUC), regulated by the United States Public Health Service (USPHS). Carotid ligations were performed in 10 week old mice. Briefly, animals were anesthetized using intraperitoneal ketamine/xylazine (80 and 12 mg/kg, respectively) followed by a small incision in the neck to expose the carotid artery. Then the left carotid was ligated at the carotid bifurcation level using a 8-0 silk suture. At 21 days mice were sacrificed and carotids were collected for histological analysis. Approximately 98% of wild type mice developed stenotic lesions. Mice that developed thrombosis of the ligated carotid were excluded from the study (~1-2%). Malat1 knockout mice were kindly provided by Dr. David Spector (Cold Spring Harbor, N.Y.). Hdac9 flox/flox/Talgn-cre mice were generated as previously reported (10). Ezh2 fl/fl/ (STOCK Ezh2tm2Sho/J) and Myh11-cre-GFP (B6.Cg-Tg(Myh11-cre,-EGFP)2Mik/J) were crossed to generate smooth muscle cell-Ezh2 deficient mice. All above mice and wild-type mice (C57BL/6J) were purchased from Jackson laboratory. For tissue analysis, animals were euthanized through inhalational isoflurane (Sigma, St, Louis, Mo.) prior to tissue collection. All carotid ligation (left carotid) procedures were performed at 10 weeks of age. All experiments were performed on male and female animals at a 1:1 ratio.

Histology.

Left and right carotids were cryosectioned using OCT standard protocol and sectioning. The right carotid artery was unligated and served as an internal control. Neoinitima analysis was performed from hematoxylin and eosin (H & E) stained horizontal cross-sections embedded in Optimal Cutting Temperature compound (OCT). Briefly, the distal 0.2 mm of carotid from the ligation suture site were discarded followed by generation of 20 slides (10 pM). Slides 1, 5, 10, and 15 were H&E stained for quantification of neointima. For quantification of the neointima, internal and external elastic lamina perimeters and medial thickness from 4 quadrants were measured and averaged using Image J software from the National Institutes of Health (NIH). Slides 2-4, 6-9, and 11-14 were used for immunofluorescence staining. All antibodies are listed in Table 2.

TABLE 2

Table listing antibodies, catalog number, samples and application.

| Ab name | Cat. # | Sample | Application |
|---|---|---|---|
| BRG1 | ab110641 | Cell, Tissue | ChIP, FISH-IF |
| CNN1 | ab46794 | Tissue | IF |
| H3K27me3 | mAbcam 6002 | Cells | ChIP |
| HDAC9 | ab59718 | Cells, Tissue | ChIP, FISH-IF |
| HDAC9 | sc-398003 | Tissue | IF, FISH-IF |
| HDAC9 | sc-28732 | Tissue | IF |
| SM22α | ab14106 | Tissue | IF |
| CD31 | ab28364 | Tissue | IF |
| MMP9 | sc-13520 | Tissue | IF |
| p-PDGFR-b | sc-365464 | Tssue | IF |
| p-FAK | sc-81493 | Tissue | IF |
| α-SMA | ab5694 | Tissue | IF |

RNA Isolation and RT-qPCR Analysis

Dissected carotids were collected into 1.5 mL tube containing 700 pL of Trizol and total RNA was prepared using RNeasy kit (Qiagen) following the manufacturer's protocol. The cDNA was prepared by reverse transcription, and gene expression was analyzed by qPCR on SYBR green system (Applied Biosystems). Expression results were analyzed by the &OCT method, and GAPDH (encoding glyceraldehyde-3-phosphate dehydrogenase) was used as a housekeeping gene. FCs were calculated by taking the average over all of the control carotid as the baseline. All primers are listed in Table 3.

TABLE 3

Table listing primers.
Table 3 discloses the "F_primer" sequences as SEQ NOS 19-42 and the "R_primer" sequences as SEQ ID NOS 43-63, 63, and 64-65, respectively, in order of appearance.

| Primer ID | F_primer | R_primer | Application | Specimen |
|---|---|---|---|---|
| COL1A1 | GCTCCTCTTAGGGGCCACT | ATTGGGGACCCTTAGGCCAT | QPCR | Mouse |
| COL3A1 | CTGTAACATGGAAACTGGGGAAA | CCATAGCTGAACTGAAAACCACC | QPCR | Mouse |
| GJA1 | ACAAGGTCCAAGCCTACTCCA | CCGGGTTGTTGAGTGTTACAG | QPCR | Mouse |
| DCN | GTCATCTTCGAGTGGTGCAGT | CAAGGTTGTGTCGGGTGGAAA | QPCR | Mouse |
| MMP2 | GTCTCAAGAGCGTGAAGTTTGGAAG | TCAGCACCTTTCTTTGGGCACA | QPCR | Mouse |
| MMP3 | GGCCTGGAACAGTCTTGGC | TGTCCATCGTTCATCATCGTCA | QPCR | Mouse |
| MMP9 | GCAGAGGCATACTTGTACCG | TGATGTTATGATGGTCCCACTTG | QPCR | Mouse |
| MMP14 | ACCCACACACAACGCTCAC | GCCTGTCACTTGTAAACCATAGA | QPCR | Mouse |
| OLFML3 | CACCTTGTGGAGTACATGGAAC | CTACCTCCCTTTCAAGACGGT | QPCR | Mouse |
| MYH9 | AGAAGTTGGTATGGGTGCCTT | CCCTGAGTAGTATCGCTCCTTG | QPCR | Mouse |
| MY10 | TCCCGAGAGGTATCTCTTTGTG | GCGTTCCGATGGAATCCAC | QPCR | Mouse |
| S100A4 | TCCACAAATACTCAGGCAAAGAG | GCAGCTCCCTGGTCAGTAG | QPCR | Mouse |
| ACTA2 | CCCAGACATCAGGGAGTAATGG | TCTATCGGATACTTCAGCGTCA | QPCR | Mouse |

TABLE 3-continued

Table listing primers.
Table 3 discloses the "F_primer" sequences as SEQ NOS 19-42 and the
"R_primer" sequences as SEQ ID NOS 43-63, 63, and 64-65, respectively,
in order of appearance.

| Primer ID | F_primer | R_primer | Application | Specimen |
|---|---|---|---|---|
| CNN1 | TCTGCACATTTTAACCGAGGTC | GCCAGCTTGTTCTTTACTTCAGC | QPCR | Mouse |
| DES | CCTGGAGCGCAGAATCGAAT | TGAGTCAAGTCTGAAACCTTGGA | QPCR | Mouse |
| ELN | TGTCCCACTGGGTTATCCCAT | CAGCTACTCCATAGGGCAATTTC | QPCR | Mouse |
| MYH11 | ATGAGGTGGTCGTGGAGTTG | GCCTGAGAAGTATCGCTCCC | QPCR | Mouse |
| SM22a | CCAACAAGGGTCCATCCTACG | ATCTGGGCGGCCTACATCA | QPCR | Mouse |
| SMTN1 | GAGCGGCAAGACAACAAGGA | CAGTCTCCCTGCCAATCGT | QPCR | Mouse |
| VCL1 | TCTCGCACCTGGTGATTATGC | TGAACAGTCTCTTTTCCAACCC | QPCR | Mouse |
| EZH2_1 | AGCACAAGTCATCCCGTTAAAG | AATTCTGTTGTAAGGGCGACC | QPCR | Mouse |
| EZH2_2 | AGTGACTTGGATTTTCCAGCAC | AATTCTGTTGTAAGGGCGACC | QPCR | Mouse |
| ChiP_ACTA2_Pro1 | accaagcagaaatcaccatg | gaagcagtggttaagccggag | ChiP-qPCR | Human |
| ChiP_ACTA2_Pro2 | ggtgtaatclggatatcagatg | atcaaagagacgtggatccag | ChiP-qPCR | Human |

In Vivo MMP Activity.

Mice were tail vein injected with 600 uL of MMPSense 750 FAST, a near-infrared fluorescence sensor for MMP2 and MMP9 activity, (PerkinElmer, USA). Mice were sacrificed 24 h post injection and aortas were dissected and analyzed using a Kodak image station 4000MM Pro for macroscopic fluorescence reflectance molecular imaging.

Sequential FISH and Immunofluorescence Microscopy.

Stellaris® FISH Probes recognizing mouse Malat1 (SMF-3008-1: Stellaris® FISH Probes, Mouse Malat1 with Quasar® 570 Dye) and labeled with Quasar® 570-labeled oligos (Biosearch Technologies, Inc., Petaluma, Calif.) were hybridized to tissue samples, followed by incubation with primary and secondary antibodies following the manufacturer's instructions available online at www.biosearchtech.com/stellarisprotocols. Imaging and analysis were performed using Volocity 5.2 software. Three-dimensional and quantitative fluorescence co-localization analysis were performed as described previously (10). Two-dimensional and white light images were analyzed using ImageJ software.

ChIP-Seq and ChIP-qPCR

Human wild-type or aneurysm (ACTA2R179" or TGFR2G357w) (10) smooth muscle cells (10 million) were fixed with 1% of formaldehyde at 37 C for 20 min, quenched with 125 mM glycine for 5 min (RT) and protein lysates were prepared using EpiTect ChIP kit according to the manufacturer's instructions (Qiagen, USA). Next, total protein lysates were sonicated to shear chromatin to an average length of 500-1,000 bp, followed by centrifugation for 10 minutes at max speed. Supernatants were collected into a 2 mL tube containing 6 pg of monoclonal antibody against HDAC9 (ab59718), BGR1 (ab110641), H3K27me3 (Abcam, ab4729) or IgG isotype control (ab171870) and 1 ml of lysis buffer supplemented with 1× of protease inhibitor cocktail (Roche Diagnostics), followed by incubation overnight (14 hours) at 4° C. Immunoprecipitates were analyzed using EpiTect ChIP kit according to the manufacturer's instructions (Qiagen). Then, ChIP-ed DNA was quantified and used for DNA-end repair (3'-dA) followed by PCR amplification and size selection (usually 100-400 bp, including adaptor sequence). The, qualified libraries were used for Hi seq sequencing (Illumina HiSeq 50 SE sequencing). Then, fastqs files were aligned to the human genome (hg19, ENSEMBL version 75) using bowtie2 aligner (23) with up to 50 alignments reported. Reads that were multimapped, duplicated or those that contained more than 2 mismatches were filtered out using samtools v1.3.1(24). The filtered alignment files in the form of bam files were indexed for the ability to view them on Integrative Genome Viewer (25). Peak calling was performed using macs2 v. caller between aneurysm (ACTA2R179" or TGFR2G357w) smooth muscle cells and their corresponding control sample at a p-value threshold of 0.05. The annotation of the peaks from macs2 was performed using the ChipSeeker package in R (26). Briefly, the reads that are mapped to unplaced scaffolds are removed from the analysis. Before annotating the peaks with UCSC's hg19 knownGene database, the genomic coordinates are first converted from ENSEMBL to UCSC and all peaks with a transcription start site region defined at 5 kilobases of the gene location are annotated. Pathway analysis was performed using DAVID (27) with all genes that contained differentially expressed peaks at a p-value <10-4 that were in both groups of comparisons ACTA2R179" or TGFR2G357w cells vs Wild-type cells. For ChIP-qPCR, Human wild-type or aneurysm (ACTA2R17911) smooth muscle cells at 60% of confluence in a T-75 flask were transfected with siRNA targeting MALAT1 (30 pM) or siRNA negative control (30 pM) for 48 hrs in OPTIMUM media followed by 24 hrs with complete growing media. Then, cells were fixed with 1% of formaldehyde at 37° C. for 10 minutes and quenched with 125 mM glycine for 5 minutes at RT, followed by preparation of total protein lysates using EpiTect ChIP kit according to the manufacturer's instructions (Qiagen, USA). Next, sheared DNA was incubated with 6 pg of monoclonal antibody against H3K27me3 (Abcam, ab4729) or IgG isotype control (ab171870). QPCR was used to analysis signals in input and immunoprecipitates. The percentage of immunoprecipitates signals was calculated over the input signals. Experiments were performed in triplicates, with independent samples. All primers and antibodies are listed in Table 2 and Table 3. All relevant data are available from authors. Genomic data from ChiP-seq experiments was deposited to GEO under the access number GSE120394.

In Vivo GSK343 and Malat1 Antisense LNA Treatments.

Cohorts of 10-week-old wild-type mice were treated with oral administration in drinking water of GSK343 24 hrs before left carotid ligation and following treatment for 3 weeks. GSK343 inhibitor (25 mg) was dissolved in 1 mL of DMSO to obtain a stock solution of 46 mM. Then, 250 ml of drinking water was supplemented with 250 pl of GSK343 stock solution. Control group for was given with equal volumes of sterile water. Bottles containing GSK343 were replaced with fresh water supplied with drug every 3 days. For Malat1 antisense LNA treatments, cohorts of 10-week-old wild-type mice were injected with 15 nmol in saline solution 24 hrs before left carotid ligation following by a second injection 7 days post-ligation.

TABLE 4

GapmeR antisense oligonucleotides against MALAT1

| Name | Sequences | ID |
|---|---|---|
| gapmeR-malat1 | GTCACAATGCATTCTA (SEQ ID NO: 1) | 339516LG0000008 |
| gapmeR-malat1-3'FAM | GTCACAATGCATTCTA/36-FAM/ (SEQ ID NO: 2) | 339516LG0000008-FFC |

Statistics.

Results are given as mean SD Student's t test (2-tailed) was applied to determine the statistical significance of difference between control and treated groups (*$P<0.05$, $P<0.01$ and *$P<0.001$). For all experiments, at least 3 experimental replicates were performed. Scatter graphs show mean SD. One-way analysis of variance (ANOVA) was used to analyze histology data involving multiple mouse genotypes (95% confidence interval is plotted). P-values represent one-way ANOVA followed by Tukey's honestly significant difference (HSD) post-hoc test. All graphs were produced using GraphPad Prism 7.0.

REFERENCES

Ailawadi G, Moehle C W, Pei H, Walton S P, Yang Z, Kron I L, Lau C L, and Owens G K. Smooth muscle phenotypic modulation is an early event in aortic aneurysms. The Journal of thoracic and cardiovascular surgery. 2009; 138(6):1392-9.

Alexander M R, and Owens G K. Epigenetic control of smooth muscle cell differentiation and phenotypic switching in vascular development and disease. Annu Rev Physiol. 2012; 74(13-40.

Guo D C, Pannu H, Tran-Fadulu V, Papke C L, Yu R K, Avidan N, Bourgeois S, Estrera A L, Safi Hi, Sparks E, et al. Mutations in smooth muscle alpha-actin (ACTA2) lead to thoracic aortic aneurysms and dissections. Nat Genet. 2007; 39(12):1488-93.

Pannu H, Tran-Fadulu V, Papke C L, Scherer S, Liu Y, Presley C, Guo D, Estrera A L, Safi Hi, Brasier A R, et al. MYH11 mutations result in a distinct vascular pathology driven by insulin-like growth factor 1 and angiotensin II. Hum Mol Genet. 2007; 16(20):2453-62.

Milewicz D M, Guo D C, Tran-Fadulu V, Lafont A L, Papke C L, Inamoto S, Kwartler C S, and Pannu H. Genetic basis of thoracic aortic aneurysms and dissections: focus on smooth muscle cell contractile dysfunction. Annu Rev Genomics Hum Genet. 2008; 9(283-302.

Guo D C, Papke C L, Tran-Fadulu V, Regalado E S, Avidan N, Johnson R J, Kim D H, Pannu H, Willing M C, Sparks E, et al. Mutations in smooth muscle alpha-actin (ACTA2) cause coronary artery disease, stroke, and Moyamoya disease, along with thoracic aortic disease. American journal of human genetics. 2009; 84(5):617-27.

Milewicz D M, Ostergaard J R, Ala-Kokko L M, Khan N, Grange D K, Mendoza-Londono R, Bradley T J, Olney A H, Ades L, Maher J F, et al. De novo ACTA2 mutation causes a novel syndrome of multisystemic smooth muscle dysfunction. American journal of medical genetics Part A. 2010; 152A(10):2437-43.Keylock A, Hong Y, Saunders D, Omoyinmi E, Mulhern C, Roebuck D, Brogan P, Ganesan V, and Eleftheriou D. Moyamoya-like cerebrovascular disease in a child with a novel mutation in myosin heavy chain 11. Neurology. 2018; 90(3):136-8.

Huang J, Wang T, Wright A C, Yang J, Zhou S, Li L, Yang 1, Small A, and Parmacek M S. Myocardin is required for maintenance of vascular and visceral smooth muscle homeostasis during postnatal development. Proc Natl Acad Sci USA. 2015; 112(14):4447-52.

Lino Cardenas C L, Kessinger C W, Cheng Y, MacDonald C, MacGillivray T, Ghoshhajra B, Huleihel L, Nuri S, Yeri A S, Jaffer F A, et al. An HDAC9-MALAT1-BRG1 complex mediates smooth muscle dysfunction in thoracic aortic aneurysm. Nat Commun. 2018; 9(1):1009.

Lino Cardenas C L, Kessinger C W, MacDonald C, Jassar A S, Isselbacher E M, Jaffer F A, and Lindsay M E. Inhibition of the methyltranferase EZH2 improves aortic performance in experimental thoracic aortic aneurysm. JO Insight. 2018; 3(5).

International Stroke Genetics C, Wellcome Trust Case Control C, Bellenguez C, Bevan S, Gschwendtner A, Spencer C C, Burgess A I, Pirinen M, Jackson C A, Traylor M, et al. Genome-wide association study identifies a variant in HDAC9 associated with large vessel ischemic stroke. Nat Genet. 2012; 44(3):328-33.

Consortium C A D, Deloukas P, Kanoni S, Willenborg C, Farrall M, Assimes T L, Thompson J R, Ingelsson E, Saleheen D, Erdmann J, et al. Large-scale association analysis identifies new risk loci for coronary artery disease. Nat Genet. 2013; 45(1):25-33.

Zhang B, Arun G, Mao Y S, Lazar Z, Hung G, Bhattacharjee G, Xiao X, Booth C J, Wu J, Zhang C, et al. The lncRNA Malat1 is dispensable for mouse development but its transcription plays a cis-regulatory role in the adult. Cell Rep. 2012; 2(1):111-23.

Owens L V, Xu L, Marston W A, Yang X, Farber M A, Iacocca M V, Cance W G, and Keagy B A. Overexpression of the focal adhesion kinase (p125FAK) in the vascular smooth muscle cells of intimal hyperplasia. Journal of vascular surgery. 2001; 34(2):344-9.

Ferns G A, Raines E W, Sprugel K H, Motani A S, Reidy M A, and Ross R. Inhibition of neointimal smooth muscle accumulation after angioplasty by an antibody to PDGF. Science. 1991; 253(5024):1129-32.

Papke C L, Cao J, Kwartler C S, Villamizar C, Byanova K L, Lim S M, Sreenivasappa H, Fischer G, Pham J, Rees M, et al. Smooth muscle hyperplasia due to loss of smooth muscle alpha-actin is driven by activation of focal adhesion kinase, altered p53 localization and increased levels of platelet-derived growth factor receptor-beta. Hum Mol Genet. 2013; 22(15):3123-37.

Talasila A, Yu H, Ackers-Johnson M, Bot M, van Berkel T, Bennett M R, Bot I, and Sinha S. Myocardin regulates vascular response to injury through miR-24/-29a and platelet-derived growth factor receptor-beta. Arteriosclerosis, thrombosis, and vascular biology. 2013; 33(10): 2355-65.

Boyer L A, Plath K, Zeitlinger J, Brambrink T, Medeiros L A, Lee T I, Levine S S, Wernig M, Tajonar A, Ray M K, et al. Polycomb complexes repress developmental regulators in murine embryonic stem cells. Nature. 2006; 441(7091):349-53.

Owens G K, Kumar M S, and Wamhoff B R. Molecular regulation of vascular smooth muscle cell differentiation in development and disease. Physiol Rev. 2004; 84(3): 767-801.

Georgescu M M, Pinho Mda C, Richardson T E, Torrealba J, Buja L M, Milewicz D M, Raisanen J M, and Burns D K. The defining pathology of the new clinical and histopathologic entity ACTA2-related cerebrovascular disease. Acta Neuropathol Commun. 2015; 3(81.

Buccheri D, Piraino D, Andolina G, and Cortese B. Understanding and managing in-stent restenosis: a review of clinical data, from pathogenesis to treatment. J Thorac Dis. 2016; 8(10):E1150-E62.

Langmead B, and Salzberg S L. Fast gapped-read alignment with Bowtie 2. Nature methods. 2012; 9(4):357-9.

Li H, Handsaker B, Wysoker A, Fennell T, Ruan J, Homer N, Marth G, Abecasis G, Durbin R, and Genome Project Data Processing S. The Sequence Alignment/Map format and SAMtools. Bioinformatics. 2009; 25(16):2078-9.

Robinson J T, Thorvaldsdottir H, Winckler W, Guttman M, Lander E S, Getz G, and Mesirov J P. Integrative genomics viewer. Nat Biotechnol. 2011; 29(1):24-6.

Yu G, Wang L G, and He Q Y. ChIPseeker: an R/Bioconductor package for ChIP peak annotation, comparison and visualization. Bioinformatics. 2015; 31(14):2382-3.

Huang D W, Sherman B T, Tan Q, Kir J, Liu D, Bryant D, Guo Y, Stephens R, Baseler M W, Lane H C, et al. DAVID Bioinformatics Resources: expanded annotation database and novel algorithms to better extract biology from large gene lists. Nucleic Acids Res. 2007; 35(Web Server issue):W169-75.

Example 2: Inhibition of the Methyltranferase EZH2 Improves Aortic Performance in Experimental Thoracic Aortic Aneurysm (TAA)

Loss-of-function mutations in genes encoding contractile proteins have been observed in thoracic aortic aneurysm (TAA). To gain insight into the contribution of contractile protein deficiency in the pathogenesis of TAA, the inventors examined human aneurysm samples. The inventors found multiple contractile gene products deficient in TAA samples and in particular expression of SM22a was inversely correlated with aneurysm size. SM22a-deficient mice demonstrated pregnancy-induced aortic dissection and SM22a-deficiency worsened aortic aneurysm in Fbn/cl° 39G/+ (Marfan) mice, validating this gene product as a TAA effector. The inventors found that repression of SM22a was enforced by increased activity of the methyltransferase EZH2. TGF-β effectors such as SMAD3 were excluded from binding SM22a-encoding chromatin (TAGLN) in TAA samples, while treatment with the EZH2 inhibitor GSK343 improved cytoskeletal architecture and restored SM22a. expression. Finally, inhibition of EZH2 improved aortic performance in Fbn1c1° 39G/+ mice in association with restoration of contractile protein expression (including SM22a). Together, these data inform our understanding of contractile protein deficiency in TAA, and support the pursuit of chromatin modifying factors as therapeutic targets in aortic disease.

Contractile proteins are vital components of the vascular smooth muscle cell (VSMC) cytoskeleton and perform kinetic and static regulatory functions in both health and disease. Loss of contractile protein expression has been observed in various forms of vascular disease including aneurysms (1-3), atherosclerosis (4-6), and vascular stenosis (7, 8). Such observations may be more than correlative as multiple genes involved in the VSMC contractile apparatus have been implicated in familial forms of thoracic aortic aneurysm (TAA). For instance, pathogenic variation in the genes ACTA2 and MYH11, encoding the complementary components of the smooth muscle actin-myosin apparatus, alpha-smooth muscle actin (D-SMA) and smooth muscle myosin heavy chain (smMHC), both have been shown to cause TAA in humans (9, 10). Additionally, regulators of this interaction have been implicated in TAA including loss of function mutations in MYLK, encoding myosin light chain kinase and a recurrent gain of function mutation in PRKG1, a negative regulator of myosin light chain phosphatase (11, 12). These genetic data directly implicate gene products involved in vascular smooth muscle cell contraction in the pathogenesis of TAA. Disruption in a second group of matrix independent gene products have been implicated in TAA. Syndromic presentations (ie. Loeys-Dietz syndrome, Aneurysms-Osteoarthritis syndrome, or Marfan syndrome) have been described with loss of function mutations in genes encoding various members of the TGF-β signaling cascade including TGFBRI, TGFBR2, TGFB2, TGFB3, and SMAD3 amongst others (13-17). These genes encode TGF-β ligands (TGFB2/3), TGF-β receptors (TGFR1/2), and downstream mediators of canonical TGF-β signaling (such as SMAD3). Both syndromic and nonsyndromic presentations of TAA affect similar anatomic portions of the aorta and show similar disruption of tissue architecture suggesting a shared pathogenesis (18).

The expression of contractile protein elements such as a-SMA, SM22a, and smoothelin can be induced in experimental contexts by exogenously applied TGF-β (19-22) leading to models whereby loss of function genetic variation in the canonical TGF-β signaling cascade may lead directly to deficiency of contractile elements. However, increased levels of TGF-β signaling, as assessed by phosphorylation of Smad proteins (p-Smad2/3) have routinely been observed in both genetically-triggered as well as sporadic aortic samples (18, 23). Despite increased TGF-β signaling, contractile protein elements in aortic specimens from TAA are often deficient and antagonism of TGF-β signaling has been shown to be therapeutic in non-inflammatory experimental TAA (24). These observations suggest a discrepancy between transcriptional circuits operating in VSMCs in health versus those in TAA.

In this study the inventors analyzed human aneurysm samples to examine proteins of the contractile apparatus in TAA. Multiple gene products are deficient in human and murine TAA samples and in particular expression of the protein SM22a. The inventors first demonstrated that loss of SM22a is a direct effector of aneurysm progression and aortic dissection in vivo. Investigation of SM22a transcriptional regulation revealed hypermethylation of consensus sequences containing SMADs-transcription factor binding sites (TFBS) at the locus of the TAGLN (SM22a-encoding) gene in human aneurysm tissue associating with histone 3 lysine 27 trimethylation (H3K27me3) modifications. Targeting the methyltransferase EZH2, (catalyzing H3K27me3 modifications), with the small molecule inhibitor GSK343 improved aortic performance in Fbn1$^{cl°39w+}$ mice in association with restoration of contractile protein expression. The therapeutic benefit of GSK343 inhibitor was comparable to losartan, however these compounds exhibited distinct molecular mechanisms. These data illuminate the critical role of vascular smooth muscle cell contractile proteins in aortic homeostasis, describe novel epigenetic modification in thoracic aortic disease, and expand the therapeutic options for thoracic aortic aneurysm.

Results:

Contractile Protein Expression is Associated with TAA Pathology.

Contractile protein down regulation has been observed in various forms of vascular disease. To study how this phenomenon may relate to disease progression in TAA the inventors choose to evaluate transcript expression of previously described markers of the VSMC phenotypic state (25) in aortic tissue taken at the time of surgery. Several genes indicative of the VSMC "synthetic state" were upregulated in comparison to control aortas. Conversely, transcripts encoding the contractile proteins were significantly deficient in tissue from TAA repair and patients who have experienced aortic dissection (FIG. 1A and Supplemental Table 1 available on the world wide web at ncbi.nlm.nih.gov/pmc/articles/PMC5922285/bin/jciinsight-3-97493-s002.xlsx).

The TAGLN gene, encoding SM22a, in particular has been reported to be downregulated (Fold Change=0.12) in patients with aortic dissection (26, 27) and the inventors therefore chose to examine this factor further. Expression of SM22a protein in aneurysm samples collected from patients with TAA at the time of cardiac surgery demonstrate significant repression from patients with syndromic and/or nonsyndromic aortic disease (FIG. 1B). Examination of human TAA samples via immunohistochemistry similarly demonstrates that the decrement in contractile proteins localize to the aortic media (FIG. 1C). To study SM22a regulation in a more controlled system, the inventors examined expression in the FbnIcl°39G1+ mouse model of Marfan syndrome and found a similar repression at both mRNA and protein level (FIG. 1D and FIG. 1E). Interestingly, the expression of SM22a was found to be closely and inversely correlated with aneurysm size (FIG. 1F). These observations led us to examine the effect of SM22a deficiency on VSMC behavior. Targeting SM22a expression with siRNA mediated silencing induced cytoskeletal destabilization as well as well as vacuole formation (FIGS. 1G and 1H), two cellular phenotypes directly visualized in classic electron microscopic examination of TAA tissue from human patients (28). Furthermore, matrix metalloproteinase (MMP) activity known to be associated with aortic aneurysms was activated in SM22a siRNA treated VSMCs (FIG. 11), consistent with previous reports of SM22a as a negative regulator of MMP expression (29).

SM22a is Required for Aortic Homeostasis.

Figure 2A:
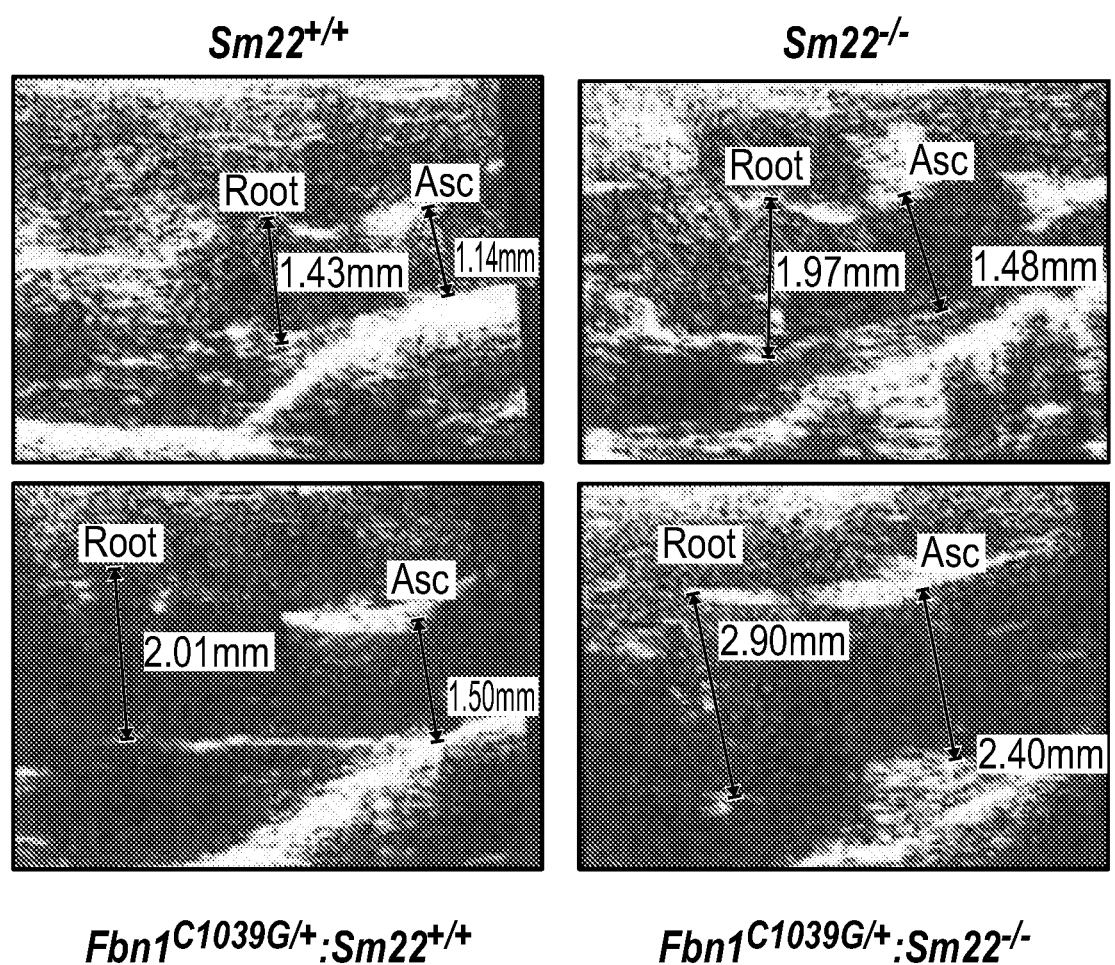
FIGS. 2A-2G demonstrate that the loss of SM22a is a direct effector of aneurysm progression and dissection.
Figure 2B:
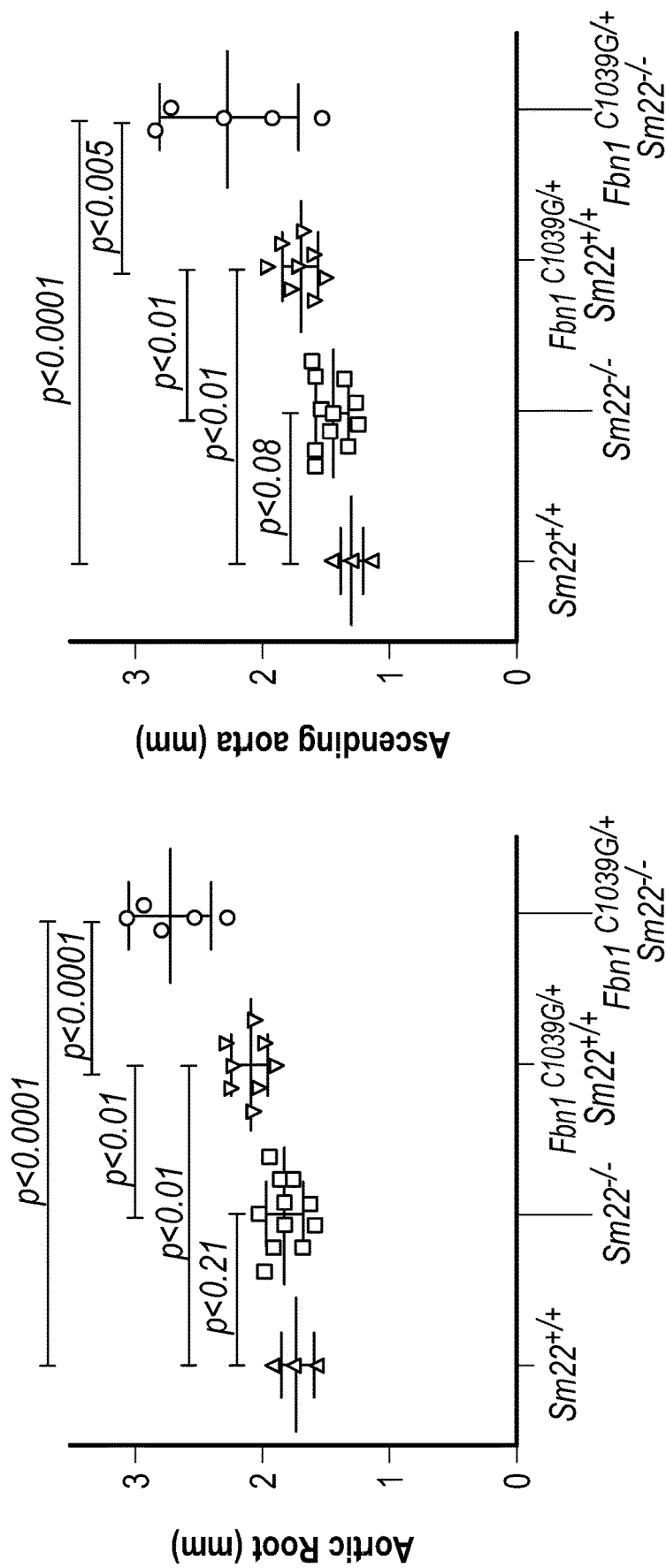
Figure 2C:
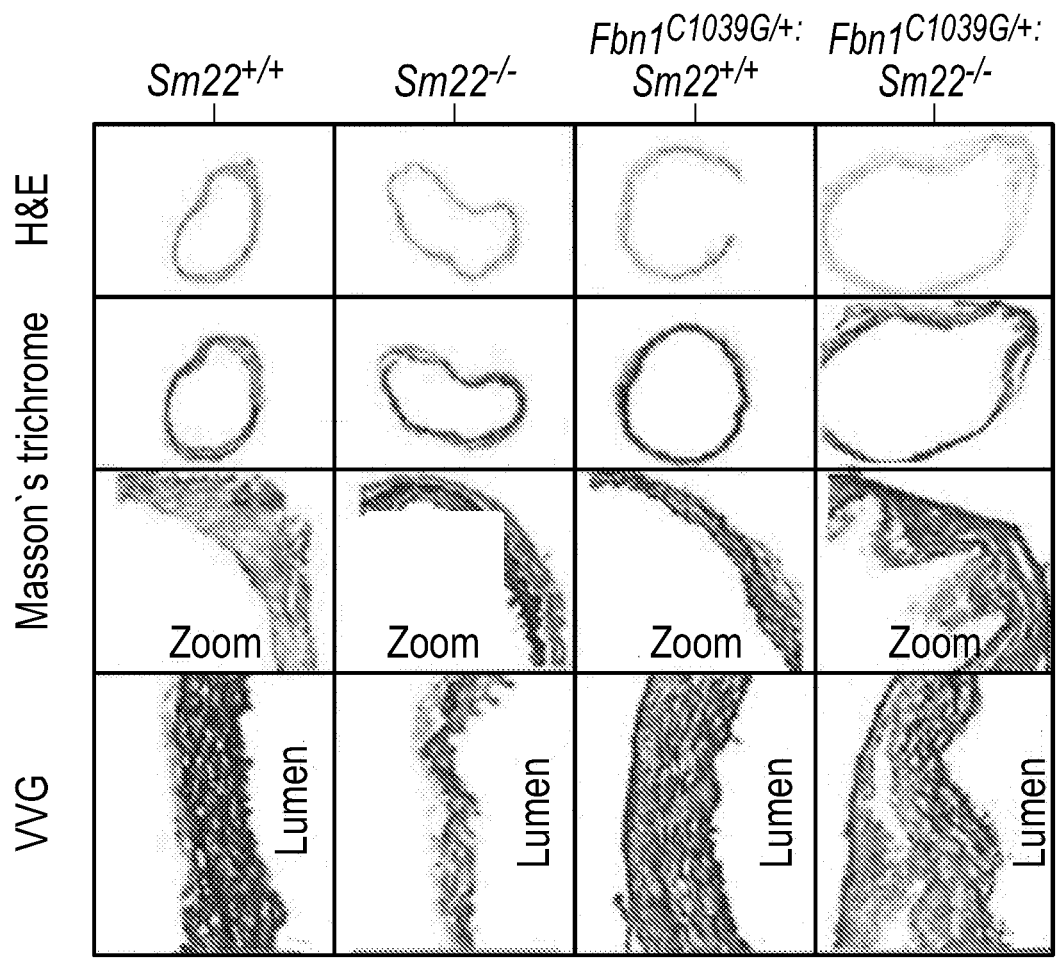
Figure 2D:
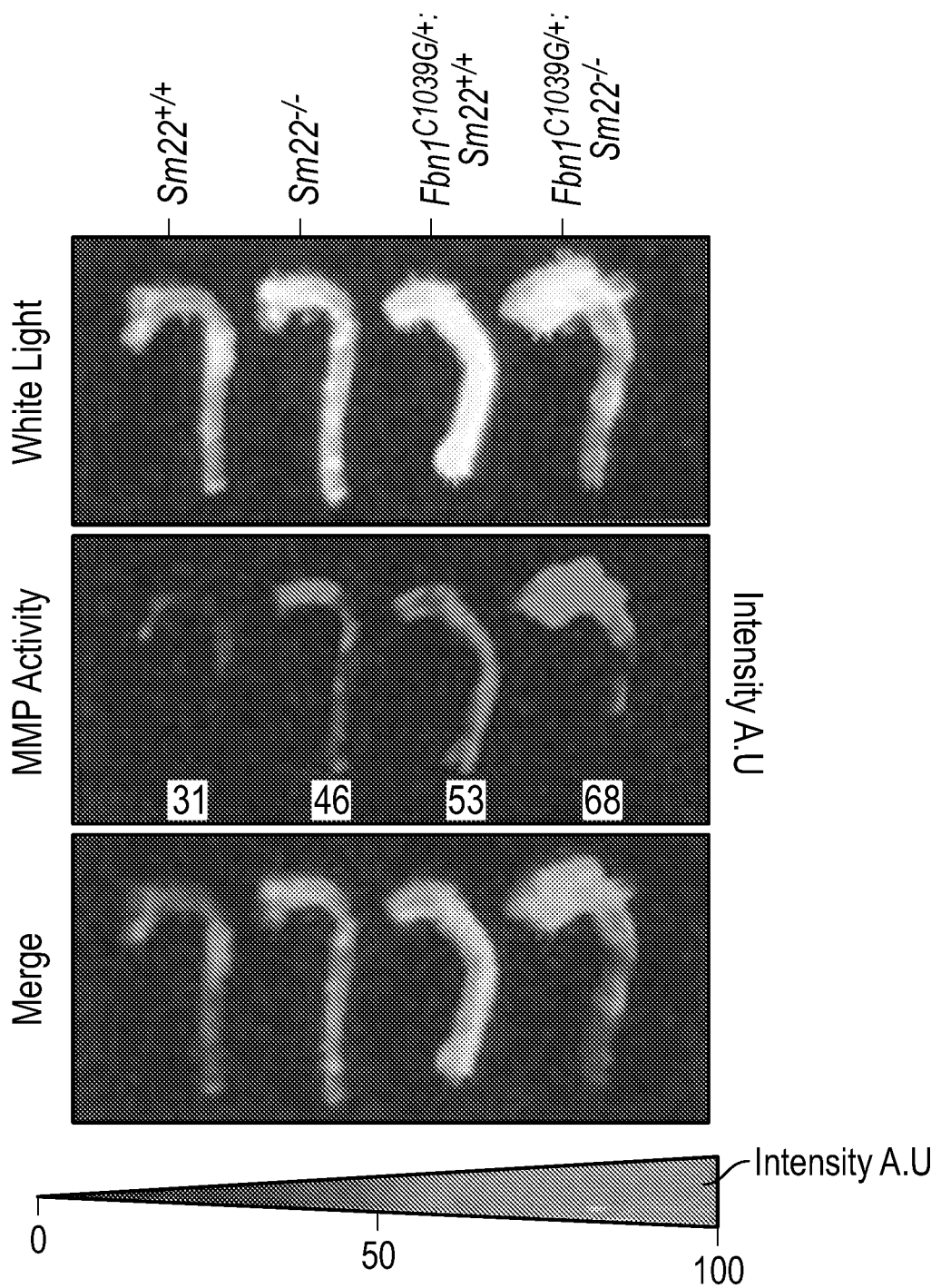

These data suggest that loss of SM22a expression may contribute to the aneurysm progression in TAA. To examine this concept, the inventors crossed SM22a-deficient mice (Tagle or Sm22) to Fbn1$^{cl°39gl+}$ mice to generate SM22a-deficient Fbni$^{cl°39G1+}$ animals and examined aortic aneurysm progression. Consistent with the role of SM22a as an important determinant of aortic homeostasis, Fbni$^{cl°39G1+}$:Sm22$^{4-}$ mice exhibited larger aortas and more rapid aortic growth than age-matched Fbn/$^{cl°39G+}$:Sm22$^{+/+}$ mice (FIG. 2A and FIG. 2B). Histochemical examination of Sm22 aortas revealed increased levels of collagen deposition in the adventitia when compared to wild type mice (FIG. 2C). In Fbni$^{cl°39/+}$:Sm22$^{-/-}$ mice collagen deposition was further accentuated and aortic wall architecture more disrupted than age-matched Fbni$^{ci°39G/+}$:Sm22$^{+/+}$ mice (FIG. 2C). These changes were accompanied by increased MMP activity in Fbni$^{cl°39Gif}$: Sm22$^{-/-}$ mice when compared to Fbni$^{cl°39G1+:Sm}$22$^{4+}$ mice (FIG. 2D).

Figure 2F:
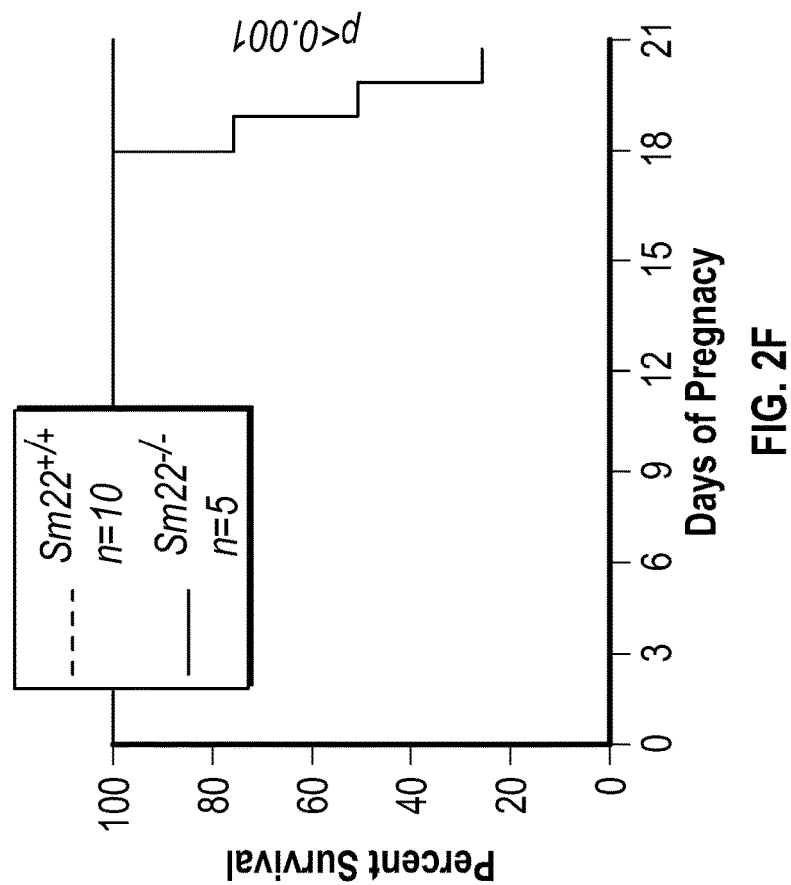
Figure 2E:
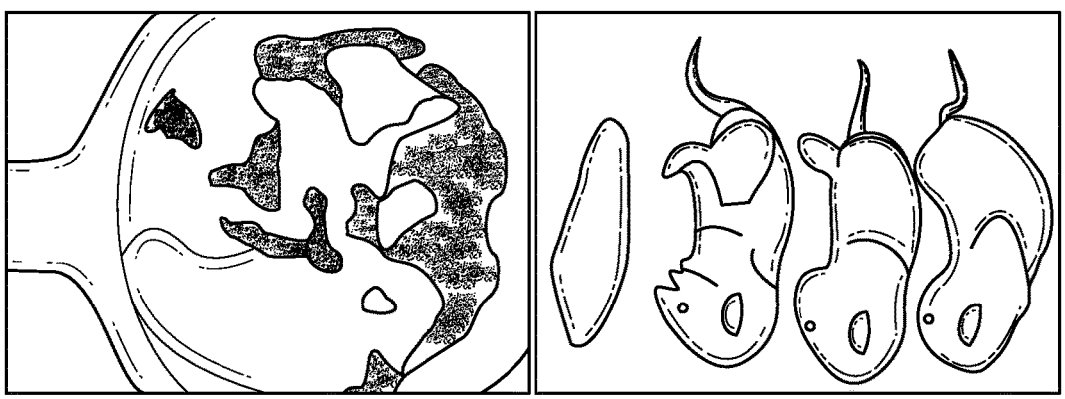
Figure 2G:
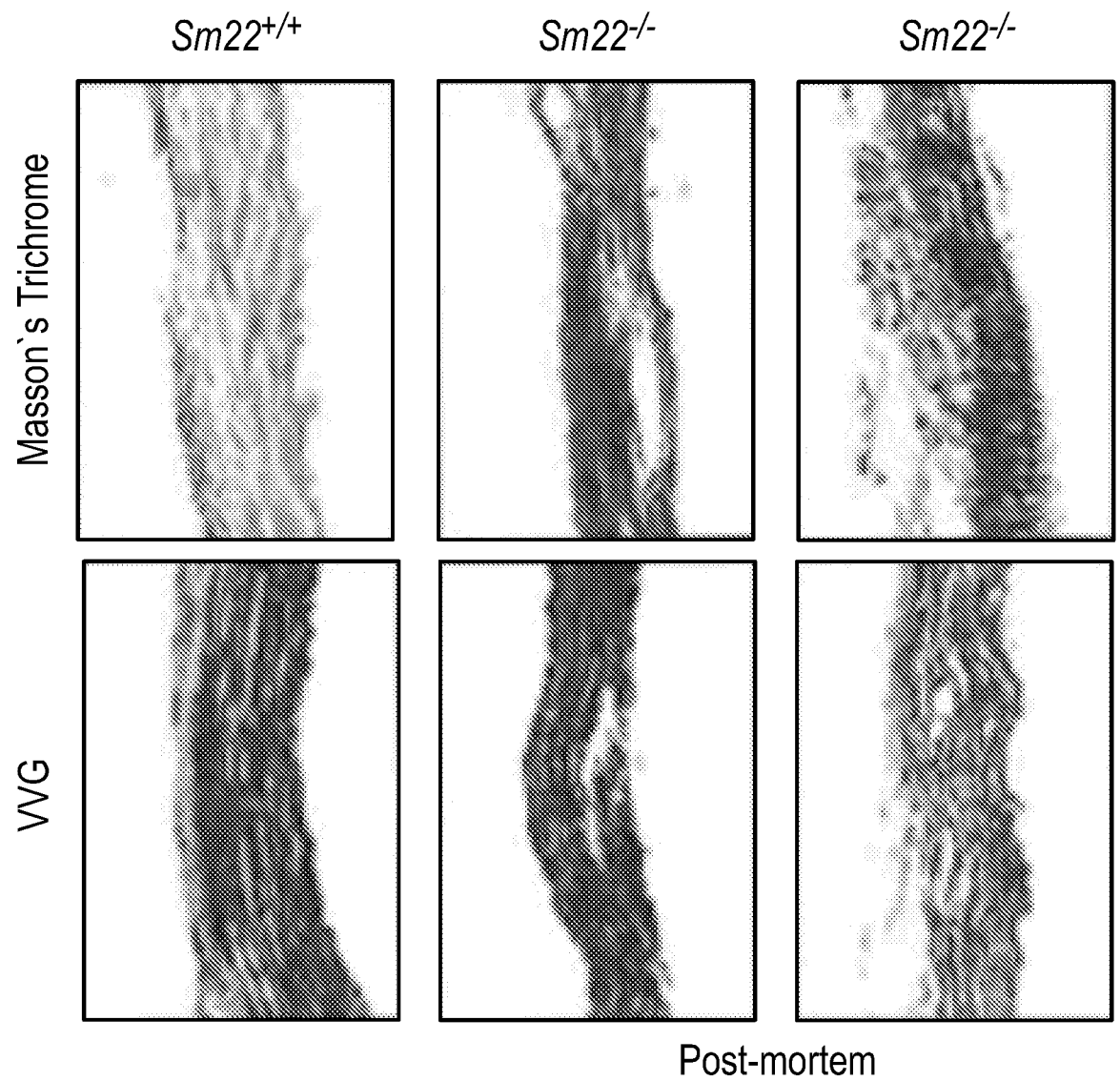

Examination of aortas from Sm22$^{-/-}$ demonstrated only mild, non-significant aortic enlargement when compared to Sm22$^{+/+}$ mice (FIG. 2B). However, during the breeding the inventors noted premature lethality in Sm22 dams. Postmortem examination of pregnant mice demonstrated evidence of hemothorax caused by aortic rupture, suggesting a susceptibility of the Sm22 aorta to pregnancy-induced aortic disease (FIG. 2E). Lethality predominantly occurred during the terminal stages of pregnancy, similar to pregnancy-induced aortic dissection in humans (FIG. 2F). Examination of post mortem aortic tissue demonstrated increased collagen deposition across the aortic media (FIG. 2G).

Inhibition of EZH2 Activity Improves SM22a Expression in Cellular Models.

Figure 3A:
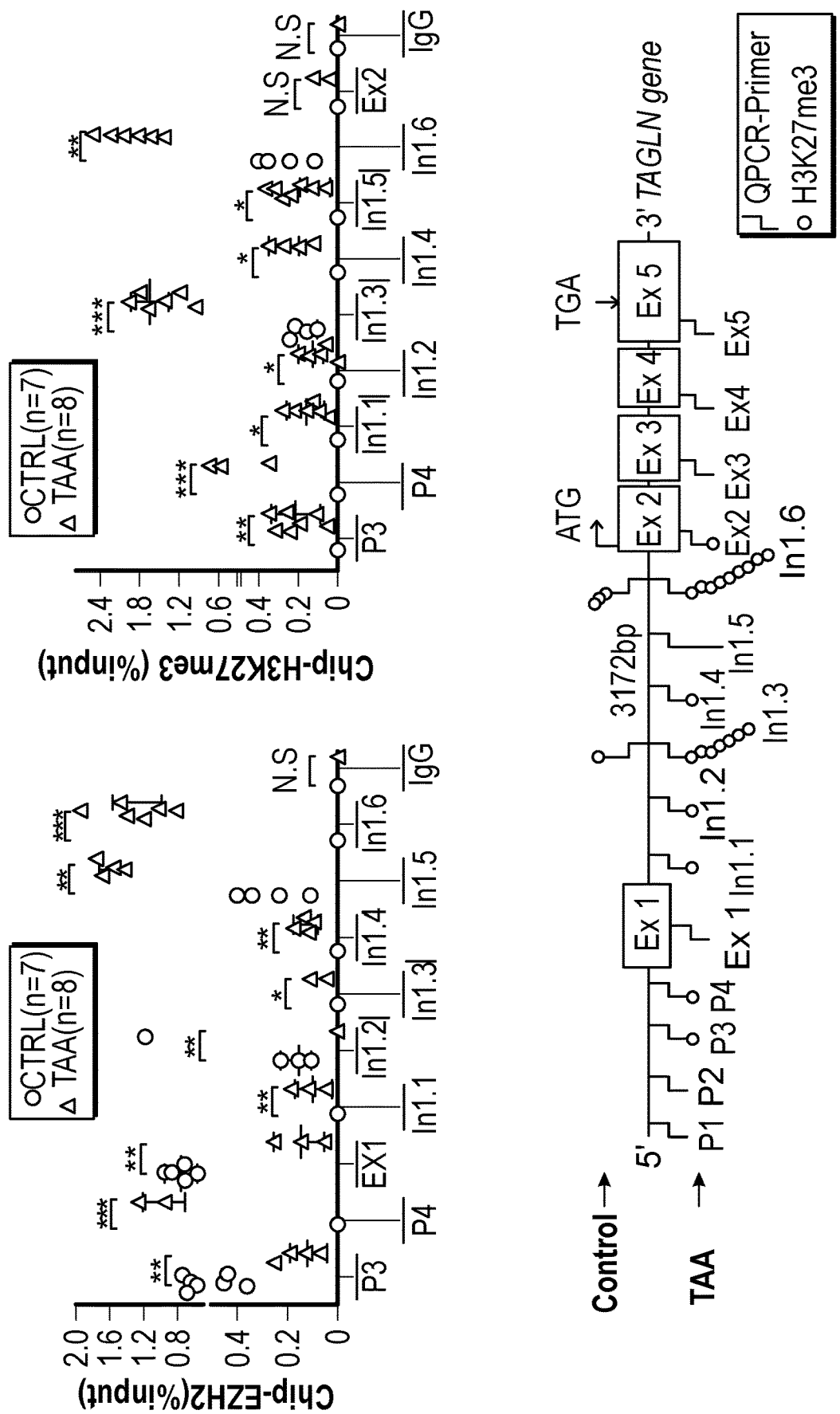
FIGS. 3A-3K demonstrate that the Inhibition of the methyltransferase, EZH2 restores SM22a expression.
Figure 3B:
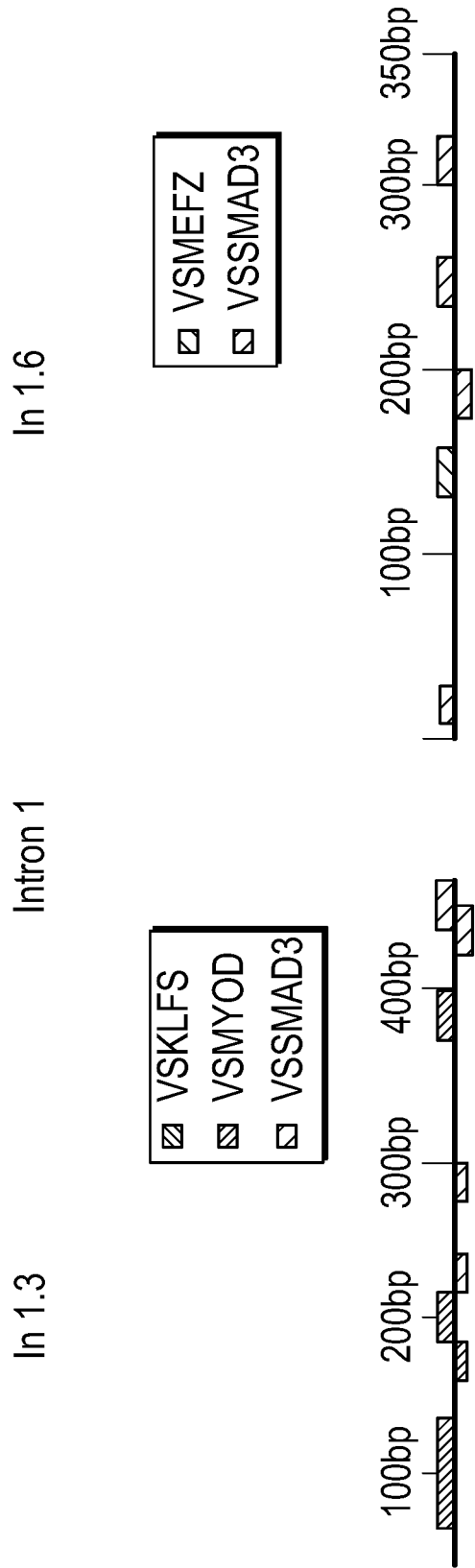
Figure 3C:
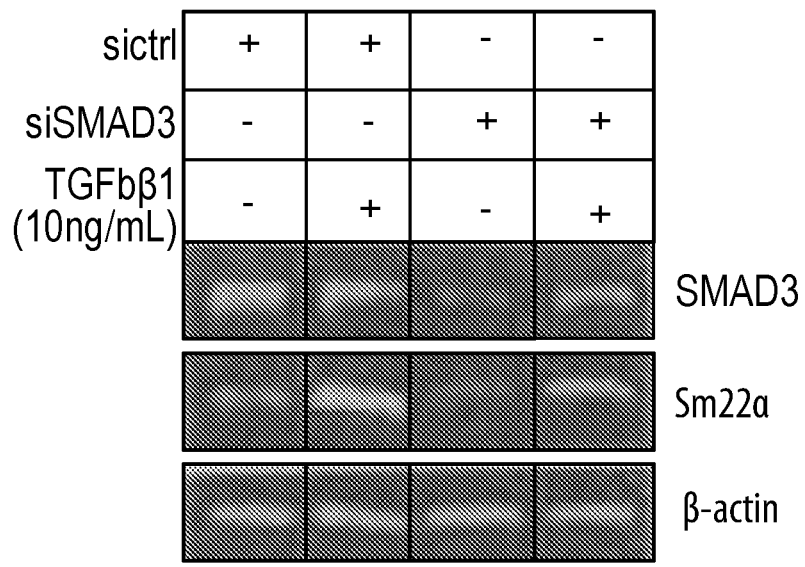
Figure 3D:
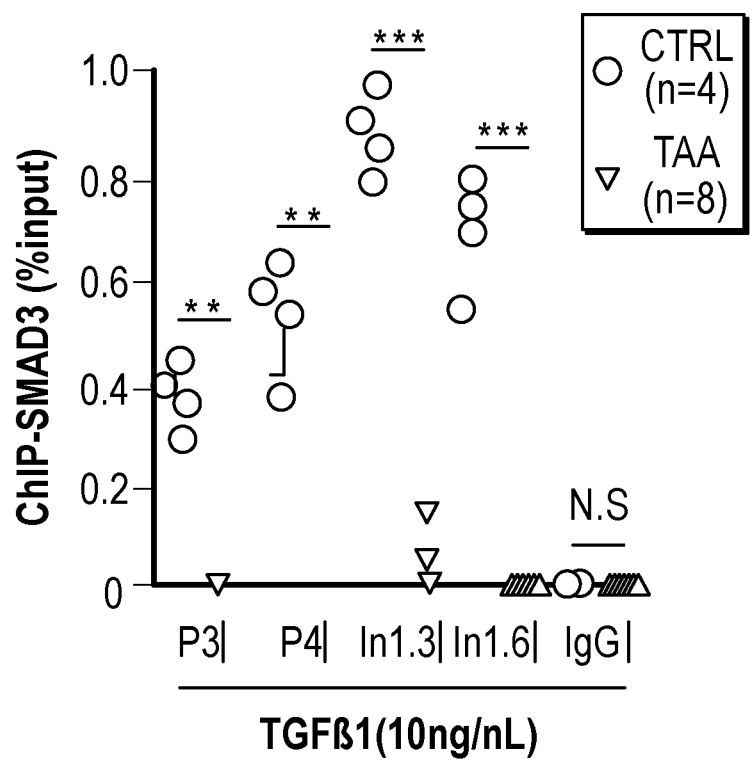
Figure 3E:
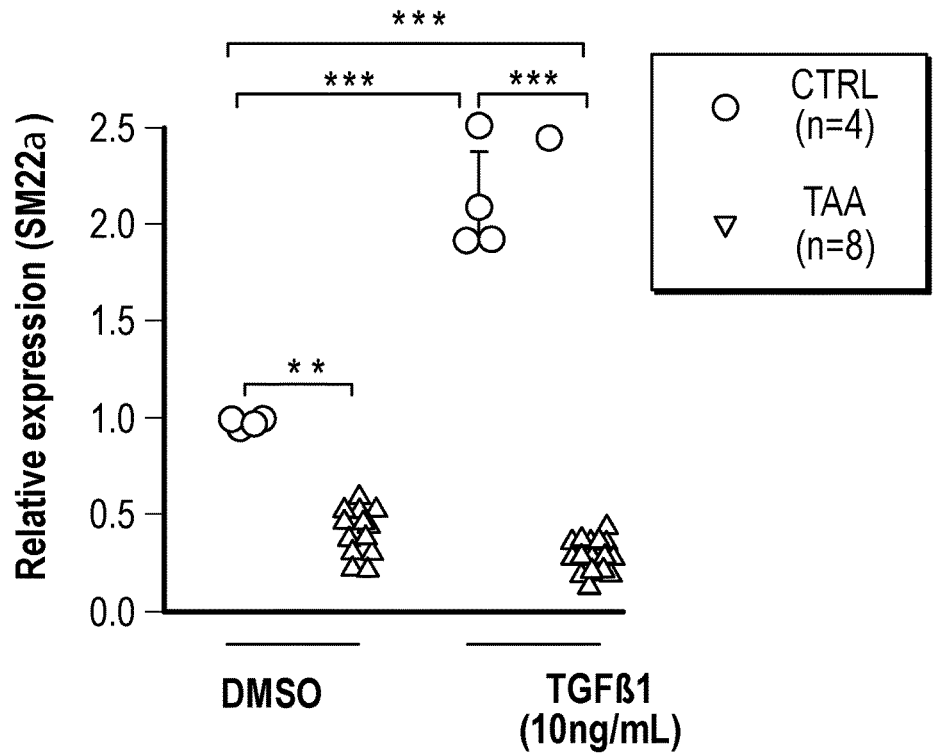
Figure 3F:
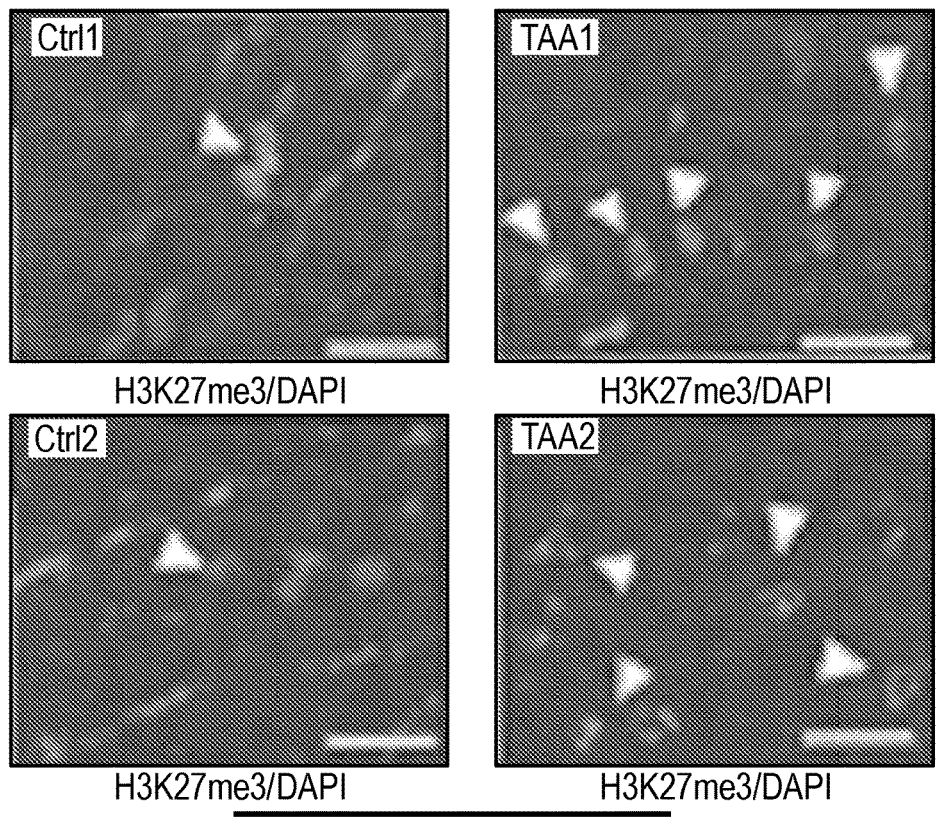
Figure 3G:
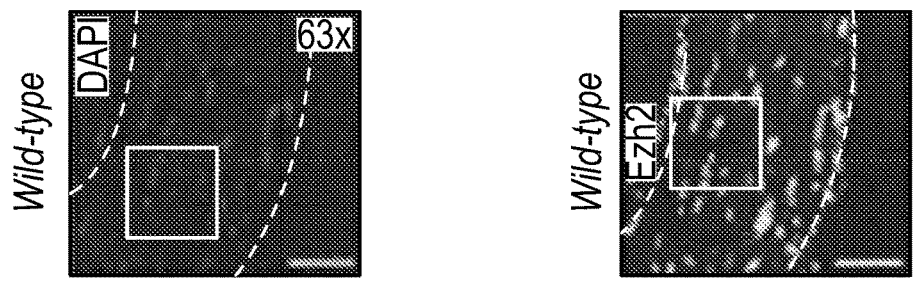

These data support the concept that SM22a deficiency represents a critical mediator of TAA pathogenesis. To examine the transcriptional regulation of the SM22a (TAGLN gene), the inventors chose to examine the chromatin state directly from human aortic aneurysm samples. By using chromatin-immunoprecipitation (ChIP-qPCR) assays, the inventors demonstrate that loss of SM22a is caused via an increased activity of the methyltransferase EZH2, the catalytic subunit of PRC2 complex, at the promoter and gene body of the TAGLN gene. The inventors also found a robust enrichment of H3K27me3, the catalytic product of EZH2, in two regions within intron 1 (ln1.3 and In1.6) (FIG. 3A). The inventors therefore analyzed the primary sequence of these two regions for possible transcription factor binding sites using Genomatix (FIG. 3B). The inventors identified putative binding sites for SMAD3, Myocardin, KLF factors and MEF2 via bioinformatics profiling. Due to the well known association of TAA with TGF-β signaling the inventors chose to examine SMAD3 activity in relation to SM22a expression. Silencing of SMAD3 in VSMCs revealed that both basal and TGF-β induced SM22a expression are mediated in part by SMAD3 expression (FIG. 3C). The inventors therefore examined SMAD3 binding to the In1.3 and In1.6 intronic region in the presence of exogenously added TGF-3. Interestingly, SMAD3 binding was detected in control VSMC cultures, but not from VSMCs cultured from TAA samples (FIG. 3D). The inability of SMAD3 to access these promoter regions correlates with an inability of TGF-β to induce TAGLN transcript expression (FIG. 3E). Immunofluorescent staining in TAA aortas showed increased levels of H3K27me3 marks (FIG. 3F). The inventors therefore tested the ability of GSK343, a potent inhibitor of EZH2, to influence SMAD3-mediated SM22a transcriptional regulation. Indeed, isolated TAA VSMCs treated with GSK343 inhibitor recovered the ability to induce SM22a expression after stimulation with recombinant TGF-f31 (FIG. 3G).

Figure 1B:
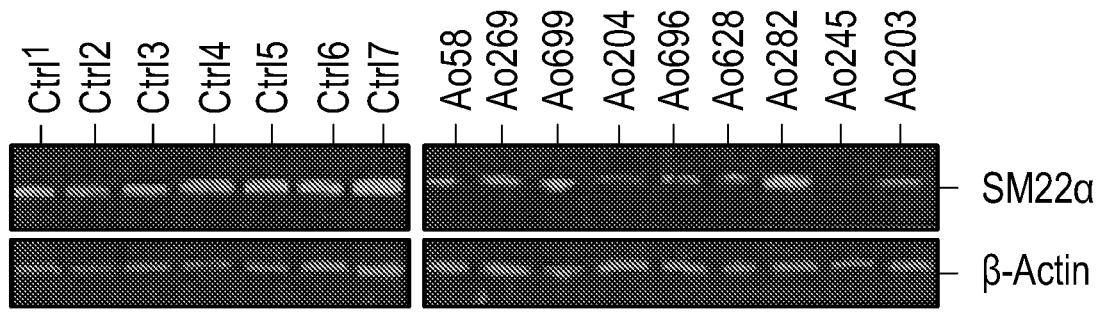
Figure 1B:
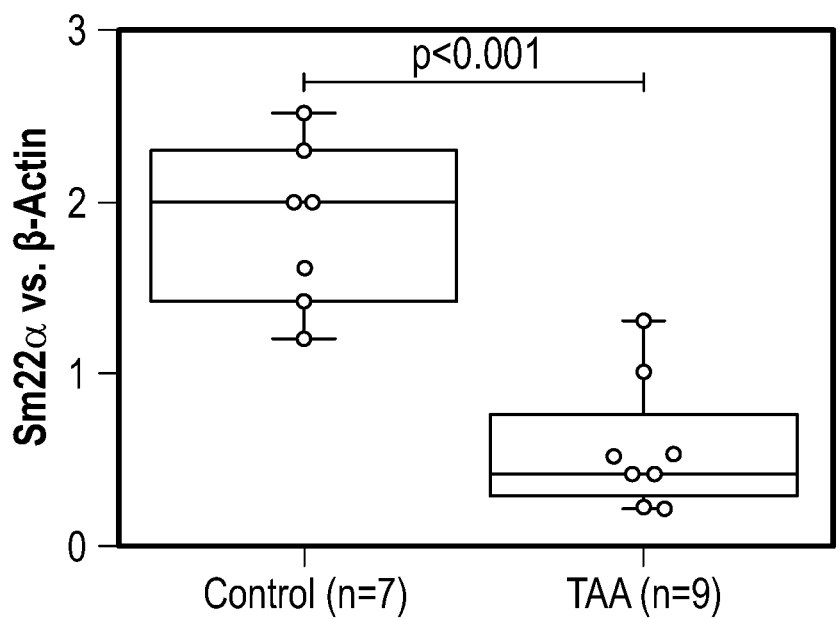
Figure 1C:
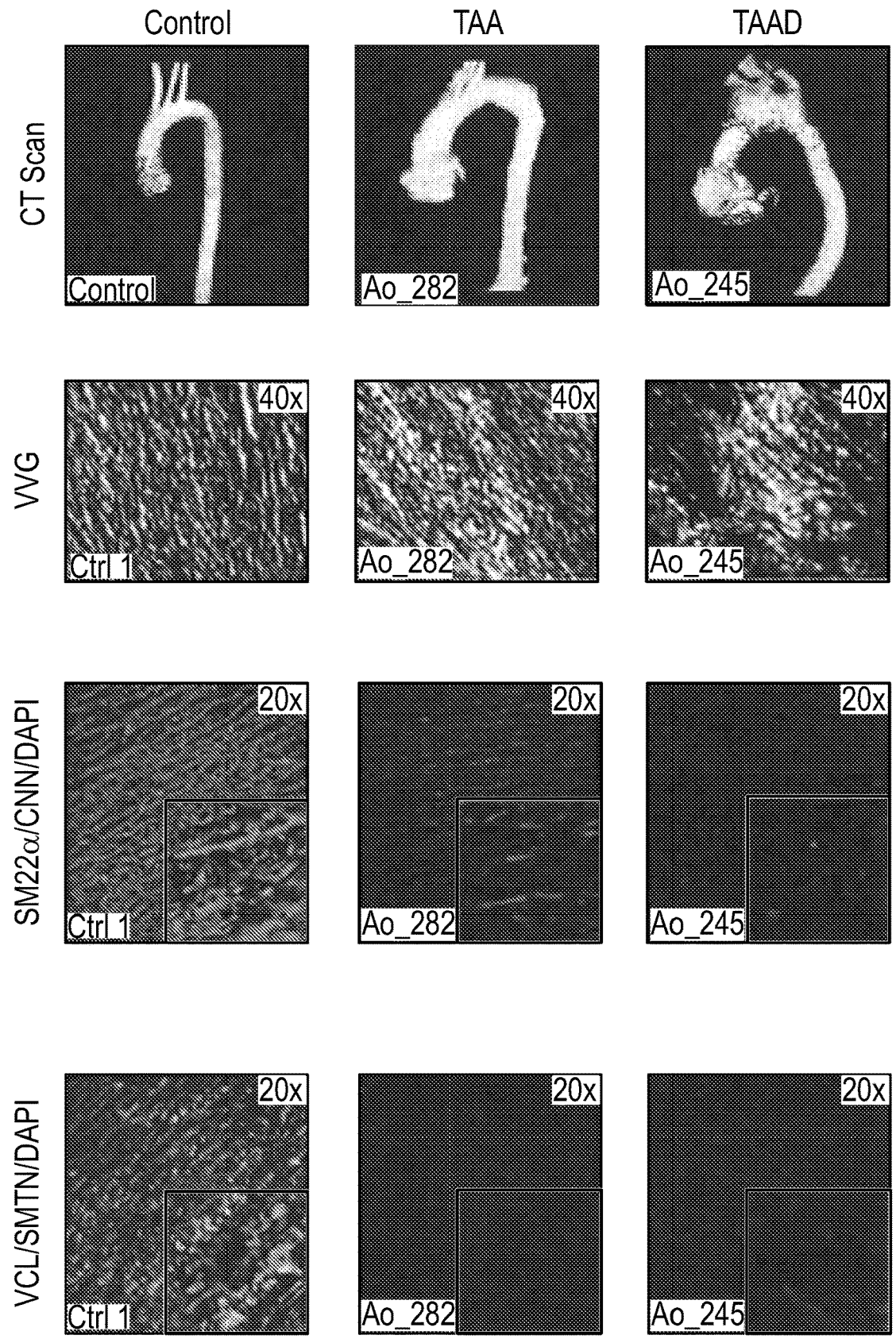
Figure 1D:
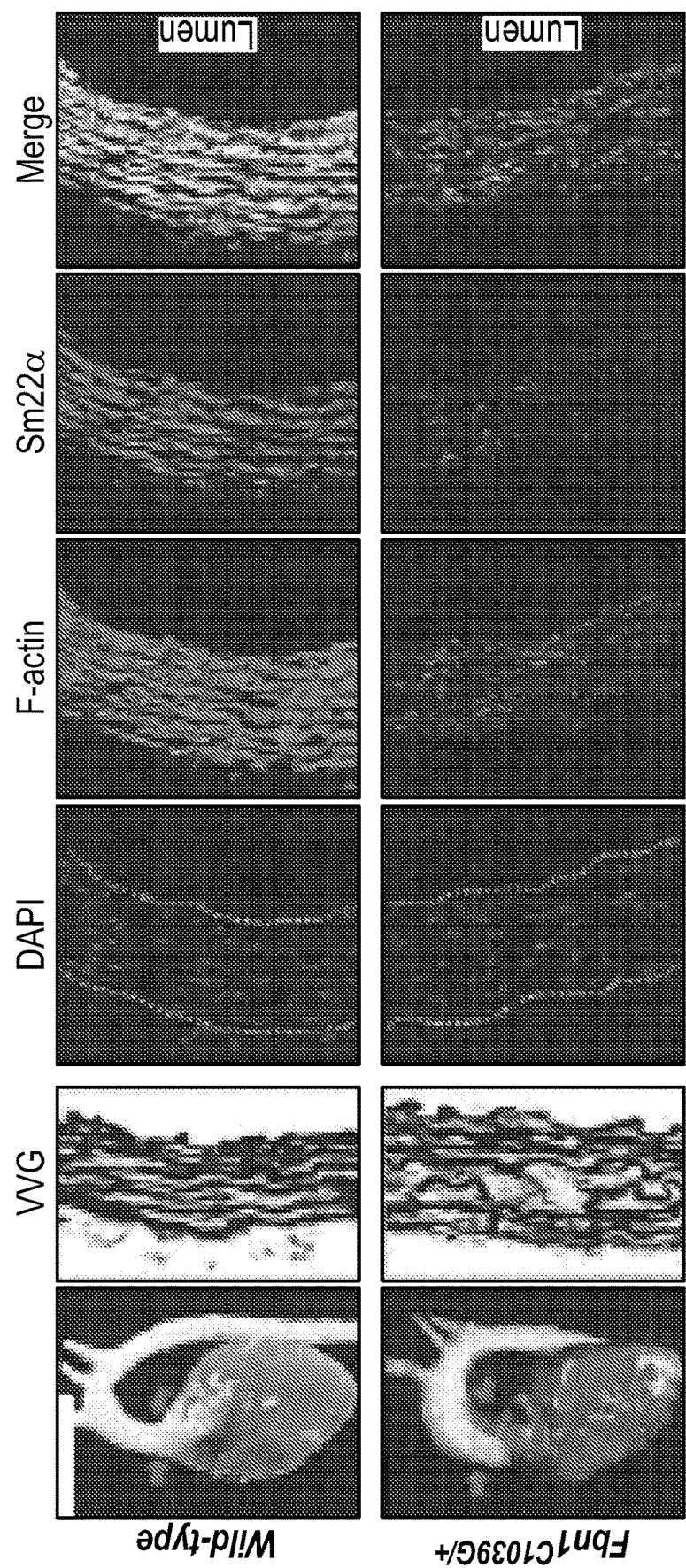
Figure 1E:
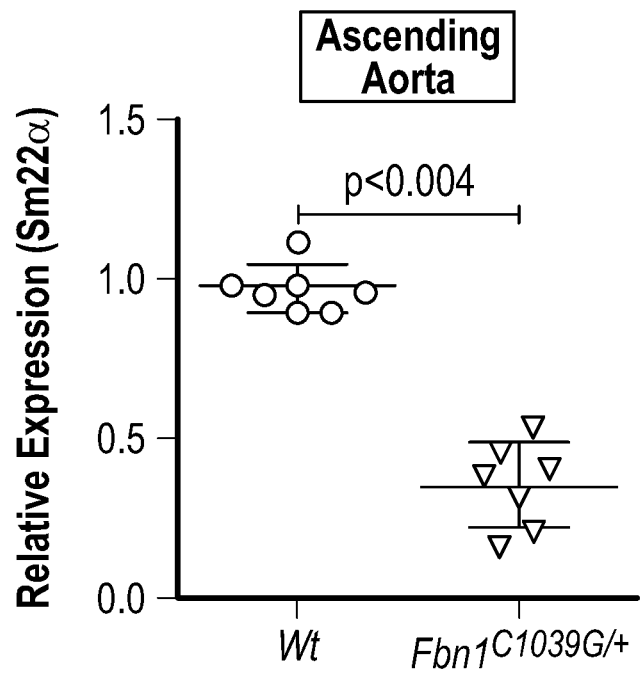
Figure 1E:
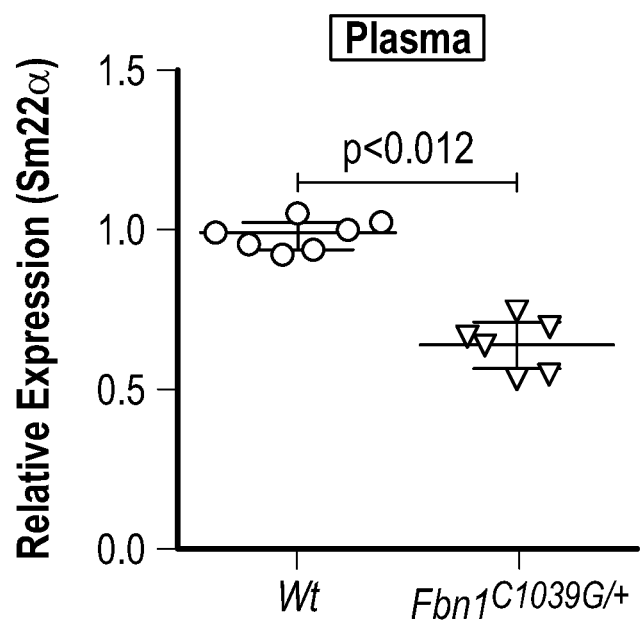
Figure 1F:
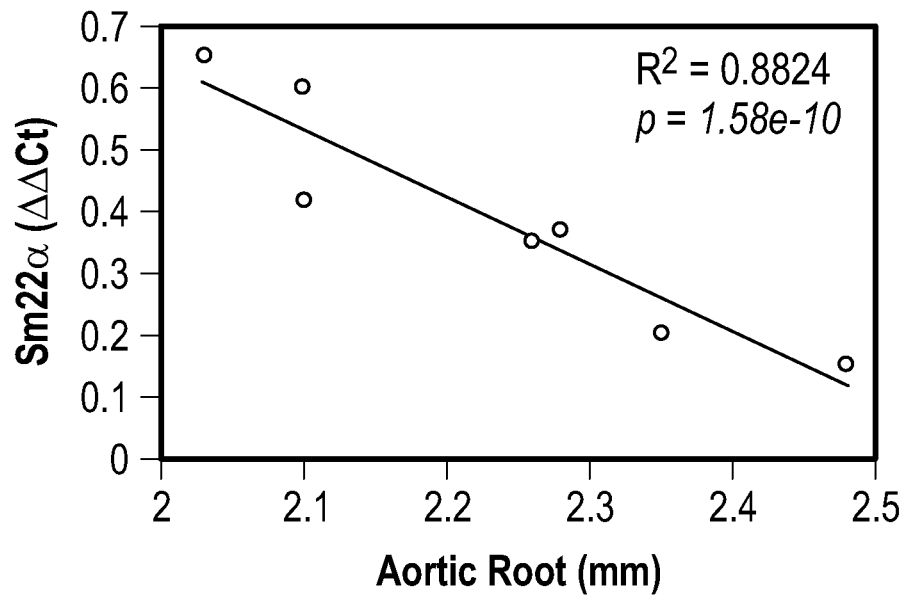
Figure 1F:
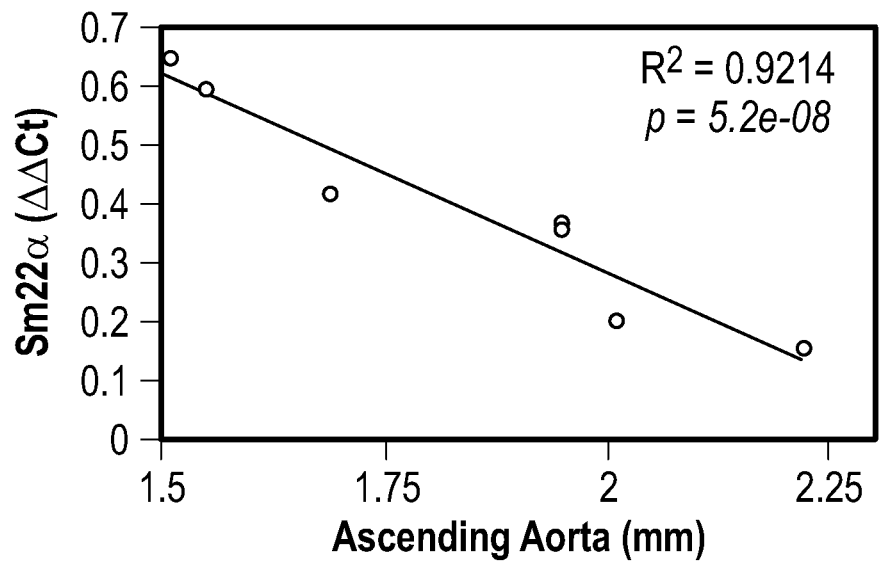
Figure 1G:
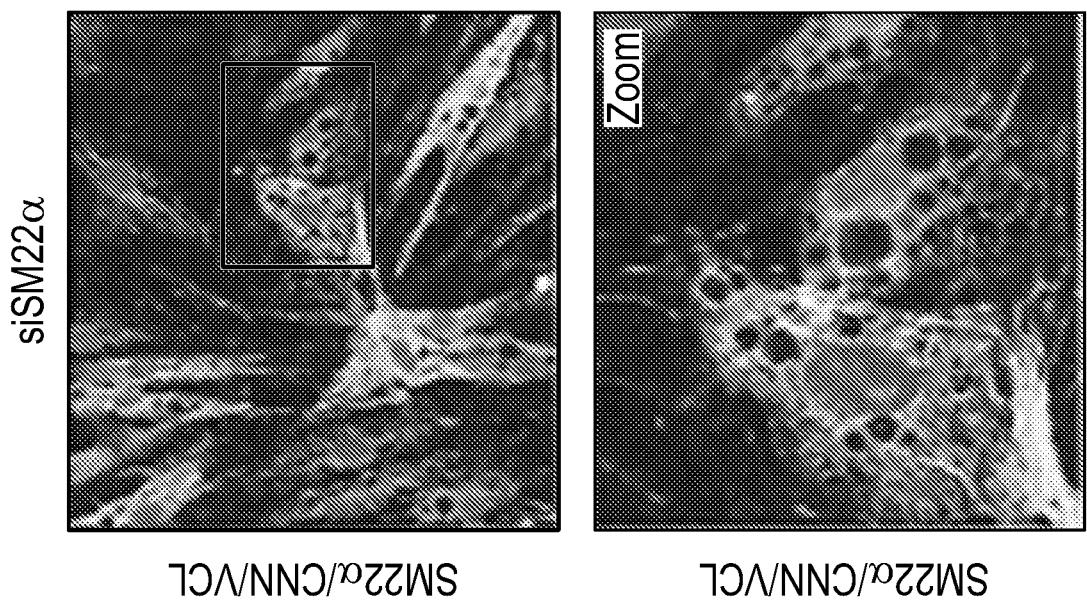
Figure 1G:
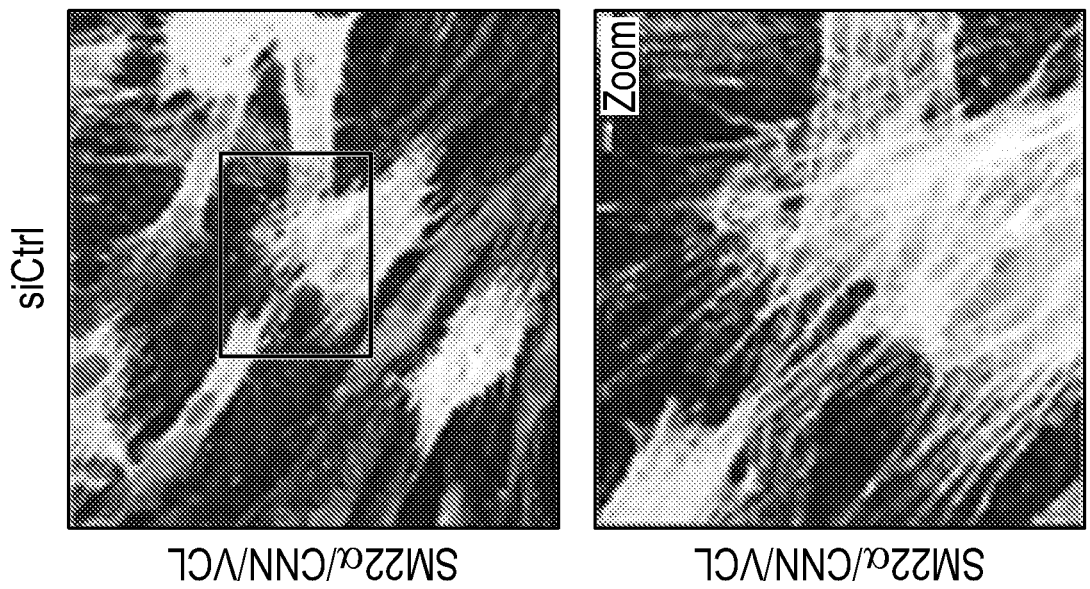
Figure 1H:
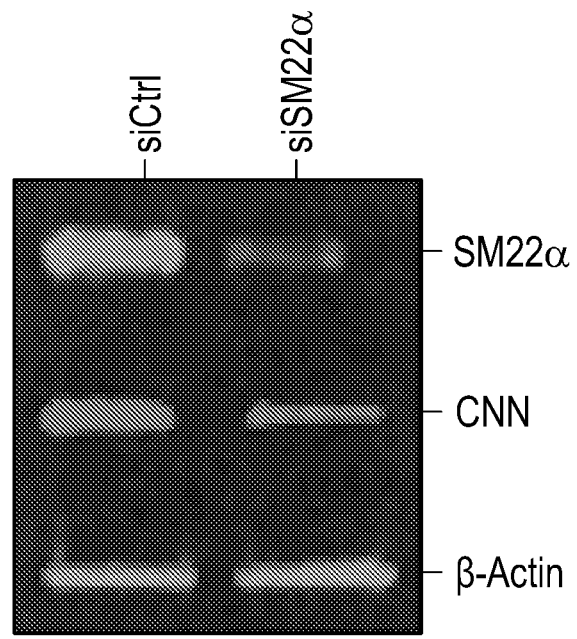
Figure 1H:
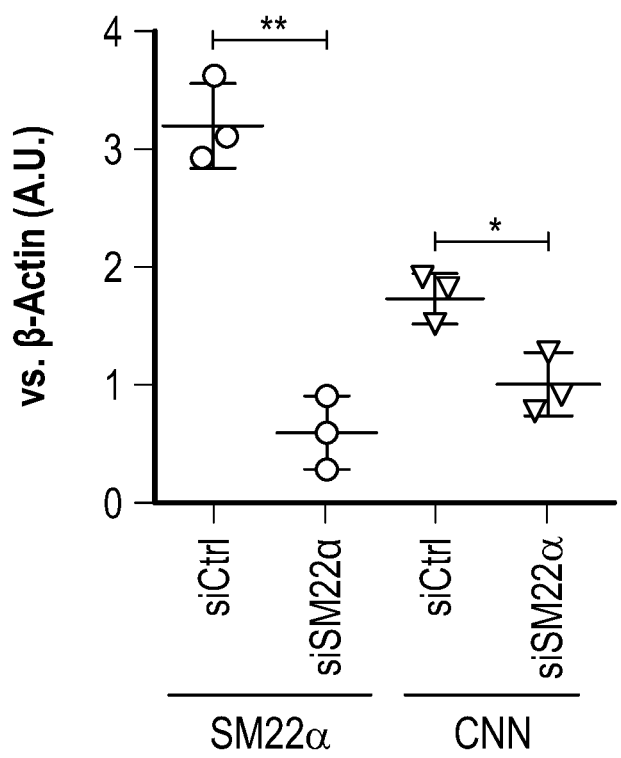
Figure 1I:
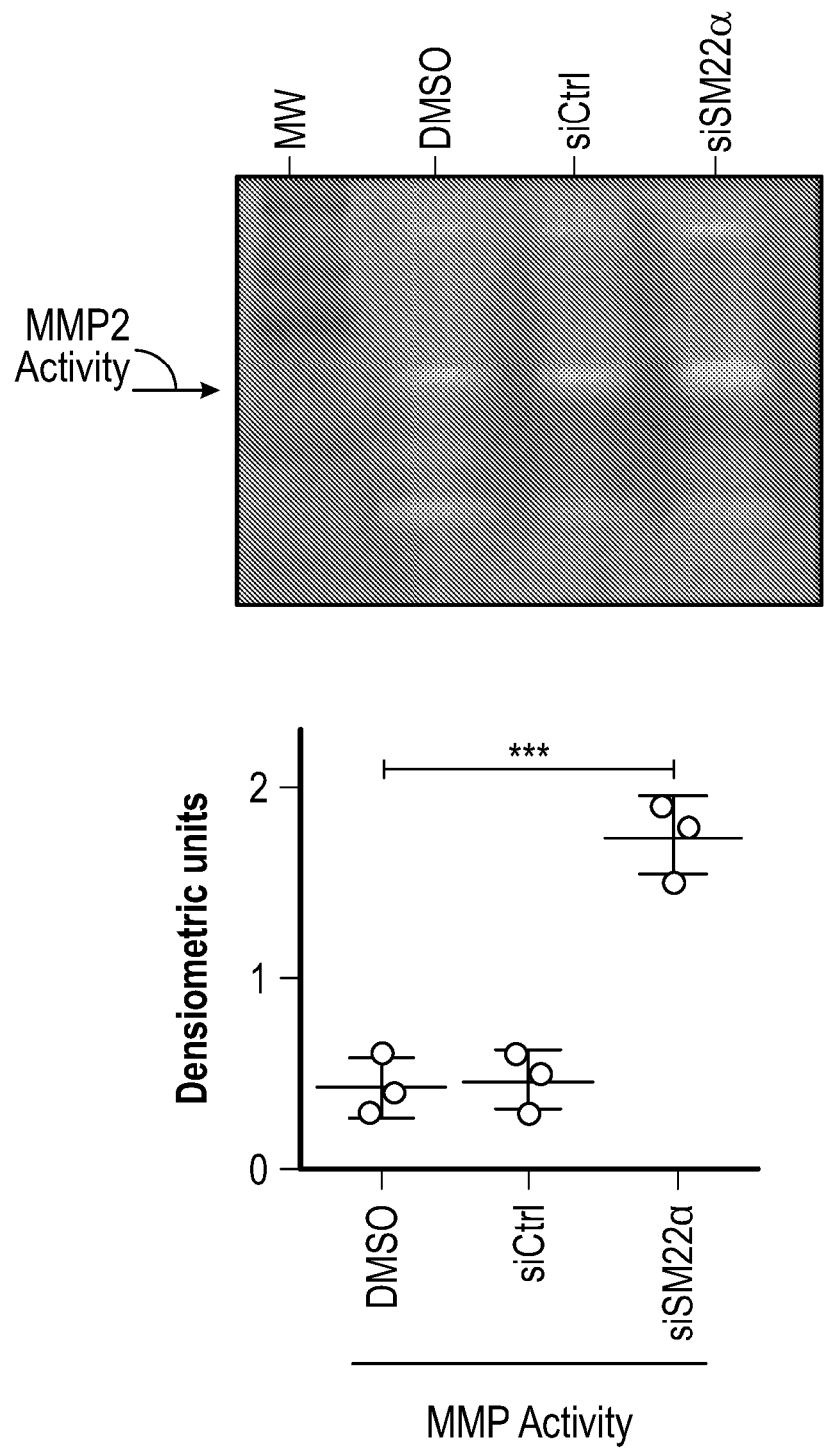
Figure 3H:
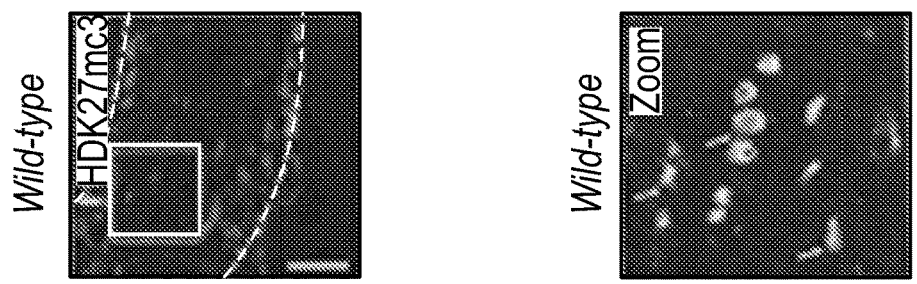
Figure 3H:
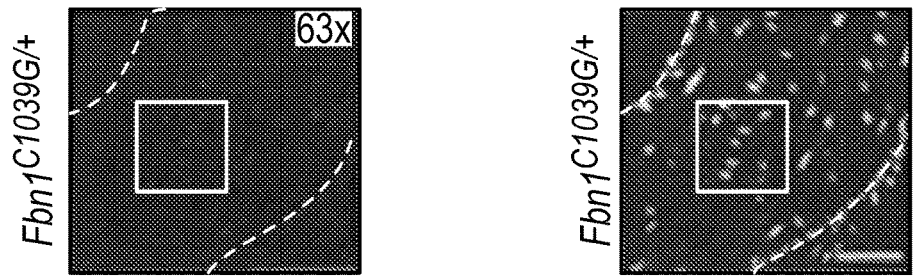
Figure 3H:
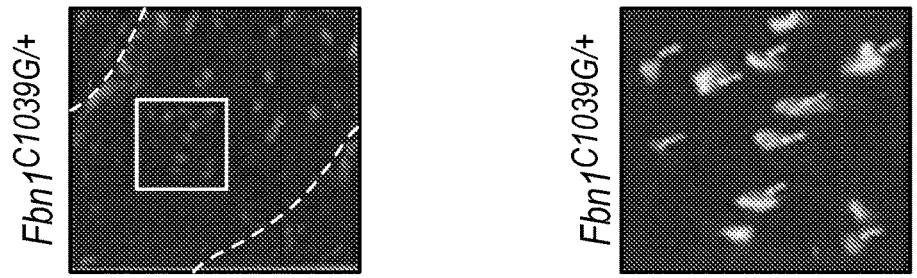
Figure 3I:
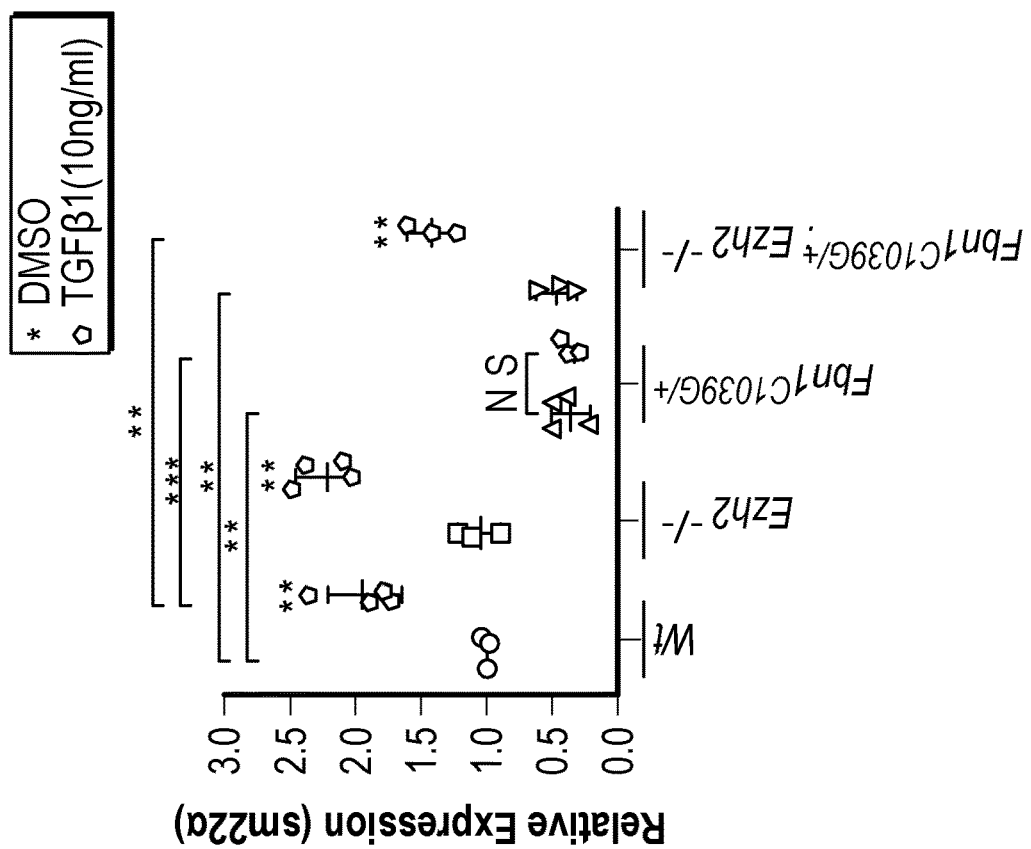
Figure 3I:
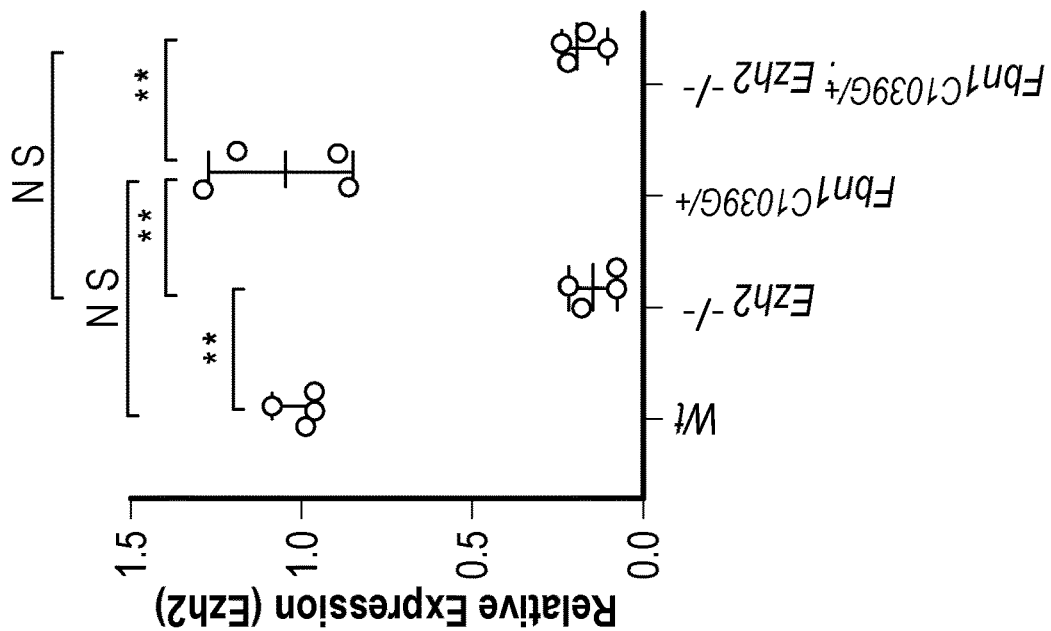
Figure 3J:
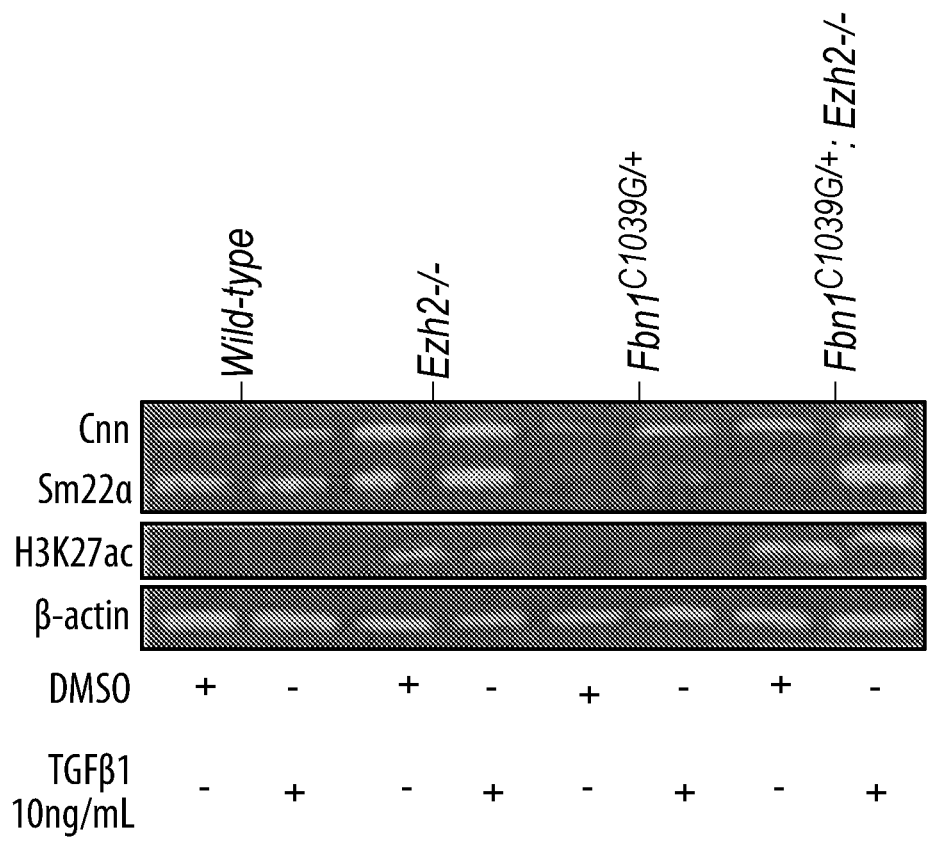
Figure 3K:
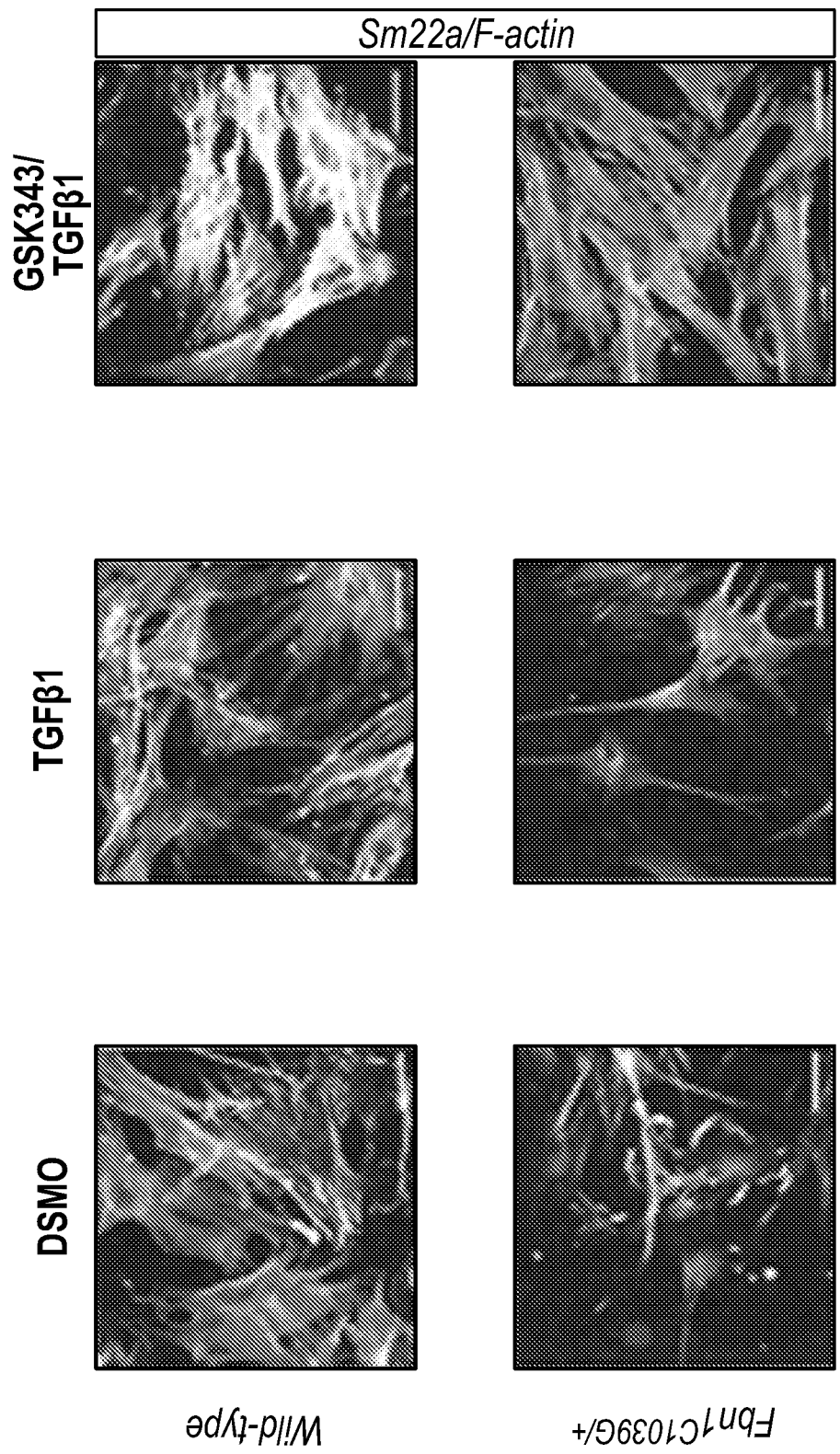

Immunostaining in the murine aorta showed increased levels of H3K27me3 and increased colocalization of Ezh2 and H3K27me3 in Fbni$^{ci°39G/+}$ versus wild type mice, (FIG. 3H and FIG. 1A). To determine if Ezh2 may be silencing genes related to aortic homeostasis, such as SM22a, the inventors studied VSMCs isolated from a murine line capable of Ezh2 deletion crossed to Fbni$^{ci°39Gi+}$ mice. Strikingly, the inability of TGF-β to induce SM22a expression in Fbn1$^{ci°39Gif}$ if cells was recovered in cells from Fbn/$^{cl°39G/+}$ mice in which Ezh2 had been deleted (FIG. 3I and FIG. 3J, and Supplemental FIG. 1B available on the world wide web at ncbi.nlm.nih.gov/pmc/articles/PMC5922285/bin/jciinsight-3-97493-s001.pdf). Consistent with this finding, overexpression of Ezh2 in VSMCs suppressed SM22a expression (Supplemental FIGS. 1C and 1D available on the world wide web at ncbi.nlm.nih.gov/pmc/articles/PMC5922285/bin/jciinsight-3-97493-s001.pdf). In addition to recovery of SM22a expression, inhibition of Ezh2 enhanced TGF-β induced stress fiber formation. (FIG. 3K and Supplemental FIG. 1E available on the world wide web at ncbi.nlm.nih.gov/pmc/articles/PMC5922285/bin/jciinsight-3-97493-s001.pdf).

Inhibition of PRC2 Activity Ameliorates Experimental TAA Progression.

Figure 4A:
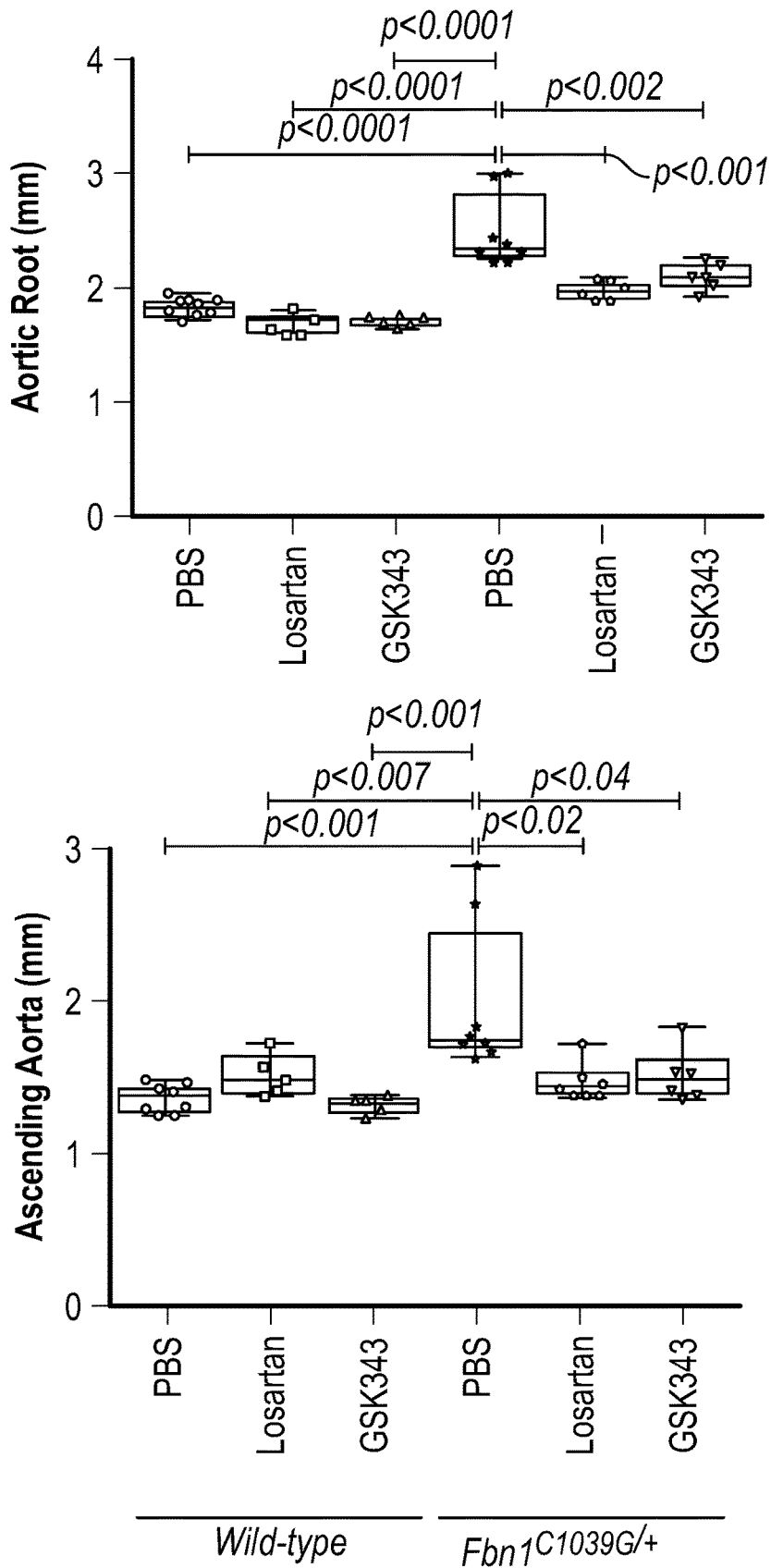
FIGS. 4A-4C demonstrate the in vivo inhibition of EZH2 activity palliates experimental aortic aneurysm.
Figure 4B:
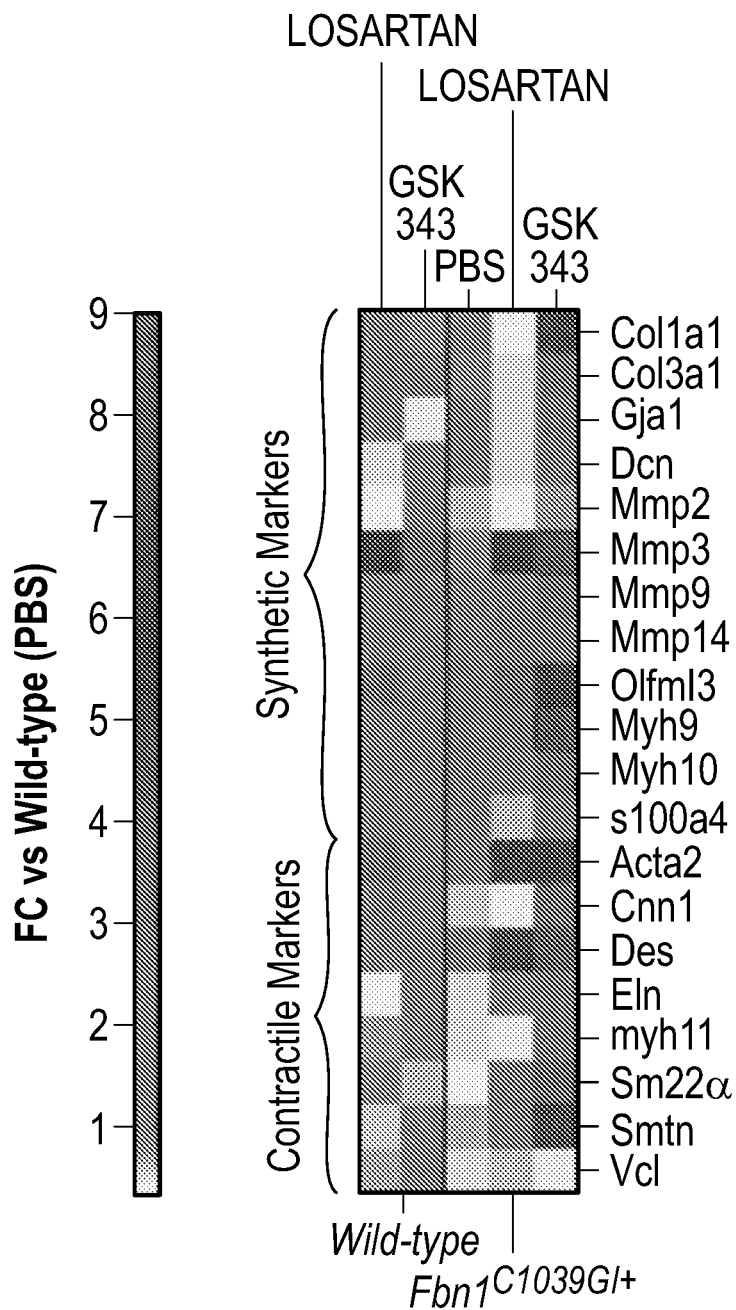
Figure 4C:
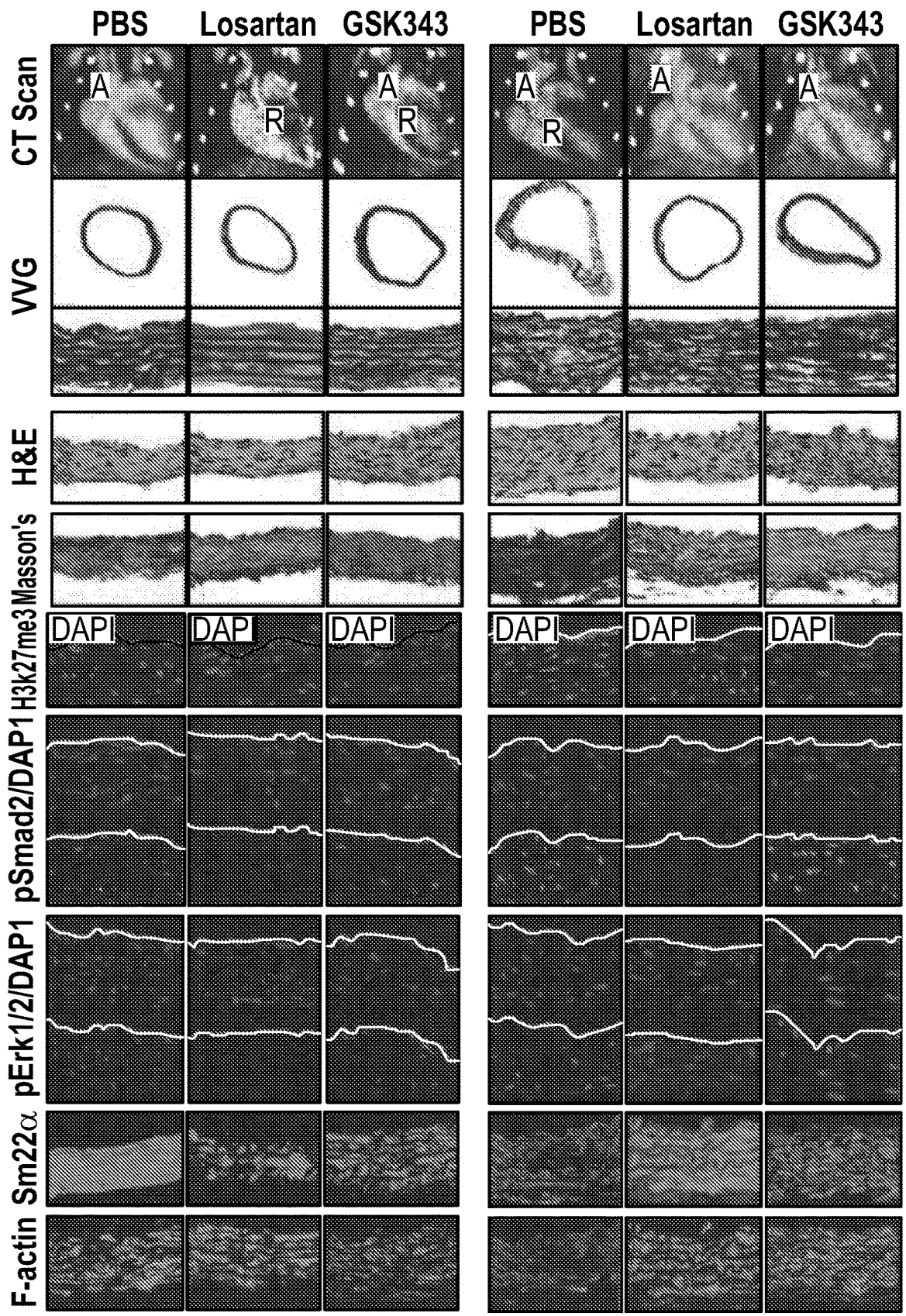
Figure 4C:
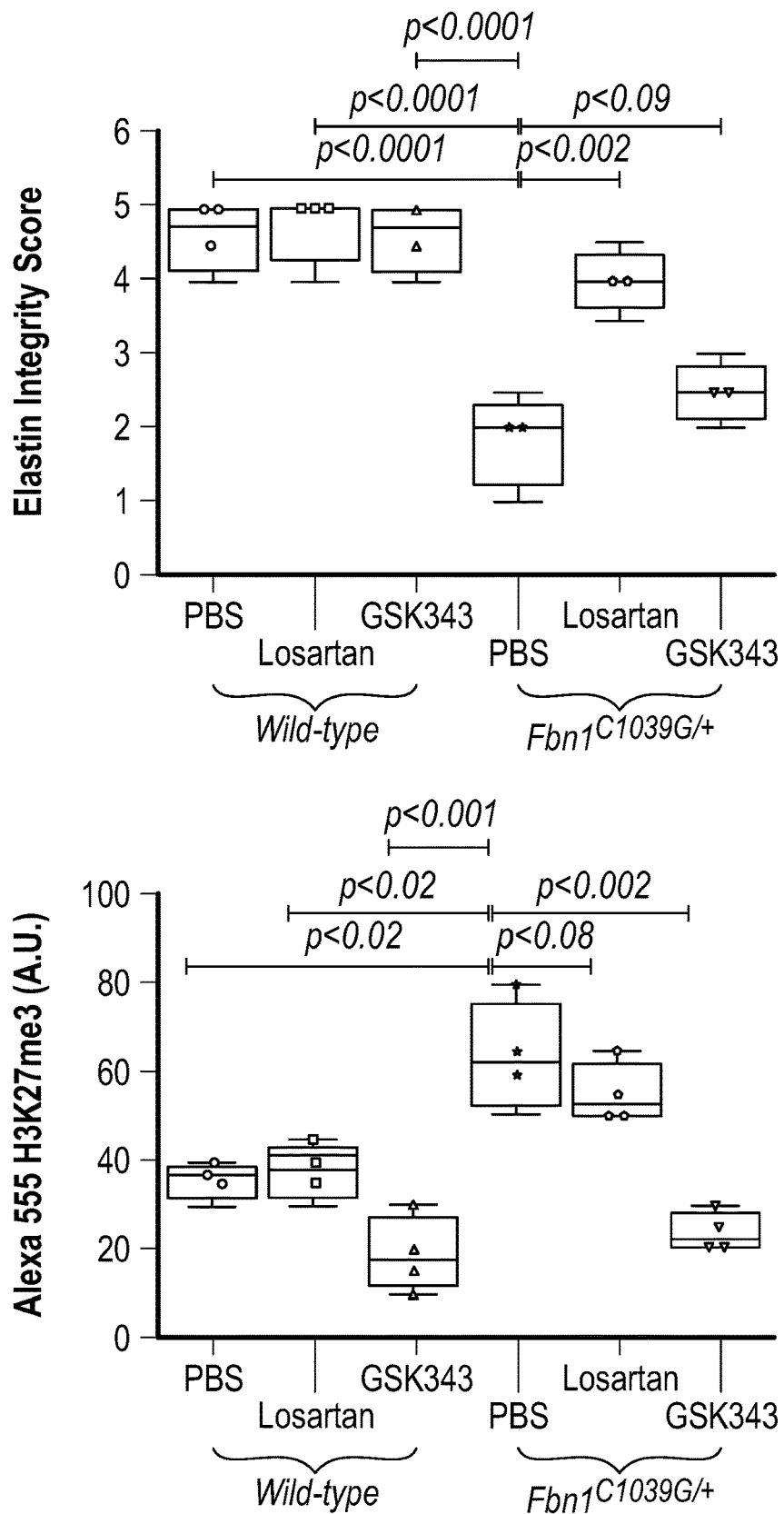
Figure 4C:
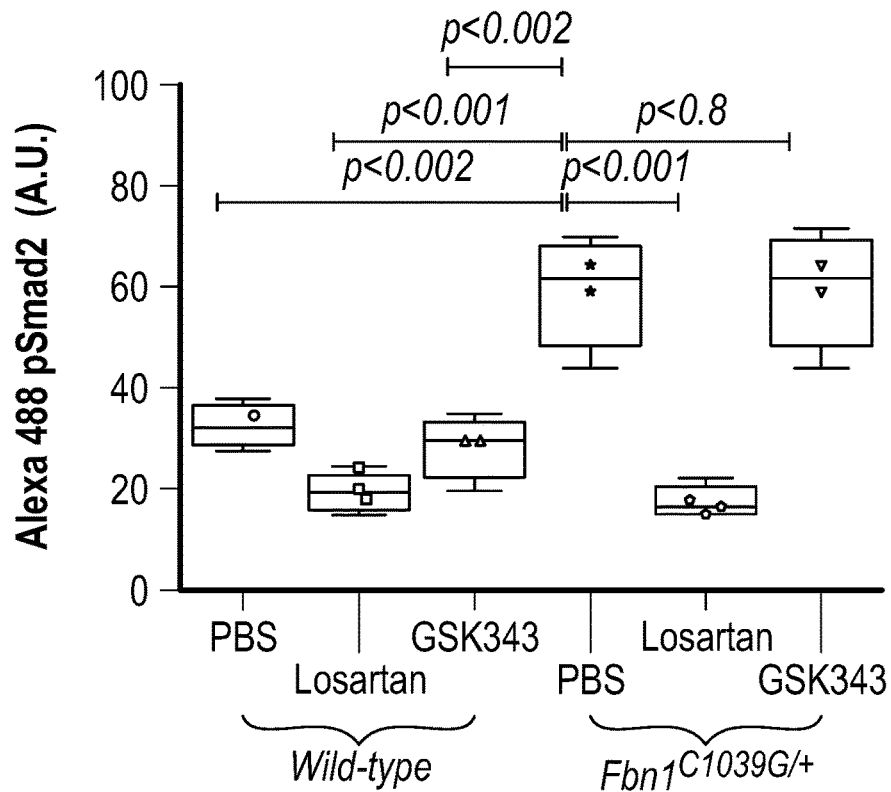
Figure 4C:
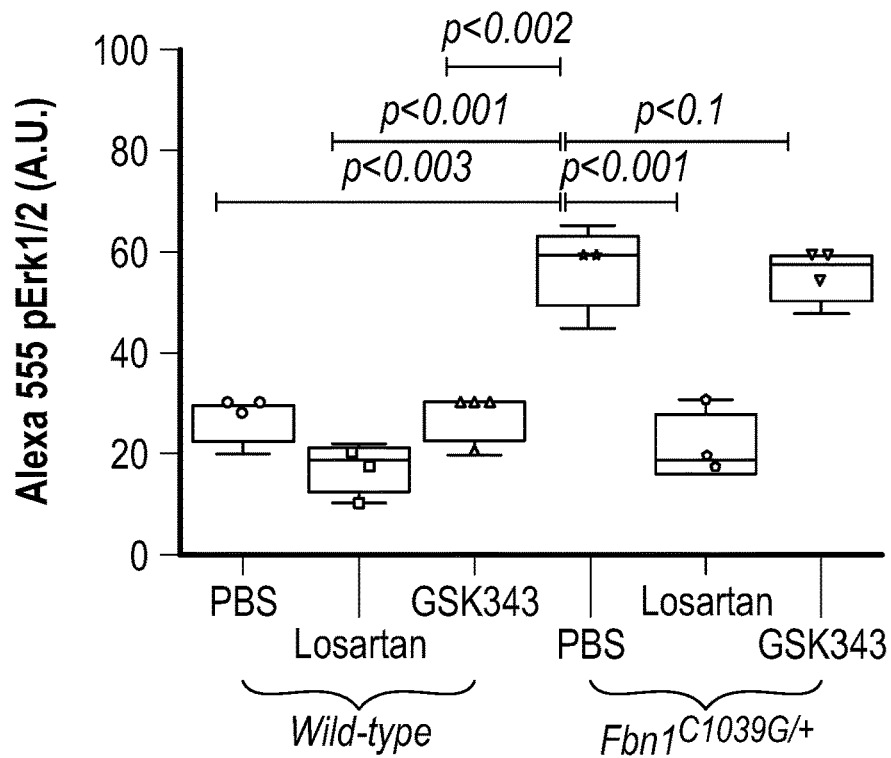
Figure 4C:
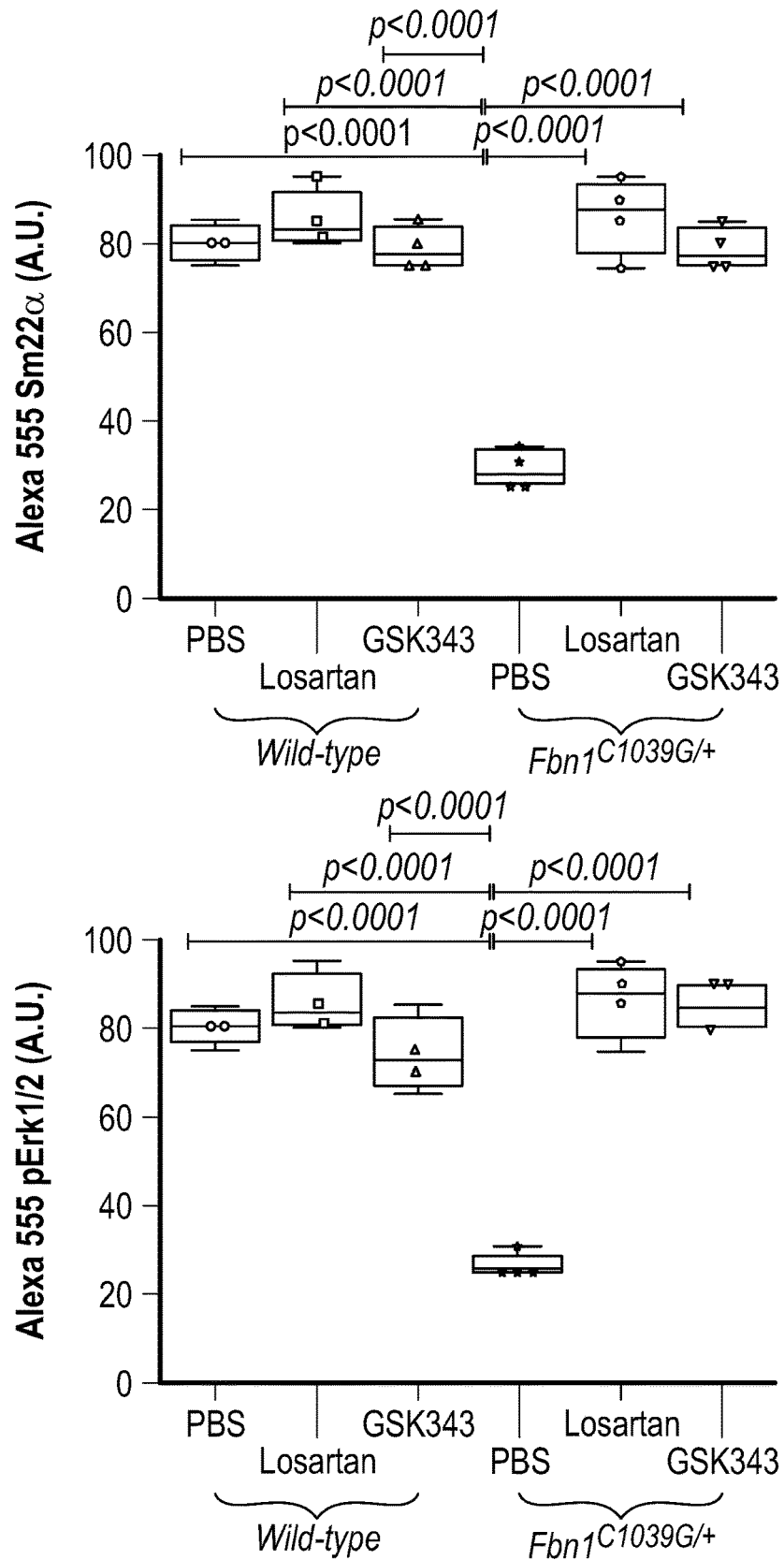

Increased TGF-β activity as assayed by phosphorylation of smad proteins and increased ligand expression has been reported repeatedly in TAA tissue[10]. The inventors reasoned that contractile genes important for aortic homeostasis (such as TAGLN) that may be induced by TGF-β activity in health are repressed through epigenetic modification in Fbn1$^{Ci°39G/+}$ murine aorta. The ability of GSK343 to restore TGF-mediated SM22a expression in cell culture prompted us to examine EZH2 inhibition as a therapeutic strategy in experimental aneurysm. To address this concept, the inventors treated Fbni$^{cl°39w+}$ mice with either the angiotensin-2 type 1 receptor blocker, losartan or GSK343 from two to six months of life. Activity of GSK343 compound was verified through examination of tissue levels of H3K27me3 (Supplemental FIG. 2 available on the world wide web at ncbi. nlm.nih.gov/pmc/articles/PMC5922285/bin/jciinsight-3-97493-s001.pdf). Both losartan and GSK343 demonstrated the ability to improve aortic dimensions in Fbn1$^{cl°39Gi+}$ mice (FIG. 4A). Examination of VSMC phenotypic markers demonstrated a distinct molecular mechanism for each agent. Losartan treatment showed a better ability to decrease the well-known pathologic markers including Col1a1, Col3a1, Gja1, Mmp2 (synthetic markers) (FIG. 4B) and improve elastin integrity overall (FIG. 4C). While the GSK343 inhibitor showed a better recovery of contractile elements but not a significant improvement in elastin fiber integrity possibly due to its inability to repress synthetic markers (FIG. 4B and FIG. 4C). Both losartan or GSK343 demonstrated an improvement in aortic architecture and filamentous actin content (FIG. 4C). Histologic staining shows a significant suppression of H3K27me3 staining in Fbn1$^{cl°39G/+}$ aortas from GSK343 treated animals when compared to either control or losartan treated Fbn/$^{c/°3°G/4}$ mice. Interestingly, despite effective control of aortic aneurysm formation, the GSK343 compound did not suppress TGF-13 activity as assessed by phosphorylation of Smad2 or Erk1 protein (FIG. 4C). Immunostaining of aortas demonstrated recovery of SM22a protein expression in both treatments when compared to control Fbni$^{cl°39G/1−}$ mice (FIG. 4C).

Example 3: EZH2 is the Catalytic Subunit of the Polycomb Repressive Complex 2 (PRC2) and Mediates Methylation of Lysine 27 of Histone Subunit 3 (H3K27Me3) Therefore Silencing Specific Gene Loci EZH2 is the catalytic subunit of the polycomb repressive complex 2 (PRC2) and mediates methylation of lysine 27 of histone subunit 3 (H3K27me3) therefore silencing specific gene loci. EZH2 is recruited during development to suppress genes associated with cell fate (33, 34). In some scenarios, such as in cancer stem cells, EZH2 is targeted to genes associated with lineage specification and therefore acts to suppress differentiation (35). However, this generalization has exceptions, and in some cell types EZH2 is required for the maintenance of cell lineage (36). Although the inventors studied primarily contractile protein regulation, this mechanism may also target transcription factors required for the maintenance of VSMC identity. In our system, the observed chromatin changes correlated with inability of transcriptional mediators such as SMAD3 to bind to promoter sequence. Increased TGF-β signaling, as assayed by SMAD protein phosphorylation, has been a redundant observation in human and murine TAA tissue and suppression of TGF-signaling has demonstrated a therapeutic response in experimental aneurysm in the Fbnicl°39G1+ mouse model. (24, 37). However, similar suppression of TGF-β signaling with anti-TGF-β neutralizing antibodies exacerbated aortic disease in angiotensin 2-infused mice (38). Furthermore, loss-of-function mutations in canonical TGF-β mediators such as TGFB2 and SMAD3 underlie syndromic aortic disease, but aortic tissue from patients with these mutations consistently shows upregulation of TGF-β signaling (14, 16, 17). These seeming contradictions of the role of TGF-β in aortic aneurysm etiology and progression continue to be controversial (39). Differential transcriptional responsiveness caused by epigenetic silencing such as described in this study may help to explain some, but not all, of these paradoxical observations. These data offer a paradigm where epigenetic modifications in TAA prevent normal transcriptional responsiveness in critical genes that would otherwise improve aortic homeostasis in the context of increased TGF-β activity, routinely observed in TAA samples. Deficient canonical TGF-β signaling may induce both epigenetic remodeling of VMSCs as well as set the stage for compensatory upregulation of TGF-β signaling during aneurysm progression. Some effects downstream of TGF-β signaling including fibrotic cascades (mediating arterial stiffness) and MMP upregulation (mediating extracellular matrix destruction) are harmful to aortic homeostasis and antagonism of such products may improve performance, hence a rationale for TGF-β antagonism. However, VSMCs are sensitive to intrinsic inhibition of TGF-β signaling as demonstrated in models that genetically inhibit members of the canonical signaling cascade (such as experiments in Tgfbr2 deficient mice) (40-42), or human conditions mediated by loss-of-function mutations in TGF-β mediators (13, 14, 16, 17). Therefore, restoration of intrinsic TGF-β signaling activity within VSMCs in TAA may also prove beneficial. Simple models of TGF-β signaling as either simply harmful or beneficial fail to incorporate the complexity of compensatory signaling events in VSMC biology. Epigenetic silencing of contractile loci may explain the ineffectual nature of TGF-13 signaling in improving contractile protein expression (SM22a, a-SMA, smMHC, amongst others) in aortic aneurysms. This type of mechanism is more relevant to ascending aortic aneurysm which has a unique clinical profile even in the absence of Mendelian association (43) a mechanistic correlate which has been noted in the differential susceptibility to intrinsic VSMC TGF-13 inhibition in model systems, when compared to descending aortic VSMCs (42).

Figure 5A:
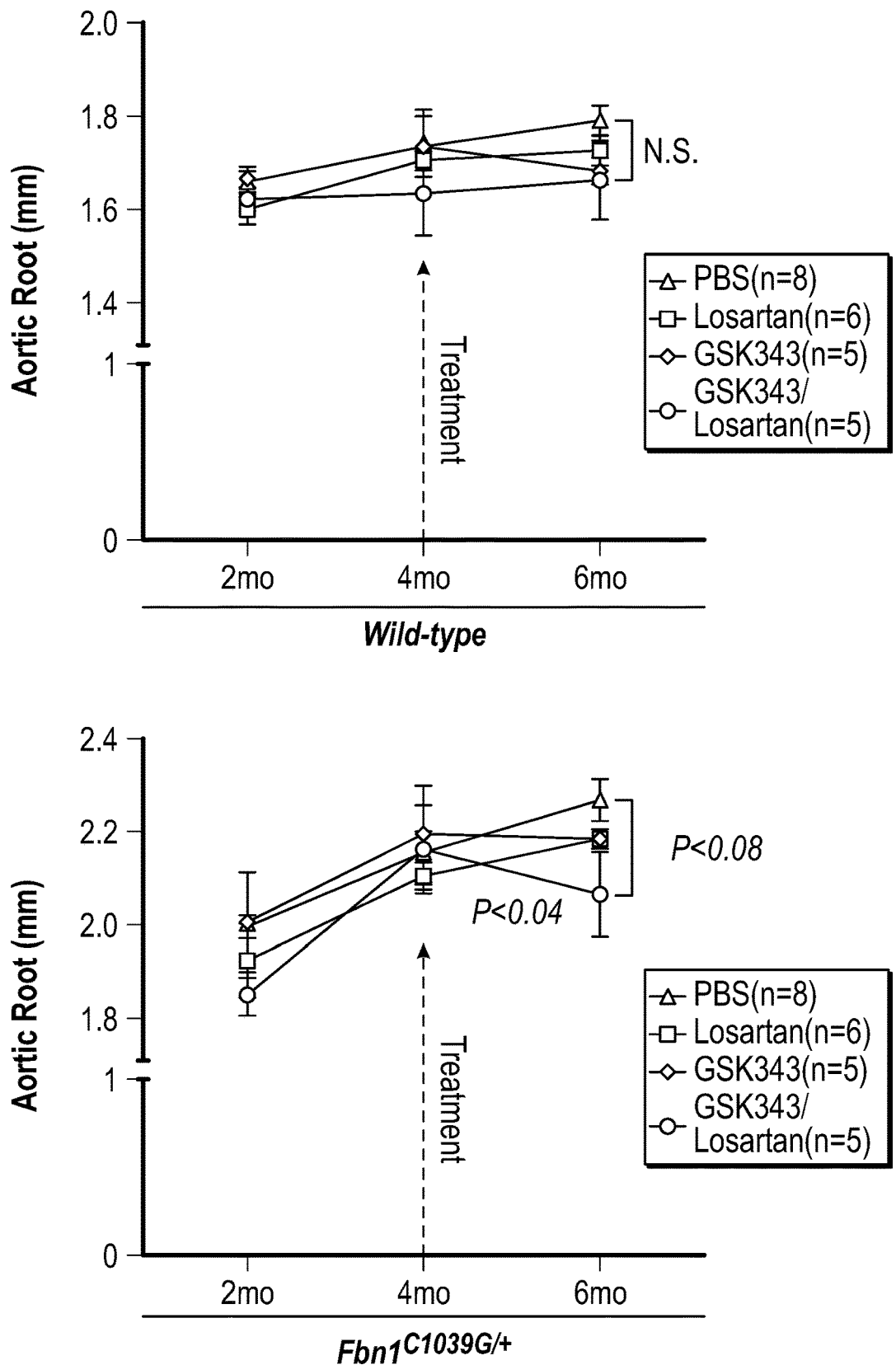
FIGS. 5A-5C demonstrate that the combination treatment improves aortic dimensions in established aortic enlargement.
Figure 5A:
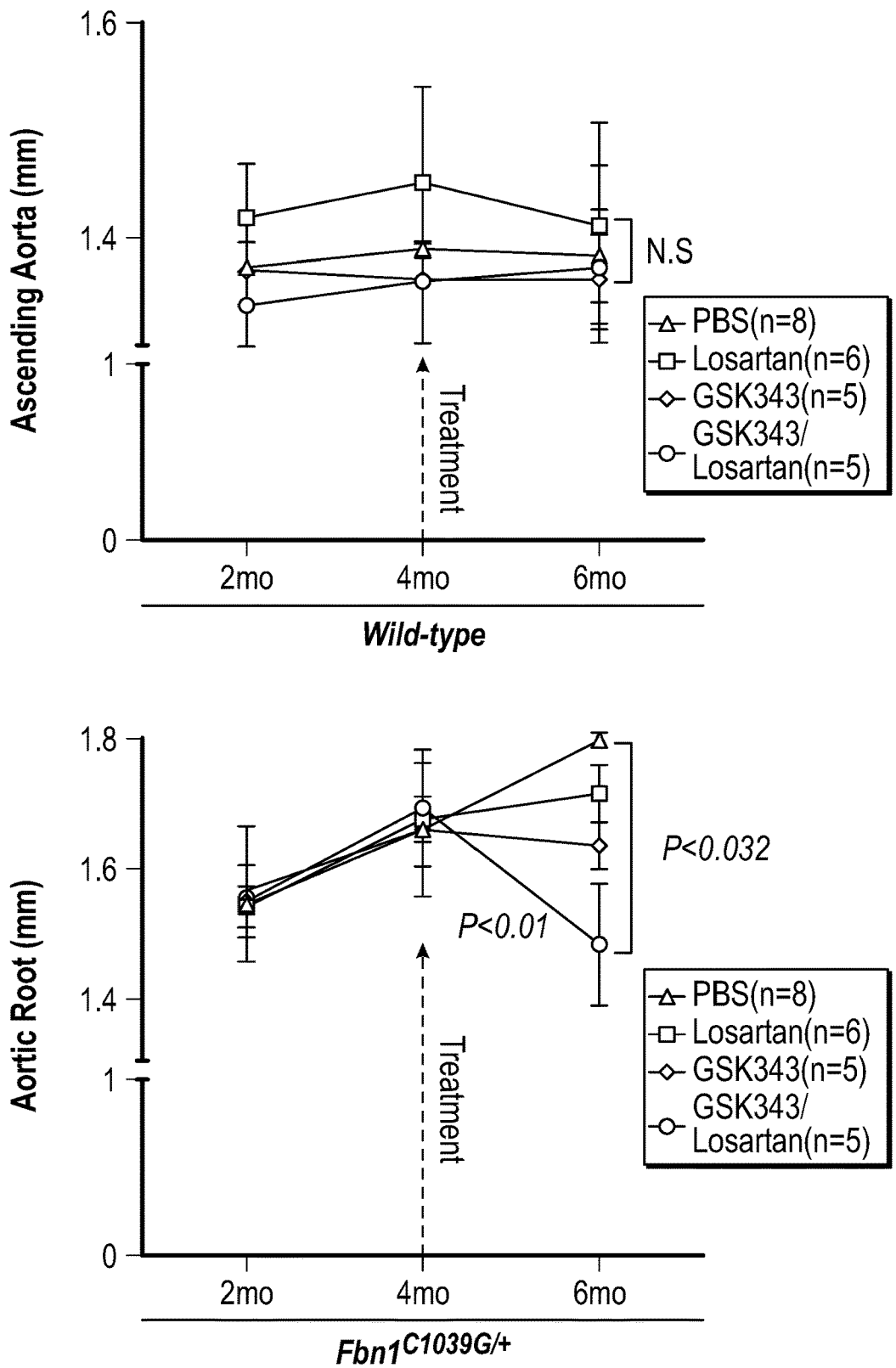
Figure 5B:
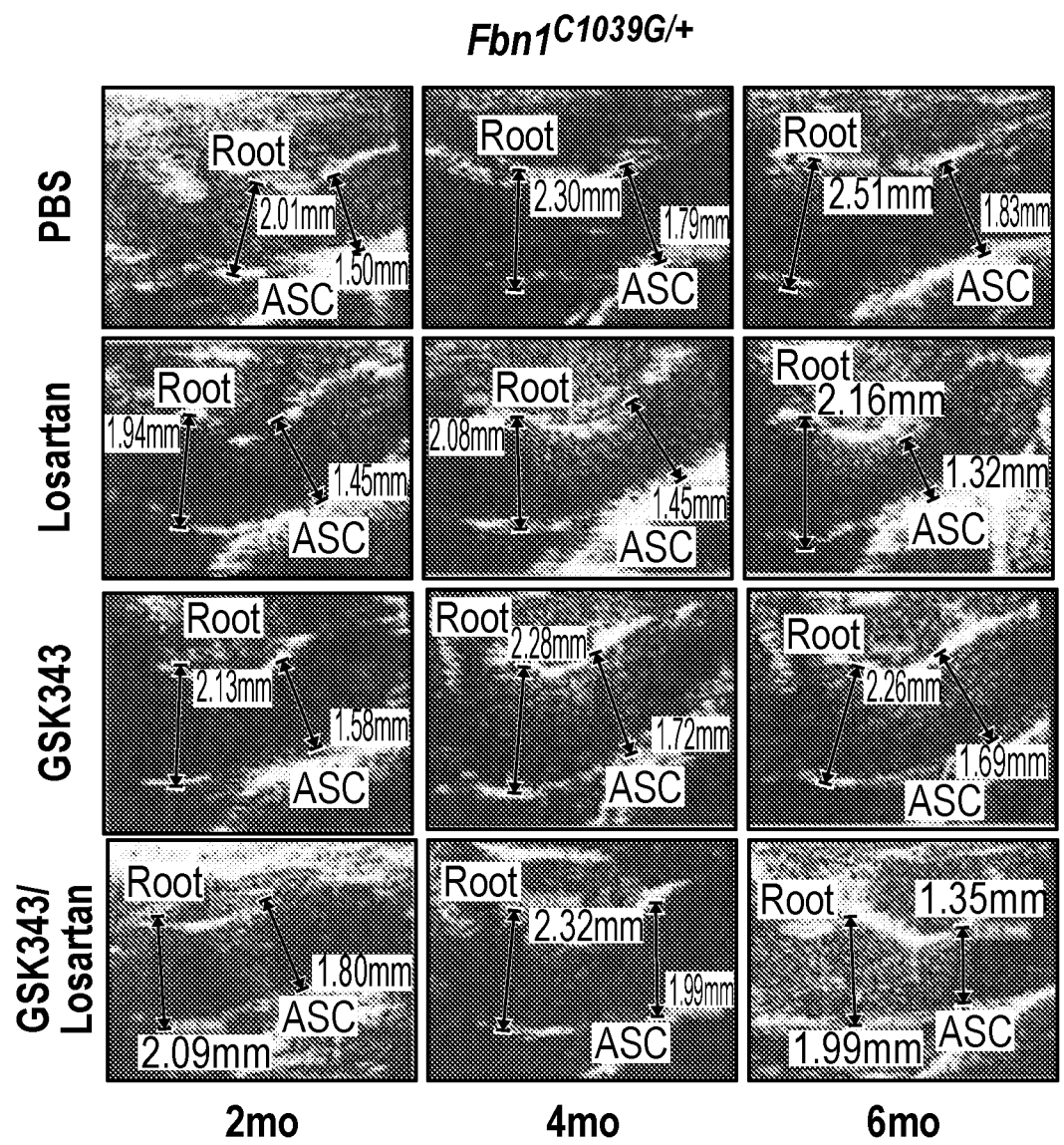
Figure 5C:
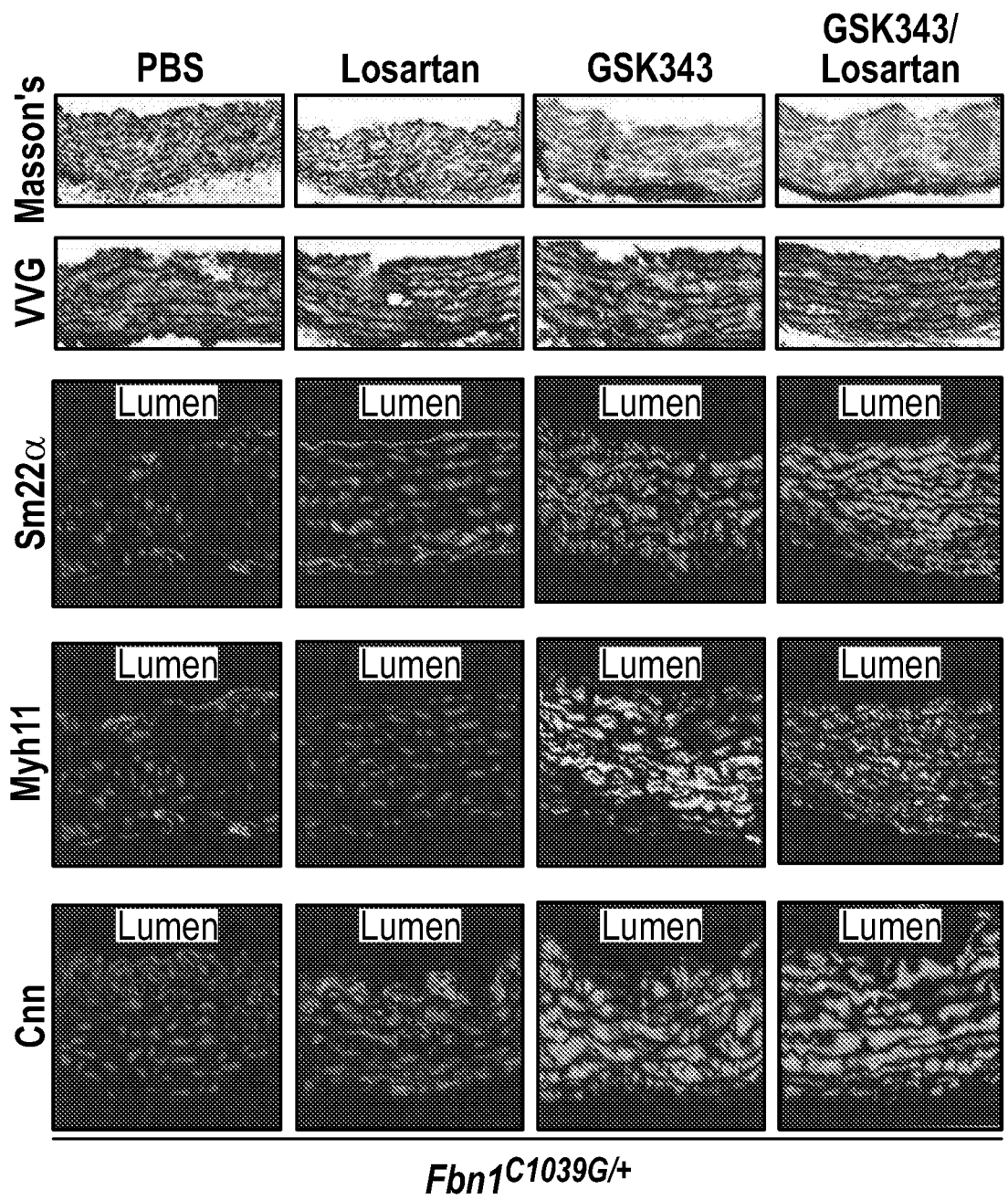
Figure 5C:
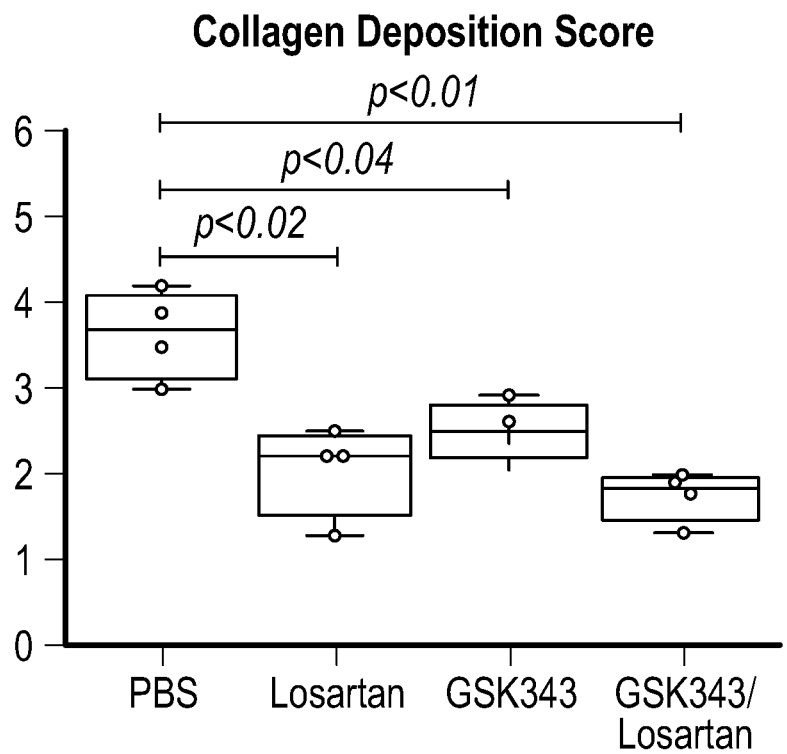
Figure 5C:
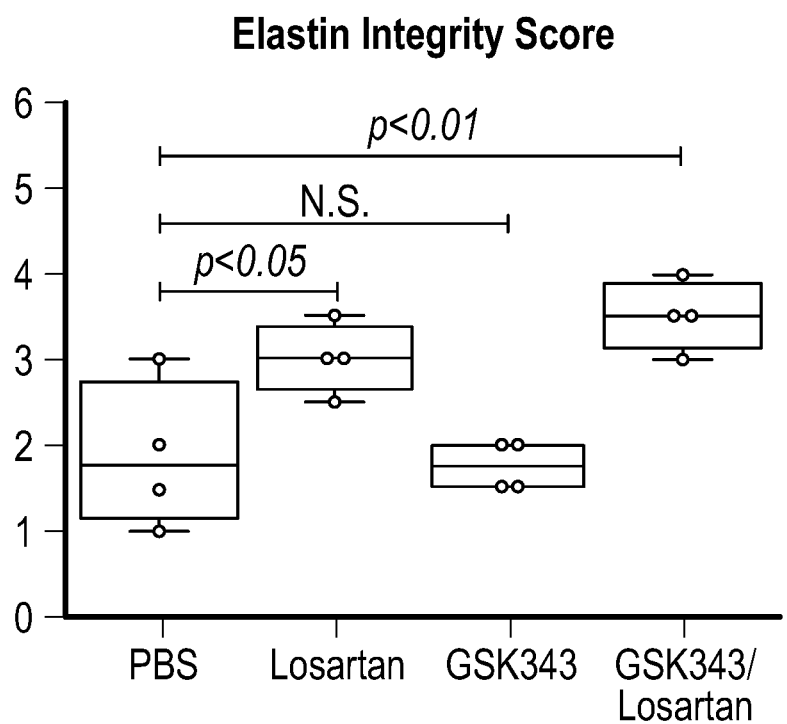
Figure 5C:
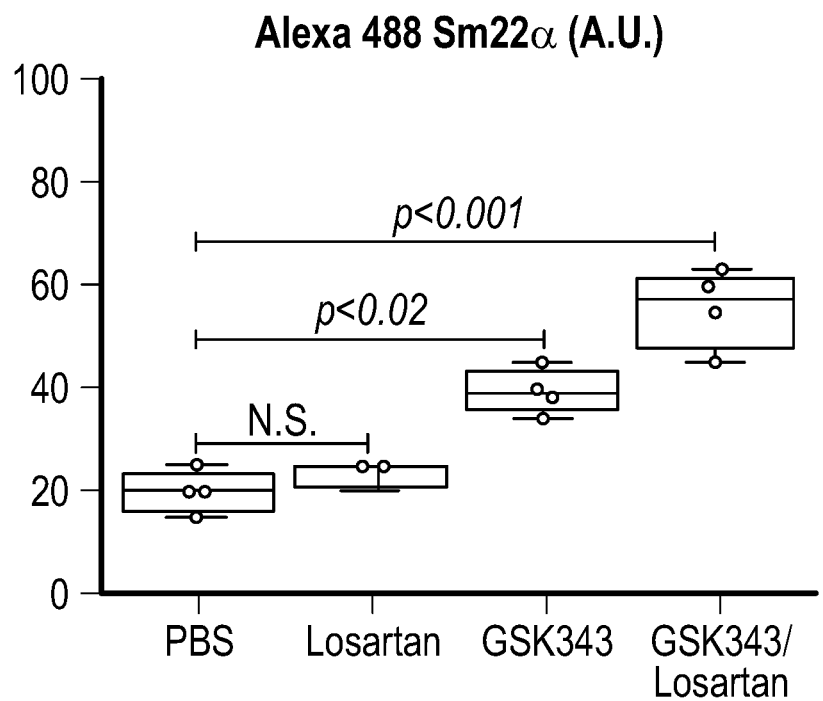
Figure 5C:
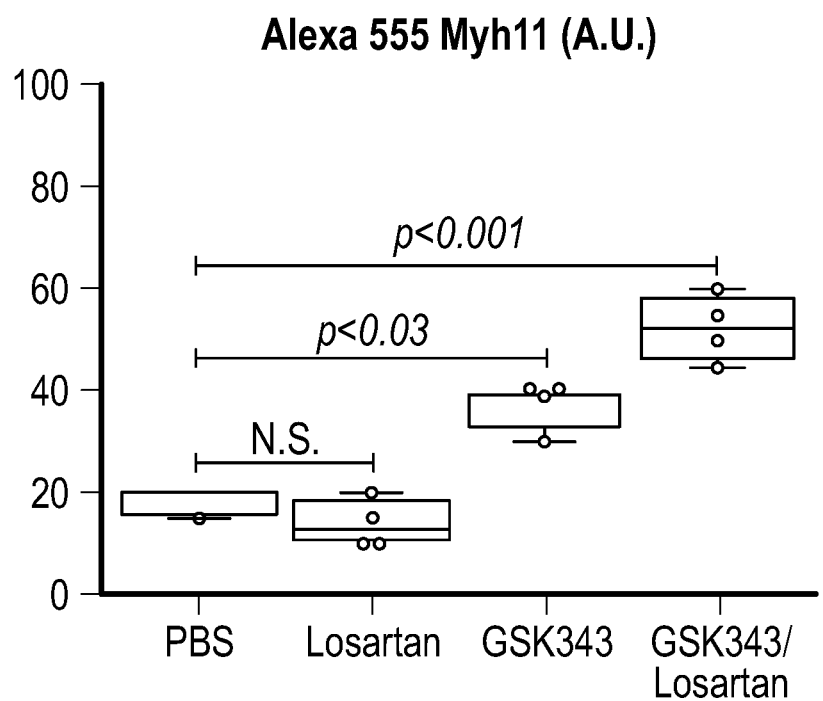
Figure 5C:
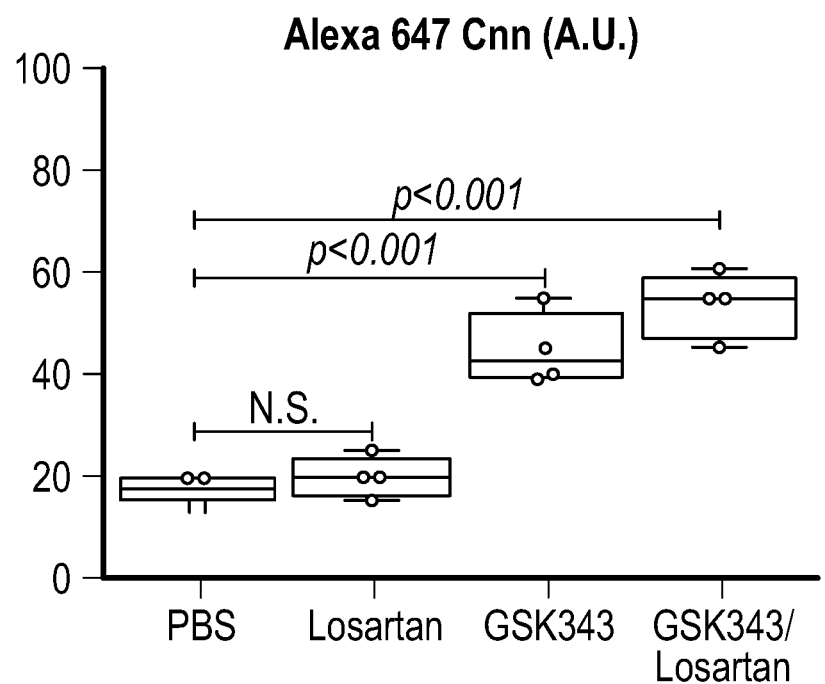
Figure 6A:
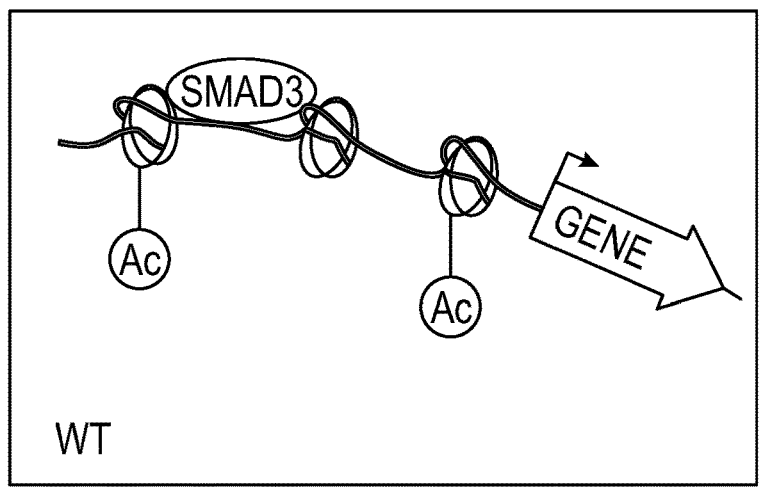
FIGS. 6A-6C show a schematic representation of epigenetic repression in TAA.
Figure 6B:
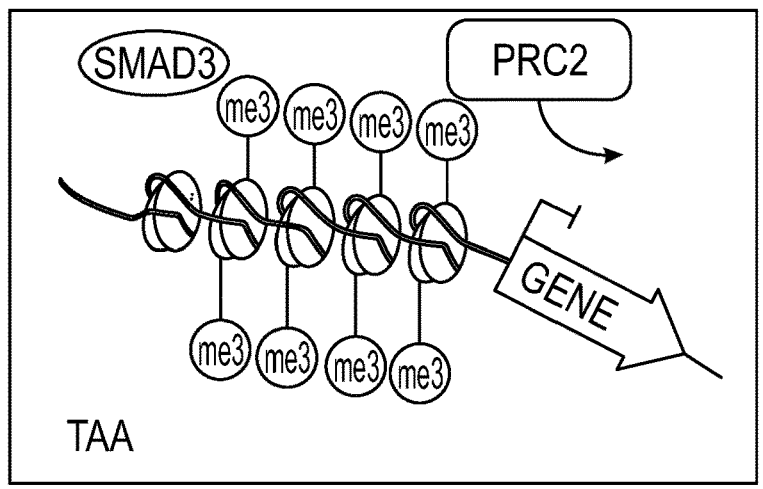
Figure 6C:
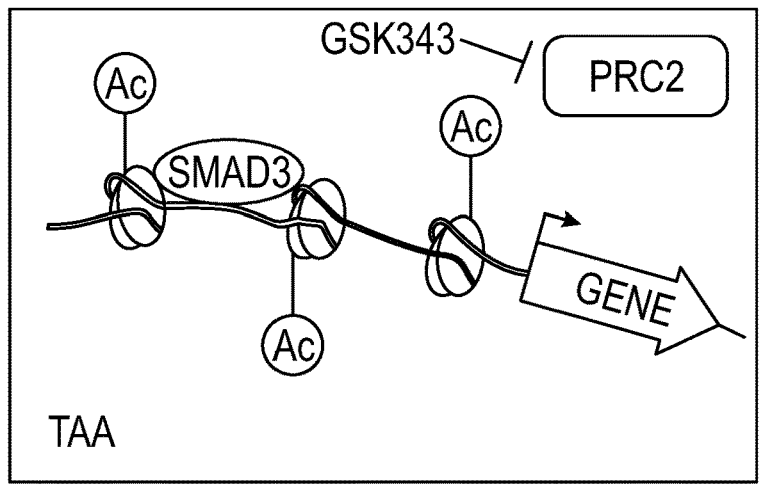

The observation that EZH2 inhibition allows for more efficient expression of SM22a, a protein necessary for proper aortic homeostasis (FIGS. 2A-2G), suggested the opportunity to use this agent as a therapeutic agent to treat aortic aneurysm. To this end the inventors treated experimental aortic aneurysm in Fbn1cl°39Gi+ mice and found a therapeutic response comparable to therapy with losartan. The effect seems to work through a distinct molecular mechanism. TGF-β signaling as assessed by suppression of smad2 phosphorylation was reduced in losartan treated aortic tissue but not in GSK343 treated animals. Conversely, GSK343 significantly decreased aortic medial H3K27me3 modifications, while losartan did not. These observations led the inventors to investigate combinatorial therapy, which offered additional benefit (FIGS. 5A-5C). The clinical benefits of using combinatorial therapies for chronic disease are clear for other cardiovascular diseases such as heart failure, hyperlipidemia, and diabetes and such may be the case in TAA. Despite this promise, EZH2 inhibitors would be expected to have major off target biologic effects, especially if their use is contemplated for a chronib condition such as aneurysm. For this reason, therapeutic strategies hoping to take advantage of pathogenic epigenetic events will require agents with greater target specificity or more precise tissue targeting properties.

In general, medical therapy for TAA is limited to different classes of anti-hypertensive medications, some with anti-TGF-β activity such as ARBs or ACE-inhibitors. This proof of concept experiment, demonstrating a therapeutic effect of a chromatin modifying agent, suggests that unsuspected classes of medication may have a role in the future medical treatment of TAA.

Methods

Aortic Samples

Aortic samples were collected from patients undergoing cardiac surgery at the Massachusetts General Hospital (MGH). Upon tissue collection, the media layer was dissected and stored at −80 C for analysis of RNA and protein expression. Control aortic tissue was obtained from patients undergoing orthotopic cardiac transplant. IRB permissions do not allow for demographic information from discarded tissue to be collected or stored.

Primary Aortic Smooth Muscle Cell Lines

Primary human aortic smooth muscle cells (HAoSMC) from healthy donors were purchased from Cell Applications Inc., California, USA (Cat. #354K-05a). Primary aneurysm aortic SMCs were isolated from fresh TAA tissue at the moment of surgery by standard explant of the aortic media. Mouse aortic SMCs were isolated by standard explant of the ascending section of the aortas from wild-type or Fbn1ci°39G1+ mice. Smooth muscle cell identity was assessed by immunofluorescence staining of contractile markers including SM22a, Calponin, Smoothelin and Vinculin. In order to preserve cell identity all experiments were carried out at passages 1-5 (Timraz et al., 2016). Human and murine SMCs were grown with smooth muscle cell growth medium from Cell Applications Inc. (Cat. #311-500).

RNA Extraction and Real-Time qPCR Analysis.

Total RNA was prepared from tissue or primary cells using RNeasy kit (Qiagen) following the manufacturer's protocol. The cDNA was prepared by reverse transcription, and expression of SMC contractile genes were analyzed by qRT-PCR on SYBR green system (Applied Biosystem, Foster city, CA). 50 pL of plasma from wild-type or Fbn1cl° 39G1+ mice were used to prepare total RNA as mentioned above. Expression results were analyzed by the ddCT method and GAPDH (encoding glyceraldehyde-3-phosphate dehydrogenase) was used as a housekeeping gene. Fold change were calculated by taking the average over all the control samples as the baseline. Plasmatic levels of the murine Tagin (SM22a) transcript were measured using 100 pL of plasma in 2 mL of sterile PBS followed by 2 hours of ultracentrifugation at 100,000 G. The supernatant was removed and the vesicular fraction was resuspended with 750 pL of TRizol reagent followed by RNA extraction using the RNeasy kit (Qiagen) according to the manufacturer's protocol.

Expression results were analyzed by the □□CT method and GAPDH was used as a housekeeping as described above. We settled on GAPDH as the most stable housekeeping gene both in healthy SMCs and in our plasma samples through direct testing under our experimental conditions. To achieve this observation the inventors ran qPCR assays using the RT profiler PCR array from Qiagen (human cat no. 330231/PAHS-055Z and mouse cat no. 330231/PAMM-055Z). This array contains 5 commonly used housekeeping genes such ACTB (beta-actin), B2M (beta-2-VSMCs and in our plasma samples through direct testing under our experimental conditions. To achieve this observation the inventors ran qPCR assays using the RT profiler PCR array from Qiagen (human cat no. 330231/PAHS-055Z and mouse cat no. 330231/PAMM-055Z). This array contains 5 commonly used housekeeping genes such ACTB (beta-actin), B2M (beta-2-microglobulin, GAPDH (Glyceraldehyde-3-phospho dehydrogenase), HPRT1 hypoxanthine phosphoribosyltransferase 1, RPLPO (Ribosomal protein, large, P0). Additionally, the arrays contain 1 human genomic DNA contamination control, 3 reverse transcription control and 3 positive PCR control. PCR primers and siRNAs are listed in Supplemental Table 2 available on the world wide web at ncbi.nlm.nih.gov/pmc/articles/PMC5922285/#.

ChIP-qPCR

For ChIP-qPCR from human aortic tissue, 200 mg of frozen sectioned aortic media from controls or TAA donors were fixed with 1% of formaldehyde at 37 C for 20 min, quenched with 125 mM glycine for 5 min at RT, supplemented with 1× of protease inhibitor cocktail (Roche) followed by preparation of total protein lysates. Next 50 ug of total protein lysates were sonicated to shear chromatin to an average length of 500-1500 bp followed by centrifugation for 10 min at max speed. Supernatants were collected in 2 mL tube containing 6 pg of monoclonal antibodies against EZH2 (clone AC22, active motif, USA) or H3K27me3 (Abcam, USA) and 1 mL of lysis buffer supplemented with 1× of protease inhibitor cocktail (Roche), followed by incubation overnight (14 hrs) at 4 C. Immunoprecipitates were analyzed using EpiTect ChIP kit according to the manufacturer's instructions (Qiagen, USA). Primers used to scan the promotor and gene body of TAGLN gene are listed in table 1. For ChIP-qPCR from cells, 5 million cells from healthy or isolated aortic aneurysm VSMCs were first treated with 0.1% of DMSO or 10 ng/mL of human recombinant TGFf31 (Abcam, USA) for 24 hrs in growing medium. Then cells were fixed with 1% of formaldehyde at 37 C for 1 Onnin, quenched with 125 mM glycine for 5 min at RT followed by preparation of total protein lysates. Next, monoclonal antibodies against SMAD3 was incubated with 20 pg of lysates and analyzed as described above. PCR primers, siRNAs, and antibodies are listed in Supplemental Table 2 available on the world wide web at ncbi.nlm.nih.gov/pmc/articles/PMC5922285/#.

siRNA Inhibition

Healthy VSMCs were transfected with 30 nM of siCtrl, siSMAD3 or siSM22a for 48 hrs with lipofectamine 2000 (Thermo Fisher Scientific) at 5 pL/mL followed by 24 hrs of normal growing medium. Then 30 pg of total protein was prepared from siRNAs treated cells to analyze the silencing of targeted transcripts by immunoblotting or nucleic acid analysis. siRNAs are listed in Supplemental Table 2 available on the world wide web at ncbi.nlm.nih.gov/pmc/articles/PMC5922285/#.

MMP Activity

For in vitro MMPs activity, healthy VSMCs were transfected with 30 nM of siCtrl or siSM22a as described above. 30 ug of total proteins were prepared from untransfected, siCtrl and siSM22a treated cells to measure the MMPs activity by gelatin zymography and analyzed by Image J software (NIH). For in vivo MMP activity assay, mice were tail vein injected with 300 pL of MMPSense 680 FAST, a near-infrared fluorescence sensor for MMP2 and MMP9 activity, (PerkinElmer, USA). Mice were sacrificed 24 hrs post injection and aortas were dissected and analyzed using a Kodak image station 4000MM Pro for macroscopic fluorescence reflectance molecular imaging (44).

Generation of Ezh24-1/SMCs

BeCause of genetic depletion of VSMC-targeted Ezh2 exhibited embryonic lethality. We crossed Fbn1c1° 93Gi+ to Ezh2fvfl mice. Then ascending aortas of Fbn1c1° 93G/+: Ezh2fvfl or Ezh2fut1 mice at 4 month of age were isolated as described above. At passage one, isolated VSMC cells were transduced with lentivirus overexpressing CMV-cre to deplete Ezh2 gene expression (pFUGW-H1 empty vector, Addgene plasmid #25870). Following 72 hours of infection cells were incubated with normal growing media for 24 hrs before TGFβ stimulation as described above.

Over Expression of a High Chromatin Affinity EZH2 Isoform.

Replacement of the serine 21 by Alanine in the EZH2 (EZH2S21A) protein induces 2-4 fold more affinity to bind with histone 3 than its wild type counterpart (45). The pcDNA3-3myc-6His-EZH2 21A construct was acquired from Addgene (Plasmid #42663,). 1-2 pg of plasmid was transiently transfected into human smooth muscle cells using lipofectamine TLX (Thermo Fisher Scientific) and opti-MEM medium (Thermo Fisher Scientific) for 48 hrs. Then cells were supplied with fresh growing media containing recombinant TGF131 (10 ng/mL) overnight (14 hrs).

Echocardiograms and Micro-CT Scan

Dimensions from each animal represent averages of measurements made on still frames in systole of the maximal internal diameter of the aortic valve annulus, aortic sinuses, sinotubular junction, or ascending aorta by a cardiologist blinded to genotype. The aorta was imaged using a standard parasternal long axis view. Based on historic controls, the mean diameter of the wild type aortic root at 4 months of life is 1.73+/−0.2 mm while in our disease model (Fbn1ci°39G/+) the mean diameter is 2.15+/−0.3 mm. This gives a window to observe therapeutic improvement of 0.42 mm. the mean diameter of the wild type aortic root at 6 months of life is 1.76+/−0.2 mm while Fbn1c1° 39Gi+ the mean diameter is 2.22+/−0.25 mm. This gives a window to observe therapeutic improvement of 0.46 mm. Nair hair removal cream was used on all mice the day prior to echocardiograms. All echocardiograms were performed on awake, unsedated mice using the Visualsonics Vevo imaging system and a 30 MHz transducer. All CT images were acquired using an Inveon small animal micro CT (Siemens Medical Solutions Inc., Malven, Pa.). All mice received intravenous iodinated contrast (Isovue-370, Bracco Diagnostic Inc.) at 20 pL/min during the scan. CT images had an isometric voxel of 0.11 mm. Images were visualized and analyzed in OsiriX software.

Histology

Latex was injected into the left ventricular apex under low pressure until it was visible in the femoral artery. Animals were then fixed in Formalin (10%) for 24 hours before transfer to 70% ethanol for dissection and storage. Aortas were then removed from the animals or dissected in situ for photography prior to paraffinization and sectioning (10 pM). Slides were produced for tissue staining or stained with standard stains including H&E staining, collagen deposition (Trichrome Stain (Masson) Kit, Sigma, USA), elastin (Verhoeff-Van Gieson, Thermo Scientific, MI, USA) or F-actin (ActinGreen™ 488 ReadyProbes, ThermoFisher Scientific, USA) for quantitative analysis. Elastin integrity score was rated by blinded observers and graded on an arbitrary scale of 5 (indicating high quality elastic fiber) to 1 (indicating severe elastin fragmentation). For nuclear staining aortas from human and mice were cryosectioned using OCT standard protocol as described previously (Fischer et al., 2008).

In Vitro GSK343 Treatment

VSMCs at 60-70% confluence were supplemented with opti-MEM 24 hrs before treatment with complete growing media containing GSK343 at a concentration of 10 pM for 4 days. Fresh media containing GSK343 was supplied daily. For GSK343/TGF81 (10 ng/mL) combo treatment, cells were first treated with complete media containing GSK343 at concentration of 10 nM during the 2 first days followed by GSK343/TGFβ combination treatment the next 2 days. Prior to cellular collection cells were washed with sterile PBS and RNA or protein extraction were performed as described above.

In Vivo Drug Treatments

Cohorts of 8-week-old wild-type or Fbn1cw3gGi+ mice were treated with oral administration in drinking water of either Losartan or GSK343 for 20 weeks (FIG. 5). Losartan was dissolved in drinking water and filtered to reach a concentration of 0.6 g/L, giving an estimate of 60 mg/Kg/day, as described previously (41). 25 mg of GSK343 inhibitor was dissolved in 1 mL of DMSO to obtain a stock solution of 46 mM. Then 200 mL of drinking water was supplemented with 250 pL of GSK343 stock solution. Control group for either drug treatment was given with equal volumes of sterile water. Bottles containing either losartan or GSKS343 were replaced with fresh water supplied with drugs every 3 days. For experiments described in FIG. 5A-5C, 16-week-old wild-type or Fbnicw3gGi+ mice were treated for 8 weeks and as described above. Additionally, a group of mice were given a combination of both losartan and GSK343 at the same concentrations as of other single drug treatments. Aortic dimensions were monitored monthly by echocardiograms as mentioned above.

Statistics

Results are given as mean S.D. Student's test (2-tailed) was applied to determine the statistical significance of difference between control and treated groups (*=$p<0.05$, =$p<0.01$ and *=$p<0.001$). For all experiments at least three experimental replicates were performed. Least squares method was used to fit line in FIG. 1F. Scatter graphs show mean SD. Data were analyzed and graphs were prepared with Prism 6.0 (GraphPad Software). Differences between multiple groups (echocardiography and histologic analysis) were assessed and p-values generated by 1-way ANOVA followed by Tukey's honestly significance difference (HSD) post-hoc test (95% CI is plotted). P-values of less than 0.05 were considered statistically significant.

REFERENCES

1. Grewal N, Gittenberger-de Groot A C, Poelmann R E, Klautz R J, Lindeman J H, Goumans M J, Palmen M, Mohamed S A, Sievers H H, Bogers A J, et al. Ascending aorta dilation in association with bicuspid aortic valve: a maturation defect of the aortic wall. *The Journal of thoracic and cardiovascular surgery.* 2014; 148(4):1583-90.
2. Ailawadi G, Moehle C W, Pei H, Walton S P, Yang Z, Kron I L, Lau C L, and Owens G K. Smooth muscle phenotypic modulation is an early event in aortic aneurysms. *The Journal of thoracic and cardiovascular surgery.* 2009; 138(6):1392-9.
3. Inamoto S, Kwartler C S, Lafont A L, Liang Y Y, Fadulu V T, Duraisamy S, Willing M, Estrera A, Safi H, Hannibal M C, et al. TGFBR2 mutations alter smooth muscle cell phenotype and predispose to thoracic aortic aneurysms and dissections. *Cardiovascular research.* 2010; 88(3): 520-9.
4. Shen J, Yang M, Ju D, Jiang H, Zheng J P, Xu Z, and Li L. Disruption of SM22 promotes inflammation after artery injury via nuclear factor kappaB activation. *Circulation research.* 2010; 106(8):1351-62.
5. Feil S, Hofmann F, and Feil R. SM22alpha modulates vascular smooth muscle cell phenotype during atherogenesis. *Circulation research.* 2004; 94(7):863-5.
6. Dong L H, Li L, Song Y, Duan Z L, Sun S G, Lin Y L, Miao S B, Yin Y J, Shu Y N, Li H, et al. TRAF6-Mediated SM22alpha K21 Ubiquitination Promotes G6P D Activation and NADPH Production, Contributing to GSH Homeostasis and VSMC Survival In Vitro and In Vivo. *Circulation research.* 2015; 117(8):684-94.
7. Rinaldi B, Finicelli M, Donniacuo M, Bernardo G D, Gritti G, Gaudio S D, Forte A, Peluso G, Cipollaro M, Rossi F, et al. G-CSF contributes at the healing of tunica media of arteriotomy-injured rat carotids by promoting differentiation of vascular smooth muscle cells. *J Cell Physiol.* 2016; 231(1):215-23.
8. Hibino N, Cismowski M J, Lilly B, McConnell P I, Shinoka T, Cheatham J P, Lucchesi P A, Galantowicz M E, and Trask A J. Potential Molecular Mechanism of Retrograde Aortic Arch Stenosis in the Hybrid Approach to Hypoplastic Left Heart Syndrome. *The Annals of thoracic surgery.* 2015; 100(3):1013-9; discussion 9-20.
9. Guo D C, Pannu H, Tran-Fadulu V, Papke C L, Yu R K, Avidan N, Bourgeois S, Estrera A L, Safi Hi, Sparks E, et al. Mutations in smooth muscle alpha-actin (ACTA2) lead to thoracic aortic aneurysms and dissections. *Nat Genet.* 2007; 39(12):1488-93.
10. Zhu L, Vranckx R, Khau Van Kien P, Lalande A, Boisset N, Mathieu F, Wegman M, Glancy L, Gasc J M, Brunotte F, et al. Mutations in myosin heavy chain 11 cause a syndrome associating thoracic aortic aneurysm/aortic dissection and patent ductus arteriosus. *Nat Genet.* 2006; 38(3):343-9.
11. Guo D C, Regalado E, Casteel D E, Santos-Cortez R L, Gong L, Kim J J, Dyack S, Home S G, Chang G, Jondeau G, et al. Recurrent Gain-of-Function Mutation in PRKG1 Causes Thoracic Aortic Aneurysms and Acute Aortic Dissections. *American journal of human genetics.* 2013
12. Wang L, Guo D C, Cao J, Gong L, Kamm K E, Regalado E, Li L, Shete S, He W Q, Zhu M S, et al. Mutations in myosin light chain kinase cause familial aortic dissections. *American journal of human genetics.* 2011; 87(5): 701-7.
12. Loeys B L, Chen J, Neptune E R, Judge D P, Podowski M, Holm T, Meyers J, Leitch C C, Katsanis N, Sharifi N, et al. A syndrome of altered cardiovascular, craniofacial, neurocognitive and skeletal development caused by mutations in TGFBR1 or TGFBR2. *Nat Genet.* 2005; 37(3): 275-81.
13. Lindsay M E, Schepers D, Bolar N A, Doyle J J, Gallo E, Fert-Bober 1, Kempers M J, Fishman E K, Chen Y, Myers L, et al. Loss-of-function mutations in TGFB2 cause a syndromic presentation of thoracic aortic aneurysm. *Nat Genet.* 2012; 44(8):922-7.
14. Bertoli-Avella A M, Gillis E, Morisaki H, Verhagen J M, de Graaf B M, van de Beek G, Gallo E, Kruithof B P, Venselaar H, Myers L A, et al. Mutations in a TGF-beta Ligand, TGFB3, Cause Syndromic Aortic Aneurysms and Dissections. *Journal of the American College of Cardiology.* 2015; 65(13):1324-36.
15. van de Laar I M, Oldenburg R A, Pals G, Roos-Hesselink I W, de Graaf B M, Verhagen J M, Hoedemaekers Y M, Willemsen R, Severijnen L A, Venselaar H, et al. Mutations in SMAD3 cause a syndromic form of aortic aneurysms and dissections with early-onset osteoarthritis. *Nat Genet.* 2011; 43(2):121-6.
16. Boileau C, Guo D C, Hanna N, Regalado E S, Detaint D, Gong L, Varret M, Prakash S K, Li A H, d'Indy H, et al. TGFB2 mutations cause familial thoracic aortic aneurysms and dissections associated with mild systemic features of Marfan syndrome. *Nat Genet.* 2012; 44(8): 916-21.
17. Isselbacher E M, Lino Cardenas C L, and Lindsay M E. Hereditary Influence in Thoracic Aortic Aneurysm and Dissection. *Circulation.* 2016; 133(24):2516-28.
18. Qiu P, Feng X H, and Li L. Interaction of Smad3 and SRF-associated complex mediates TGF-betal signals to regulate SM22 transcription during myofibroblast differentiation. *J Mol Cell Cardiol.* 2003; 35(12):1407-20.
19. Zhang P, Hou S, Chen J, Zhang J, Lin F, Ju R, Cheng X, Ma X, Song V. Zhang Y, et al. Smad4 Deficiency in Smooth Muscle Cells Initiates the Formation of Aortic Aneurysm. *Circulation research.* 2016; 118(3):388-99.
20. Chen S, Kulik M, and Lechleider R I. Smad proteins regulate transcriptional induction of the SM22alpha gene by TGF-beta. *Nucleic Acids Res.* 2003; 31(4):1302-10.
21. Qiu P, Ritchie R P, Gong X Q, Hamamori Y, and Li L. Dynamic changes in chromatin acetylation and the expression of histone acetyltransferases and histone deacetylases regulate the SM22alpha transcription in response to Smad3-mediated TGFbeta1 signaling. *Biochemical and biophysical research communications.* 2006; 348(2):351-8.
22. Renard M, Holm T, Veith R, Callewaert B L, Ades L C, Baspinar O, Pickart A, Dasouki M, Hoyer J, Rauch A, et al. Altered TGFbeta signaling and cardiovascular manifestations in patients with autosomal recessive cutis laxa type I caused by fibulin-4 deficiency. *European journal of human genetics: EJHG.* 2010.

23. Habashi J P, Judge D P, Holm T M, Cohn R D, Loeys B L, Cooper T K, Myers L, Klein E C, Liu G, Calvi C, et al. Losartan, an AT1 antagonist, prevents aortic aneurysm in a mouse model of Marfan syndrome. *Science.* 2006; 312(5770):117-21.
24. Rensen S S, Doevendans P A, and van Eys G J. Regulation and characteristics of vascular smooth muscle cell phenotypic diversity. *Neth Heart J.* 2007; 15(3):100-8.
25. Zhang L, Yu C, Chang Q, Luo X, Qiu J, and Liu S. Comparison of gene expression profiles in aortic dissection and normal human aortic tissues. *Biomed Rep.* 2016; 5(4):421-7.
26. Sun Y, Zhao Z, Hou L, Xiao Y, Qin F, Yan J, Zhou J, and Jing Z. The regulatory role of smooth muscle 22 on the proliferation of aortic smooth muscle cells participates in the development of aortic dissection. *Journal of vascular surgery.* 2017; 66(3):875-82.
27. Lesauskaite V, Tanganelli P, Sassi C, Neri E, Diciolla F, Ivanoviene L, Epistolato M C, Lalinga A V, Alessandrini C, and Spina D. Smooth muscle cells of the media in the dilatative pathology of ascending thoracic aorta: morphology, immunoreactivity for osteopontin, matrix metalloproteinases, and their inhibitors. *Human pathology.* 2001; 32(9):1003-11.
28. Nair R R, Solway J, and Boyd D D. Expression cloning identifies transgelin (SM22) as a novel repressor of 92-kDa type I V collagenase (MMP-9) expression. *J Biol Chem.* 2006; 281(36):26424-36.
29. Thompson O, Moghraby J S, Ayscough K R, and Winder S J. Depletion of the actin bundling protein SM22/transgelin increases actin dynamics and enhances the tumourigenic phenotypes of cells. *BMC Cell Biol.* 2012; 13(1.
30. Yamamura H, Yoshikawa H, Tatsuta M, Akedo H, and Takahashi K. Expression of the smooth muscle calponin gene in human osteosarcoma and its possible association with prognosis. *International journal of cancer.* 1998; 79(3):245-50.
31. Prasad P D, Stanton J A, and Assinder S J. Expression of the actin-associated protein transgelin (SM22) is decreased in prostate cancer. *Cell and tissue research.* 2010; 339(2):337-47.
32. Boyer L A, Plath K, Zeitlinger J, Brambrink T, Medeiros L A, Lee T I, Levine S S, Wernig M, Tajonar A, Ray M K, et al. Polycomb complexes repress developmental regulators in murine embryonic stem cells. *Nature.* 2006; 441(7091):349-53.
33. Ezhkova E, Pasolli H A, Parker J S, Stokes N, Su I H, Hannon G, Tarakhovsky A, and Fuchs E. Ezh2 orchestrates gene expression for the stepwise differentiation of tissue-specific stem cells. *Cell.* 2009; 136(6):1122-35.
34. Chang C J, Yang J Y, Xia W, Chen C T, Xie X, Chao C H, Woodward W A, Hsu J M, Hortobagyi G N, and Hung M C. EZH2 promotes expansion of breast tumor initiating cells through activation of RAF1-beta-catenin signaling. *Cancer Cell.* 2011; 19(1):86-100.
35. Wang L, Jin Q, Lee J E, Su I H, and Ge K. Histone H3K27 methyltransferase Ezh2 represses Wnt genes to facilitate adipogenesis. *Proc Natl Acad Sci USA.* 2010; 107(16):7317-22.
36. Renard M, Callewaert B, Baetens M, Campens L, Macdermot K, Fryns J P, Bonduelle M, Dietz H C, Gaspar I M, Cavaco D, et al. Novel MYH11 and ACTA2 mutations reveal a role for enhanced TGFbeta signaling in FTAAD. *International journal of cardiology.* 2011.
37. Wang Y, Ait-Oufella H, Herbin O, Bonnin P, Ramkhelawon B, Taleb S, Huang J, Offenstadt G, Combadiere C, Renia L, et al. TGF-beta activity protects against inflammatory aortic aneurysm progression and complications in angiotensin II-infused mice. *J Clin Invest.* 2010; 120(2):422-32.
38. Mallat Z, Ait-Oufella H, and Tedgui A. The Pathogenic Transforming Growth Factor-beta Overdrive Hypothesis in Aortic Aneurysms and Dissections: A Mirage? *Circulation research.* 2017; 120(11):1718-20.
39. Li W, Li O, Jiao Y, Qin L, Al R, Zhou J, Ferruzzi J, Kim R W, Geirsson A, Dietz H C, et al. Tgfbr2 disruption in postnatal smooth muscle impairs aortic wall homeostasis. *J Clin Invest.* 2014; 124(2):755-67.
40. Gallo E M, Loch D C, Habashi J P, Calderon J F, Chen Y, Bedja D, van Erp C, Gerber E E, Parker S J, Sauls K, et al. Angiotensin II-dependent TGF-beta signaling contributes to Loeys-Dietz syndrome vascular pathogenesis. *J Clin Invest.* 2014; 124(1):448-60.
41. Angelov S N, Hu J H, Wei H, Airhart N, Shi M, and Dichek D A. TGF-beta (Transforming Growth Factor-beta) Signaling Protects the Thoracic and Abdominal Aorta from Angiotensin I I-Induced Pathology by Distinct Mechanisms. *Arteriosclerosis, thrombosis, and vascular biology.* 2017; 37(142102-13.
42. Vapnik J S, Kim J B, Isselbacher E M, Ghoshhajra B B, Cheng Y, Sundt T M, 3rd, MacGillivray T E, Cambria R P, and Lindsay M E. Characteristics and Outcomes of Ascending Versus Descending Thoracic Aortic Aneurysms. *The American journal of cardiology.* 2016; 117 (10):1683-90.
43. Chang K, Francis S A, Aikawa E, Figueiredo J L, Kohler R H, McCarthy J R, Weissleder R, Plutzky J, and Jaffer F A. Pioglitazone suppresses inflammation in vivo in murine carotid atherosclerosis: novel detection by dual-target fluorescence molecular imaging. *Arteriosclerosis, thrombosis, and vascular biology.* 2010; 30(10):1933-9.
44. Cha T L, Zhou B P, Xia W, Wu Y, Yang C C, Chen C T, Ping B, Otte A P, and Hung M C. Akt-mediated phosphorylation of EZH2 suppresses methylation of lysine 27 in histone H3. *Science.* 2005; 310(5746):306-10.

What is claimed herein is:

1. A method of treating a thoracic aortic aneurysm, the method comprising administering to a subject in need thereof a therapeutically effective dose of GSK343.

2. The method of claim 1, wherein the subject is administered a therapeutically effective dose of GSK343 and losartan.

* * * * *